US012630590B2

(12) United States Patent
Chilkoti et al.

(10) Patent No.: US 12,630,590 B2
(45) Date of Patent: May 19, 2026

(54) ORDER AND DISORDER AS A DESIGN PRINCIPLE FOR STIMULI-RESPONSIVE BIOPOLYMER NETWORKS

(71) Applicant: Duke University, Durham, NC (US)

(72) Inventors: Ashutosh Chilkoti, Durham, NC (US); Stefan Roberts, Raleigh, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 18/303,530

(22) Filed: Apr. 19, 2023

(65) Prior Publication Data

US 2024/0083952 A1     Mar. 14, 2024

Related U.S. Application Data

(63) Continuation of application No. 16/625,899, filed as application No. PCT/US2018/040409 on Jun. 29, 2018, now Pat. No. 11,680,083.

(60) Provisional application No. 62/534,019, filed on Jul. 18, 2017, provisional application No. 62/527,836, filed on Jun. 30, 2017.

(51) Int. Cl.
| | |
|---|---|
| *C07K 14/00* | (2006.01) |
| *A61K 9/00* | (2006.01) |
| *A61K 9/51* | (2006.01) |
| *A61K 35/12* | (2015.01) |
| *A61K 35/74* | (2015.01) |

(52) U.S. Cl.
CPC .......... *C07K 14/001* (2013.01); *A61K 9/0024* (2013.01); *A61K 9/5169* (2013.01); *A61K 35/12* (2013.01); *A61K 35/74* (2013.01)

(58) Field of Classification Search
CPC .. C07K 14/001; A61K 9/0024; A61K 9/5169; A61K 35/12; A61K 35/74
See application file for complete search history.

(56) References Cited

U.S. PATENT DOCUMENTS

| | | | |
|---|---|---|---|
| 4,415,732 | A | 11/1983 | Caruthers et al. |
| 4,458,066 | A | 7/1984 | Caruthers et al. |
| 4,500,707 | A | 2/1985 | Caruthers et al. |
| 4,554,101 | A | 11/1985 | Hopp |
| 4,668,777 | A | 5/1987 | Caruthers et al. |
| 4,973,679 | A | 11/1990 | Caruthers et al. |
| 4,976,734 | A | 12/1990 | Urry et al. |
| 5,153,319 | A | 10/1992 | Caruthers et al. |
| 5,250,516 | A | 10/1993 | Urry |
| 5,278,302 | A | 1/1994 | Caruthers et al. |
| 5,336,256 | A | 8/1994 | Urry |
| 5,453,496 | A | 9/1995 | Caruthers et al. |
| 5,534,408 | A | 7/1996 | Green et al. |
| 5,578,577 | A | 11/1996 | Ching et al. |
| 5,580,859 | A | 12/1996 | Felgner et al. |
| 5,602,244 | A | 2/1997 | Caruthers et al. |
| 5,676,646 | A | 10/1997 | Hofmann et al. |
| 5,679,647 | A | 10/1997 | Carson et al. |
| 5,702,359 | A | 12/1997 | Hofmann et al. |
| 5,703,055 | A | 12/1997 | Felgner et al. |
| 5,935,776 | A | 8/1999 | Green et al. |
| 6,013,763 | A | 1/2000 | Braisted et al. |
| 6,068,650 | A | 5/2000 | Hofmann et al. |
| 6,096,020 | A | 8/2000 | Hofmann |
| 6,120,493 | A | 9/2000 | Hofmann |
| 6,150,148 | A | 11/2000 | Nanda et al. |
| 6,181,964 | B1 | 1/2001 | Hofmann et al. |
| 6,192,270 | B1 | 2/2001 | Hofmann et al. |
| 6,207,749 | B1 | 3/2001 | Mayes et al. |
| 6,208,893 | B1 | 3/2001 | Hofmann |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,245,515 | B1 | 6/2001 | Vogelstein et al. |
| 6,296,831 | B1 | 10/2001 | Weller et al. |
| 6,302,874 | B1 | 10/2001 | Zhang et al. |
| 6,413,587 | B1 | 7/2002 | Hawker et al. |
| 6,512,060 | B1 | 1/2003 | Matyjaszewski et al. |
| 6,541,580 | B1 | 4/2003 | Matyjaszewski et al. |
| 6,623,950 | B1 | 9/2003 | Osten et al. |
| 6,649,138 | B2 | 11/2003 | Adams et al. |
| 6,660,247 | B1 | 12/2003 | Gutowska et al. |
| 6,841,617 | B2 | 1/2005 | Jeong et al. |
| 6,852,834 | B2 | 2/2005 | Chilkoti |
| 6,869,588 | B2 | 3/2005 | Weller et al. |
| 7,033,571 | B2 | 4/2006 | Gutowska et al. |
| 7,087,244 | B2 | 8/2006 | Jeong et al. |
| 7,300,922 | B2 | 11/2007 | Sullenger et al. |

(Continued)

FOREIGN PATENT DOCUMENTS

| | | | |
|---|---|---|---|
| AU | 2007265628 | B2 | 12/2012 |
| CA | 2327325 | A1 | 11/1999 |

(Continued)

OTHER PUBLICATIONS

U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.

(Continued)

*Primary Examiner* — Robert S Cabral
(74) *Attorney, Agent, or Firm* — Michael Best & Friedrich LLP

(57)     ABSTRACT

Disclosed herein are partially ordered polypeptides, which include a plurality of disordered domains and a plurality of structured domains. The partially ordered polypeptides may have phase transition behavior and form aggregates at, above, or below certain temperatures. Further provided are cellular scaffolds comprised of the partially ordered polypeptides.

21 Claims, 115 Drawing Sheets

Specification includes a Sequence Listing.

(56)                    References Cited

U.S. PATENT DOCUMENTS

| | | | |
|---|---|---|---|
| 7,429,458 | B2 | 9/2008 | Chilkoti |
| 7,531,524 | B2 | 5/2009 | Rusconi |
| 7,664,545 | B2 | 2/2010 | Westersten et al. |
| 7,674,882 | B2 | 3/2010 | Kaplan et al. |
| 7,846,445 | B2 | 12/2010 | Schellenberger et al. |
| 8,129,330 | B2 | 3/2012 | Martinez et al. |
| 8,283,125 | B2 | 10/2012 | Cebolla Ramirez et al. |
| 8,470,967 | B2 | 6/2013 | Chilkoti et al. |
| 8,497,356 | B2 | 7/2013 | Chilkoti et al. |
| 8,506,963 | B2 | 8/2013 | Li et al. |
| 8,586,347 | B2 | 11/2013 | Lochhead et al. |
| 8,841,414 | B1 | 9/2014 | Raucher et al. |
| 8,912,310 | B2 | 12/2014 | Chilkoti et al. |
| 8,937,153 | B2 | 1/2015 | Abrahmsén et al. |
| 9,127,047 | B2 | 9/2015 | Chilkoti |
| 9,132,178 | B2 | 9/2015 | Philip |
| 9,138,743 | B2 | 9/2015 | Yager et al. |
| 9,482,664 | B2 | 11/2016 | Chilkoti et al. |
| 9,592,303 | B2 | 3/2017 | Chilkoti et al. |
| 9,662,422 | B2 | 5/2017 | Pollock et al. |
| 9,771,396 | B2 | 9/2017 | Chilkoti et al. |
| 9,804,170 | B2 | 10/2017 | Krishna et al. |
| 9,890,420 | B2 | 2/2018 | Chilkoti et al. |
| 10,064,954 | B2 | 9/2018 | Wu |
| 10,131,690 | B2 | 11/2018 | Bonny et al. |
| 10,138,291 | B2 | 11/2018 | Chhabra et al. |
| 10,302,636 | B2 | 5/2019 | Chilkoti et al. |
| 10,364,451 | B2 | 7/2019 | Chilkoti et al. |
| 10,385,115 | B2 | 8/2019 | Chilkoti et al. |
| 10,434,182 | B2 | 10/2019 | Weng et al. |
| 11,169,150 | B2 | 11/2021 | Chilkoti et al. |
| 2001/0034050 | A1 | 10/2001 | Chilkoti |
| 2002/0052443 | A1 | 5/2002 | Greenwald et al. |
| 2002/0146794 | A1 | 10/2002 | Tomycz |
| 2003/0008308 | A1 | 1/2003 | Enzelberger et al. |
| 2003/0138829 | A1 | 7/2003 | Unger et al. |
| 2003/0161816 | A1 | 8/2003 | Fraser et al. |
| 2003/0175290 | A1 | 9/2003 | Renner et al. |
| 2003/0185741 | A1 | 10/2003 | Matyjaszewski et al. |
| 2003/0225251 | A1 | 12/2003 | Sallberg et al. |
| 2003/0233675 | A1 | 12/2003 | Cao et al. |
| 2004/0053976 | A1 | 3/2004 | Martinez et al. |
| 2004/0101852 | A1 | 5/2004 | Bennett et al. |
| 2004/0192072 | A1 | 9/2004 | Snow et al. |
| 2005/0037967 | A1 | 2/2005 | Rosenblum |
| 2005/0186214 | A1 | 8/2005 | Liu et al. |
| 2005/0255554 | A1 | 11/2005 | Chilkoti |
| 2005/0288229 | A1 | 12/2005 | Sindrey et al. |
| 2006/0025524 | A1 | 2/2006 | Schneider et al. |
| 2006/0034796 | A1 | 2/2006 | Ashwell et al. |
| 2006/0051798 | A1 | 3/2006 | Mirkin et al. |
| 2006/0073101 | A1 | 4/2006 | Oldfield et al. |
| 2007/0087114 | A1 | 4/2007 | Chilkoti et al. |
| 2007/0117173 | A1 | 5/2007 | Levison et al. |
| 2008/0181861 | A1 | 7/2008 | Jiang et al. |
| 2009/0098652 | A1 | 4/2009 | Stupp et al. |
| 2009/0215194 | A1 | 8/2009 | Magni et al. |
| 2009/0247424 | A1 | 10/2009 | Chilkoti et al. |
| 2010/0015070 | A1 | 1/2010 | Bollschweiler et al. |
| 2010/0022455 | A1 | 1/2010 | Chilkoti |
| 2010/0048473 | A1 | 2/2010 | Chaikof et al. |
| 2010/0120018 | A1 | 5/2010 | Quake et al. |
| 2010/0241054 | A1 | 9/2010 | Dacey et al. |
| 2010/0311059 | A1 | 12/2010 | Didion et al. |
| 2010/0311669 | A1 | 12/2010 | Greene et al. |
| 2010/0325765 | P1 | 12/2010 | Pait et al. |
| 2011/0060032 | A1 | 3/2011 | MacLachlan et al. |
| 2011/0082283 | A1 | 4/2011 | Dagher et al. |
| 2011/0110866 | A1 | 5/2011 | Chilkoti et al. |
| 2011/0119778 | A1 | 5/2011 | Liss |
| 2011/0165557 | A1 | 7/2011 | Ah et al. |
| 2011/0207673 | A1 | 8/2011 | Chilkoti et al. |
| 2011/0248698 | A1 | 10/2011 | Kikuchi et al. |
| 2011/0294189 | A1 | 12/2011 | Chilkoti et al. |
| 2011/0303303 | A1 | 12/2011 | Proper et al. |
| 2011/0305718 | A1 | 12/2011 | Mugica et al. |
| 2012/0172298 | A1 | 7/2012 | Andersen et al. |
| 2012/0208742 | A1 | 8/2012 | Primiano et al. |
| 2013/0039927 | A1 | 2/2013 | Dewhurst et al. |
| 2013/0079277 | A1 | 3/2013 | Chilkoti |
| 2013/0079280 | A1 | 3/2013 | Baca et al. |
| 2013/0096058 | A1 | 4/2013 | Baca et al. |
| 2013/0102993 | A1 | 4/2013 | Kim et al. |
| 2013/0130384 | A1 | 5/2013 | Okamoto et al. |
| 2013/0150432 | A1 | 6/2013 | Thodeti et al. |
| 2013/0157889 | A1 | 6/2013 | Chilkoti et al. |
| 2013/0165389 | A1 | 6/2013 | Schellenberger et al. |
| 2013/0172274 | A1 | 7/2013 | Chilkoti |
| 2013/0197359 | A1 | 8/2013 | Park et al. |
| 2013/0315823 | A1 | 11/2013 | Trieu |
| 2013/0330335 | A1 | 12/2013 | Bremel et al. |
| 2014/0024600 | A1 | 1/2014 | Chilkoti et al. |
| 2014/0163201 | A1 | 6/2014 | Winter et al. |
| 2014/0275227 | A1 | 9/2014 | Hoge et al. |
| 2014/0294932 | A1 | 10/2014 | Kim et al. |
| 2015/0094270 | A1 | 4/2015 | Harris et al. |
| 2015/0099707 | A1 | 4/2015 | Pastan et al. |
| 2015/0112022 | A1 | 4/2015 | Chilkoti et al. |
| 2016/0017278 | A1 | 1/2016 | Montclare et al. |
| 2016/0114053 | A1 | 4/2016 | Chilkoti |
| 2016/0120952 | A1 | 5/2016 | Chilkoti |
| 2016/0187239 | A1 | 6/2016 | Givens et al. |
| 2016/0200787 | A1 | 7/2016 | Matern et al. |
| 2016/0209356 | A1 | 7/2016 | Herget et al. |
| 2016/0220727 | A1 | 8/2016 | Lu et al. |
| 2016/0250165 | A1 | 9/2016 | Sullenger et al. |
| 2016/0271262 | A1 | 9/2016 | Lopez et al. |
| 2016/0303091 | A1 | 10/2016 | Wang |
| 2016/0348147 | A1 | 12/2016 | Lopez et al. |
| 2016/0355802 | A1 | 12/2016 | Isaacs et al. |
| 2017/0020961 | A1 | 1/2017 | Rosenblatt et al. |
| 2017/0088670 | A1 | 3/2017 | Rowan et al. |
| 2017/0102357 | A1 | 4/2017 | Liang et al. |
| 2017/0166621 | A1 | 6/2017 | Boettcher et al. |
| 2017/0170142 | A1 | 6/2017 | Edelstein et al. |
| 2017/0189545 | A1 | 7/2017 | Lee et al. |
| 2017/0209601 | A1 | 7/2017 | Kumar et al. |
| 2017/0233714 | A1 | 8/2017 | Chilkoti et al. |
| 2017/0239363 | A1 | 8/2017 | Chilkoti et al. |
| 2017/0369651 | A1 | 12/2017 | Cheng et al. |
| 2018/0037609 | A1 | 2/2018 | Chilkoti et al. |
| 2018/0133401 | A1 | 5/2018 | Schwab et al. |
| 2018/0135060 | A1 | 5/2018 | Romero Ramos et al. |
| 2018/0161772 | A1 | 6/2018 | Rammohan et al. |
| 2018/0171337 | A1 | 6/2018 | O'Neill et al. |
| 2018/0200196 | A1 | 7/2018 | Fahmy et al. |
| 2018/0217136 | A1 | 8/2018 | Chilkoti et al. |
| 2018/0231469 | A1 | 8/2018 | Gibbons et al. |
| 2018/0238864 | A1 | 8/2018 | Burd et al. |
| 2018/0258157 | A1 | 9/2018 | Chilkoti et al. |
| 2018/0326044 | A1 | 11/2018 | Carter |
| 2018/0327752 | A1 | 11/2018 | Pillay et al. |
| 2018/0369399 | A1 | 12/2018 | Hershfield et al. |
| 2019/0015520 | A1 | 1/2019 | Chilkoti et al. |
| 2019/0016763 | A1 | 1/2019 | Kitazawa et al. |
| 2019/0204309 | A1 | 7/2019 | Gibbs |
| 2019/0285623 | A1 | 9/2019 | Chilkoti et al. |
| 2019/0292549 | A1 | 9/2019 | Zhang et al. |
| 2019/0345228 | A1 | 11/2019 | Chilkoti et al. |
| 2020/0030496 | A1 | 1/2020 | Reddy et al. |
| 2020/0078313 | A1 | 3/2020 | Roy et al. |
| 2020/0121809 | A1 | 4/2020 | Hope et al. |
| 2020/0148724 | A1 | 5/2020 | Chilkoti et al. |
| 2020/0163878 | A1 | 5/2020 | Baumhof et al. |
| 2020/0181555 | A1 | 6/2020 | Hinojosa et al. |
| 2020/0241020 | A1 | 7/2020 | Oshinski |
| 2021/0046188 | A1 | 2/2021 | Hucknall et al. |
| 2021/0128734 | A1 | 5/2021 | Chilkoti et al. |
| 2021/0154143 | A1 | 5/2021 | Chilkoti et al. |
| 2021/0333278 | A1 | 10/2021 | Mangan |
| 2021/0346570 | A1 | 11/2021 | Wu et al. |
| 2022/0074938 | A1 | 3/2022 | Omir et al. |
| 2022/0347489 | A1 | 11/2022 | Brachman et al. |
| 2022/0379308 | A1 | 12/2022 | Shing et al. |

(56)             References Cited

U.S. PATENT DOCUMENTS

| 2023/0098149 A1 | 3/2023 | Chilkoti et al. |
| 2023/0225998 A1 | 7/2023 | Mansour et al. |
| 2024/0050642 A1 | 2/2024 | Tal et al. |

FOREIGN PATENT DOCUMENTS

| CA | 2423488 A1 | 4/2002 |
| CN | 102575229 A | 7/2012 |
| CN | 104725628 B | 4/2018 |
| CN | 112946261 A | 6/2021 |
| CN | 112961065 A | 6/2021 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | WO2006/110292 A2 | 10/2006 |
| WO | WO2007/073486 A2 | 6/2007 |
| WO | WO2007/108013 A2 | 9/2007 |
| WO | WO2007/134245 A2 | 11/2007 |
| WO | WO2008/012543 A1 | 1/2008 |
| WO | WO2008/030968 A2 | 3/2008 |
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | WO2011/025572 A1 | 3/2011 |
| WO | WO2011/123813 A2 | 10/2011 |
| WO | 2012/156058 A1 | 11/2012 |
| WO | WO2012/162426 A1 | 11/2012 |
| WO | WO2013/049234 A2 | 4/2013 |
| WO | WO2013/065009 A1 | 5/2013 |
| WO | WO2013/106715 A1 | 7/2013 |
| WO | WO2014/037373 A1 | 3/2014 |
| WO | WO2014/194244 A1 | 12/2014 |
| WO | WO2015/011231 A1 | 1/2015 |
| WO | WO2015/130846 A2 | 9/2015 |
| WO | WO2016/065273 A1 | 4/2016 |
| WO | WO2016/065300 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO2017/192449 A1 | 11/2017 |
| WO | WO2018/115401 A1 | 6/2018 |
| WO | WO2018/144854 A1 | 8/2018 |
| WO | 2018/231834 A1 | 12/2018 |
| WO | WO2019/103744 A1 | 5/2019 |
| WO | WO2019/147954 A1 | 8/2019 |
| WO | WO2019/213150 A1 | 11/2019 |
| WO | 2020/037100 A1 | 2/2020 |
| WO | WO2020/037214 A1 | 2/2020 |
| WO | WO2020/051220 A1 | 3/2020 |
| WO | WO2020/051223 A1 | 3/2020 |
| WO | WO2020/160472 A1 | 8/2020 |
| WO | WO2021/178898 A1 | 9/2021 |
| WO | WO2022/016089 A2 | 1/2022 |
| WO | 2023/028072 A1 | 3/2022 |
| WO | WO2022/178438 A1 | 8/2022 |
| WO | 2022/216821 A1 | 10/2022 |
| WO | 2022/066635 A1 | 3/2023 |

OTHER PUBLICATIONS

U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.

PCT/US2017/052887, Sep. 22, 2017, WO2018/057847, Mar. 29, 2018.
U.S. Appl. No. 16/335,734, filed Mar. 22, 2019, U.S. Pat. No. 11,155,584, Oct. 26, 2021.
U.S. Appl. No. 17/477,192, filed Sep. 16, 2021, 2022/0098248, Mar. 31, 2022.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US2016/032785, May 15, 2018, WO2018/213320, Nov. 22, 2018.
U.S. Appl. No. 16/614,282, filed Nov. 15, 2019, U.S. Pat. No. 11,554,097, Jan. 17, 2023.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, U.S. Pat. No. 11,458,205, Oct. 4, 2022.
U.S. Appl. No. 62/394,662, filed Sep. 14, 2016.
PCT/US2017/051661, Sep. 14, 2017 WO2018/053201, Mar. 22, 2018.
U.S. Appl. No. 16/332,865, filed Mar. 13, 2019, U.S. Pat. No. 11,135,301, May 10, 2021.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, U.S. Pat. No. 11,648,200, May 16, 2023.
U.S. Appl. No. 62/527,836, filed Jun. 30, 2017.
U.S. Appl. No. 62/534,019, filed Jul. 18, 2017.
PCT/US2018/040409, Jun, 29, 2018, WO2019/006374, Jan. 3, 2019.
U.S. Appl. No. 16/625,899, filed Dec. 23, 2019, U.S. Pat. No. 11,680,083, Jun. 20, 2023.
U.S. Appl. No. 18/303,530, filed Apr. 19, 2023.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018, U.S. Pat. No. 11,467,156, Oct. 11, 2022.
U.S. Appl. No. 62/728,582, filed Sep. 7, 2018.
PCT/US2019/050077, Sep. 6, 2019, WO2020/051541, Mar. 12, 2020.
U.S. Appl. No. 17/272,887, filed Mar. 2, 2021, 2021/0316007, Oct. 14, 2021.
U.S. Appl. No. 62/767,736, filed Nov. 15, 2018.
PCT/US2019/061144, Nov. 13, 2019, WO2020/102324, May 22, 2020.
U.S. Appl. No. 17/294,368, filed May 14, 2021, 2022/0008567, Jan. 13, 2022.
U.S. Appl. No. 62/622,249, filed Jan. 26, 2018.

(56)          References Cited

OTHER PUBLICATIONS

PCT/US2019/015176, Jan, 25, 2019, WO2019/147954, Aug. 1, 2019.
U.S. Appl. No. 16/964,832, filed Jul. 24, 2020, 2021/0060171, Mar. 4, 2021.
U.S. Appl. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 17/051,202, filed Oct. 28, 2020.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020, 2021/0009999, Jan. 14, 2021.
U.S. Appl. No. 18/051,487, filed Oct. 31, 2022.
U.S. Appl. No. 62/713,752, filed Aug. 2, 2018.
PCT/US2019/044911, Aug. 2, 2019, WO2020/028806, Feb. 6, 2020.
U.S. Appl. No. 17/265,165, filed Feb. 1, 2021, U.S. Pat. No. 11,649,275, May 16, 2023.
U.S. Appl. No. 18/296,961, filed Apr. 6, 2023.
U.S. Appl. No. 62/985,174, filed Mar. 4, 2020.
PCT/US2021/020589, Mar. 3, 2021, WO2021/178481, Sep. 10, 2021.
U.S. Appl. No. 17/908,415, filed Aug. 31, 2022, 2023/0086188, Mar. 23, 2023.
U.S. Appl. No. 62/985,179, filed Mar. 4, 2020.
PCT/US2021/020591, Mar. 3, 2021, WO2021/178483, Sep. 10, 2021.
U.S. Appl. No. 17/908,427, filed Aug. 31, 2022, 2023/0086188, Mar. 23, 2023.
U.S. Appl. No. 62/898,353, filed Sep. 12, 2019.
U.S. Appl. No. 17/015,315, filed Sep. 9, 2020, 2021/0046188, Feb. 18, 2021.
U.S. Appl. No. 62/975,479, filed Feb. 12, 2020.
PCT/US2021/017809, Feb. 12, 2021, WO2021/163445, Aug. 19, 2021.
U.S. Appl. No. 17/798,868, filed Aug. 10, 2022, 2023/0105233, Apr. 6, 2023.
U.S. Appl. No. 63/035,173, filed Jun. 5, 2020.
PCT/US2021/035823, Jun. 4, 2021, WO2021/247952, Dec. 9, 2021.
U.S. Appl. No. 18/007,879, filed Dec. 2, 2022.
U.S. Appl. No. 63/068,432, filed Aug. 21, 2020.
U.S. Appl. No. 63/116,511, filed Nov. 20, 2020.
PCT/US2021/046833, Aug. 20, 2021, WO2022/040495, Feb. 24, 2022.
U.S. Appl. No. 18/042,032, filed Feb. 17, 2023.
U.S. Appl. No. 63/236,064, filed Aug. 23, 2021.
PCT/US2022/041251, Aug. 23, 2022, WO2023/028072, Mar. 2, 2023.
U.S. Appl. No. 63/169,541, filed Apr. 1, 2021.
PCT/US2022/023158, Apr. 1, 2022, WO2022/212911, Oct. 6, 2022.
U.S. Appl. No. 63/151,878, filed Feb. 22, 2021.
U.S. Appl. No. 63/274,839, filed Nov. 2, 2021.
PCT/US2022/017349, Feb. 22, 2022, WO2022/178438, Aug. 25, 2022.
U.S. Appl. No. 63/271,595, filed Oct. 25, 2021.
PCT/US2022/078659, Oct. 25, 2022, WO2023/076902, May 4, 2023.
U.S. Appl. No. 63/250,813, filed Sep. 30, 2021.
U.S. Appl. No. 17/957,373, filed Sep. 30, 2022, 2023/0098149, Mar. 30, 2023.
U.S. Appl. No. 63/325,708, filed Mar. 31, 2022.
U.S. Appl. No. 18/194,417, filed Mar. 31, 2023.
U.S. Appl. No. 63/429,316, filed Dec. 1, 2022.
Cereghetti et al., "Reversible, functional amyloids: towards an understanding of their regulation in yeast and humans," Cell Cycle, 2018, 17(13): 1545-1558.

Uversky et al., "Life in Phases: Intra- and Inter-Molecular Phase Transitions in Protein Solutions," Biomolecules, 2019, 9(12): 842.
McPherson, "Product purification by reversible phase transition following *Escherichia coli* expression of genes encoding up to 251 repeats of the elastomeric pentapeptide GVGVP," Protein Expression and Purification, 1996, 7: 51-57.
Cascarina et al., "Generalizable Compositional Features Influencing the Proteostatic Fates of Polar Low-Complexity Domains," International Journal of Molecular Sciences, 2021, 22(16): 8944.
Krainer et al., "Reentrant liquid condensate phase of proteins is stabilized by hydrophobic and non-ionic interactions," Nature Communications, 2021, 12(1): 1085.
United States Patent Office Action for U.S. Appl. No. 17/477,192 dated Jan. 4, 2024 (11 pages).
United States Patent Office Notice of Allowance for U.S. Appl. No. 18/051,487 dated Dec. 11, 2023 (5 pages).
United States Patent Office Action for U.S. Appl. No. 16/964,832 dated Jan. 19, 2024 (9 pages).
United States Patent Office Action for U.S. Appl. No. 17/051,202 dated Jan. 19, 2024 (5 pages).
Liu et al., "Stable Evans Blue Derived Exendin-4 Peptide for Type 2 Diabetes Treatment," Bioconjugate Chem, 2016, 27: 54058.
United States Patent Office Action for U.S. Appl. No. 17/051,202 dated Jun. 21, 2023 (10 pages).
United States Patent Office Notice of Allowance for U.S. Appl. No. 17/015,315 dated Apr. 26, 2023 (7 pages).
Singh et al., "Polymeric microneedles for controlled transdermal drug delivery," Journal of Controlled Release, 2019, 315: 97-113.
Vancoillie et al., "Thermoresponsive poly(oligo ethylene glycol acrylates)," Progress in Polymer Science, 2014, 39(6): 1074-1095.
Zhang et al., "A triple thermoresponsive schizophrenic diblock copolymer," Polymer Chemistry, 2013, 4(16): 4322-4325.
International Search Report and Written Opinion for Application No. PCT/US2024/050476 dated Nov. 25, 2024 (18 pages).
United States Patent Office Notice of Allowance for U.S. Appl. No. 16/964,832 dated Jan. 6, 2025 (14 pages).
United States Patent Office Action for U.S. Appl. No. 17/272,887 dated Nov. 21, 2024 (13 pages).
United States Patent Office Notice of Allowance for U.S. Appl. No. 17/051,202 dated Nov. 15, 2024 (7 pages).
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6):1247-1260.
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Agarwal et al., "One-step microfluidic generation of pre-hatching embryo-like core-shell microcapsules for miniaturized 3D culture of pluripotent stem cells," Lab Chip, 2013, 13: 4525-4533.
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Aladini et al., "Chemical Synthesis and Characterization of Elastin-Like Polypeptides (ELPs) With Variable Guest Residues," J Pept Sci, May 2016, vol. 22, Issue 5, pp. 334-342.

(56)          References Cited

OTHER PUBLICATIONS

Alarcon et al., "Exendin 4 controls insulin production in rat islet beta cells predominantly by potentiation of glucose-stimulated proinsulin biosynthesis at the translational level," Diabetologia, 2006, 49(12):2920-2929.

Albanese et al., "The effect of nanoparticle size, shape, and surface chemistry on biological systems," Annu. Rev. Biomed. Eng., Aug. 2012, vol. 14, pp. 1-16.

Alconcel et al., "FDA-approved poly(ethylene glycol)-protein conjugate drugs," Polym. Chem., vol. 2, Apr. 2011, Issue 7, pp. 1442-1448.

Alghoul et al., "The effect of hyaluronan hydrogel on fat graft survival," Aesthet Surg J, 2012, 32: 622-633.

Allen et al., "Liposomal drug delivery systems: from concept to clinical applications," Adv Drug Deliv Rev, Elsevier, Jan. 2013, 65(1):36-48.

Alley et al., "Feasibility of drug screening with panels of human tumor cell lines using a microculture tetrazolium assay," Cancer Res., 1988, 48, 589-601.

Aluri et al., "Elastin-like peptide amphiphiles Form nanofibers with tunable length," Biomacromolecules, Sep. 2012, vol. 13, Issue 9, pp. 2645-2654.

Alves et al., "Influence of doxorubicin on model cell membrane properties: insight from in vitro and in silico studies," Sci Rep, 2017, 7(1): 6343.

Amanat et al., "A serological assay to detect SARS-CoV-2 seroconversion in humans," Nat Med, 2020, 26(7): 1033-1036.

American Diabetes Association, Standards of medical care in diabetes—2018. Diabetes Care, Jan. 2018, vol. 41, Supplement 1, pp. S1-S159.

American Hospital Association, "AHA Hospital Statistics," 2020 edition. Available at: <https://www.aha.org/statistics/fast-facts-us-hospitals>.

American Society of Plastic Surgeons, "2017 Plastic Surgery Statistics Report," Oct. 2018, 25 pages.

Amiram et al., "A depot-forming glucagon-like peptide-1 fusion protein reduces blood glucose for five days with a single injection," J. Control. Release, Nov. 2013, vol. 172, Issue, pp. 144-151.

Amiram et al., "Evolution of translation machinery in recoded bacteria enables multi-site incorporation of nonstandard amino acids," Nat Biotechnol, 2015, 33: 1272-1279.

Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.

Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.

Anselmo et al., "Nanoparticles in the clinic," Bioeng Transl Med, Jun. 2016, 1(1):10-29.

Antos et al., "Lipid Modification of Proteins through Sortase-Catalyzed Transpeptidation," J. Am. Chem. Soc., Dec. 2008, vol. 130, Issue 48, pp. 16338-16343.

Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.

Appleyard et al., "Multiplexed protein quantification with barcoded hydrogel microparticles," Anal Chem, 2011, 83: 193-199.

Arami et al., "In vivo delivery, pharmacokinetics, biodistribution and toxicity of iron oxide nanoparticles," Chem Soc Rev, Dec. 2015, 44(23):8576-8607.

Arias et al., "Superior preclinical efficacy of gemcitabine developed as chitosan nanoparticulate system," Biomacromolecules, Jan. 2011, vol. 12, Issue 1, pp. 97-104.

Armbruster et al., "Limit of blank, limit of detection and limit of quantitation," Clin Biochem Rev, 2008, 29 Suppl 1: S49-52.

Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.

Armstrong et al., "The Hydrodynamic Radii of Macromolecules and Their Effect on Red Blood Cell Aggregation," Biophys. J., 2004, 87, 4259-4270.

Arner et al., "FGF21 attenuates lipolysis in human adipocytes—a possible link to improved insulin sensitivity," FEBS Lett, May 2008, vol. 582, Issue 12, pp. 1725-1730.

Arnida et al., "Geometry and surface characteristics of gold nanoparticles influence their biodistribution and uptake by macrophages," Eur J Pharm Biopharm, Apr. 2011, vol. 77, Issue 3, pp. 417-423.

Arshavsky-Graham et al., "Lab-on-a-Chip Devices for Point-of-Care Medical Diagnostics," Advances in Biochemical Engineering/Biotechnology, 2020, 19 pages.

Asai et al., "Protein polymer hydrogels by in situ, rapid and reversible self-gelation," Biomaterials, Jul. 2012, vol. 33, Issue 21, pp. 5451-5458.

Astete et al., "Synthesis and characterization of PLGA nanoparticles," Journal of Biomaterials Science, Polymer Edition 2006, 17(3):247-289.

Atun et al., "Expanding global access to radiotherapy," Lancet Oncol, Sep. 2015, vol. 16, Issue 10, pp. 1153-1186.

Atyeo et al., "Distinct Early Serological Signatures Track with SARS-CoV-2 Survival," Immunity, 2020, 53: 524-532.

Averick et al., "ATRP under biologically relevant conditions: grafting from a protein," ACS Macro. Lett., Jan. 2012, vol. 1, Issue 1, pp. 6-10.

Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.

Awai et al., "Studies of the metabolism of I-131-labeled human transferrin," J. Lab. Clin. Med. 61, 1963, 363-396.

Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.

Awasthi et al., "Evaluation of combination treatment benefits of nab-paclitaxel in experimental pancreatic cancer," Journal of Clinical Oncology, 2012, 30, 170.

Axup et al., "Synthesis of site-specific antibody-drug conjugates using unnatural amino acids," Proc Natl Acad Sci USA, Feb. 2012, vol. 109, Issue 40, pp. 16101-16106.

Azhdarinia et al., "Regional radiochemotherapy using in situ hydrogel," Pharm Res., 2005, 22, 776-783.

Babu, "The contribution of intrinsically disordered regions to protein function, cellular complexity, and human disease," Biochem Soc Trans, Oct. 2016, 44(5):1185-1200.

Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.

Badi, "Non-linear PEG-based thermoresponsive polymer systems," Progress in Polymer Science, Mar. 2017, vol. 66, pp. 54-79.

Bae et al., "Targeted drug delivery to tumors: myths, reality and possibility," J Control Release, Elsevier, Aug. 2011, 153(3):198-205.

Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.

Baggio et al., "Biology of Incretins: GLP-1 and GIP," Gastroenterology, May 2007, vol. 132, Issue 6, pp. 2131-2157.

Bailey et al., "Genomic analyses identify molecular subtypes of pancreatic cancer," Nature, Mar. 2016, vol. 531, Issue 7592, pp. 47-52.

Bain et al., "Formation of monolayer films by the spontaneous assembly of organic thiols from solution onto gold," Journal of the American Chemical Society, 1989, 111: 321-335.

Balaji, "Subdermal fat grafting for Parry-Romberg syndrome," Ann Maxillofac Surg, 2014, 4: 55-59.

Balu et al., "An16-resilin: an advanced multi-stimuli-responsive resilin-mimetic protein polymer," Acta Biomater, Nov. 2014, 10:4768-4777.

Bamford et al., "The COSMIC (Catalogue of Somatic Mutations in Cancer) database and website," British Journal of Cancer, 2004, 91, 355-358.

(56) References Cited

OTHER PUBLICATIONS

Banani et al., "Biomolecular condensates: organizers of cellular biochemistry," Nat Rev Mol Cell Biol, May 2017, 18(5):285-298.

Banerjee et al., "Nanoparticles in cancer chemotherapy," Prog Mol Biol Transl Sci, Elsevier, Nov. 2011, 104:489-507.

Banga et al., "Parenteral controlled delivery and parmacokinetics of therapeutic peptides and proteins," (CRC Press, Boca Raton, FL, 2005).

Banjade et al., "Phase transitions of multivalent proteins can promote clustering of membrane receptors," Elife, Oct. 2014, 3:e04123.

Bansal et al., "PEGylation improves pharmacokinetic profile, liver uptake and efficacy of Interferon gamma in liver fibrosis," J. Control. Release, Sep. 2011, vol. 154, Issue 3, pp. 233-240.

Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.

Banyard et al., "Preparation, Characterization, and Clinical Implications of Human Decellularized Adipose Tissue Extracellular Matrix (hDAM): A Comprehensive Review," Aesthet Surg J, 2016, 36: 349-357.

Baraf et al., "Infusion-related reactions with pegloticase, a recombinant uricase for the treatment of chronic gout refractory to conventional therapy," J Clin Rheumatol, 2014, 20: 427-432.

Barbuti et al., "Paclitaxel through the ages of anticancer therapy: Exploring its role in chemoresistance and radiation therapy," Cancers, Dec. 2015, vol. 7, Issue 4, pp. 2360-2371.

Barnett et al., "Normal tissue reactions to radiotherapy: towards tailoring treatment dose by genotype," Nat Rev Cancer, Feb. 2009, vol. 9, Issue 2, pp. 134-142.

Barton et al., "Estimating the demand for radiotherapy form the evidence: A review of changes from 2003 to 2012," Radiother Oncol, Jul. 2014, vol. 112, Issue 1, pp. 140-144.

Baskar et al., "Cancer and Radiation Therapy: Current Advances and Future Directions," Int. J. Med. Sci., Feb. 2012, vol. 9, Issue 3, pp. 193-199.

Bates et al., "Block copolymer thermodynamics: theory and experiment," Annu Rev. Phys. Chem., 1990, 41:525-57.

Bedford et al., "WW domain-mediated interactions reveal a spliceosome-associated protein that binds a third class of proline-rich motif: The proline glycine and methionine-rich motif," PNAS, 1998, 95: 10602-10607.

Beenken et al., "The FGF family: biology, pathophysiology and therapy," Nat Rev Drug Discov, Mar. 2009, vol. 8, Issue 3, pp. 235-253.

Begg et al., "Strategies to improve radiotherapy with targeted drugs," Nat Rev Cancer, Apr. 2011, vol. 11, Issue 4, pp. 239-253.

Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.

Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.

Bender et al., "Synthesis, Crystallization, and Biological Evaluation of an Orally Active Prodrug of Gemcitabine," J. Med. Chem., Nov. 2009, vol. 52, Issue 22, pp. 6958-6961.

Benn et al., "Physiology of Hyperuricemia and Urate-Lowering Treatments," Front Med (Lausanne), 2018, 5: 160, 28 pages.

Bennett et al., "Association of Fat Grafting With Patient-Reported Outcomes in Postmastectomy Breast Reconstruction," JAMA Surg, 2017, 152: 944-950.

Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.

Bernacki et al., "Length-dependent aggregation of uninterrupted polyalanine peptides," Biochemistry, Sep. 2011, vol. 50, Issue 43, pp. 9200-9211.

Berndt et al., "Synthetic lipidation of peptides and amino acids: Monolayer structure and properties," J. Am. Chem. Soc., 1995, 117, 9515-9522.

Berry et al., "Development and characterisation of neutralising monoclonal antibody to the SARS-coronavirus," J Virol Methods, 2004, 120: 87-96.

Bessa et al., "Thermoresponsive self-assembled elastin-based nanoparticles for delivery of BMPs," Journal of Controlled Release, Mar. 2010, vol. 142, Issue 3, pp. 312-318.

Best, "Computational and theoretical advances in studies of intrinsically disordered proteins," Curr Opin Struct Biol, Feb. 2017, 42:147-154.

Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.

Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.

Bidwell et al., "Development of elastin-like polypeptide for thermally targeted delivery of doxorubicin," Biochemical Pharmacology, Mar. 2007, vol. 73, Issue 5, pp. 620-631.

Binz et al., "Engineering novel binding proteins from nonimmunoglobulin domains," Nat Biotechnol, 2005, 23(10):1257-68.

Blanco et al., "Principles of nanoparticle design for overcoming biological barriers to drug delivery," Nat Biotechnol, Sep. 2015, 33(9):941-51.

Blasko et al., "Brachytherapy for carcinoma of the prostate: Techniques, patient selection, and clinical outcomes," Seminars in Radiation Oncology, 2002, 12, 81-94.

Blasko et al., "The role of external beam radiotherapy with I-125/Pd-103 brachytherapy for prostate carcinoma," Radiother Oncol, 2000, 57, 273-278.

Blasko et al., "Transperineal percutaneous iodine-125 implantation for prostatic carcinoma using transrectal ultrasound and template guidance," Endocurietherapy/Hyperthermia Oncology, 1987, 3, 131-139.

Bley et al., "Microtubule stabilising agents and ionising radiation: Multiple exploitable mechanisms for combined treatment," Eur J Cancer, Jan. 2013, vol. 49, Issue 1, pp. 245-253.

Bobo et al., "Nanoparticle-based medicines: a review of FDA-approved materials and clinical trials to date." Pharmaceutical research, Oct. 2016, vol. 33, Issue 10, pp. 2373-2387.

Bocci et al., "The pharmacological bases of the antiangiogenic activity of paclitaxel," Angiogenesis, Jul. 2013, vol. 16, Issue 3, pp. 481-492.

Bochicchio et al., "Investigating by CD the molecular mechanism of elasticity of elastomeric proteins," Chirality, Sep. 2008, vol. 20, Issue 9, pp. 985-994.

Boekhorst et al., "Genome-wide detection and analysis of cell wall-bound proteins with LPxTG-like sorting motifs," J. Bacteriol. 187, 2005, 4928-4934.

Boeynaems et al., "Protein Phase Separation: A New Phase in Cell Biology," Trends Cell Biol, Jun. 2018, 28(6):420-435.

Boeynaems et al., "Spontaneous driving forces give rise to protein-RNA condensates with coexisting phases and complex material properties," Proc Natl Acad Sci U S A, 2019, 116:7889-7898.

Boldt, "Use of albumin: an update," Br J. Anaesth., Mar. 2010, vol. 104, Issue 3, pp. 276-284.

Bond, "Exenatide (Byetta) as a novel treatment option for type 2 diabetes mellitus," Proc. (Bayl. Univ. Med. Cent.), Jul. 2006, vol. 19, Issue 3, pp. 281-284.

Bontempo et al., "Streptavidin as a macroinitiator for polymerization: in situ protein-polymer conjugate formation," J. Am. Chem. Soc., 2005, 6508-6509.

Borst et al., "The Therapeutic Antibody LM609 Selectively Inhibits Ligand Binding to Human αVβ3 Integrin via Steric Hindrance," Structure, Nov. 2017, 25(11):1732-1739.e5.

Bowditch et al., "Identification of a novel integrin binding site in fibronectin. Differential utilization by β3 integrins," Journal of Biological Chemistry, 1994, 269(14):10856-10863.

(56)  References Cited

OTHER PUBLICATIONS

Boyer et al., "Well-Defined Protein-Polymer Conjugates via in Situ RAFT Polymerization," J. Am. Chem. Soc., Jun. 2007, vol. 129, Issue 22, pp. 7145-7154.

Branco et al., "Self-assembling materials for therapeutic delivery," Acta Biomaterialia, Mar. 2009, vol. 5, Issue 3, pp. 817-831.

Brangwynne et al., "Polymer physics of intracellular phase transitions," Nature Physics, Nov. 2015, 11(11):899-904.

Brannon-Peppas et al., "Nanoparticle and targeted systems for cancer therapy," Advanced Drug Delivery Reviews, Elsevier, Sep. 2012, 64(11):206-212.

Broome et al., "Expanding the utility of beta-galactosidase complementation: piece by piece," Mol Pharm, ACS Publications, Feb. 2010, 7(1):60-74.

Broyer et al., "Emerging synthetic approaches for protein-polymer conjugations," Chem. Commun., Feb. 2011, vol. 47, Issue 8, pp. 2212-2226.

Brusa et al., "Antitumor activity and pharmacokinetics of liposomes containing lipophilic gemcitabine prodrugs," Anticancer Res., Jan. 2007, vol. 27, Issue 1A, pp. 195-199.

Bryant et al., "Serology for SARS-CoV-2: Apprehensions, opportunities, and the path forward," Sci Immunol, 2020, 5: eabc6347, 4 pages.

Brzezienski et al., "Autologous Fat Grafting to the Breast Using REVOLVE System to Reduce Clinical Costs," Ann Plast Surg, 2016, 77: 286-289.

Burchard, "Light Scattering Techniques," Physical techniques for the study of food biopolymers, 1994, 151-213.

Burke et al., "Multimodal nanoparticle imaging agents: design and applications," Philos Trans A Math Phys Eng Sci, Nov. 2017, 375:20170261.

Burnouf, "Modern plasma fractionation," Transfus. Med. Rev., Apr. 2007, vol. 21, Issue 2, pp. 101-117.

Buteau et al., "Glucagon-like peptide-1 prevents beta cell glucolipotoxicity," Diabetologia, 2004, 47(5):806-815.

Butler et al., "B-Cell Deficit and Increased B-Cell Apoptosis in Humans With Type 2 Diabetes," Diabetes, 2003, 52(1):102-110.

Cabral et al., "Accumulation of sub-100 nm polymeric micelles in poorly permeable tumours depends on size," Nature Nanotechnology, Oct. 2011, vol. 6, Issue 12, pp. 815-823.

Cabrera et al., "Automated, High-Throughput Assays for Evaluation of Human Pancreatic Islet Function," Cell Transplant, First published Nov. 2007, vol. 16, Issue 10, pp. 1039-1048.

Cabrera et al., "Glutamate Is a Positive Autocrine Signal for Glucagon Release," Cell Metab, Jun. 2008, vol. 7, Issue 6, pp. 545-554.

Cai et al., "Long-acting preparations of exenatide," Drug Des. Devel. Ther., Sep. 2013, vol. 7, pp. 963-970.

Calabrese et al., "Frequency, distribution and immunologic nature of infusion reactions in subjects receiving pegloticase for chronic refractory gout," Arthritis Res Ther, 2017, 19: 191, 7 pages.

Caliceti et al., "Pharmacokinetic and biodistribution properties of poly(ethylene glycol)-protein conjugates," Adv. Drug Deliv. Rev, 2003, 55, 1261-1277.

Callahan et al., "Triple stimulus-responsive polypeptide nanoparticles that enhance intratumoral spatial distribution," Nano Letters, Mar. 2012, vol. 12, Issue 4, pp. 2165-2170.

Camilloni et al., "Determination of secondary structure populations in disordered states of proteins using nuclear magnetic resonance chemical shifts," Biochemistry, Feb. 2012, vol. 51, Issue 11, pp. 2224-2231.

Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.

Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.

Cardenes et al., "Locally advanced pancreatic cancer: Current therapeutic approach," The Oncologist, Jun. 2006, vol. 11, Issue 6, pp. 612-623.

Carreiras et al., "Expression and localization of alpha v integrins and their ligand vitronectin in normal ovarian epithelium and in ovarian carcinoma," Gynecol Oncol, 1996, 62(2):260-7.

Carrico et al., "Introducing genetically encoded aldehydes into proteins," Nat Chem Biol, Jun. 2007, vol. 3, Issue 6, pp. 321-322.

Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.

Caves et al., "Thermal inactivation of uricase (urate oxidase): mechanism and effects of additives," Biochemistry, 2013, 52: 497-507.

Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.

Ceska et al., "A new and rapid method for the clinical determination of $\alpha$-amylase activities in human serum and urine. Optimal conditions," Clinica Chimica Acta, 1969, 26, 437-444.

Cha et al., "Microfluidics-assisted fabrication of gelatin-silica coreshell microgels for injectable tissue constructs," Biomacromolecules, 2014, 15: 283-290.

Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.

Chakrabartty et al., "Stability of $\alpha$-Helices," Adv Protein Chem, 1995, 46, 141-176.

Champion et al., "Particle shape: a new design parameter for micro- and nanoscale drug delivery carriers," J Control Release, Elsevier, Aug. 2007, 121(1-2):3-9.

Champion et al., "Role of particle size in phagocytosis of polymeric microspheres," Pharm Res, Srpinger, Mar. 2008, 25(8):1815-21.

Champion et al., "Role of target geometry in phagocytosis," Proc Natl Acad Sci U S A, The National Academy of Sciences of the USA, Mar. 2006, 103(13):4930-4.

Champion et al., "Shape induced inhibition of phagocytosis of polymer particles," Pharm Res, Springer, Jan. 2009, 26(1):244-9.

Chan et al., "A randomized, repeat-dose, pharmacodynamic and safety study of an antidote-controlled factor IXa inhibitor," J Thromb Haemost, 2008, 6(5): 789-796.

Chan et al., "Phase 1b randomized study of antidote-controlled modulation of factor IXa activity in patients with stable coronary artery disease," Circulation, 2008, 117(22): 2865-2874.

Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.

Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.

Chapin et al., "Rapid microRNA profiling on encoded gel microparticles," Angew Chem Int Ed Engl, 2011, 50: 2289-2293.

Chappell et al., "Computational design of small transcription activating RNAs for versatile and dynamic gene regulation," Nat Commun, 2017, 8(1): 1051.

Chappell et al., "Creating small transcription activating RNAs," Nat Chem Biol, 2015, 11(3): 214-220.

Chase et al., "Single-Stranded DNA Binding Proteins Required for DNA Replication," Ann. Rev. Biochem., 1986, 55: 103-136.

Chatterjee et al., "Type 2 diabetes," The Lancet, Jun. 2017, vol. 389, Issue 10085, pp. 2239-2251.

Chaudhury et al., "The major histocompatibility complex-related Fc receptor for IgG (FcRn) binds albumin and prolongs its lifespan," J Exp Med, 2003, 197(3): p. 315-22.

Chen et al., "Anisotropic hydrogels fabricated with directional freezing and radiation-induced polymerization and crosslinking method," Materials Letters, Dec. 2012, vol. 89, pp. 104-107.

Chen et al., "Anti-hypervariable region antibody induced by a defined peptide: An approach for studying the structural correlates of idiotypes," PNAS, 1984, 81:1784-1788.

(56)                    References Cited

OTHER PUBLICATIONS

Chen et al., "Bioinspired Modular Synthesis of Elastin-Mimic Polymers to Probe the Mechanism of Elastin Elasticity," J. Am. Chem. Soc., Mar. 2010, vol. 132, Issue 13, pp. 4577-4579.

Chen et al., "Real-world patterns of pegloticase use for treatment of gout: descriptive multidatabase cohort study," BMJ Open, 2020, 10: e041167, 6 pages.

Chen et al., "Rheology of Soft Materials," Annual Review of Condensed Matter Physics, May 2010, vol. 1, pp. 301-322.

Chen et al., "Site-specific labeling of cell surface proteins with biophysical probes using biotin ligase," Nat Methods, 2005, 2(2):99-104.

Chen et al., "The influence of polymer topology on pharmacokinetics: differences between cyclic and linear PEGylated poly(acrylic acid) comb polymers," J Control Release, 2009, 140: 203-209.

Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.

Chen, "Small-molecule delivery by nanoparticles for anticancer therapy," Trends Mol Med, Cell Press, Dec. 2010, 16(12):594-602.

Chilkoti et al., "Design of thermally responsive, recombinant polypeptide carriers for targeted drug delivery," Advance Drug Delivery Reviews, 2002, 54:1093-1111.

Chilkoti et al., "Stimulus responsive elastin biopolymers: applications in medicine and biotechnology," Curr Opin Chem Biol, Dec. 2006, vol. 10, Issue 6, pp. 652-657.

Chilkoti et al., "Targeted drug delivery by thermally responsive polymers," Advanced Drug Delivery Reviews, 2002, 54:613-630.

Chin et al., "Addition of p-azido-I-phenylalanine to the genetic code of Escherichia coli," Journal of the American Chemical Society, 2002, 124: 9026-9027.

Chithrani et al., "Determining the size and shape dependence of gold nanoparticle uptake into mammalian cells," Nano Lett, Apr. 2006, vol. 6, Issue 4, pp. 662-668.

Chithrani et al., "Elucidating the mechanism of cellular uptake and removal of protein-coated gold nanoparticles of different sizes and shapes," Nano letters, ACS Publications, Jun. 2007, 7(6):1542-1550.

Chitkara et al., "Self-Assembling, Amphiphilic Polymer-Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.

Cho et al., "Effects of hofmeister anions on the phase transition temperature of elastin-like polypeptides," J. Phys. Chem. B., Nov. 2008, vol. 112, Issue 44, pp. 13765-13771.

Cho et al., "Hydrogen bonding of β-turn structure is stabilized in D(2)O," J Am Chem Soc, Oct. 2009, vol. 131, Issue 42, pp. 15188-15193.

Cho et al., "Therapeutic nanoparticles for drug delivery in cancer," Clin. Cancer Res., Mar. 2008, vol. 14, Issue 5, pp. 1310-1316.

Chockalingam et al., "Design and application of stimulus-responsive peptide systems," Protein Engineering, Design & Selection, Apr. 2007, 20(4):155-161.

Choi et al., "Multiplexed detection of mRNA using porosity-tuned hydrogel microparticles," Anal Chem, 2012, 84: 9370-9378.

Choi et al., "Recent advances in engineering microparticles and their nascent utilization in biomedical delivery and diagnostic applications," Lab Chip, 2017, 17: 591-613.

Choi et al., "Renal Clearance of Nanoparticles," Nature biotechnology, Oct. 2007, vol. 25, Issue 10, pp. 1165-1170.

Chow et al., "Peptide-based biopolymers in biomedicine and biotechnology," Mater. Sci. Eng. R Reports, Jan. 2008, vol. 62, Issue 4, pp. 125-155.

Chow et al., "Ultra-High Expression of a Thermally Responsive Recombinant Fusion Protein in E. coli," Biotechnology Progress, Sep. 2006, vol. 22, Issue 3, pp. 638-646.

Choy et al., "Investigation of taxol as a potential radiation sensitizer," Cancer, 1993, 71, 3774-3778.

Christensen et al., "Fusion order controls expression level and activity of elastin-like polypeptide fusion proteins," Protein Science, Jul. 2009, vol. 18, Issue 7, pp. 1377-1387.

Christensen et al., "Predicting Transition Temperatures of Elastin-Like Polypeptide Fusion Proteins," Biomacromolecules, Mar. 2013, vol. 14, Issue 5, pp. 1514-1519.

Chu et al., "Controllable monodisperse multiple emulsions," Angew Chem Int Ed Engl, 2007, 46: 8970-8974.

Chu et al., "Molecular Diagnosis of a Novel Coronavirus (2019-nCOV) Causing an Outbreak of Pneumonia," Clin Chem, 2020, 66(4): 549-555.

Cid-Arregui et al., "Perspectives in the treatment of pancreatic adenocarcinoma," World Journal of Gastroenterology, Aug. 2015, vol. 21, Issue 31, pp. 9297-9316.

Ciezki et al., "Brachytherapy or surgery? A composite view," Oncology, Oct. 2009, vol. 23, Issue 11, pp. 960-964.

Cima, "AVMA Guidelines for the Euthanasia of Animal: 2013 Edition," Journal of the American Veterinary Medical Association, Jan. 2013, vol. 242, 102 pages.

Cirulis et al., "Viscoelastic properties and gelation of an elastin-like polypeptide," Journal of Rheology, Sep. 2009, vol. 53, Issue 5, pp. 1215-1228.

Clarke et al., "Tropoelastin massively associates during coacervation to form quantized protein spheres," Biochemistry, Jul. 2006, vol. 45, Issue 33, pp. 9989-9996.

Clavé et al., "Amylase, lipase, pancreatic isoamylase, and phospholipase A in diagnosis of acute pancreatitis," Clinical Chemistry, 1995, 41, 1129-1134.

Cohen et al., "First clinical application of an actively reversible direct factor IXa inhibitor as an anticoagulation strategy in patients undergoing percutaneous coronary intervention," Circulation, 2010, 122(6): 614-622.

Coin et al., "Solid-phase peptide synthesis: from standard procedures to the synthesis of difficult sequences," Nat. Protoc., Dec. 2007, vol. 2, Issue 12, 3247-3256.

Colomb et al., "Radiation-Convertible Polymers from Norbornenyl Derivatives. Crosslinking with Ionizing Radiation," Journal of Applied Polymer Science, 1970, 14, 1659-1670.

Cong et al., "Nucleocapsid Protein Recruitment to Replication-Transcription Complexes Plays a Crucial Role in Coronaviral Life Cycle," J Virol, 2020, 94: e01925-19, 21 pages.

Conner et al., "Regulated portals of entry into the cell," Nature, 2003, 422(6927):37-44.

Conrad et al., "ELPylated anti-human TNF therapeutic single-domain antibodies for prevention of lethal septic shock," Plant Biotechnology Journal, Jan. 2011, vol. 9, Issue 1, pp. 22-31.

Coskun et al., "Fibroblast Growth Factor 21 Corrects Obesity in Mice," Endocrinology, Dec. 2008, vol. 149, Issue 12, pp. 6018-6027.

Costa et al., "Active Targeting of Cancer Cells by Nanobody Decorated Polypeptide Micelle with Bio-orthogonally Conjugated Drug," Nano letters, Dec. 2018, 19(1):247-254.

Costa et al., "Photo-crosslinkable unnatural amino acids enable facile synthesis of thermoresponsive nano- to microgels of intrinsically disordered polypeptides," Adv Mater, 2018, 30(5): 1704878.

Craik et al., "The future of peptide-based drugs," Chemical biology & drug design 81, Dec. 2013, vol. 81, Issue 1, pp. 136-147.

Crowther, "The ELISA guidebook," Methods Mol Biol, 2000, 149(III-IV): 1-413.

Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.

Cui et al., "Self-assembly of peptide amphiphiles: from molecules to nanostructures to biomaterials," Biopolymers, Jan. 2010, vol. 94, Issue 1, pp. 1-18.

Da Pieve Chiara et al., "Modification of Thiol Functionalized Aptamers by Conjugation of Synthetic Polymers," Bioconjugate Chemistry, 2009, 1(1): 169-174.

Dai et al., "Versatile biomanufacturing through stimulus-responsive cell-material feedback," Nature chemical biology, Sep. 2019, 15(10):1017-1024.

(56) References Cited

OTHER PUBLICATIONS

Dale et al., "Direct covalent mercuration of nucleotides and polynucleotides," Biochemistry, 1975, 14(11): 2447-2457.

Dalhaimer et al., "Single Molecule Visualization of Stable, Stiffness-Tunable, Flow-Conforming Worm Micelles," Macromolecules, 2003, 36(18):6873-6877.

Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.

Darling et al., "Viscoelastic properties of zonal articular chondrocytes measured by atomic force microscopy," Osteoarthritis Cartilage, 2006, 14: 571-579.

Darzynkiewicz et al., "DNA content measurement for DNA ploidy and cell cycle analysis," Current Protocols in Cytometry, 2001, 7.5.1-7.5.24.

Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.

Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.

Davis et al., "Antibodies and the RNA World: A Role for Low-molecular-weight Effectors in Biochemical Evolution," RNA World, 1993, Chapter 8, p. 185-204.

Day et al., "A new glucagon and GLP-1 co-agonist eliminates obesity in rodents," Nat Chem Biol, Oct. 2009, 5:749.

De et al., "Temperature-Regulated Activity of Responsive Polymer-Protein Conjugates Prepared by Grafting-from via RAFT Polymerization," J. Am. Chem. Soc. Jul. 2008, 130, 11288-11289.

De Leon-Rodriguez et al., "Multifunctional thermoresponsive designer peptide hydrogels," Acta Biomaterialia, 2017, 47: 40-49.

De Simone et al., "Accurate random coil chemical shifts from an analysis of loop regions in native states of proteins," J Am Chem Soc, Nov. 2009, 131, 16332-16333.

Deer et al., "Phenotype and genotype of pancreatic cancer cell lines," Pancreas, May 2010, 39, 425-435.

Dejana et al., "The role of adherens junctions and VE-cadherin in the control of vascular permeability," J Cell Sci, Jul. 2008, 121, 2115-2122.

Delaglio et al., "NMRPipe: A multidimensional spectral processing system based on UNIX pipes," Journal of Biomolecular NMR 6, 1995, 277-293.

Delisser et al., "Vascular endothelial platelet endothelial cell adhesion molecule 1(PECAM-1) regulates advanced metastatic progression," PNAS, Oct. 2010, 107, 18616-18621.

Dennis et al., "Albumin binding as a general strategy for improving the pharmacokinetics of proteins," J Biol Chem, 2002, 277(38): p. 35035-43.

Dennis et al., "Co-Translational Myristoylation Alters the Quaternary Structure of HIV-1 Nef in Solution," Proteins: Structure, Function, and Bioinformatics, 2005, 60:658-669.

Depp et al., "Native protein-initiated ATRP: A viable and potentially superior alternative to PEGylation for stabilizing biologics," Acta Biomater. Feb. 2009, 5, 560-569.

Deshayes et al., "Radium 223 dichloride for prostate cancer treatment," Drug Des Devel Ther, Sep. 2017, 11, 2643-2651.

Deyoung et al., "Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.

Diana et al., "Prognostic role and correlation of CA9, CD31, CD68 and CD20 with the desmoplastic stroma in pancreatic ductal adenocarcinoma," Oncotarget, Nov. 2016, 7, 72819-72832.

Diehl et al., "A Good Practice Guide to the Administration of Substances and Removal of Blood Including Routes and Volumes," J Appl Toxicol, 2001, 21, 15-23.

Dignon et al., "Relation between single-molecule properties and phase behavior of intrinsically disordered proteins," Proc Natl Acad Sci U S A, Oct. 2018, 115(40):9929-9934.

Dignon et al., "Sequence determinants of protein phase behavior from a coarse-grained model," PLoS Comput Biol, Jan. 2018, 14(1):e1005941.

Dincer et al., "Multiplexed Point-of-Care Testing—xPOCT," Trends Biotechnol, 2017, 35(8): 728-742.

Ding et al., "Mechanism for the alpha-helix to beta-hairpin transition," Proteins, 2003, 53, 220-228.

Ding et al., "BKlotho Is Required for Fibroblast Growth Factor 21 Effects on Growth and Metabolism," Cell Metab, Sep. 2012, 16(3):387-393.

Dong et al., "An interactive web-based dashboard to track COVID-19 in real time," Lancet Infect Dis, 2020, 20: 533-534.

Donnelly et al., "DNA Vaccines," Ann. Rev. Immunol., 1997, 15, 617-648.

Dreher et al., "Evaluation of an elastin-like polypeptide-doxorubicin conjugate for cancer therapy," J. of Controlled Release, 2003, 91:31-43.

Dreher et al., "Temperature triggered self-assembly of polypeptides into multivalent spherical micelles," J. Am. Chem. Soc. Jan. 2008, 130, 687-694.

Dreher et al., "Thermal cycling enhances the accumulation of a temperature-sensitive biopolymer in solid tumors," Cancer Res, May 2007, 67, 4418-4424.

Dreher, M. R. Ph.D. Thesis, Duke University, Durham, NC, Apr. 2006.

Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.

Drucker "Mechanisms of Action and Therapeutic Application of Glucagon-like Peptide-1," Cell Metab, Apr. 2018, 27(4):740-756.

Drucker et al., "The incretin system: glucagon-like peptide-1 receptor agonists and dipeptidyl peptidase-4 inhibitors in type 2 diabetes," Lancet 368, Nov. 2006, 1696-1705.

Drucker, "Glucagon-like peptides," Diabetes 47, 1998, 159-169.

Drucker, "Incretin action in the pancreas: potential promise, possible perils, and pathological pitfalls," Diabetes, Oct. 2013, 62, 3316-3323.

Du et al., "Endoscope-assisted brachytherapy for pancreatic cancer: From tumor killing to pain relief and drainage," Journal of interventional gastroenterology, Jan. 2011, 1, 23-27.

Du et al., "Tailor-made dual pH-sensitive polymer-doxorubicin nanoparticles for efficient anticancer drug delivery," J. Am. Chem. Soc., Oct. 2011, 133, 17560-17563.

Duan et al., "Fibronectin type III domain based monobody with high activity," Biochemistry, Oct. 2007 46(44):12656-12664.

Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.

Dubey et al., "Development and evaluation of folate functionalized albumin nanoparticles for targeted delivery of gemcitabine," Int J Pharm., Aug. 2015, 492(1-2):80-91.

Ducreux et al., "Radiation plus docetaxel and cisplatin in locally advanced pancreatic carcinoma: A non-comparative randomized phase II trial," Digestive and Liver Disease, Oct. 2014, 46, 950-955.

Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.

Duncan, "The dawning era of polymer therapeutics," Nature Reviews Drug Discovery, 2003, 2, 347-360.

Duncan, R. "Polymer conjugates as anticancer nanomedicines," Nat. Rev. Cancer, Sep. 2006, 6, 688-701.

Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.

Dutta et al., "The Nucleocapsid Protein of SARS-CoV-2: a Target for Vaccine Development," J Virol, 2020, 94(13): e00647-20, 2 pages.

(56)         References Cited

OTHER PUBLICATIONS

Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.

Dyrberg et al., "Peptide as Atigens," J. Exp. Med., 1986, 164:1344-1349.

Dzuricky et al., "Avidity and Cell Uptake of Integrin Targeting Polypeptide Micelles is Strongly Shape Dependent," Nano letters, Sep. 2019, 19(9):6124-6132.

Dzuricky et al., "The Convergence of Artificial Protein Polymers and Intrinsically Disordered Proteins," Biochemistry, May 2018, 57(17):2405-2414.

Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.

Ehlerding et al., "Biodegradable and Renal Clearable Inorganic Nanoparticles," Adv Sci (Weinh), Feb. 2016, 3(2):1500223.

Eichhorn et al., "Interactions of metal ions with polynucleotides and related compounds. XII. The relative effect of various metal ions on DNA helicity," J. Am. Chem. Soc, 1968, 90: 7323-7328.

Eisenhaber et al., "Prediction of lipid posttranslational modifications and localization signals from protein sequences: Big-Π, NMT and PTS1," Nucleic Acids Res., 2003, 31, 3631-3634.

Eisenhauer et al., "New response evaluation criteria in solid tumours: Revised RECIST guideline (version 1.1)," Eur J Cancer, Jan. 2009, 45(2):228-247.

Ekladious et al., "Polymer-drug conjugate therapeutics: advances, insights and prospects," Nature Reviews Drug Discovery, 2019, 18: 273-294.

El-Assaad et al., "Saturated Fatty Acids Synergize with Elevated Glucose to Cause Pancreatic β-Cell Death," Endocrinology, 2003, 144(9):4154-4163.

Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.

Ellis, "Macromolecular crowding: obvious but underappreciated," Trends Biochem. Sci., 2001, 26 (10), 597-604.

Elsabahy et al., "Design of polymeric nanoparticles for biomedical delivery applications," Chem Soc Rev, Royal Society of Chemistry, Apr. 2012, 41(7):2545-61.

Elvin et al., "Synthesis and properties of crosslinked recombinant pro-resilin," Nature, 2005, 437(7061):999-1002.

Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.

Engin et al., "Thermoradiotherapy in the management of superficial malignant tumors," Clinical Cancer Research, 1995, 1, 139-145.

Eom et al., "The number of operations required for completing breast reconstruction," Plast Reconstr Surg Glob Open, 2012, 2: e242.

Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.

Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.

Etrych et al., "HPMA Copolymer Conjugates of Paclitaxe; and Docetaxel with pH-Controlled Drug Release," Molecular Pharmaceutics, Jun. 2010, 7(4):1015-1026.

Falk et al., "Hyperthermia in oncology," Int J Hyperthermia, 2001, 17, 1-18.

Farazi et al., "Structures of Saccharomyces cerevisiae N-myristoyltransferase with bound myristoylCoA and peptide provide insights about substrate recognition and catalysis," Biochemistry, 2001, 40, 6335-6343.

Farmer et al., "Conformational behavior of chemically reactive alanine-rich repetitive protein polymers," Biomacromolecules, 2005, 6, 1531-1539.

Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.

Fathallah et al., "Immunogenicity of Subcutaneously Administered Therapeutic Proteins-a Mechanistic Perspective," The AAPS Journal, 2013, 15(4): 897-900.

Feng et al., "Protein resistant surfaces: comparison of acrylate graft polymers bearing oligo-ethylene oxide and phosphorylcholine side chains," Biointerphases, Mar. 2006, 1 (1), 50.

Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.

Finan et al., "A rationally designed monomeric peptide triagonist corrects obesity and diabetes in rodents," Nat Med, Jan. 2015, 21:27-36.

Finan et al., "Unimolecular Dual Incretins Maximize Metabolic Benefits in Rodents, Monkeys, and Humans," Sci Transl Med, Oct. 2013, 5(209):209ra151.

Fluegel et al., "Chain stiffness of elastin-like polypeptides," Biomacromolecules, Oct. 2010, 11, 3216-3218.

Fosgerau et al., "Peptide therapeutics: current status and future directions," Drug Discovery Today, Jan. 2015, 20, 122-128.

Fox et al., "Soluble polymer carriers for the treatment of cancer: the importance of molecular architecture," Acc Chem Res, 2009, 42(8): 1141-1151.

Frandsen et al., "Recombinant protein-based polymers for advanced drug delivery," Chem Soc Rev, 2012, 41: 2696-2706.

Franzmann et al., "Phase separation of a yeast prion protein promotes cellular fitness," Science, Jan. 2018, 359(6371):eaao5654.

Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.

Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.

Frilling et al., "Recommendations for management of patients with neuroendocrine liver metastases," The lancet oncology, Jan. 2014, 15, e8-21.

Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.

Fujiwara et al., "Modulating effect of the PI3-kinase inhibitor LY294002 on cisplatin in human pancreatic cancer cells," Journal of Experimental & Clinical Cancer Research, Nov. 2008, 27, 76.

Furgeson et al., "Structural optimization of a "smart" doxorubicin-polypeptide conjugate for thermally targeted delivery to solid tumors," Journal of Controlled Release, Jan. 2006, 110:362-369.

Furumoto et al., "Effect of coupling of albumin onto surface of PEG liposome on its In vivo disposition," International Journal of Pharmaceutics, Mar. 2007, 329(1-2): p. 110-116.

Gaberc-Porekar et al., "Obstacles and pitfalls in the PEGylation of therapeutic proteins," Curr. Opin. Drug Discov. Devel. 11, Mar. 2008, 242-250.

Gabizon et al., "Prolonged circulation time and enhanced accumulation in malignant exudates of doxorubicin encapsulated in polyethylene-glycol coated liposomes," Cancer Res., Feb. 1994, 54, 987-992.

Gabriel et al., "Fat grafting and breast reconstruction: tips for ensuring predictability," Gland Surg, 2015, 4: 232-243.

Gaich et al., "The Effects of LY2405319, an FGF21 Analog, in Obese Human Subjects with Type 2 Diabetes," Cell Metab, Sep. 2013, 18(3):333-340.

(56)                    References Cited

OTHER PUBLICATIONS

Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.

Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.

Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.

Gao et al., "In situ growth of a PEG-like polymer from the C terminus of an intein fusion protein improves pharmacokinetics and tumor accumulation" PNAS Early Edition, Jul. 2010, vol. 107, 1-6.

Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.

Gao et al., "In situ growth of a stoichiometric PEG-like conjugate at a protein's N-terminus with significantly improved pharmacokinetics," Proc. Natl. Acad. Sci., Sep. 2009, 15231-15236.

Gao, "Site-specific and in situ growth of stealth polymer conjugates of proteins with significally improved pharmacology," Journal of Controlled Release, Nov. 2013, 172(1):e116-e117.

Garanger et al., "Structural Evolution of a Stimulus-Responsive Diblock Polypeptide Micelle by Temperature Tunable Compaction of its Core," Macromolecules, Sep. 2015, 48, 6617-6627.

Garay et al., "Antibodies against polyethylene glycol in healthy subjects and in patients treated with PEG-conjugated agents," Expert Opinion. Drug Deliv. 9, Nov. 2012, 1319-1323.

Garay et al., "Therapeutic perspectives on uricases for gout," Joint Bone Spine, 2012, 79: 237-242.

Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D11972.pdf?sequence=I&isAllowed=y.

Gauthier et al., "Peptide/protein-polymer conjugates: synthetic strategies and design concepts," Chem. Commun., Jul. 2008, 2591-2611.

Ge et al., "Self-Cleavable Stimulus Responsive Tags for Protein Purification without Chromatography" J. Am. Chem. Soc., 2005, 127: 11228-11229.

Genbank Accession NM_001182082.1 (Mar. 2017).

Geng et al., Shape effects of filaments versus spherical particles in flow and drug delivery, Nat Nanotechnol, Nature Research, Apr. 2007, 2(4):249-55.

Ghoorchian et al., "Molecular architecture influences the thermally induced aggregation behavior of elastin-like polypeptides," Biomacromolecules, Oct. 2011, 12, 4022-4029.

Gianni et al., "Nonlinear pharmacokinetics and metabolism of paclitaxel and its pharmacokinetic/pharmacodynamic relationships in humans," J. Clin. Oncol., 1995, 13 (1), 180-190.

Giberti et al., "Radical retropubic prostatectomy versus brachytherapy for low-risk prostatic cancer: a prospective study," World J Urol, Oct. 2009, 27, 607-612.

Gibson et al., "Enzymatic assembly of DNA molecules up to several hundred kilobases," Nat Methods, May 2009, 6, 343-345.

Gilbreth et al., "Structural insights for engineering binding proteins based on non-antibody scaffolds," Curr Opin Struct Biol, Elsevier, Jun. 2012, 22(4):413-20.

Gillies et al., "Dendrimers and dendritic polymers in drug delivery," Drug Discovery Today, 2005, 10(1):35-43.

Gilroy et al., "Fusion of fibroblast growth factor 21 to a thermally responsive biopolymer forms an injectable depot with sustained anti-diabetic action," J Control Release, May 2018, 277:154-164.

Gilroy et al., "Sustained release of a GLP-1 and FGF21 dual agonist from an injectable depot protects mice from obesity and hyperglycemia," Science Advances, 2020, 6(35): eaaz9890, 12 pages.

Glassman et al., "Toughening of Thermoresponsive Arrested Networks of Elastin-Like Polypeptides to Engineer Cytocompatible Tissue Scaffolds," Biomacromolecules, Feb. 2016, 17, 415-426.

Gluck et al., "Single Vector System for Efficient N-myristoylation of Recombinant Proteins in E. coli," Plos One, Apr. 2010, 5(4) e100881.

Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.

Gold et al., "Aptamers and the RNA World, Past and Present," Cold Spring Harbor Perspect. Biol., 2012, 4: a003582, 9 pages.

Goldsmith et al., "Enzyme engineering: reaching the maximal catalytic efficiency peak," Curr Opin Struct Biol, Dec. 2017, 47:140-150.

Gordon et al., "Protein N-myristoylation," J. Biol. Chem., 1991, 266, 8647-8650.

Gosline et al., "Elastic proteins: biological roles and mechanical properties," Philos Trans R Soc Lond B Biol Sci, 2002, 357, 121-132.

Gottlieb et al., "NMR chemical shifts of common laboratory solvents as trace impurities," J. Org. Chem., 1997, 62, 7512-7515.

Goutelle et al., "The Hill equation: a review of its capabilities in pharmacological modelling. Fundam," Clin. Pharmacol. 22, Dec. 2008, 633-648.

Graff et al., "Theoretical analysis of antibody targeting of tumor spheroids: importance of dosage for penetration, and affinity for retention," Cancer Research, 2003, 63(6):1288-1296.

Gratton et al., "The effect of particle design on cellular internalization pathways," Proc Natl Acad Sci U S A, The National Academy of Sciences of the USA, Aug. 2008, 105(33):11613-8.

Greco et al., "The search for synergy: a critical review from a response surface perspective," Pharmacological Reviews, 1995, 24, 331-385.

Green et al., "Abraxane®, a novel Cremophor®-free, albumin-bound particle form of paclitaxel for the treatment of advanced non-small-cell lung cancer," Annals of Oncology, Aug. 2006, 17, 1263-1268.

Green et al., "Novel dipeptidyl peptidase IV resistant analogues of glucagon-like peptide-1(7-36) amide have preserved biological activities in vitro conferring improved glucose-lowering action in vivo" J. of Mol. Endocrin., 2003, 31(3): 529-540.

Greenfield, "Using circular dichroism spectra to estimate protein secondary structure," Nat. Protoc., Dec. 2006, 1(6):2876-90.

Griffin et al., "Accelerated wound healing by injectable microporous gel scaffolds assembled from annealed building blocks," Nat Mater, 2015, 14: 737-744.

Grimm et al., "Advances in Brachytherapy," Reviews in Urology, 2004, 6, S37-S48.

Grover et al., "Protein-Polymer Conjugates: Synthetic Approaches by Controlled Radical Polymerizations & Interesting Applications", Curr Opin Chem Bioi., Dec. 2010; 14(6): 818-827.

Gu et al., "Enzymatic Synthesis of Nucleobase-Modified Single-Stranded DNA Offers Turnable Resistance to Nuclease Degradation," Biomacromolecules, Jul. 2018, 19, 3525-3535.

Gu et al., "Photocontrolled micellar aggregation of amphiphilic DNA-azobenzene conjugates," Colloids Surfaces B: Biointerfaces, Nov. 2015, 135, 126-132.

Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.

Gungor et al., "Pancreatic cancer," British Journal of Pharmacology, Jan. 2014, 171, 849-858.

Guo et al., "Nanoparticles escaping RES and endosome: challenges for siRNA delivery for cancer therapy," J. Nanomaterials, Aug. 2011, 2011: 1-12.

Gustafsson, "Nonlinear structured-illumination microscopy: wide-field fluorescence imaging with theoretically unlimited resolution," Proc Natl Acad Sci U S A, 2005, 102, 13081-13086.

Gustafsson, "Surpassing the lateral resolution limit by a factor of two using structured illumination microscopy," Short Communication. Journal of Microscopy, 2000, 198, 82-87.

(56)                    References Cited

OTHER PUBLICATIONS

Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.

Gylbert, "Applanation tonometry for the evaluation of breast compressibility," Scand J Plast Reconstr Surg Hand Surg, 1989, 23: 223-229.

Ha et al., "Immunoglobulin Fc Heterodimer Platform Technology: From Design to Applications in Therapeutic Antibodies and Proteins," Front Immunol, Oct. 2016, 7(394) (in English).

Haider et al., "Genetically engineered polymers: Status and prospects for controlled release," J. Control. Release, 2004, 95, 1-26.

Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.

Hamada et al., "Novel therapeutic strategies targeting tumor-stromal interactions in pancreatic cancer," Frontiers in Physiology, Nov. 2013, vol. 4, Article 331, 7 pages.

Hamidi et al., "Pharmacokinetic Consequences of Pegylation," Drug Deliv., Dec. 2006, 13, 399-409.

Hamley, "Self-assembly of amphiphilic peptides," Soft Matter, Feb. 2011, 7, 4122.

Hampp et al., "Use of Antidiabetic Drugs in the U.S., 2003-2012," Diabetes Care, May 2014, 37: 1367-1374.

Han et al., "Survival of patients with advanced pancreatic cancer after iodine125 seeds implantation brachytherapy: A meta-analysis," Medicine, Feb. 2017, 96, e5719.

Harmon et al., "A Model for Hysteresis Observed in Phase Transitions of Thermally Responsive Intrinsically Disordered Protein Polymers," Biophysical Journal, Feb. 2017, 112(3):207a.

Harries et al., "Nanoparticle Albumin-Bound Paclitaxel for Metastatic Breast Cancer," J. Clin. Oncol., 2005, 23(31):7768-7771.

Harris et al., "Effect of pegylation on pharmaceuticals," Nature Reviews Drug Discovery, 2003, 2: 214-221.

Harris et al., "Pegylation," Clinical Pharmacokinetics, 2001, 40(7):539-551.

Hart et al., "Attenuation of FGF signalling in mouse β-cells leads to diabetes," Nature, 2000, 408:864.

Hartgerink et al., "Self-assembly and mineralization of peptide-amphiphile nanofibers," Science, 2001, 294, 1684-8.

Hassouneh et al., "Elastin-like Polypeptide Diblock Copolymers Self-Assemble into Weak Micelles," Macromolecules, Jun. 2015, 48, 4183-4195.

Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.

Hassouneh et al., "Fusions of elastin-like polypeptides to pharmaceutical proteins," Methods Enzymol., Jan. 2012, 502, 215-37.

Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.

Hathout et al., "Analysis of seed loss and pulmonary seed migration in patients treated with virtual needle guidance and robotic seed delivery," American journal of clinical oncology, Oct. 2011, 34, 449-453.

He et al., "Comparative genomics of elastin: Sequence analysis of a highly repetitive protein," Matrix Biology, Sep. 2007, 26:524-540.

He et al., "Improving protein resistance of α-Al2O3 membranes by modification with POEGMA brushes," Applied Surface Science, Nov. 2011, 258(3):1038-1044.

Heagerty et al., Biometrics, "Time-dependent ROC curves for censored survival data and a diagnostic marker," Jun. 2000, 56(2):337-44.

Heal et al., "N-Myristoyl transferase-mediated protein labelling in vivo," Org. Biomol. Chem., Aug. 2008, 6(13):2308-2315.

Heal et al., "Site-specific N-terminal labelling of proteins in vitro and in vivo using N-myristoyl transferase and bioorthogonal ligation chemistry," Chem. Commun., Jan. 2008, 3, 480-482.

Heggestad et al., "In Pursuit of Zero 2.0: Recent Developments in Nonfouling Polymer Brushes for Immunoassays," Adv Mater, 2020, 32: e1903285.

Heredia et al., "In Situ Preparation of Protein-"Smart" Polymer Conjugates with Retention of Bioactivity," J. Am. Chem. Soc. Jan. 2006, 127, 16955-16960.

Hermanson et al., "Peginesatide for the treatment of anemia due to chronic kidney disease—an unfulfilled promise," Expert Opin Drug Saf, 2016, 15(10): 1421-1426.

Herrero-Vanrell et al., "Self-assembled particles of an elastin-like polymer as vehicles for controlled drug release," J Control Release, 2005, 102, 113-122.

Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.

Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.

Hess et al., "Graphene Transistors for Multifunctional Polymer Brushes for Biosensing Applications," Applied Materials & Interfaces, 2014, 6: 9705-9710.

Heus, "RNA aptamers," Nat Struct Biol, 1997, 4(8): 597-600.

Hidalgo, "Pancreatic Cancer," N Engl J Med, Apr. 2010, 362, 1605-1617.

Hingorani et al., "Phase Ib Study of PEGylated Recombinant Human Hyaluronidase and Gemcitabine in Patients with Advanced Pancreatic Cancer," Clinical Cancer Research, Jun. 2016, 22, 2848-2854.

Ho et al., "Chemoenzymatic Labeling of Proteins for Imaging in Bacterial Cells," J. Am. Chem. Soc., Nov. 2016, 138(46):15098-15101.

Ho et al., "Internal radiation therapy for patients with primary or metastatic hepatic cancer: a review," Cancer, 1998, 83, 1894-1907.

Hober et al., "Protein A chromatography for antibody purification," Journal of Chromatography B 848, Mar. 2007, pp. 40-47.

Hochkoeppler, "Expanding the landscape of recombinant protein production in Escherichia coli," Biotechnol. Lett., Dec. 2013, 35, 1971-1981.

Hofmann et al., "A kinetic study on the enzymatic hydrolysis of fluoresceindiacetate and fluorescein-di-β-D-galactopyranoside," Analytical biochemistry, 1983, 131(1):180-186.

Holehouse et al., "CIDER: Classification of Intrinsically Disordered Ensemble Regions," Biophysical Journal, Feb. 2015, vol. 108, Issue 2, Supplement 1, p. 228a.

Holehouse et al., "Functional Implications of Intracellular Phase Transitions," Biochemistry, May 2018, 57(17):2415-2423.

Holm et al., "Transperineal $^{125}$iodine seed implantation in prostatic cancer guided by transrectal ultrasonography," The Journal of urology, 2002, 167, 985-988.

Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.

Hortobagyi, "Anthracyclines in the Treatment of Cancer," Drugs, 1997, vol. 54, No. 4, pp. 1-7.

Howell et al., "The MIRD Perspective 1999," J Nucl Med, 1999, 40, 3S-10S.

Hruby et al., "New bioerodable thermoresponsive polymers for possible radiotherapeutic applications," Journal of Controlled Release, May 2007, 119, 25-33.

Hruby et al., "Thermoresponsive polymeric radionuclide delivery system—an injectable brachytherapy," Eur J Pharm Sci., Feb. 2011, 42, 484-488.

Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.

(56) References Cited

OTHER PUBLICATIONS

Hsu et al., "Fat grafting's past, present, and future: why adipose tissue is emerging as a critical link to the advancement of regenerative medicine," Aesthet Surg J, 2015, 32: 892-899.

Hu et al., "Design of tumor-homing and pH-responsive polypeptide-doxorubicin nanoparticles with enhanced anticancer efficacy and reduced side effects," Chemical Communications, Jun. 2015, 51, 11405-11408.

Hu et al., "Nanografting De Novo Proteins onto Gold Surfaces," Langmuir, 2005, vol. 21:9103-9109.

Hu et al., "Site-specific in situ growth of a cyclized protein-polymer conjugate with improved stability and tumor retention," Biomaterials, 2015, 47:13-19.

Huang et al., "Clinical features of patients infected with 2019 novel coronavirus in Wuhan," China. Lancet, 2020, 395: 497-506.

Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.

Huber et al., "Designer amphiphilic proteins as building blocks for the intracellular formation of organelle-like compartments," Nat Mater, Jan. 2015, 14(1):125-132.

Hucknall et al., "Simple Fabrication of Antibody Microarrays on Nonfouling Polymer Brushes with Femtomolar Sensitivity for Protein Analytes in Serum and Blood," Adv Mater, 2009, 21(19):1968-1971.

Hucknall et al., "Simple Fabrication of Antibody Microarrays on Nonfouling Polymer Brushes with Femtomolar Sensitivity for Protein Analytes in Serum and Blood," Adv Mater, 2009, 21:1968-1971.

Huotari et al., "Endosome maturation," EMBO J, Aug. 2011, 30 (17), 3481-3500.

Hutter et al., "Calibration of atomic-force microscope tips," Review of Scientific Instruments, 1993, 64: 1868-1873.

Hwang et al., "Caprolactonic poloxamer analog: PEG-PCL-PEG," Biomacromolecules, 2005, 6, 885-890.

Hwang et al., "Differentially degradable janus particles for controlled release applications," Macromol Rapid Commun, 2012, 33: 1178-1183.

Hwang et al., "Gene therapy for primary and metastatic pancreatic cancer with intraperitoneal retroviral vector bearing the wild-type p53 gene," Surgery, 1998, 124, 143-151.

Hwang et al., "Inhibition of gene expression in human cells through small molecule-RNA interactions," Proc. Natl. Acad. Sci. USA, 1999, 96(23): 12997-13002.

Hwang et al., "Synthesis and Characterization of Polystyrene Brushes for Organic Thin Film Transistors," Journal of Nanoscience and Nanotechnology, 2012, 12: 4137-4141.

Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.

Ilangovan et al., "Structure of sortase, the transpeptidase that anchors proteins to the cell wall of Staphylococcus aureus," Proc. Natl. Acad. Sci. 98, 2001, 6056-6061.

Inostroza-Brito et al., "Co-assembly, spatiotemporal control and morphogenesis of a hybrid protein-peptide system," Nat. Chem., Nov. 2015, 7, 1-8.

Ishida et al., "Accelerated blood clearance (ABC) phenomenon upon repeated injection of PEGylated liposomes," International Journal of Pharmaceutics, May 2008, 354(1-2):56-62.

Ito et al., "Impaired negative feedback suppression of bile acid synthesis in mice lacking ßKlotho," J Clin Invest, 2005, 115(8):2202-2208.

Ito et al., "In vivo antitumor effect of the mTOR inhibitor CCI-779 and gemcitabine in xenograft models of human pancreatic cancer," International Journal of Cancer, May 2006, 118, 2337-2343.

Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.

Jain, "Barriers to Drug-Delivery in Solid Tumors," Sci Am, 1994, 271, 58-65.

Jakubowski et al., "Activators regenerated by electron transfer for atom-transfer radical polymerization of (meth)acrylates and related block copolymers," Angew. Chem. Int. Ed., Jun. 2006, 4482-4486.

Janes et al., "Chitosan nanoparticles as delivery systems for doxorubicin," J. Control Release, 2001, 73, 255-267.

Jang et al., "Engineering Globular Protein Vesicles through Tunable Self-Assembly of Recombinant Fusion Proteins," Small, 2017, 13(36): 1700399.

Jenkins et al., In vivo monitoring of tumor relapse and metastasis using bioluminescent PC-3M-luc-C6 cells in murine models of human prostate cancer. Clinical & Experimental Metastasis, 2003, 20, 745-756.

Ji et al., "RGD-conjugated albumin nanoparticles as a novel delivery vehicle in pancreatic cancer therapy," Cancer Biology & Therapy, Feb. 2012, 13, 206-215.

Jia et al., "Preparation, physicochemical characterization and cytotoxicity in vitro of gemcitabine- loaded PEG-PDLLA nanovesicles," World J. Gastroenterol., Feb. 2010, 16(8):1008-1013.

Jiang et al., "Nanoparticle-mediated cellular response is size-dependent," Nat Nanotechnol, Nature Research, Mar. 2008, 3(3):145-50.

Jiang et al., "Neutralizing Antibodies against SARS-CoV-2 and Other Human Coronaviruses," Trends Immunol, 2020, 41(5): 355-359.

Jiang et al., "The internal structure of self-assembled peptide amphiphiles nanofibers," Soft Matter, Feb. 2007, 3, 454.

Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.

Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.

Joh et al., "Inkjet-printed point-of-care immunoassay on a nanoscale polymer brush enables subpicomolar detection of analytes in blood," Proc Natl Acad Sci U S A, 2017, 114: E7054-E7062.

Johansson et al., "Structure, Specificity, and Mode of Interaction for Bacterial Albumin-binding Modules," J. Biol. Chem. 2002, 277 (10), 8114-8120.

Johansson et al., "The GA module, a mobile albumin-binding bacterial domain, adopts a three-helix-bundle structure," FEBS Lett, 1995, 374(2): 257-261.

Johnson et al., "Fibroblast Growth Factor 21 Reduces the Severity of Cerulein-Induced Pancreatitis in Mice," Gastroenterology, Nov. 2009, 137(5):1795-1804.

Jokerst et al., "Nanoparticle PEGylation for imaging and therapy," Nanomedicine (Lond), Future Medicine, Jun. 2011, 6(4):715-28.

Jonsson et al., "Engineering of a femtomolar affinity binding protein to human serum albumin," Protein Engineering Design and Selection, Aug. 2008, 21(8): 515-527.

Junutula et al., "Site-specific conjugation of a cytotoxic drug to an antibody improves the therapeutic index," Nat Biotechnol, Aug. 2008, 26(8): 925-932.

Jurney et al., "Unique size and shape-dependent uptake behaviors of non-spherical nanoparticles by endothelial cells due to a shearing flow," J Control Release, Jan. 2017, 245:170-176.

Kaighn et al., "Establishment and characterization of a human prostatic carcinoma cell line (PC-3)," Investigative urology, 1979, 17, 16-23.

Kaitin et al., "Pharmaceutical innovation in the 21st century: new drug approvals in the first decade, 2000-2009," Clin Pharmacol Ther, Feb. 2011, 89, 183-188.

Kamaly et al., "Targeted polymeric therapeutic nanoparticles: design, development and clinical translation," Chem Soc Rev, Royal Society of Chemistry, Apr. 2012, 41(7):2971-3010.

Kamisawa et al., "Pancreatic cancer," Lancet, Jul. 2016, 388, 73-85.

Kang et al., "Crystal structure of SARS-CoV-2 nucleocapsid protein RNA binding domain reveals potential unique drug targeting sites," Acta Pharm Sin B, 2020, 10(7): 1228-1238.

(56)         References Cited

OTHER PUBLICATIONS

Kanoski et al., "The role of nausea in food intake and body weight suppression by peripheral GLP-1 receptor agonists, exendin-4 and liraglutide," Neuropharmacology 62, Apr. 2012, 1916-1927.

Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.

Karagoz et al., "Polymerization-Induced Self-Assembly (PISA)—control over the morphology of nanoparticles for drug delivery applications," Polym. Chem., Jan. 2014, 5(2):350-355.

Karamanolis et al., "Increased expression of VEGF and CD31 in postradiation rectal tissue: implications for radiation proctitis," Mediators Inflamm, May 2013, 515048.

Karperien, A. FracLac for Image J, version 2.5 <http://rsb.info.nih.gov/ij/plugins/fraclac/FLHelp/Introduction.htm> 1999-2012.

Kaspar et al., "Future directions for peptide therapeutics development," Drug Discovery Today, Sep. 2013, 18, 807-817.

Katakura, "Nuclear Data Sheets for A=125," Nuclear Data Sheets, Mar. 2011, 112, 495-705.

Kataoka et al., "Block copolymer micelles for drug delivery: Design, characterization and biological significance," Advanced Drug Delivery Reviews, 2001, 47:113-131.

Kato et al., "Acidic extracellular microenvironment and cancer," Cancer Cell Int, Sep. 2013, 13, 89, 8 pages.

Katti et al., "Amino acid repeat patterns in protein sequences: Their diversity and structural-functional implications," Protein Science, 2000, 9: 1203-1209.

Keefe et al., "Aptamers as therapeutics," Nature Reviews Drug Discovery, 2010, 9: 537-550.

Keefe et al., "Poly(zwitterionic)protein conjugates offer increased stability without sacrificing binding affinity or bioactivity," Nat Chem, Jan. 2012, 4(1):59-63.

Keller et al., "Empirical Statistical Model to Estimate the Accuracy of Peptide Identifications Made by MS/MS and Database Search," Anal. Chem. 2002, 74, 5383-5392.

Kelly et al., "How to study proteins by circular dichroism," Biochim. Byophys. Acta—Proteins Proteomics, 2005, 1751(2): 119-39.

Kelly et al., "Shape-specific, monodisperse nano-molding of protein particles," J Am Chem Soc, ACS Publications, Apr. 2008, 130(16):5438-9.

Kesharwani et al., "Dendrimer as nanocarrier for drug delivery," Progress in Polymer Science, Feb. 2014, 39(2):268-307.

Keten et al., "Nanoconfinement controls stiffness, strength and mechanical toughness of ß-sheet crystals in silk," Nat Mater, Mar. 2010, 9, 359-367.

Khademhosseini et al., "Micromolding of photocrosslinkable hyaluronic acid for cell encapsulation and entrapment," J Biomed Mater Res A, 2006, 79: 522-532.

Khailany et al., "Genomic characterization of a novel SARS-CoV-2," Gene Rep, 2020, 9:100682, 6 pages.

Khandare et al., "Polymer-drug conjugates: Progress in polymeric drugs," Prog. Polym. Sci., 2005, vol. 31, pp. 359-397.

Khanna et al., "The dog as a cancer model," Nat. Biotechnol., Sep. 2006, 24, 1065-1066.

Kharitonenkov et al., "FGF-21 as a novel metabolic regulator," J Clin Invest, 2005, 115(6):1627-1635.

Kharitonenkov et al., "FGF21 Revolutions: Recent Advances Illuminating FGF21 Biology and Medicinal Properties," Trends Endocrinol Metab, Nov. 2015, 26(11):608-617.

Kharitonenkov et al., "Fibroblast growth factor 21 night watch: advances and uncertainties in the field," J Intern Med, Nov. 2016, 281(3):233-246.

Kharitonenkov et al., "Inventing new medicines: The FGF21 story," Mol Metab, Jun. 2014, 3(3):221-229.

Khazov et al., "Nuclear Data Sheets for A=131," Nuclear Data Sheets, 2006, 107, 2715-2930.

Khoo et al., "Activation of mitogen-activating protein kinase by glucose is not required for insulin secretion," Proc Natl Acad Sci USA, 1997, 94(11):5599-5604.

Khoo et al., "Regulation of Insulin Gene Transcription by ERK1 and ERK2 in Pancreatic βCells," J Biol Chem, 2003, 278(35):32969-32977.

Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.

Kim et al., "Generation of core-shell microcapsules with three-dimensional focusing device for efficient formation of cell spheroid," Lab Chip, 2011, 11: 246-252.

Kim et al., "Recombinant elastin-mimetic biomaterials: Emerging applications in medicine," Adv Drug Deliv Rev, Dec. 2010, 62, 1468-1478.

Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.

Kim et al., "Ultrasensitive Carbon nanotube-based biosensors using antibody-binding fragments," Analytical Biochemistry, Jul. 2008, 381, 193-198.

Knop et al., "Poly(ethylene glycol) in Drug Delivery: Pros and Cons as Well as Potential Alternatives," Angewandte Chemie International Edition, Aug. 2010, 49(36):6288-6308.

Knudsen, "Glucagon-like Peptide-1: The Basis of a New Class of Treatment for Type 2 Diabetes" J. Med. Chem, 2004, 47: 4128-4134.

Kobashigawa et al., "Attachment of an NMR-Invisible Solubility Enhancement Tag Using a Sortase-Mediated Protein Ligation Method," J Biomol NMR. Mar. 2009, vol. 43, No. 3; pp. 145-150.

Kobayashi et al., "Summary of recombinant human serum albumin development," Biologicals, Mar. 2006, 34(1): 55-59.

Koehler et al., "Albumin affinity tags increase peptide half-life In vivo," Bioorganic & Medicinal Chemistry Letters, 2002, 12(20): 2883-2886.

Kontos et al., "Drug development: longer-lived proteins," Chemical Society Reviews, Feb. 2012, 41(7):2686-2695.

Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.

Korte et al., "Short activated partial thromboplastin times are related to increased thrombin generation and an increased risk for thromboembolism," Am J Clin Pathol, 2000, 113(1): 123-127.

Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.

Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.

Kozel et al., "Point-of-care testing for infectious diseases: past, present, and future," J Clin Microbiol, 2017, 55: 2313-2320.

Kozma et al., "Anti-PEG antibodies: Properties, formation, testing and role in adverse immune reactions to PEGylated nano-biopharmaceuticals," Adv Drug Deliv Rev, 2020, 154-155, 163-175.

Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.

Krammer et al., "Serology assays to manage COVID-19," Science, 2020, 368: 1060-1061.

Kraulis et al., "The serum albumin-binding domain of streptococcal protein G is a three-helical bundle: a heteronuclear NMR study," FEBS letters, 1996, 378(2): p. 190-194.

Krause et al., "Structure and function of claudins," Biochmica et Biophysica Acta, Mar. 2008, 1778, 631-645.

Krempien et al., "Neoadjuvant chemoradiation in patients with pancreatic adenocarcinoma," HPB (Oxford), Feb. 2006, 8(1):22-28.

Kronowitz et al., "Delayed-Immediate Breast Reconstruction," Plastic and Reconstructive Surgery, 2004, 113: 1617-1628.

Kruger et al., "Analysis of the Substrate Specificity of the *Staphylococcus aureus* Sortase Transpeptidase SrtAt," Biochemistry, 2004, 43, 1541-1551.

(56)			References Cited

OTHER PUBLICATIONS

Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kuo et al., "Global epidemiology of gout: prevalence, incidence and risk factors," Nature Reviews Rheumatology, 2015, 11: 649-662.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of ßKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Laing et al., "A dynamic COVID-19 immune signature includes associations with poor prognosis," Nat Med, 2020, 26:1623-1635.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.

Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in Escherichia coli," Appl Environ Microb., Nov. 2011, 77(22):8114-28.
Leung et al., "Bio-Click Chemistry: Enzymatic Functionalization of PEGylated Capsules for Targeting Applications** ," Angew. Chem. Int. Ed. Jul. 2012, 51, 7132-7136.
Levine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS One, Feb. 2014, 9(2): e87704, 9 pages.
Lewis et al., "Use of digitized video microscopy with a fluorogenic enzyme substrate to demonstrate cell-and compartment-specific gene expression in Salmonella enteritidis and Bacillus subtilis," Molecular microbiology, 1994, 13:655-662.
Li et al., "Elastin is an essential determinant of arterial morphogenesis," Nature, 1998, 393, 276-280.
Li et al., "Ferric Chloride-induced Murine Thrombosis Models," J. Vis. Exp., 2016, 115: e54479, 12 pages.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading the Reticuloendothelial System: Role of the Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macromol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered E. coli methionine aminopeptidase," Prot. Sci. 13, 2004, 1802-1810.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers for tissue repair," Biomacromolecules, Feb. 2008, 9, 222-230.

(56) References Cited

OTHER PUBLICATIONS

Lim et al., "In vivo post-translational modifications of recombinant mussel adhesive protein in insect cells," Biotechnol. Prog., September-Oct. 2011, 27(5):1390-1396.

Lin et al., "Adiponectin Mediates the Metabolic Effects of FGF21 on Glucose Homeostasis and Insulin Sensitivity in Mice," Cell Metab, May 2013, 17(5):779-789.

Lin et al., "Formation and Maturation of Phase-Separated Liquid Droplets by RNA-Binding Proteins," Mol Cell, Oct. 2015, 60(2):208-219.

Lin et al., "Functional expression of a biologically active fragment of soluble gp130 as an ELP-fusion protein in transgenic plants: purification via inverse transition cycling," Biochem J, Sep. 2006, 398(3):577-583.

Lin et al., "Intrinsically disordered sequences enable modulation of protein phase separation through distributed tyrosine motifs," J Biol Chem, Nov. 2017, 292(46):19110-19120.

Lin et al., "Phase Separation and Single-Chain Compactness of Charged Disordered Proteins Are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17):178101.

Lin et al., "Statistical properties of the traditional algorithm-based designs for phase I cancer clinical trials," Biostatistics, 2001, 2(2):203-215.

Lin et al., "Utility of immunohistochemistry in the pancreatobiliary tract," Arch Pathol Lab Med, Jan. 2015, 139, 24-38.

Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.

Linder et al., "Lipid Modifications of G Protein Subunits," J. Biol. Chem., 1991, 266(7):4654-4659.

Ling et al., "Protein thioester synthesis enabled by sortase," J. Am Chem Soc, Jul. 2012, 134(26):10749-10752.

Liong et al., "Multifunctional inorganic nanoparticles for imaging, targeting, and drug delivery," ACS Nano, ACS Publications, May 2008, 2(5):889-96.

Lippard et al., "Platinum complexes: probes of polynucleotide structure and antitumor drugs," Acc. Chem. Res., 1978, 11(5): 211-217.

Lipsitch et al., "Antibody testing will enhance the power and accuracy of COVID-19-prevention trials," Nat Med, 2020, 26: 818-819.

Lipsky et al., "Pegloticase immunogenicity: the relationship between efficacy and antibody development in patients treated for refractory chronic gout," Arthritis Res Ther, 2014, 16: R60.

Lisboa Bastos et al., "Diagnostic accuracy of serological tests for covid-19: systematic review and meta-analysis," BMJ, 2020, 370: m2516.

Litiere et al., "RECIST—learning from the past to build the future," Nat Rev Clin Oncol, Mar. 2017, 14, 187-192.

Liu et al., "Brachytherapy using injectable seeds that are self-assembled from genetically encoded polypeptides in situ," Cancer Res, Nov. 2012, 72, 5956-5965.

Liu et al., "High neutralizing antibody titer in intensive care unit patients with COVID-19," Emerg Microbes Infect, 2020, 9: 1664-1670.

Liu et al., "Hydrophobic modifications of cationic polymers for gene delivery," Prog. In Polym. Sci., Sep. 2010, 35, 1144-1162.

Liu et al., "In Situ Formation of Protein-Polymer Conjugates through Reversible Addition Fragmentation Chain Transfer Polymerization** ," Angew. Chem. Int. Ed. Apr. 2007, 46, 3099-3103.

Liu et al., "Injectable intratumoral depot of thermally responsive polypeptide-radionuclide conjugates delays tumor progression in a mouse model," J. Control Release, May 2010, 144(1):2-9.

Liu et al., "Integrin $\alpha_v\beta_3$-Targeted Cancer Therapy," Drug Dev Res, Wiley, Sep. 2008, 69(6):329-339.

Liu et al., "Semi-permeable coatings fabricated from comb-polymers efficiently protect proteins in vivo," Nature Communications, 2014, 5: 5526.

Liu et al., "The experiences of health-care providers during the COVID-19 crisis in China: a qualitative study," Lancet Glob Health, 2020, 8: e790-e798.

Liu et al., "Tracking the in vivo fate of recombinant polypeptides by isotopic labeling," Journal of Controlled Release, Sep. 2006, 114, 184-192.

Liu et al., "Tumor accumulation, degradation and pharmacokinetics of elastin-like polypeptides in nude mice," Journal of Controlled Release, Nov. 2006, 116, 170-178.

Liu, L et al., "Monodisperse core-shell chitosan microcapsules for pH-responsive burst release of hydrophobic drugs," Soft Matter, 2011, 7: 4821-4827.

Livingstone, "Theoretical property predictions. Curr Top Med Chem FIELD Full Journal Title: Current topics in medicinal chemistry," Curr. Top. Med. Chem. 2003, 3, 1171-1192.

Loh et al., "Utilising inorganic nanocarriers for gene delivery," Biomater Sci, Jan. 2016, 4(1):70-86.

Lopresti et al., "Polymersomes: nature inspired nanometer sized compartments," Journal of Materials Chemistry, RSC Publishing, Jun. 2009, 19(22):3576-3590.

Lovshin et al., "Incretin-based therapies for type 2 diabetes mellitus," Nat. Rev. Endocrinol. 5, Jun. 2009, 262-269.

Lu et al., "Genomic characterisation and epidemiology of 2019 novel coronavirus: implications for virus origins and receptor binding," Lancet, 2020, 395: 565-574.

Ludden, "Nonlinear pharmacokinetics: clinical Implications," Clin. Pharmacokinet., 1991, 20 (6), 429-446.

Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.

Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.

Lukyanov et al., "Micelles From Lipid Derivatives of Water-Soluble Polymers as Delivery Systems for Poorly Soluble Drugs," Adv. Drug Deliver. Rev., 2004, 56(9):1273-1289.

Lukyanov et al., "Tumor-targeted liposomes: doxorubicin-loaded long-circulating liposomes modified with anti-cancer antibody," J Control Release, 2004, 100(1):135-44.

Lund et al., "Phase II study of gemcitabine (2',2'-difluorodeoxycytidine) in previously treated ovarian cancer patients," J. Natl. Cancer. Inst. 1994, 86(20):1530-1533.

Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.

Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.

Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.

Lyons et al., "Comparisons of Recombinant Resilin-like Proteins: Repetitive Domains Are Sufficient to Confer Resilin-like Properties," Biomacromolecules, ACS Publications, Oct. 2009, 10(11):3009-3014.

Lyons et al., "Design and facile production of recombinant resilin-like polypeptides: Gene construction and a rapid protein purification method," Protein Engineering Design & Selection, Oxford university Press, Jan. 2007, 20(1):25-32.

Ma et al., "Core-shell hydrogel microcapsules for improved islets encapsulation," Adv Healthc Mater, 2013, 2: 667-672.

Ma et al., "Non-fouling" oligo(ethylene glycol)-functionalized polymer brushes synthesized by surface-initiated atom transfer radical polymerization, Advanced Materials 2004, 16 (4), 338.

(56)　　　　References Cited

OTHER PUBLICATIONS

Ma et al., "Protein-resistant polymer coatings on silicon oxide by surface-initiated atom transfer radical polymerization," Langmuir: the ACS journal of surfaces and colloids, Mar. 2006, 22 (8), 3751-6.

Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.

MacEwan et al., "Applications of elastin-like polypeptides in drug delivery," Journal of Controlled Release, Sep. 2014, 190: p. 314-330.

MacEwan et al., "Controlled apoptosis by a thermally toggled nanoscale amplifier of cellular uptake," Nano Letters, Apr. 2014, 14, 2058-2064.

MacEwan et al., "Digital switching of local arginine density in a genetically encoded self- assembled polypeptide nanoparticle controls cellular uptake," Nano Lett., Jun. 2012, 12, 3322-3328.

MacEwan et al., "Elastin-like polypeptides: Biomedical applications of tunable biopolymers," Biopolymers, Jan. 2010, 94, 60-77.

MacEwan et al., "Non-chromatographic Purification of Recombinant Elastin-like Polypeptides and their Fusions with Peptides and Proteins from Escherichia coli," Jun. 2014, 88, p. e51583.

MacEwan et al., "Phase Behavior and Self-Assembly of Perfectly Sequence-Defined and Monodisperse Multiblock Copolypeptides," Biomacromolecules, Jan. 2017, 18(2):599-609.

Mack et al., "Antiobesity action of peripheral exenatide (exendin-4) in rodents: effects on food intake, body weight, metabolic status and side-effect measures," Int. J. Obes. 30, Sep. 2006, 1332-1340.

MacKay et al., "Self-assembling chimeric polypeptide-doxorubicin conjugate nanoparticles the abolish tumors after single injection," Nat Mater, Dec. 2009, 8(12):993-999.

Maeda et al., "Tumor vascular permeability and the EPR effect in macromolecular therapeutics: a review," J. Control. Release, Mar. 2000, 65(1-2)271-284.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Magnusson et al., "In Situ Growth of Side-Chain PEG Polymers from Functionalized Human Growth Hormone-A New Technique for Preparation of Enhanced Protein-Polymer Conjugates," Bioconjugate Chem. 21, Mar. 2010, 671-678.

Magnusson et al., "Ion-Sensitive "Isothermal" Responsive Polymers Prepared in Water," Journal of the American Chemical Society, Aug. 2008, 130, 10852-10853.

Maier et al., "From selection hits to clinical leads: progress in aptamer discovery," Mol. Ther. Methods Clin. Dev., 2016, 3: 16014, 10 pages.

Maitra et al., "Pancreatic Cancer," Annu Rev Pathol Mech Dis, Feb. 2008, 3, 157-188.

Malam et al., "Liposomes and nanoparticles: nanosized vehicles for drug delivery in cancer," Trends Pharmacol Sci, Cell Press, Nov. 2009, 30(11):592-9.

Malik et al., "Recent advances in protein and peptide drug delivery systems," Curr. Drug Deliv. 2, Apr. 2007, 141-151.

Manders et al., "Dynamics of three-dimensional replication patterns during the S-phase, analysed by double labelling of DNA and confocal microscopy," Journal of cell science, 1992, 103(Pt 3):857-862.

Mann et al., "Proteomic analysis of post-translational modifications," Nat. Biotechnol., 2003, 21, 255-61.

Manzoor et al., "Overcoming limitations in nanoparticle drug delivery: triggered, intravascular release to improve drug penetration into tumors," Cancer Res, Nov. 2012, 72, 5566-5575.

Mao et al., "DNA repair by nonhomologous end joining and homologous recombination during cell cycle in human cells," Cell cycle, Sep. 2008, 7, 2902-2906.

Mao et al., "Net charge per residue modulates conformational ensembles of intrinsically disordered proteins," Proc Natl Acad Sci U S A, 2010, 107(18):8183-8188.

Mao et al., "Sortase-mediated protein ligation: a new method for protein engineering," J. Am. Chem. Soc., 2004, 126(9):2670-2671.

Maraffini et al., "Sortases and the art of anchoring proteins to the envelopes of Gram-positive bacteria," Microbiol Mol Biol Rev, Mar. 2006, 70(1):192-221.

Mariam et al., "Albumin corona on nanoparticles—a strategic approach in drug delivery," Drug Deliv., Oct. 2016, 23 (8), 2668-2676.

Marr et al., "Effect of Temperature on the Composition of Fatty Acids in Escherichia coli," J Bacteriol., 1962, 84(6):1260-7.

Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.

Maskarinec et al., "Protein engineering approaches to biomaterials design," Curr. Opin. Biotechnol., 2005, 16, 422-426.

Masood, "Polymeric nanoparticles for targeted drug delivery system for cancer therapy," Mater Sci Eng C Mater Biol Appl, Mar. 2016, 60:569-578.

Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.

Mastria et al., "Doxorubicin-conjugated polypeptide nanoparticles inhibit metastasis in two murine models of carcinoma," J Control Release, Jun. 2015, 208:52-8.

Mastria et al., "Nanoparticle formulation improves doxorubicin efficacy by enhancing host antitumor immunity," J Control Release, Jan. 2018, 269:364-373.

Matsumura et al., "A new concept for macromolecular therapeutics in cancer chemotherapy: mechanism of tumoritropic accumulation of proteins and the antitumor agent smancs," Cancer Res. 1986, 46, 6387-6392.

Matsumura, "Cancer stromal targeting (CAST) therapy," Advanced Drug Delivery Reviews, Jun. 2012, 64, 710-719.

Matsunaga et al., "Molding cell beads for rapid construction of macroscopic 3D tissue architecture," Adv Mater, 2011, 23: H90-94.

Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.

Matyjaszewski et al., "Atom transfer radical polymerization," Chem. Rev. 101, Sep. 2001, 2921-2990.

Matyjaszewski et al., "Macromolecular engineering by atom transfer radical polymerization," J. Am. Chem. Soc. 136, 2014, 6513-6533.

Maurer-Stroh et al., "N-terminal N-myristoylation of proteins: prediction of substrate proteins from amino acid sequence" J Mol Biol., 2002, 317(4):541-557.

Maurer-Stroh et al., "N-terminal N-myristoylation of proteins: Refinement of the sequence motif and its taxon-specific differences," J Mol Biol., 2002, 317(4):523-540.

Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McConkey et al., "Molecular Characterization of Pancreatic Cancer Cell Lines," Pancreatic Cancer, Jan. 2010, 457-469.

McDaniel et al., "A unified model for de novo design of elastin-like polypeptides with tunable inverse transition temperatures," Biomacromolecules, Aug. 2013, 14(8):2866-2872.

(56) References Cited

OTHER PUBLICATIONS

McDaniel et al., "Actively targeting solid tumours with thermoresponsive drug delivery systems that respond to mild hyperthermia," Int J Hyperthermia, Aug. 2013, 29, 501-510.

McDaniel et al., "Doxorubicin-conjugated chimeric polypeptide nanoparticles that respond to mild hyperthermia," Control. Release, May 2012, 159 (3), 362-367.

McDaniel et al., "Drug delivery to solid tumors by elastin-like polypeptides," Adc. Drug Deliver. Rev., Dec. 2010, 62(15):1456-1467.

McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.

McDaniel et al., "Rational design of "heat seeking" drug loaded polypeptide nanoparticles that thermally target solid tumors," Nano Letters, Apr. 2014, 14, 2890-2895.

McDaniel et al., "Recursive Directional Ligation by Plasmid Reconstruction Allows Rapid and Seamless Cloning of Oligomeric Genes," Biomacromolecules, Feb. 2010, 11(4):944-952.

McDaniel et al., "Self-assembly of thermally responsive nanoparticles of a genetically encoded peptide polymer by drug conjugation," Chem. Int. Ed. Feb. 2013, 52, 1683-1687.

McDaniel et al., "Assembly of Highly Asymmetric Genetically-Encoded Amphiphiles for Thermally Targeted Delivery of Therapeutics," Dissertation, 2013, 295 pages, Published Mar. 1, 2014.

McElvaney et al., "A linear prognostic score based on the ratio of interleukin-6 to interleukin-10 predicts outcomes in COVID-19," EBioMedicine, 2020, 61: 103026, 8 pages.

McHale et al., "Synthesis and in vitro evaluation of enzymatically cross-linked elastin-like polypeptide gels for cartilaginous tissue repair," Tissue Eng., 2005, 11, 1768-1779.

McIlhinney et al., "Characterization of a polyhistidine-tagged form of human myristoyl-CoA: protein N-myristoyltransferase produced in *Escherichia coli*," European Journal of Biochemistry, 1994, 222(1):137-146.

McKenzie et al., "Multivalent Binding of a Ligand-Coated Particle: Role of Shape, Size, and Ligand Heterogeneity," Biophys J, Apr. 2018, 114(8):1830-1846.

McManus et al., "Gene silencing in mammals by small interfering RNAs," Nat Rev Genet, 2002, 3(10): 737-747.

Meier et al., "Determination of Optimal Sample Size for Quantification of β-Cell Area, Amyloid Area and β-Cell Apoptosis in Isolated Islets," J Histochem Cytochem, Aug. 2015, 63(8):663-673.

Mejía-Salazar et al., "Microfluidic Point-of-Care Devices: New Trends and Future Prospects for eHealth Diagnostics," Sensors, 2020, 20: 1951, 19 pages.

Mejuch et al., "Synthesis of lipidated proteins," Bioconjug. Chem. 27, Jul. 2016, 1771-1783.

Meng et al., "Stimuli-responsive polymersomes for programmed drug delivery," Biomacromolecules, ACS Publications, Feb. 2009, 10(2):197-209.

Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.

Mero et al., "Transglutaminase-mediated PEGylation of proteins: direct identification of the sites protein medification by mass spectrometry using a novel monodisperse PEG," Bioconjug Chem, Feb. 2009, 20(2):384-389.

Merriam Webster Dictionary, "Plurality," <https://www.merriam-webster.com/dictionary/plurality> webpage accessed Jun. 25, 2020.

Merrick et al., "Seed fixity in the prostate/periprostatic region following brachytherapy," International journal of radiation oncology, biology, physics, 2000, 46, 215-220.

Meyer et al., "Drug targeting using thermally responsive polymers and local hyperthermia," Journal of Controlled Release, 2001, 74, 213-224.

Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.

Meyer et al., "Purification of recombinant proteins by fusion with thermally-responsive polypeptide," Nat. Biotechnol., 1999, 17(11):1112-1115.

Meyer et al., "Quantification of the effects of chain length and concentration on the thermal behavior of elastin-like polypeptides," Biomacromolecules, 2004, 5(3):846-51.

Meyer et al., "Targeting a Genetically Engineered Elastin-Like Polypeptide to Solid Tumors by Local Hyperthermia," Cancer Res., 2001, 61(4):1548-1554.

Miao et al., "Sequence and domain arrangements influence mechanical properties of elastin-like polymeric elastomers," Biopolymers, Jun. 2013, 99, 392-407.

Miao et al., "Structural determinants of cross-linking and hydrophobic domains for self-assembly of elastin-like polypeptides," Biochemistry, 2005, 44, 14367-14375.

Michl et al., "Current concepts and novel targets in advanced pancreatic cancer," Gut, Jan. 2013, 62, 317-326.

Micsonai et al. "Accurate secondary structure prediction and fold recognition for circular dichroism spectroscopy," Proc Natl Acad Sci U S A, Jun. 2015, 112, E3095-3103.

Milenic et al., "Antibody-targeted radiation cancer therapy," Nature Reviews Drug Discovery, 2004, 3, 488-498.

Miller et al., "Disease and healthcare burden of COVID-19 in the United States, " Nat Med, 2020, 26: 1212-1217.

Miller et al., "Solubilized, Spaced Polyalanines: A Context-Free System for Determining Amino Acid α-Helix Propensities," Journal of the American Chemical Society, 2002, 124, 945-962.

Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.

Mitragotri et al., "Physical approaches to biomaterial design," J. Nat Mater, Nature Publishing Group, Jan. 2009, 8(1):15-23.

Miyata et al., "Polymeric micelles for nano-scale drug delivery," Reaction & Functional Polymers, Mar. 2011, 71, 227-234.

Mjelle et al., "Cell cycle regulation of human DNA repair and chromatin remodeling genes," DNA Repair, Jun. 2015, 30, 53-67.

Modery et al., "Heteromultivalent liposomal nanoconstructs for enhanced targeting and shear-stable binding to active platelets for site-selective vascular drug delivery," Biomaterials, Elsevier, Dec. 2011, 32(35):9504-9514.

Molliex et al., "Phase separation by low complexity domains promotes stress granule assembly and drives pathological fibrillization," Cell, Sep. 2015, 163(1):123-133.

Moosmann et al., "Alpha complementation of LacZ in mammalian cells," Nucleic Acids Res, 1996, 24(6):1171-1172.

Moreno et al., "Anti-PEG Antibodies Inhibit the Anticoagulant Activity of PEGylated Aptamers," Cell Chem Biol, 2019, 26(5): 634-644.e3.

Morgan et al., "The combination of epidermal growth factor receptor inhibitors with gemcitabine and radiation in pancreatic cancer," Clin Cancer Res, Aug. 2008, 14, 5142-5149.

Mosbach et al., "Formation of proinsulin by immobilized Bacillus subtilis," Nature, 1983, 302, 543-545.

Mozhdehi et al., "Genetically Encoded Cholesterol-Modified Polypeptides," Journal of the American Chemical Society, Jan. 2019, 141(2):945-951.

Mozhdehi et al., "Genetically encoded lipid-polypeptide hybrid biomaterials that exhibit temperature-triggered hierarchical self-assembly," Nature chemistry, May 2018, 10(5):496-505.

Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.

Muiznieks et al., "Modulated growth, stability and interactions of liquid-like coacervate assemblies of elastin," Matrix Biology 36, Jun. 2014, pp. 39-50.

Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.

(56) References Cited

OTHER PUBLICATIONS

Muiznieks et al., "Structural changes and facilitated association of tropoelastin," Archives of Biochemistry and Biophysics, 2003, 410, 317-323.

Muñoz et al., "Elucidating the folding problem of helical peptides using empirical parameters," Nature Structural Biology, 1994, 1, 399-409.

Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.

Muñoz et al., "Elucidating the folding problem of helical peptides using empirical parameters. III. Temperature and pH dependence," J Mol Biol, 1995, 245, 297-308.

Muralidharan et al., "Protein Ligation: an Enabling Technology for the Biophysical Analysis of Proteins," Nature Methods, Jun. 2006, vol. 3, No. 6, pp. 429-438.

Muro, "Challenges in design and characterization of ligand-targeted drug delivery systems," J Control Release, Elsevier, Dec. 2012, 164(2):125-37.

Murphy et al., "A dosimetric model of duodenal toxicity after stereotactic body radiotherapy for pancreatic cancer," Int J Radiation Oncology Biol Phys, Dec. 2010, 78, 1420-1426.

Na et al., "Thermoresponsive pore structure of biopolymer microspheres for a smart drug carrier," Langmuir, Jun. 2010, 26, 11165-11169.

Nagarsekar et al., "Genetically Engineered Polymers for Drug Delivery," Journal of Drug Targeting, 1999, 7(1):11-32.

Nahire et al., "Multifunctional Polymersomes for Cytosolic Delivery of Gemcitabine and Doxorubicin to Cancer Cells," Biomaterials, Aug. 2014, 35(24):6482-6497.

Nairn et al., "A Synthetic Resilin Is Largely Unstructured," Biophysical Journal, Oct. 2008, vol. 95 3358-3365.

Nakaoka et al., "Prolongation of the serum half-life period of superoxide dismutase by poly(ethylene glycol) modification," Journal of Controlled Release, 1997, 46(3):253-261.

Nalla et al., "Comparative Performance of SARS-CoV-2 Detection Assays Using Seven Different Primer-Probe Sets and One Assay Kit," J Clin Microbiol, 2020, 58: e00557-20, 6 pages.

Nanoprecision Medical, "Pipeline, Type II Diabetes," <http://www.nanoprecisionmedical.com/pipeline/diabetes> webpage available as early as Aug. 2018.

Napier et al., "Nanoparticle drug delivery platform," Journal of Macromolecular Science, Part C: Polymer Reviews, Taylor & Francis Group, LLC, Aug. 2007, 47(3):321-327.

National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).

Nauck "Glucagon-like Peptide 1 (GLP-1) in the Treatment of Diabetes," Horm Metab Res, 2004, 36(11/12):852-858 (in English).

Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.

Neidigh et al., "Exendin-4 and glucagon-like-peptide-q: NMR structural comparisons in the solution and micelle-associated states," Biochemistry 40, 2001, 13188-13200.

Nettles et al., "Applications of elastin-like polypeptides in tissue engineering," Adv Drug Deliv Rev, Dec. 2010, 62, 1479-1485.

Nettles et al., "In situ crosslinking elastin-like polypeptide gels for application to articular cartilage repair in a goat osteochondral defect model," Tissue Eng Part A, Jul. 2008, 14, 1133-1140.

Newcomb et al., "Advances in cryogenic transmission electron microscopy for the characterization of dynamic self-assembling nanostructures," Current Opinion in Colloid and Interface Science, Dec. 2012, 17, 350-359.

Newton et al., "Commissioning a small-field biological irradiator using point, 2D, and 3D dosimetry techniques," Medical Physics, Dec. 2011, 38, 6754-6762.

Ni et al., "Engineering of inorganic nanoparticles as magnetic resonance imaging contrast agents," Chem Soc Rev, Nov. 2017, 46(23):7438-7468.

Nichols et al., "Claudin 4 protein expression in primary and metastatic pancreatic cancer," Am J Clin Pathol, 2004, 121, 226-230.

Nicolas et al., "Fluorescently tagged polymer bioconjugates from protein derived macroinitiators," Chem. Commun. Jan. 2007, 45, 4697-4699.

Nie, "Understanding and overcoming major barriers in cancer nanomedicine," Nanomedicine (Lond) Jun. 2010, 5 (4), 523-528.

Nielsen, "Incretin mimetics and DPP-IV inhibitors for the treatment of type 2 diabetes," Drug Discov. Today 10, 2005, 703-710.

Nies et al., "Fibroblast Growth Factor Signaling in Metabolic Regulation," Front Endocrinol, Jan. 2016, 6(193) (in English).

Nikolic et al., "Structural basis for the recognition of LDL-receptor family members by VSV glycoprotein," Nature Communications, 2018, 9: 1029, 12 pages.

Nilvebrant et al., "The albumin-binding domain as a scaffold for protein engineering," Computational and Structural Biotechnology Journal, Mar. 2013, 6: e201303009, 8 pages.

Nimjee et al., "Aptamers as Therapeutics," Annu Rev Pharmacol Toxicol, 2017, 57: 61-79.

Niu et al., "The role of adhesion molecules, $\alpha v\beta 3$, $\alpha v\beta 5$ and their ligands in the tumor cell and endothelial cell adhesion," Eur J Cancer Prev, Wolters Kluwer, Dec. 2007, 16(6):517-27.

Norman et al., "Ultrasensitive high-resolution profiling of early seroconversion in patients with COVID-19," Nat Biomed Eng, 2020, 11 pages.

Nott et al., "Phase transition of a disordered nuage protein generates environmentally responsive membraneless organelles," Mol Cell, Mar. 2015, 57(5):936-947.

Nucci et al., "The therapeutic value of poly(ethylene glycol)-modified proteins," Adv. Drug Deliv. Rev., 1991, 6(2):133-151.

Nuhn et al., "Secondary structure formation and LCST behavior of short elastin-like peptides," Biomacromolecules, Sep. 2008, 9, 2755-2763.

Nunn et al., "Crystal Structure of Tobacco Etch Virus Protease Shows the Protein C Terminus Bound within the Active Site," Journal of Molecular Biology, 2005, 350: 145-155.

Nyborg et al., "A Therapeutic Uricase with Reduced Immunogenicity Risk and Improved Development Properties," PLoS One, 2016, 11(12): e0167935, 23 pages.

O'Day et al., "Therapeutic Protein-polymer Conjugates: Advancing beyond PEGylation," J. Am. Chem. Soc., Sep. 2014, vol. 136, pp. 14323-14332.

Ogawara et al., "Pre-coating with serum albumin reduces receptor-mediated hepatic disposition of polystyrene nanosphere: implications for rational design of nanoparticles," Journal of Controlled Release, 2004, 100(3): 451-455.

Oh et al., "The development of microgels/nanogels for drug delivery applications," Progress in Polymer Science, 2008, 33(4): 448-477.

Okba et al., "Severe Acute Respiratory Syndrome Coronavirus 2-Specific Antibody Responses in Coronavirus Disease Patients," Emerg Infect Dis, 2020, 26: 1478-1488.

Olafsen et al., "Covalent disulfide-linked anti-CEA diabody allows site-specific conjugation and radiolabeling for tumor targeting applications," Protein Engineering, Design & Selection, 2004, 17(1):21-27.

Ortega et al., "Hydrodynamic properties of rodlike and dislike particles in dilute solution," The Journal of Chemical Physics, 2003, 119(18):9914-9919.

Ortony et al., "Internal dynamics of a supramolecular nanofibre," Nat. Mater., Aug. 2014, 13, 1-5.

Ozer et al., "Effect of Molecular Architecture on Cell Interactions and Stealth Properties of PEG," Biomacromolecules, 2017, 18: 2699-2710.

Ozer et al., "Injectable non-immunogenic PEG-like conjugate that forms a subcutaneous depot and enables sustained delivery of a peptide drug," Research Square, 2021, 38 pages.

(56)         References Cited

OTHER PUBLICATIONS

Ozer et al., "PEG-like brush polymer conjugate of RNA aptamer that shows reversible anticoagulant activity and minimal immune response," Advanced Materials, 2022, 34(10):210852.

Ozer et al., "Site-Specific and Stoichiometric Stealth Polymer Conjugates of Therapeutic Peptides and Proteins," Bioconjug Chem, Mar. 2017, 28(3):713-723.

Pace et al., "How to measure and predict the molar absorption coefficient of a protein" Protein Science 1995, 4: 2411-2423.

Pagani et al., "International guidelines for management of metastatic breast cancer: can metastatic breast cancer be cured?," Journal of the National Cancer Institute, Apr. 2010, 102, 456-463.

Pak et al., "Sequence Determinants of Intracellular Phase Separation by Complex Coacervation of a Disordered Protein," Mol Cell, Jul. 2016, 63(1):72-85.

Palmerston Mendes et al., "Dendrimers as Nanocarriers for Nucleic Acid and Drug Delivery in Cancer Therapy," Molecules, Aug. 2017, 22(9):1401.

Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology• Physics, Oct. 2016, 96, S204-S205.

Palva et al., "Secretion of interferon by Bacillus subtilis," Gene, 1983, 22, 229-235.

Pan et al., "A Pig Model for the Histological Analysis of Adipocytes after Co-injections of Autologous Fat with Fillers," International Journal of Surgery & Surgical Techniques, 2016, 2: 7 pages.

Panda et al., "Stop-flow lithography to generate cell-laden microgel particles," Lab Chip, 2008, 8: 1056-1061.

Pang et al., "A Modular Method for the High-Yield Synthesis of Site-Specific Protein-Polymer Therapeutics," Angew Chem Int Ed Engl, Jul. 2016, 55, 10296-10300.

Paolino et al., "Folate-targeted supramolecular vesicular aggregates as a new frontier for effective anticancer treatment in in vivo model," Eur. J. Pharm. Biopharm., Jun. 2012, 82(1):94-102.

Paolino et al., "Gemcitabine-loaded PEGylated unilamellar liposomes vs GEMZAR: biodistribution, pharmacokinetic features and in vivo antitumor activity," J. Control. Release Jun. 2010, 144(2):144-150.

Paoloni et al., "Translation of new cancer treatments from pet dogs to humans," Nat. Rev. Cancer Feb. 2008, 8 (2), 147-156.

Papa et al., "PEGylated Liposomal Gemcitabine: Insights Into a Potential Breast Cancer Therapeutic," Cell Oncol. (Dordr), Oct. 2013, 36(6):449-457.

Paramonov et al., "Self-assembly of peptide-amphiphile nanofibers: The roles of hydrogen bonding and amphiphilic packing," J. Am. Chem. Soc., May 2006, 128, 7291-7298.

Pardridge, "The blood-brain barrier: bottleneck in brain drug development," NeuroRx, 2005, 2(1):3-14.

Park et al., "Exendin-4 and exercise improve hepatic glucose homeostasis by promoting insulin signaling in diabetic rats," Metabolism, Jan. 2010, 59, 123-133.

Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.

Park et al., "Polymer Brush as a Facile Dielectric Surface Treatment for High-Performance, Stable, Soluble Acene-Based Transistors," Chemistry of Materials, 2010, 22: 5377-5382.

Park et al., "Protein stitchery: Design of a protein for selective binding to a specific DNA sequence," PNAS, 1992, vol. 89:9094-9096.

Parker et al., "Antibody mimics based on human fibronectin type three domain engineered for thermostability and high-affinity binding to vascular endothelial growth factor receptor two," Protein Eng Des Sel, 2005, 18(9):435-44.

Parkes et al. "Discovery and development of exenatide: the first antidiabetic agent to leverage the multiple benefits of the incretin hormone, GLP-1," Expert Opinion. Drug Deliv., Feb. 2013, 8(2):219-244.

Parveen et al., "Nanomedicine," Clinical Pharmacokinetics, Oct. 2006, 45(10):965-988.

Pastuszka et al., "A tunable and reversible platform for the intracellular formation of genetically engineered protein microdomains," Biomacromolecules, ACS Publications, Oct. 2012, 13(11):3439-3444.

Patil et al., "Cellular delivery of doxorubicin via pH-controlled hydrazone linkage using multifunctional nano vehicle based on poly(beta-I-malic acid)," Int J Mol Sci, Sep. 2012, 13, 11681-11693.

Paulsen et al., "Optofluidic fabrication for 3D-shaped particles," Nat Commun, 2015, 6: 6976.

Pecoraro et al., "A systematic evaluation of immunoassay point-of-care testing to define impact on patients' outcomes," Ann Clin Biochem, 2017, 54(4): 420-431.

Peeler et al., "Genetically encoded initiator for polymer growth from proteins," J. Am. Chem. Soc. 132, Oct. 2010, 13575-13577.

Peng et al., "Length-dependent prediction of protein intrinsic disorder," BMC Bioinformatics, Springer Nature, Apr. 2006, 7:208.

Peters, "Serum albumin," Adv. Protein Chem. 37, 1985, 161-245.

Petitdemange et al., "Tuning Thermoresponsive Properties of Cationic Elastin-like Polypeptides by Varying Counterions and Side-Chains," Bioconjug. Chem., May 2017, 28(5):1403-1412.

Petros et al., "Strategies in the design of nanoparticles for therapeutic applications," Nat Rev Drug Discov, Nature Research, Aug. 2010, 9(8):615-27.

Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.

Pinkas et al., "Tunable, post-translational hydroxylation of collagen domains in Escherichia coli," ACS Chem. Biol., Apr. 2011, 6(4):320-324.

Pisal et al., "Delivery of therapeutic proteins," Journal of Pharmaceutical Sciences, 2010, 99(6):2557-2575.

Pliarchopoulou et al., "Pancreatic cancer: Current and future treatment strategies," Cancer Treatment Reviews, Aug. 2009, 35, 431-436.

Poitout et al., "Glucolipotoxicity: Fuel Excess and β-Cell Dysfunction," Endocr Rev, May 2008, 29(3):351-366.

Pometun et al., "Quantitative observation of backbone disorder in native elastin," J Biol Chem, 2004, 279, 7982-7987.

Ponti et al., "Biomarkers associated with COVID-19 disease progression," Crit Rev Clin Lab Sci, 2020, 57, 11 pages.

Popp et al., "Site-specific labeling via sortase-mediated transpeptidation," Curr. Protoc. Protein Sci. 56, Apr. 2009, 15.13.1-15.13.9.

Popp et al., "Sortase-Catalyzed Transformations That Improve the Properties of Cytokines," PNAS, Feb. 2011, vol. 108, No. 8, pp. 3169-3174.

Posthuma-Trumpie et al., "Lateral flow (immuno)assay: its strengths, weaknesses, opportunities and threats. A literature survey," Anal Bioanal Chem, 2009, 393: 569-582.

Potters et al., "12-year outcomes following permanent prostate brachytherapy in patients with clinically localized prostate cancer," The Journal of urology, 2005, 173, 1562-1566.

Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.

Potters et al., "Potency after permanent prostate brachytherapy for localized prostate cancer," International journal of radiation oncology, biology, physics, 2001, 50(5): 1235-1242.

Potthoff et al., "Endocrine fibroblast growth factors 15/19 and 21: from feast to famine," Genes Dev, Feb. 2012, 26(4):312-324.

Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.

(56)                    References Cited

OTHER PUBLICATIONS

Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.
Purtell et al., "Isoelectric point of albumin: effect on renal handling of albumin," Kidney Int, 1979, 16(3): 366-376.
Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for A brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation-moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.

Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Rasmussen et al., "A Novel Porcine Model for Future Studies of Cell-enriched Fat Grafting," Plast Reconstr Surg Glob Open, 2018, 6: e1735.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravichandran et al., "Antibody signature induced by SARS-CoV-2 spike protein immunogens in rabbits," Sci Transl Med, 2020, 10.1126/scitranslmed.abc3539, 9 pages.
Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Ren et al., "Stimulus-Responsive Polymer Prodrugs," Progress in Chemistry, 2013, 25(5): 10 pages.
Resh, "Covalent Lipid Modifications of Proteins," Curr Biol., May 2013, 23(10): R431-R435.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human αvβ3 integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Richter et al., "Mechanistic determinants of biotherapeutics absorption following SC administration," AAPS J, 2012, 14(3): 559-570.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rinaldi et al., "Antisense oligonucleotides: the next frontier for treatment of neurological disorders," Nat Rev Neurol, 2018, 14(1): 9-21.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.

(56)          References Cited

OTHER PUBLICATIONS

Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.

Roberts et al., "Elastin-like polypeptides as models of intrinsically disordered proteins," FEBS Lett., Sep. 2015, 589, 2477-2486.

Roberts et al., "Injectable tissue integrating networks from recombinant polypeptides with tunable order," Nature Materials, 2018, 17(12): 1154-1163.

Robinet et al. "Elastin-derived peptides enhance angiogenesis by promoting endothelial cell migration and tubulogenesis through upregulation of MT1-MMP," J. Cell Science, 2005, 118:343-356.

Roca et al., "Autologous Fat Grafting for Treatment of Breast Implant Capsular Contracture: A Study in Pigs," Aesthet Surg J, 2014, 34: 769-775.

Rodriguez-Cabello et al., "Elastin-like polypeptides in drug delivery," Adv Drug Deliv Rev, 2016, 97: 85-100.

Rodriguez-Diaz et al., "Alpha cells secrete acetylcholine as a non-neuronal paracrine signal priming beta cell function in humans," Nat Med, Jun. 2011, 17:888-892.

Rogers et al., "Isolation of potent SARS-CoV-2 neutralizing antibodies and protection from disease in a small animal model," Science, 2020, 369: 956-963.

Rolland et al., "Direct fabrication and harvesting of monodisperse, shape-specific nanobiomaterials," J Am Chem Soc, 2005, 127(28):10096-100.

Romer et al., "The elaborate structure of spider silk: structure and function of a natural high performance fiber," Prion, Nov. 2008, 2(4):154-161.

Roopenian et al., "FcRn: the neonatal Fc receptor comes of age," Nat. Rev. Immunol., Sep. 2007, vol. 7, No. 9, 715-725.

Rosadas et al., "Testing for responses to the wrong SARS-CoV-2 antigen," Lancet, 2020, 396:e23.

Rosenberg et al., "Present and future innovations in radiation oncology," Surg Oncol Clin N Am, Jul. 2013, 22(3):599-618.

Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.

Rösler et al., "Advanced drug delivery devices via self-assembly of amphiphilic block copolymers," Advanced Drug Delivery Reviews, 2001, 53:95-108.

Rothe et al., "Transmission of 2019-nCOV Infection from an Asymptomatic Contact in Germany," N Engl J Med, 2020, 382: 10, 2 pages.

Rozak et al., "G148-GA3: a streptococcal virulence module with atypical thermodynamics of folding optimally binds human serum albumin at physiological temperatures," Biochim Biophys Acta, 2005, 1753(2): p. 226-33.

Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.

Rusconi et al., "Antidote-mediated control of an anticoagulant aptamer in vivo," Nat Biotechnol, 2004, 22(11): 1423-1428.

Rusconi et al., "RNA aptamers as reversible antagonists of coagulation factor Ixa," Nature, 2002, 19(6902): 90-94.

Russo et al., "The role of neoadjuvant therapy in pancreatic cancer: a review," Future Oncol, Mar. 2016, 12(5):669-685.

Ryerson et al., "Annual report to the nation on the status of cancer, 1975-2012, featuring the Increasing incidence of liver cancer," Cancer, May 2016, 122(9): 1312-1337.

Ryu et al., "Elastin-like polypeptide for improved drug delivery for anticancer therapy: preclinical studies and future applications," Expert Opinion on Drug Delivery, Informa Healthcare, Oct. 2014, 12(4):653-667.

Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.

Safran et al., "Gemcitabine, paclitaxel, and radiation for locally advanced pancreatic cancer: A phase I trial," Int J Radiation Oncology Biol Phys, 2002, 54, 137-141.

Sagle et al., "Investigating the hydrogen-bonding model of urea denaturation," J Am Chem Soc, Jun. 2009, 131(26): 9304-9310.

Saifer et al., "Selectivity of binding of PEGs and PEG-like oligomers to anti-PEG antibodies induced by methoxyPEG-proteins," Molecular Immunology, Feb. 2014, 57(2):236-246.

Sandberg et al., "The Structure of the Elastic Fiber: An Overview," The Journal of Investigative Dermatology, 1982, 79(S1): 128s-132s.

Sandler et al., "Gemcitabine: Single-Agent and Combination Therapy in Non-Small Cell Lung Cancer," Oncologist 1999, 4(3)241-251.

Sanna et al., "Targeted therapy using nanotechnology: focus on cancer," Int J Nanomedicine, Jan. 2014, 9:467-83.

Schaal et al., "Biopolymer ß-brachytherapy delivered with concomitant paclitaxel outperforms traditional x-ray radiation to include complete regression in multiple pancreatic tumor xenograft models through synergistic modulation of the tumor microenvironment," Poster #5831, 2018.

Schaal et al., "Injectable polypeptide micelles that form radiation crosslinked hydrogels in situ for intratumoral radiotherapy," Journal of Controlled Release, Apr. 2016, 228, 58-66.

Schellenberg et al., "Gemcitabine chemotherapy and single-fraction stereotactic body radiotherapy for locally advanced pancreatic cancer," Int J Radiation Oncol Biol Phys, Nov. 2008, 72(3): 678-686.

Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.

Schellenberger et al., "A recombinant polypeptide extends the in vivo half-life of peptides and proteins in a tunable manner," Nat. Biotechnol., Dec. 2009, 27(12):1186-1188.

Schlaff et al., "Bringing the heavy: carbon ion therapy in the radiobiological clinical context," Radiation Oncology, Mar. 2014, 9, Article 88, 1-18.

Schneider et al., "NIH Image to ImageJ: 25 years of image analysis," Nature Methods, Jul. 2012, 9(7): 671-675.

Schnell et al., "Expression of integrin αvβ3 in gliomas correlates with tumor grade and is not restricted to tumor vasculature," Brain Pathol, International Society of Neuropathology, Aug. 2008, 18(3):378-86.

Schwendeman et al., "Injectable controlled release depots for large molecules," J Control Release, Sep. 2014, 190, 240-253.

Senin et al., "N-Myristoylation of recoverin enhances its efficiency as an inhibitor of rhodopsin kinase," Febs. Lett., 1995, 376, 87-90.

Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.

Seow et al., "Longitudinal evaluation and decline of antibody responses in SARS-CoV-2 infection," medRxiv, 2020, 24 pages.

Serrano et al., "An infrared spectroscopic study of the conformational transition of elastin-like polypeptides," Biophys. J., Oct. 2007, 93(7):2429-2435.

Shadwick, "Mechanical design in arteries," J Exp Biol, 1999, 202, 3305-3313.

Shang et al., "pH-Dependent Protein Conformational Changes in Albumin: Gold Nanoparticle Bioconjugates: A Spectroscopic Study," Langmuir, Feb. 2007, 23 (5), 2714-2721.

Shao et al., "Super-resolution 3D microscopy of live whole cells using structured illumination," Nat Methods, Oct. 2011, 8(12): 1044-1046.

Sharma et al., "Dendrimer nanoarchitectures for cancer diagnosis and anticancer drug delivery," Drug Discov Today, Feb. 2017, 22(2):314-326.

Sharma et al., "PLGA-based nanoparticles: A new paradigm in biomedical applications," TrAC Trends in Analytical Chemistry, Jun. 2016, 80:30-40.

(56) References Cited

OTHER PUBLICATIONS

Sharma et al., "Polymer particle shape independently influences binding and internalization by macrophages," Journal of Controlled Release, Elsevier, Nov. 2010, 147(3):408-412.

Shen et al., "Conjugation site modulates the in vivo stability and thearpeutic activity of antibody-drug conjugates," Nat Biotechnol, Jan. 2012, 30(2):184-189.

Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.

Sherman et al., "Next-Generation PEGylation Enables Reduced Immunoreactivity of PEG-Protein Conjugates," Drug and Development & Delivery, Jun. 2012, vol. 12, No. 5, 36-42.

Sherman et al., "Role of the Methoxy Group in Immune Responses to mPEG-Protein Conjugates," Bioconjugate Chemistry, Mar. 2012, 23(3): 485-499.

Shi et al., "Cell adhesion on a POEGMA-modified topographical surface," Langmuir: the ACS journal of surfaces and colloids, Dec. 2012, 28 (49), 17011-8.

Shi et al., "Triggered sorting and co-assembly of genetically engineered protein microdomains in the cytoplasm," Adv Mater, Wiley, Jan. 2014, 26(3):449-454.

Shimoboji et al., "Temperature-Induced Switching of Enzyme Activity with Smart Polymer-Enzyme Conjugates," Bioconjugate Chem. 2003, 14, 517-525.

Shin et al., "Liquid phase condensation in cell physiology and disease," Science, Sep. 2017, 357(6357):eaaf4382.

Shu et al., "GISAID: Global initiative on sharing all influenza data—from vision to reality," Euro Surveill 22, 2017, 22(13): 30494, 3 pages.

Shusharina et al., "Micelles of Diblock Copolymers with Charged and Neutral Blocks: Scaling and Mean-Field Lattice Approaches," Macromolecules, 2000, 33(10): 3892-3901.

Sickmeier et al., "DisProt: the Database of Disordered Proteins," Nucleic Acids Res, Oxford Academy, Jan. 2007, 35:D786-793.

Siegel et al., "Absorbed fractions for electrons and beta particles in spheres of various sizes," J Nucl Med, 1994, 35, 152-156.

Siegwart et al., "ATRP in the Design of Functional Materials for Biomedical Applications," Prog Polymer Science, Jan. 2012, vol. 37, No. 1, pp. 18-37.

Silberstein et al., "The SNM Practice Guideline for Therapy of Thyroid Disease with 131I, 3.0," J Nucl Med, Jul. 2012, 53, 1-19.

Silva et al., "Selective differentiation of neural progenitor cells by high-epitope density nanofibers," Science, 2004, 303, 1352-5.

Simakova et al., "Aqueous ARGET ATRP," Macromolecules, Aug. 2012, 45(16):6371-6379.

Simnick et al., "In vivo tumor targeting by a NGR-decorated micelle of a recombinant diblock copolypeptide," J Control Release, Oct. 2011, 155(2): 144-151.

Simnick et al., "Morphing low-affinity ligands into high-avidity nanoparticles by thermally triggered self-assembly of a genetically encoded polymer," ACS Nano, Apr. 2010, 4(4):2217-2227.

Simon et al., "Engineered Ribonucleoprotein Granules Inhibit Translation in Protocells," Molecular cell, Jul. 2019, 75(1):66-75.

Simon et al., "Programming molecular self-assembly of intrinsically disordered proteins containing sequences of low complexity," Nat Chem, Jun. 2017, 9(6):509-515.

Simonacci et al., "Procedure, applications, and outcomes of autologous fat grafting," Ann Med Surg (Lond), 2017, 20: 49-60.

Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.

Sisson et al., "Radiation safety in the treatment of patients with thyroid diseases by radioiodine 1311: practice recommendations of the American Thyroid Association," Thyroid, Apr. 2011, 21(4):335-346.

Skerra, "Alternative non-antibody scaffolds for molecular recognition," Curr Opin Biotechnol, Elsevier, Aug. 2007, 18(4):295-304.

Smith et al., "Coronaviruses lacking exoribonuclease activity are susceptible to lethal mutagenesis: evidence for proofreading and potential therapeutics," PLOS Pathog, 2013, 9:e1003565, 11 pages.

Smith et al., "The Role of Beta Cell Glucagon-like Peptide-1 Signaling in Glucose Regulation and Response to Diabetes Drugs," Cell Metab, Jun. 2014, 19(6):1050-1057.

Smits et al., "Elastin-Like Polypeptide Based Nanoparticled: Design Rationale Toward Nanomedicine," Macromolecular Bioscience, Macromolecular Journals, Jan. 2015, 15(1):36-51.

Sonawane et al., "Hydrazo linkages in pH responsive drug delivery systems," European Journal Pharmaceutical Sciences, Mar. 2017, 99, 45-65.

Song et al., "Budding-like division of all-aqueous emulsion droplets modulated by networks of protein nanofibrils," Nat Commun, 2018, 9: 2110.

Sorkin et al., "Signal transduction and endocytosis: close encounters of many kinds," Nat Rev Mol Cell Biol, 2002, 3(8):600-614.

Sousa et al., "Production of a polar fish antimicrobial peptide in Escherichia coli using an ELP-intein tag," J Biotechnol, Sep. 2016, 234:83-89.

Srinivas et al., "Aptamer-functionalized microgel particles for protein detection," Anal Chem, 2011, 83: 9138-9145.

Sriraman et al., "Barriers to drug delivery in solid tumors," Tissue Barriers, Jul. 2014, 2(3): 2-10.

Stanislaus et al., "A Novel Fc-FGF21 With Improved Resistance to Proteolysis, Increased Affinity Toward B-Klotho, and Enhanced Efficacy in Mice and Cynomolgus Monkeys," Endocrinology, May 2017, 158(5):1314-1327.

Stefl et al., "RNA sequence-and shape-dependent recognition by proteins in the ribonucleoprotein particle" EMBO reports (2005) 6(1):33-38.

Steichen et al., "A Review of Current Nanoparticle and Targeting Moieties for the Delivery of Cancer Therapeutics," Eur J Pharm Sci, Elsevier, Feb. 2013, 48(3):416-27.

Stock et al., "Penile erectile function after permanent raioactive seed implantation for treatment of prostate cancer," The Journal of urology, 2001, 165, 436-439.

Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.

Strohmaier et al., "Comparison of 60Co and 192Ir sources in HDR brachytherapy," J Contemp Brachyther, Dec. 2011, 3(4): 199-208.

Strong et al., "The Current State of Fat Grafting: A Review of Harvesting, Processing, and Injection Techniques," Plast Reconstr Surg, 2015, 136: 897-912.

Strulson et al., "RNA catalysis through compartmentalization," Nat Chem, Nature Publishing Group, Nov. 2012, 4(11):941-946.

Stutz et al., "Seed loss through the urinary tract after prostate brachytherapy: examining the role of cystoscopy and urine straining post implant," Medical physics, 2003, 30, 2695-2698.

Sugyo et al., "Evaluation of efficacy of radioimmunotherapy with 90Y-labeled fully human anti- transferring receptor monoclonal antibody in pancreatic cancer mouse models," PLoS One, Apr. 2015, 10, 1-17.

Suk et al., "PEGylation as a Strategy for Improving Nanoparticle-Based Drug and Gene Delivery " Adv Drug Deliv Rev, Apr. 2016, 99(Pt A):28-51.

Sumerlin, "Proteins as Initiators of Controlled Radical Polymerization: Grafting-from via ATRP and RAFT," ACS Macro Lett. Jan. 2012, 1(1): 141-145.

Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.

Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.

Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.

(56)                    References Cited

OTHER PUBLICATIONS

Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout," Arthritis Rheum, 2007, 56(3): 1021-1028.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of TRAIL Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Fractal aspects of elastin supramolecular organization," J Biomol Struct Dyn, 1995, 12: 1161-1172.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tang et al., "Laboratory Diagnosis of COVID-19: Current Issues and Challenges," J Clin Microbiol, 2020, 58: e00512-20, 9 pages.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attach-ment of PEG comb polymers using catalytic chain transfer and thiol-ene chemistry," Polymer Chemistry, Oct. 2012, 3 (10), 2743-2751.
Teicher, "In vivo/ex vivo and in situ assays used in cancer research: a brief review," Toxicol. Pathol., Jan. 2009, 37 (1), 114-122.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.
Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of Staphylococcus aureus and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Toshima et al., "Three-dimensional architecture of elastin and collagen fiber networks in the human and rat lung," Arch Histol Cytol, 2004, 67: 31-40.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, Elsevier, Nov. 2011, 32(33):8462-73.
Tsarevsky et al., "Deactivation efficiency and degree of control over polymerization in ATRP in protic solvents," Macromolecules 37, 2004, 9768-9778.
Tschop et al., "Unimolecular Polypharmacy for Treatment of Diabetes and Obesity," Cell Metab, Jul. 2016, 24(1):51-62.
Tsuda et al., "Monodisperse cell-encapsulating peptide microgel beads for 3D cell culture," Langmuir, 2010, 26: 2645-2649.

(56)         References Cited

OTHER PUBLICATIONS

Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.

Tu et al., "Stages in tropoelastin coalescence during synthetic elastin hydrogel formation," Micron, Apr. 2010, 41(3): 268-272.

Tuerk et al., "Systematic evolution of ligands by exponential enrichment: RNA ligands to bacteriophage T4 DNA polymerase," Science, 1990, 249(4968): 505-510.

Turner et al., "Challenges and Opportunities for the Subcutaneous Delivery of Therapeutic Proteins," Journal of Pharmaceutical Sciences, 2018, 107(5): 1247-1260.

Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.

Tward et al., "Survival of men with clinically localized prostate cancer treated with prostatectomy, brachytherapy, or no definitive treatment: impact of age at diagnosis," Cancer, Oct. 2006, 107(10): 2392-2400.

U.S. FDA—Classify your medical devices. Updated as of: Feb. 7, 2020. Available at: <https://www.fda.gov/medical-devices/overview-device-regulation/classify-your-medical-device>.

U.S. FDA—In Vitro Diagnostics. Updated as of: Oct. 25, 2019. Available at: <https://www.fda.gov/medical-devices/products-and-medical-procedures/vitro-diagnostics>.

Uchida et al., "Potential of adenovirus-mediated REIC/Dkk-3 gene therapy for use in the treatment of pancreatic cancer," Journal of Gastroenterology and Hepatology, Apr. 2014, 29(5):973-983.

UniProtKB—P15214 (GST_PROMI) acessed online at <https://www.uniprot.org/uniprot/P152146/> on Jun. 8, 2021, 7 pages.

Urry et al., "Calculation of distorted circular dichroism curves for poly-L-glutamic acid suspensions," Arch Biochem Biophys, 1970, 137, 214-221.

Urry et al., "Coacervation of solubilized elastin effects a notable conformational change," Nature, 1969, 222, 795-796.

Urry et al., "Differential scatter of left and right circularly polarized light by optically active particulate systems," Proc Natl Acad Sci U S A, 1970, 65, 845-852.

Urry et al., "Distortions in circular dichroism patterns of particulate (or membranous) systems," Arch Biochem Biophys, 1968, 128, 802-807.

Urry et al., "Elastic protein-based polymers in soft tissue augmentation and generation," J. Biomater. Sci. Polym. Ed., 1998, 9, 1015-1048.

Urry et al., "Hydrophobicity Scale for Proteins Based on InverseTemperature Transitions," Biopolymers, 1992, 32:1243-1250.

Urry et al., "Physical chemistry of biological free energy transduction as demonstrated by elastic protein-based polymers," J. of Phys. Chem. B., 1997, 101, 11007-11028.

Urry et al., "Temperature dependence of length of elastin and its polypentapeptide," Biochem Biophys Res Commun, 1986, 141, 749-755.

Urry et al., "Temperature of polypeptide inverse temperature transition depends on mean residue hydrophobicity," J. Am. Chem. Soc., 1991, 113(11):4346-4348.

Urry, "Free energy transduction in polypeptides and proteins based on inverse temperature transitions," Prog Biophys Mol Biol, Jan. 1992, 57(1):23-57.

Urry, "Protein elasticity based on conformations of sequential polypeptides: The biological elastic fiber," J Protein Chemistry, 1984, 3, 403-436.

Utada et al., "Monodisperse double emulsions generated from a microcapillary device," Science, 2005, 308: 537-541.

Uversky et al., "Intrinsically disordered proteins as crucial constituents of cellular aqueous two phase systems and coacervates," FEBS Lett, Jan. 2015, 589(1):15-22.

Uversky et al., "Understanding protein non-folding," Biochim Biophys Acta, Elsevier, Jun. 2010, 1804(6):1231-1264.

Uversky, "Protein intrinsic disorder-based liquid-liquid phase transitions in biological systems: Complex coacervates and membrane-less organelles," Adv Colloid Interface Sci, 2017, 239: 97-114.

Valkenburg et al., "Targeting the tumour stroma to improve cancer therapy," Nature Reviews Clinical Oncology, Jun. 2018, 15, 366-381.

Van der Lee et al., "Classification of intrinsically disordered regions and proteins," Chem Rev, Jul. 2014, 114(13): 6589-6631.

Van Roey et al., "Short linear motifs: ubiquitous and functionally diverse protein interaction modules directing cell regulation," Chem Rev, Jul. 2014, 114(13): 6733-6778.

Van Roy, "Beyond E-cadherin: roles of other cadherin superfamily members in cancer, " Nat Rev Cancer, Feb. 2014, 14(2): 121-134.

Vaninov, "In the eye of the COVID-19 cytokine storm," Nat Rev Immunol, 2020, 20: 277, 1 page.

Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.

Vashist et al., "Emerging Technologies for Next-Generation Point-of-Care Testing," Trends Biotechnol, 2015, 33(11): 692-705.

Vazquez-Lombardi et al., "Challenges and Opportunities for Non-Antibody Scaffold Drugs," Drug Discov Today, Oct. 2015, 20(10):1271-83.

Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.

Venkataraman et al., "The Effects of Polymeric Nanostructure Shape on Drug Delivery," Adv Drug Deliv Rev, Elsevier, Nov. 2011, 63(14-15):1228-46.

Verhoef et al., "Potential induction of anti-PEG antibodies and complement activation toward PEGylated therapeutics," Drug Discov Today, 2014, 19(12): 1945-1952.

Verma et al., "Effect of surface properties on nanoparticle-cell interactions," Small, Wiley, Jan. 2010, 6(1):12-21.

Veronese et al., "PEGylation, successful approach to drug delivery," Drug Discovery Today, 2005, 10(21):1451-1458.

Veronese, "Peptide and protein PEGylation: a review of problems and solutions," Biomaterials 22, 2001, 405-417.

Vicini et al., "An interinstitutional and interspecialty comparison of treatment outcome data for patients with prostate carcinoma based on predefined prognostic categories and minimum follow-up," Cancer, 2002, 95, 2126-2135.

Viegas et al., "Polyoxazoline: Chemistry, properties and applications," Bioconjugate Chem., May 2011, 22(5): 976-986.

Vlieghe et al., "Synthetic therapeutic peptides: science and market," Drug Discovery Today, Jan. 2010, 15(1-2): 40-56.

Voelker et al., "Alteration of the specificity and regulation of fatty acid synthesis of Escherichia coli by expression of a plant medium-chain acyl-acyl carrier protein thioesterase," J Bacteriol., 1994, 176(23):7320-7.

Volkova et al., "Anthracycline Cardiotoxicity: Prevalence, Pathogenesis and Treatment," Curr. Cardiol. Rev., Nov. 2011, vol. 7, No. 4, pp. 214-220.

Volodkin et al., "One-Step Formulation of Protein Microparticles with Tailored Properties: Hard Templating at Soft Conditions," Advanced Functional Materials, 2012, 22: 1914-1922.

Von Roemeling et al., "Breaking Down the Barriers to Precision Cancer Nanomedicine," Trends Biotechnol, Feb. 2017, 35(2):159-171.

Vonarbourg et al., "Evaluation of pegylated lipid nanocapsules versus complement system activation and macrophage uptake," J Biomed Mater Res A, Wiley, Sep. 2006, 78(3):620-8.

Vrhovski et al., "Biochemistry of tropoelastin," Eur J Biochem, 1998, 258, 1-18.

Vrhovski et al., "Coacervation Characteristics of Recombinant Human Tropoelastin," European Journal of Biochemistry, 1997, 250(1):92-98.

Vrignaud et al., "Strategies for the nanoencapsulation of hydrophilic molecules in polymer-based nanoparticles," Biomaterials, Nov. 2011, 32(33):8593-8604.

(56) References Cited

OTHER PUBLICATIONS

Vugmeyster et al., "Pharmacokinetics and toxicology of therapeutic proteins: Advances and challenges," World J Biol Chem, 2012, 3(4): 73-92.

Walczak, "Death Receptor-Ligand Systems in Cancer, Cell Death, and Inflammation," Cold Spring Harb. Perspect. Biol., May 2013, 5(5): a008698.

Wali et al., "Measuring Death of Pancreatic Beta Cells in Response to Stress and Cytotoxic T Cells," Methods in Molecular Biology, Mar. 2015, 1292:165-176.

Walsh et al., "Post-translational modifications in the context of therapeutic proteins," Nat. Biotechnol., Oct. 2006, 24(10): 1241-1252.

Walsh et al., "Posttranslationale Proteinmodifikation: die Chemie der Proteomdiversifizierung," Angew Chem, 2005, 117, 7508-7539.

Walsh et al., "Protein posttranslational modifications: The chemistry of proteome diversifications," Angew. Chem. Int. Ed., 2005, 44, 7342-7372.

Wang et al., "A Molecular Grammar Governing the Driving Forces for Phase Separation of Prion-like RNA Binding Proteins," Cell, Jul. 2018, 174(3):688-699.e616.

Wang et al., "Enhanced Tumor Delivery of Gemcitabine via PEG-DSPE/TPGS Mixed Micelles," Mol. Pharm., Apr. 2014, 11(4): 1140-1150.

Wang et al., "Extending Half Life of H-Ferritin Nanoparticle by Fusing Albumin Binding Domain for Doxorubicin Encapsulation," Biomacromolecules, Mar. 2018, 19(3):773-781.

Wang et al., "Functional polymeric microparticles engineered from controllable microfluidic emulsions," Acc Chem Res, 2014, 47: 373-384.

Wang et al., "More effective nanomedicines through particle design," Small, Wiley, Jul. 2011, 7(14): 1919-31.

Wang et al., "Nanoparticle delivery of cancer drugs," Annu Rev Med, Annual Reviews, Feb. 2012, 63:185-98.

Wang et al., "Pigs Can Be Used as a Large Animal Model for Autologous Fat Grafting," Ophthalmic Plast Reconstr Surg, 2016, 32: 73-74.

Wang et al., "Quantitative Mapping of the Spatial Distribution of Nanoparticles in Endo-Lysosomes by Local pH," Nano Lett., Feb. 2017, 17(2): 1226-1232.

Wang et al., "Size and dynamics of caveolae studied using nanoparticles in living endothelial cells," ACS nano, Dec. 2009, 3(12): p. 4110-4116.

Wang et al., "Stimuli-responsive Dendrimers in Drug Delivery," Biomater Sci, Mar. 2016, 4(3):375-90.

Wang et al., "The Weak Link: Optimization of the Ligand-Nanoparticle Interface to Enhance Cancer Cell Targeting by Polymer Micelles," Nano Lett Oct. 2017, 17(10):5995-6005.

Waterboer et al., "Suppression of non-specific binding in serological Luminex assays," J Immunol Methods, 2006, 309: 200-204.

Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.

Wechsel et al., "Renal Cell Carcinoma: Immunohistological Investigation of Expression of the Integrin $\alpha v \beta 3$," Anticancer research, 1999, 19(2C):1529-1532.

Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.

Wei et al., "Fibroblast growth factor 21 promotes bone loss by potentiating the effects of peroxisome proliferator-activated receptor $\gamma$," Proc Natl Acad Sci USA, Feb. 2012, 109(8):3143-3148.

Weinhandl et al., "Relative safety of peginesatide and epoetin alfa," Pharmacoepidemiology and Drug Safety, 2014, 23(10): 1003-1011.

Weis et al., "$\alpha$V Integrins in Angiogenesis and Cancer," Cold Spring Harb Perspect Med, Cold Spring Harbor Laboratory Press, Sep. 2011, 1(1):a006478.

Weitzhandler et al., "Micellar Self-Assembly of Recombinant Resilin-/Elastin-Like Block Copolypeptides," Biomacromolecules, Aug. 2017, 18(8):2419-2426.

Wendt et al., "DNA-mediated Folding and Assembly of MyoD-E47 Heterodimers," Journal of Biol. Chem., 1998, 273(10):5735-5743.

Wente et al., "Fibroblast Growth Factor-21 Improves Pancreatic $\beta$-Cell Function and Survival by Activation of Extracellular Signal-Regulated Kinase 1/2 and Akt Signaling Pathways," Diabetes, Sep. 2006, 55(9):2470-2478.

Werle et al., "Strategies to improve plasma half life time of peptide and protein drugs," Amino Acids 30, Jun. 2006, 30(4):351-367.

Werstuck et al., "Controlling gene expression in living cells through small molecule-RNA interactions," Science, 1998, 282(5387): 296-298.

Whitman et al., "Evaluation of SARS-CoV-2 serology assays reveals a range of test performance," Nat Biotechnol, 2020, 38: 1174-1183.

Wienkers et al., "Predicting in vivo drug interactions from in vitro drug discovery data," Nat. Rev. Drug. Discov. 2005, 4(10):825-833.

Wiersinga et al., "Pathophysiology, Transmission, Diagnosis, and Treatment of Coronavirus Disease 2019 (COVID-19): A Review," JAMA, 2020, 324(8): 782-793.

Wilkins et al., "Hydrodynamic Radii of Native and Denatured Proteins Measured by Pulse Field Gradient NMR Techniques," Biochemistry, 1999, 38(50):16424-16431.

Williams et al., "Targeted radionuclide therapy," Medical Physics, Jul. 2008, 35(7): 3062-3068.

Williamson et al., "Efficient N-terminal labeling of proteins by use of sortase," Angew Chem Int ed Engl, Sep. 2012, 51(37):9377-9380.

Wimley et al., "Experimentally determined hydrophobicity scale for proteins at membrane interfaces," Nature Structural & Molecular Biology, 1996, 3(10) 842-848.

Winter et al., "The important role of serology for COVID-19 control," Lancet Infect Dis, 2020, 20:758-759.

Winzell et al., "The high-fat diet-fed mouse: a model for studying mechanisms and treatment of impaired glucose tolerance and type 2 diabetes," Diabetes 53, 2004, S215-S219.

Wold, "In vivo chemical modification of proteins," Annu. Rev. Med., 1981, 50, 783-814.

Wölfel et al., "Virological assessment of hospitalized patients with COVID-2019," Nature, 2020, 581: 465-469.

Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.

Woodruff et al., "Modulation of the Coagulation Cascade Using Aptamers," Arterioscler Thromb Vasc Biol, 2015, 35(10): 2083-2091.

Wright et al., "Intrinsically disordered proteins in cellular signalling and regulation," Nat Rev Mol Cell Biol, Jan. 2015, 16(1):18-29.

Wright et al., "Self-assembly of block copolymers derived from elastin-mimetic polypeptide sequences," Advanced Drug Delivery Reviews, 2002, 54, 1057-1073.

Wright et al., "Thermoplastic elastomer hydrogels via self-assembly of an elastin-mimetic triblock polypeptide," Advanced Functional Materials, 2002, 12, 149-154.

Wu et al., "An injectable adipose matrix for soft-tissue reconstruction," Plast Reconstr Surg, 2012, 129: 1247-1257.

Wu et al., "Site-specific chemical modification of recombinant proteins produced in mammalian cells by using the genetically encoded aldehyde tag," Proc Natl Acad Sci USA, Mar. 2009, 106(9):3000-3005.

Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.

Wust et al., "Hyperthermia in combined treatment of cancer," The Lancet Oncology, 2002, 3, 487-497.

Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.

(56)         References Cited

OTHER PUBLICATIONS

Xia et al., "Tunable self-assembly of genetically engineered silk—elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic Api: Ii. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAS) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yamaoka et al., "Distribution and tissue uptake of poly(ethylene glycol) with different molecular weights after intravenous administration to mice," Journal of Pharmaceutical Sciences, 1994, 83(4): 601-606.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Plasma IP-10 and MCP-3 levels are highly associated with disease severity and predict the progression of COVID-19," J Allergy Clin Immunol, 2020, 146: 119-127.
Yang et al., "Poly(carboxybetaine) nanomaterials enable long circulation and prevent polymer-specific antibody production," Nano Today, Feb. 2014, 9(1):10-16.
Yang et al., "Uricases as therapeutic agents to treat refractory gout: Current states and future directions," Drug Dev Res, 2012, 73(2): 66-72.
Yates et al., "Contemporary management of patients with high-risk non-muscle-invasive bladder cancer who fail intravesical BCG therapy," World journal of urology, May 2011, 29(4): 415-422.
Yeh et al., "Micromolding of shape-controlled, harvestable cell-laden hydrogels," Biomaterials, 2006, 27: 5391-5398.
Yeo et al., "Coacervation of tropoelastin," Adv Colloid Interface Sci, Sep. 2011, 167(1-2): 94-103.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.

Yokoe et al., "Albumin-conjugated PEG liposome enhances tumor distribution of liposomal doxorubicin in rats," International Journal of Pharmaceutics, May 2008, 353(1-2): 28-34.
Yong et al., "Connecting clusters of COVID-19: an epidemiological and serological investigation," Lancet Infect Dis, 2020, 20: 809-815.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)I seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS One, 2012, 7(6): e39659.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Zhang et al., "Shape Effects of Nanoparticles Conjugated with Cell-Penetrating Peptides (HIV Tat PTD) on CHO Cell Uptake," Bioconjugate Chem, Sep. 2008, 19(9): 1880-1887.
Zhao et al., "A new Bliss Independence model to analyze drug combination data," J Biomol Screen, Jun. 2014, 19(5): 817-821.
Zhao et al., "Antibody responses to SARS-CoV-2 in patients of novel coronavirus disease 2019," Clin Infect Dis, 2020, 22 pages.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor avB3 Integrin Is a Therapeutic Target for Breast Cancer Bone Metastases," Cancer Res, AACR Publications, Jun. 2007, 67(12):5821-30.
Zhou et al., "Aptamers as targeted therapeutics: current potential and challenges," Nat Rev Drug Discov, 2017, 16(3): 181-202.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.

(56) References Cited

OTHER PUBLICATIONS

Zong et al., "Crystal structures of *Staphylococcus aureus* sortase A and its substrate complex," J. Biol. Chem. 279, 2004, 31383-31389.

Zununi Vahed et al., "Targeted cancer drug delivery with aptamer-functionalized polymeric nanoparticles," Journal of drug targeting, Mar. 2019, 27(3):292-299.

International Search Report and Written Opinion for Application No. PCT/US2008/084159 dated Feb. 27, 2009 (8 pages).

International Search Report and Written Opinion for Application No. PCT/US2016/024202 dated Aug. 26, 2016 (9 pages).

International Search Report and Written Opinion for Application No. PCT/US2016/045655 dated Dec. 2, 2016 (13 pages).

International Search Report and Written Opinion for Application No. PCT/US2016/068141 dated Jul. 19, 2017 (12 pages).

International Search Report and Written Opinion for Application No. PCT/US2016/068142 dated Jul. 19, 2017 (12 pages).

International Search Report and Written Opinion for Application No. PCT/US2018/032785 dated Sep. 25, 2018 (16 pages).

International Search Report and Written Opinion for Application No. PCT/US2017/035530 dated Aug. 23, 2017 (13 pages).

International Search Report and Written Opinion for Application No. PCT/US2017/052887 dated Jan. 26, 2018 (20 pages).

International Search Report and Written Opinion for Application No. PCT/US2017/051661 dated Jan. 2, 2018 (12 pages).

International Search Report and Written Opinion for Application No. PCT/US2018/013611 dated May 30, 2018 (18 pages).

International Search Report and Written Opinion for Application No. PCT/US2018/040409 dated Nov. 5, 2018 (16 pages).

International Search Report and Written Opinion for Application No. PCT/US2019/015176 dated Jun. 3, 2019 (12 pages).

International Search Report and Written Opinion for Application No. PCT/US2019/023583 dated Jul. 5, 2019 (10 pages).

International Search Report and Written Opinion for Application No. PCT/US2019/030022 dated Jul. 25, 2019 (8 pages).

International Search Report and Written Opinion for Application No. PCT/US2019/044911 dated Dec. 10, 2019 (11 pages).

International Search Report and Written Opinion for Application No. PCT/US2019/050077 dated Jan. 27, 2020 (19 pages).

International Search Report and Written Opinion for Application No. PCT/US2019/061144 dated May 21, 2020 (15 pages).

International Search Report and Written Opinion for Application No. PCT/US2021/020589 dated Jul. 15, 2021 (21 pages).

International Search Report and Written Opinion for Application No. PCT/US2021/017809 dated Jul. 22, 2021 (20 pages).

International Search Report and Written Opinion for Application No. PCT/US2021/020591 dated Oct. 7, 2021 (14 pages).

International Search Report and Written Opinion for Application No. PCT/US2021/046833 dated Nov. 8, 2021 (13 pages).

International Search Report and Written Opinion for Application No. PCT/US2021/035823 dated Dec. 8, 2021 (16 pages).

International Search Report and Written Opinion for Application No. PCT2022/023158 dated Jun. 21, 2022 (7 pages).

International Search Report and Written Opinion for Application No. PCT/US2022/017349 dated Jun. 3, 2022 (20 pages).

International Search Report and Written Opinion for Application No. PCT/US2022/041241 dated Oct. 25, 2022 (10 pages).

International Search Report and Written Opinion for Application No. PCT/US2022/078659 dated Feb. 1, 2023 (17 pages).

European Patent Office Extended Search Report for Application No. 18825502.0 dated Jun. 11, 2021 (9 pages).

United States Patent Office Action for U.S. Appl. No. 13/904,836 dated Mar. 27, 2014 (10 pages).

United States Patent Office Notice of Allowance for U.S. Appl. No. 13/904,836 dated Jul. 30, 2014 (6 pages).

United States Patent Office Action for U.S. Appl. No. 13/942,037 dated Jan. 15, 2016 (19 pages).

United States Patent Office Action for U.S. Appl. No. 13/942,037 dated Jun. 4, 2015 (33 pages).

United States Patent Office Action for U.S. Appl. No. 13/942,037 dated Nov. 28, 2016 (22 pages).

United States Patent Office Action for U.S. Appl. No. 13/942,037 dated Feb. 9, 2018 (29 pages).

United States Patent Office Notice of Allowance for U.S. Appl. No. 13/245,459 dated Feb. 27, 2013 (13 pages).

United States Patent Office Action for U.S. Appl. No. 14/572,391 dated Oct. 26, 2016 (11 pages).

United States Patent Office Notice of Allowance for U.S. Appl. No. 14/572,391 dated Jun. 16, 2017 (10 pages).

United States Patent Office Action for U.S. Appl. No. 15/387,536 dated Sep. 27, 2018 (11 pages).

United States Patent Office Action for U.S. Appl. No. 15/387,540 dated Sep. 27, 2018 (12 pages).

United States Patent Office Action for U.S. Appl. No. 15/561,799 dated Dec. 27, 2018 (8 pages).

United States Patent Office Notice of Allowance for U.S. Appl. No. 15/387,536 dated Mar. 13, 2019 (13 pages).

United States Patent Office Notice of Allowance for U.S. Appl. No. 15/561,799 dated Apr. 2, 2019 (6 pages).

United States Patent Office Notice of Allowance for U.S. Appl. No. 15/387,540 dated Apr. 17, 2019 (9 pages).

United States Patent Office Action for U.S. Appl. No. 16/058,924 dated Nov. 26, 2019 (23 pages).

United States Patent Office Action for U.S. Appl. No. 16/064,424 dated Apr. 22, 2020 (18 pages).

United States Patent Office Action for U.S. Appl. No. 16/064,425 dated Apr. 22, 2020 (18 pages).

United States Patent Office Action for U.S. Appl. No. 16/058,924 dated Jul. 6, 2020 (51 pages).

United States Patent Office Action for U.S. Appl. No. 15/749,797 dated May 11, 2020 (14 pages).

United States Patent Office Action for U.S. Appl. No. 15/749,797 dated Oct. 20, 2020 (16 pages).

United States Patent Office Action for U.S. Appl. No. 16/335,734 dated Nov. 20, 2020 (15 pages).

United States Patent Office Action for U.S. Appl. No. 16/525,374 dated Dec. 7, 2020 (9 pages).

United States Patent Office Action for U.S. Appl. No. 16/305,696 dated Jan. 28, 2021 (15 pages).

United States Patent Office Notice of Allowance for U.S. Appl. No. 16/332,865 dated Apr. 2, 2021 (10 pages).

United States Patent Office Action for U.S. Appl. No. 16/477,229 dated Apr. 12, 2021 (14 pages).

United States Patent Office Action for U.S. Appl. No. 15/749,797 dated May 12, 2021 (19 pages).

United States Patent Office Notice of Allowance for U.S. Appl. No. 16/332,865 dated May 17, 2021 (5 pages).

United States Patent Office Notice of Allowance for U.S. Appl. No. 16/335,734 dated Jun. 16, 2021 (9 pages).

United States Patent Office Action for U.S. Appl. No. 16/305,696 dated Jun. 22, 2021 (20 pages).

United States Patent Office Action for U.S. Appl. No. 16/614,282 dated Oct. 21, 2021 (14 pages).

United States Patent Office Action for U.S. Appl. No. 15/749,797 dated Nov. 29, 2021 (10 pages).

United States Patent Office Action for U.S. Appl. No. 16/477,229 dated Oct. 26, 2021 (10 pages).

United States Patent Office Action for U.S. Appl. No. 17/265,165 dated Dec. 21, 2021 (11 pages).

United States Patent Office Action for U.S. Appl. No. 16/964,832 dated Jan. 19, 2022 (12 pages).

United States Patent Office Action for U.S. Appl. No. 16/625,899 dated Dec. 15, 2021 (12 pages).

United States Patent Office Action for U.S. Appl. No. 16/927,982 dated Jan. 6, 2022 (6 pages).

United States Patent Office Action for U.S. Appl. No. 16/477,229 dated Mar. 3, 2022 (10 pages).

United States Patent Office Notice of Allowance for U.S. Appl. No. 15/749,797 dated Mar. 16, 2022 (6 pages).

United States Patent Office Action for U.S. Appl. No. 16/614,282 dated Apr. 27, 2022 (15 pages).

United States Patent Office Notice of Allowance for U.S. Appl. No. 16/305,696 dated May 23, 2022 (10 pages).

(56)          References Cited

OTHER PUBLICATIONS

United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).
United States Patent Office Action for U.S. Appl. No. 17/265,165 dated Sep. 2, 2022 (5 pages).
United States Patent Office Action for U.S. Appl. No. 17/015,315 dated Dec. 23, 2022 (10 pages).
United States Patent Office Notice of Allowance for U.S. Appl. No. 16/477,229 dated Jan. 6, 2023 (8 pages).
United States Patent Office Notice of Allowance for U.S. Appl. No. 17/265,165 dated Jan. 10, 2023 (7 pages).
United States Patent Office Notice of Allowance for U.S. Appl. No. 16/625,899 dated Jan. 18, 2023 (8 pages).
United States Patent Office Action for U.S. Appl. No. 16/964,832 dated Apr. 17, 2023 (17 pages).
Chen et al., "Polyethylene Glycol Immunogenicity: Theoretical, Clinical, and Practical Aspects of Anti-Polyethylene Glycol Antibodies," ACS Nano, 2021, 15(9): 14022-14048.
European Patent Office Partial Supplementary Search Report for Application No. 18825502.0 dated Jun. 26, 2024 (5 pages).
United States Patent Office Action for U.S. Appl. No. 17/294,368 dated Sep. 12, 2024 (11 pages).
Antonicelli et al., "Elastin-elastases and inflamm-aging," Curr Top Dev Biol, 2007, 79: 99-155.
Carvalho et al., "Modern Trends for Peripheral Nerve Repair and Regeneration: Beyond the Hollow Nerve Guidance Conduit," Front Bioeng Biotechnol, 2019, 7: 337.
Gu et al., "Construction of tissue engineered nerve grafts and their application in peripheral nerve regeneration," Prog Neurobiol, 2011, 93: 204-230.
Heggestad et al., "Rapid test to assess the escape of SARS-CoV-2 variants of concern," Science Advances, 2021, 7(49): 1-12.
Jacobs et al., "Fusion to a highly stabble consensus albumin binding domain allows for tunable pharmacokinetics," Protein Engineering, Designs & Selections, 2015, 28(10): 385-393.
Mohammad et al., "Development and validation of a rapid and easy-to-perform point-of-care lateral flow immunoassay (LFIA) for the detection of SARS-CoV-2 spike protein," Frontiers in Immunology, 2023, 14: 1-15.
Parker et al., "Nerve guidance conduit development for primary treatment of peripheral nerve transection injuries: A commercial perspective," Acta Biomater, 2021, 135: 64-86.
Roberts et al., "Complex microparticle architectures from stimuli-responsive intrinsically disordered proteins," Nat Commun, 2020, 11: 1342.
Rosso et al., "Implications of Schwann Cells Biomechanics and Mechanosensitivity for Peripheral Nervous System Physiology and Pathophysiology," Front Mol Neurosci, 2017, 10: 345.
Rosso et al., "Schwann cells and neurite outgrowth from embryonic dorsal root ganglions are highly mechanosensitive," Nanomedicine, 2017, 13: 493-501.
Saffari et al., "Surgical Angiogenesis of Decellularized Nerve Allografts Improves Early Functional Recovery in a Rat Sciatic Nerve Defect Model," Plast Reconstr Surg, 2021, 148: 561-570.
Saffari et al., "The role of vascularization in nerve regeneration of nerve graft," Neural Regen Res, 2020, 15: 1573-1579.
Shakhbazau et al., "Aligned collagen-GAG matrix as a 3D substrate for Schwann cell migration and dendrimer-based gene delivery," J Mater Sci Mater Med, 2014, 25: 1979-1989.

Taskindoust et al., "Recombinant Elastin Biomatrix Improves Autologous Fat Grafting for Soft Tissue Reconstruction," Plastic and Reconstructive Surgery Global Open, 2022, 10(10S): 74-75.
Weber, "Improving Cloning Procedures and Particle Architectures of Elastin-like Polypeptide-based Drug Delivery Vehicles," Master Thesis, Duke University, Nov. 13, 2019, 92 pages.
International Search Report and Written Opinion for Application No. PCT/US2023/082105 dated Apr. 10, 2024 (8 pages).
United States Patent Office Notice of Allowance for U.S. Appl. No. 17/477,192 dated May 9, 2024 (8 pages).
United States Patent Office Action for U.S. Appl. No. 17/272,887 dated Jun. 4, 2024 (12 pages).
United States Patent Office Action for U.S. Appl. No. 16/964,832 dated Jun. 21, 2024 (6 pages).
Adamus et al., "The revival of CpG oligonucleotide-based cancer immunotherapies," Contemp Oncol (Pozn), 2018, 22: 56-60.
Bailey-Downs et al., "Development and characterization of a preclinical model of breast cancer lung micrometastatic to macrometastatic progression," PLoS One, 2014, 9(5): e98624.
Bieniasz-Krzywiec et al., "Isolation and separation of murine tumor-associated macrophages (TAMs) subpopulations from orthotopic 4T1 breast tumors," STAR Protoc, 2021, 2(2): 100481.
Bird, "CpG-rich islands and the function of DNA methylation," Nature, 1986, 321(6067): 209-213.
Bode et al., "CpG DNA as a vaccine adjuvant," Expert Rev Vaccines, 2011, 10: 499-511.
Bonaventura et al., "Cold Tumors: A Therapeutic Challenge for Immunotherapy," Front Immunol, 2019, 10: 168.
Borden et al., "Cancer Neoantigens: Challenges and Future Directions for Prediction, Prioritization, and Validation," Frontiers in Oncology, 2022, 12: 836821.
Brincker, "Direct intratumoral chemotherapy," Critical Reviews in Oncology/Hematology, 1993, 15: 91-98.
Chen et al., "Hypoxic microenvironment in cancer: molecular mechanisms and therapeutic interventions," Signal Transduct Target Ther, 2023, 8: 70.
D'Alterio et al., "Paradoxical effects of chemotherapy on tumor relapse and metastasis promotion," Seminars in Cancer Biology, 2020, 60: 351-361.
De Gassart et al., "MHC class II stabilization at the surface of human dendritic cells is the result of maturation-dependent March I down-regulation," Proceedings of the National Academy of Sciences, 2008, 105(9): 3491-3496.
De Jong et al., "The immunostimulatory activity of unmethylated and methylated CpG oligodeoxynucleotide is dependent on their ability to colocalize with TLR9 in late endosomes," The Journal of Immunology, 2010, 184(11): 6092-6102.
Deng et al., "Doxorubicin and CpG loaded liposomal spherical nucleic acid for enhanced Cancer treatment," Journal of Nanobiotechnology, 2022, 20: 140.
Dillekås et al., "Are 90% of deaths from cancer caused by metastases?" Cancer Med, 2019, 8(12): 5574-5576.
Dongye et al., "Toll-like receptor 9 agonists and combination therapies: strategies to modulate the tumour immune microenvironment for systemic anti-tumour immunity," British Journal of Cancer, 2022, 127: 1584-1594.
Dupre et al., "Murine mammary carcinoma 4T1 induces a leukemoid reaction with splenomegaly: association with tumor-derived growth factors," Experimental and Molecular Pathology, 2007, 82: 12-24.
Erkamp et al., "Spatially non-uniform condensates emerge from dynamically arrested phase separation," Nature Communications, 2023, 14: 684.
Hosseinpour et al., "Improving tumor treatment through intratumoral injection of drug-loaded magnetic nanoparticles and low-intensity ultrasound," Scientific Reports, 2024, 14: 1452.
Hu et al., "Harnessing innate immune pathways for therapeutic advancement in cancer," Signal Transduction and Targeted Therapy, 2024, 9: 68.
Jakob et al., "Activation of Cutaneous Dendritic Cells by CpG-Containing Oligodeoxynucleotides: A Role for Dendritic Cells in the Augmentation of Th1 Responses by Immunostimulatory DNA," The Journal of Immunology, 1998, 161: 3042-3049.

(56) References Cited

OTHER PUBLICATIONS

Jenkins et al., "Genetically Encoded Elastin-Like Polypeptides for Drug Delivery," Advanced Healthcare Materials, 2021, 10(13): 2100209.

Kashkooli et al., "Controlled anti-cancer drug release through advanced nano-drug delivery systems: Static and dynamic targeting strategies," Journal of Controlled Release, 2020, 327: 316-349.

Kayraklioglu et al., "CpG Oligonucleotides as Vaccine Adjuvants," Methods Mol Biol, 2021, 2197: 51-85.

Kelly et al., "Intratumoral delivery of brachytherapy and immunotherapy by a thermally triggered polypeptide depot," J Control Release, 2022, 343: 267-276.

Kim et al., "Eradication of metastatic mouse cancers resistant to immune checkpoint blockade by suppression of myeloid-derived cells," Proceedings of the National Academy of Sciences, 2014, 111(32): 11774-11779.

Krishnamachari et al., "Innovative strategies for co-delivering antigens and CpG oligonucleotides," Adv Drug Deliv Rev, 2009, 61(3): 205-217.

Landmann et al., "Maturation of dendritic cells is accompanied by rapid transcriptional silencing of class II transactivator (CIITA) expression," J Exp Med, 2001, 194(4): 379-391.

Le et al., "Adjuvant effects of combination monophosphoryl lipid A and poly I:C on antigen-specific immune responses and protective efficacy of influenza vaccines," Scientific Reports, 2023, 13: 12231.

Lelekakis et al., "A novel orthotopic model of breast cancer metastasis to bone," Clin Exp Metastasis, 1999, 17(2): 163-170.

Liu et al., "Clinical cancer immunotherapy: Current progress and prospects," Front Immunol, 2022, 13: 961805.

Liu et al., "Injectable intratumoral depot of thermally responsive polypeptide-radionuclide conjugates delays tumor progression in a mouse model," Journal of Controlled Release, 2010, 144: 2-9.

Liu et al., "Membrane Anchored Immunostimulatory Oligonucleotides for In Vivo Cell Modification and Localized Immunotherapy," Angewandte Chemie International Edition, 2011, 50(31): 7052-7055.

Maeda ate al., "Analyses of repeated failures in cancer therapy for solid tumors: poor tumor-selective drug delivery, low therapeutic efficacy and unsustainable costs, " Clinical and Translational Medicine, 2018, 7: 11.

Mani et al., "Causes of death among people living with metastatic cancer," Nature Communications, 2024, 15: 1519.

Marciscano et al., "The role of dendritic cells in cancer and anti-tumor immunity," Semin Immunol, 2021, 52: 101481.

Martins et al., "Vaccine adjuvant uses of poly-IC and derivatives," Expert Rev Vaccines, 2015, 14(3): 447-459.

Maurer et al., "CpG-DNA aided cross-presentation of soluble antigens by dendritic cells," Eur J Immunol, 2002, 32(8): 2356-2364.

McCoy et al., "Activation of RAW264.7 Macrophages by Bacterial DNA and Lipopolysaccharide Increases Cell Surface DNA Binding and Internalization," Journal of Biological Chemistry, 2004, 279(17): 17217-17223.

Milligan et al., "A Nanoparticle's Journey to the Tumor: Strategies to Overcome First-Pass Metabolism and Their Limitations," Cancers, 2022, 14(7): 1741.

Milligan et al., "Genetically encoded elastin-like polypeptide nanoparticles for drug delivery," Current Opinion in Biotechnology, 2022, 74: 146-153.

Moseman et al., "Human plasmacytoid dendritic cells activated by CpG oligodeoxynucleotides induce the generation of CD4+CD25+ regulatory T cells," J Immunol, 2004, 173(7): 4433-4442.

Nastiuk et al., "Opportunities and challenges in combination gene cancer therapy," Adv Drug Deliv Rev, 2016, 98: 35-40.

Ouyang et al., "Overcoming cold tumors: a combination strategy of immune checkpoint inhibitors, " Front Immunol, 2024, 15: 1344272.

Roberts et al., "Differences in macrophage activation by bacterial DNA and CpG-containing oligonucleotides," The Journal of Immunology, 2005, 175(6): 3569-3576.

Schaal et al., "Brachytherapy via a depot of biopolymer-bound 131I synergizes with nanoparticle paclitaxel in therapy-resistant pancreatic tumours," Nat Biomed Eng, 2022, 6: 1148-1166.

Senapati et al., "Controlled drug delivery vehicles for cancer treatment and their performance," Signal Transduction and Targeted Therapy, 2018, 3: 7.

Shih et al., "Ultrasound-triggered release reveals optimal timing of CpG-ODN delivery from a cryogel cancer vaccine," Biomaterials, 2021, 279: 121240.

Singh-Jasuja et al., "The mouse dendritic cell marker CD11c is down-regulated upon cell activation through toll-like receptor triggering. Immunobiology," Immunobiology, 2013, 218: 28-39.

Sun et al., "Intra-tumor heterogeneity of cancer cells and its implications for cancer treatment," Acta Pharmacologica Sinica, 2015, 36(10): 1219-1227.

Tsujimura et al., "Toll-like receptor 9 signaling activates NF-kappaB through IFN regulatory factor-8/IFN consensus sequence binding protein in dendritic cells," J Immunol, 2004, 172(11): 6820-6827.

Turley et al., "Immunological hallmarks of stromal cells in the tumour microenvironment," Nature Reviews Immunology, 2015, 15(11): 669-682.

Utaisincharoen et al., "CpG ODN activates NO and iNOS production in mouse macrophage cell line (RAW 264.7), " Clin Exp Immunol, 2002, 128(3): 467-473.

Van den Boorn et al., "Chapter 1—Nucleic Acid Adjuvants: Toward an Educated Vaccine," Advances in Immunology, 2012, 114: 1-32.

Wilson et al., "Dendritic cells constitutively present self antigens in their immature state in vivo and regulate antigen presentation by controlling the rates of MHC class II synthesis and endocytosis," Blood, 2004, 103(6): 2187-2195.

Xie et al., "Neoantigens: promising targets for cancer therapy," Signal Transduction and Targeted Therapy, 2023, 8(1): 9.

Yang et al., "Advanced biomaterials for cancer immunotherapy," Acta Pharmacologica Sinica, 2020, 41(7): 911-927.

Yang et al., "Sustained release of tumor cell lysate and CpG from an injectable, cytotoxic hydrogel for melanoma immunotherapy," Nanoscale Advances, 2023, 5: 2071-2084.

Aslan et al. "Targeted Therapies for Pancreatic Cancer and Hurdles Ahead," Anticancer Research, 2018, 38: 6591-6606.

Bowen, "Particle Size Distribution Measurement from Millimeters to Nanometers and from Rods to Platelets," Journal of Dispersion Science and Technology, 2002, 631-662.

United States Patent Office Notice of Allowance for U.S. Appl. No. 17/272,887 dated Jul. 2, 2025 (10 pages).

United States Patent Office Action for U.S. Appl. No. 17/294,368 dated Jul. 7, 2025 (18 pages).

Piasecki et al., "Purified Viable Fat Suspended in Matrigel Improves Volume Longevity," Aesthetic Surg. J., 2008, 28:24-32.

United States Patent Office Notice of Allowance for Application No. 17/272,887 dated Aug.21, 2025 (9 pages).

United States Patent Office Action for U.S. Appl. No. 17/908,427 dated Oct. 15, 2025 (16 pages).

United States Patent Office Action for U.S. Appl. No. 18/042,032 dated Oct. 1, 2025 (14 pages).

Bae et al., "Intelligent biosynthetic nanobiomaterials for hyperthermic combination chemotherapy and thermal drug targeting of HSP90 inhibitor geldanamycin," Journal of Controlled Release, 2007, 122: 16-23.

WIPO English Translation of CN112946261A (Year 2021).

Punta et al., "The Rough Guide to In Silica Function Prediction, or How To Use Sequence and Structure Information To Predict Protein Function," PLOS Comput Biol, 2008, 4(10): e1000160.

Whisstock et al., "Prediction of protein function from protein sequence and structure," Quarterly Reviews in Biophysics, 2007, 36(3): 307-340.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 1990, 111: 2129-2138.

(56)            References Cited

OTHER PUBLICATIONS

Song et al., "A Single Amino Acid Change (Asp 533Ala53) Converts Survivin from Anti-apoptotic to Pro-apoptotic," Molecular Biology of the Cell, 2004, 15: 1287-1296.

Defeo-Jones et al., "Substitution of Lysine for Arginine at Position 42 of Human Transforming Growth Factor-a Eliminates Biological Activity without Changing Internal Disulfide Bonds," Molecular and Cellular Biology, Sep. 1989, p. 4083-4086.

Bork, "Powers and Pitfalls in Sequence Analysis: The 70% Hurdle," Genome Research, 2000, 10: 398-400.

United States Patent Office Action for U.S. Appl. No. 17/798,868 dated Nov. 19, 2025 (28 pages).

United States Patent Office Action for U.S. Appl. No. 17/957,373 dated Nov. 5, 2025 (19 pages).

United States Patent Office Action for U.S. Appl. No. 17/908,415 dated Nov. 25, 2025 (19 pages).

United States Patent Office Notice of Allowance for U.S. Appl. No. 17/272,887 dated Nov. 20, 2025 (9 pages).

International Search Report and Written Opinion for Application No. PCT/US2025/019969 dated Oct. 3, 2025 (14 pages).

Fletcher et al., "Designed multifunctional polymeric nanomedicines: long-term biodistribution and tumour accumulation of aptamer-targeted nanomaterials," Chem. Commun., 2018, 54: 11538.

United States Patent Office Action for U.S. Appl. No. 18/277,915 dated Apr. 6, 2026 (21 pages).

International Search Report and Written Opinion for Application No. PCT/US2025/040378 dated Dec. 30, 2025 (16 pages).

Hu et al., "Poly [oligo (ethylene glycol) methacrylate-co-glycidyl methacrylate] brush substrate for sensitive surface plasmon resonance imaging protein arrays," Advanced Functional Materials, 2020, pp. 3497-3503.

United States Patent Office Action for U.S. Appl. No. 18/007,879 dated Mar. 17, 2026 (42 pages).

Ni et al., "Chemical Modifications of Nucleic Acid Aptamers for Therapeutic Purposes," Int. J. Mol. Sci, 2017, 18: 1683.

Wilharm et al., "Energetic electron assisted synthesis of highly tunable temperature-responsive collagen/elastin gels for cyclic actuation: macroscopic switching and molecular origins," Sci Rep, 2019, 9: 12363.

International Search Report and Written Opinion for Application No. PCT/US2025/049197 dated Feb. 3, 2026 (12 pages).

a
Isolated Oligomers                    Docked Aggregate
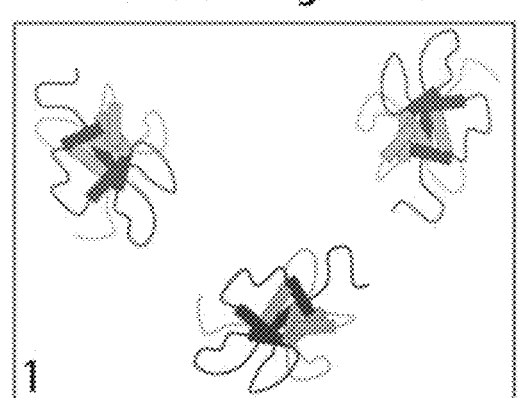
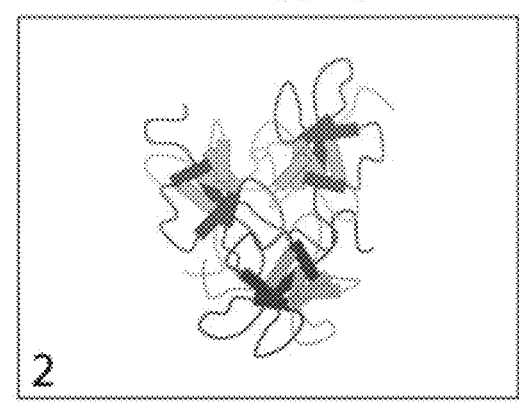
Heating
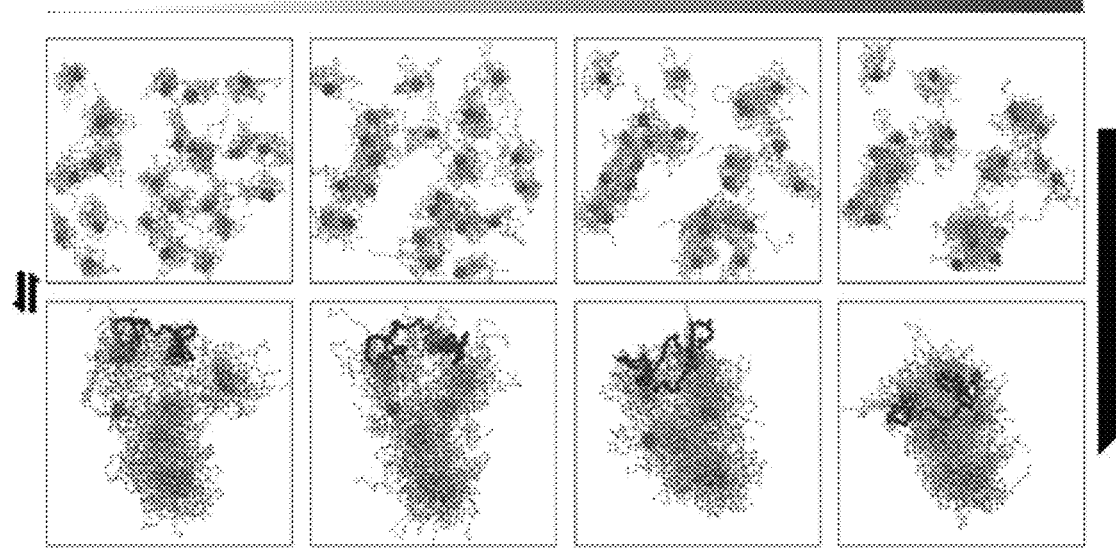
Cooling
Entangled Oligomers              Entangled Aggregate
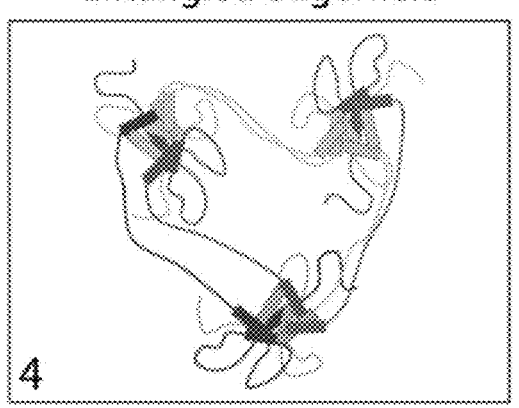
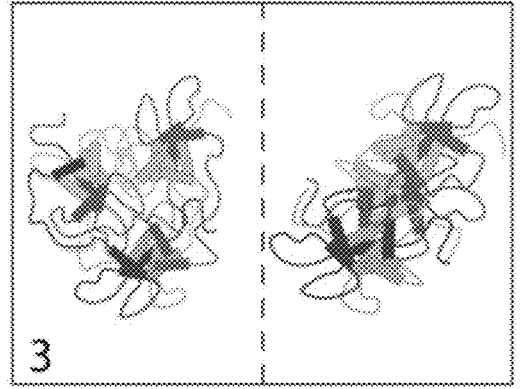
FIG 3A Entangled Aggregate

FIG. 3C

Entangled Oligomers

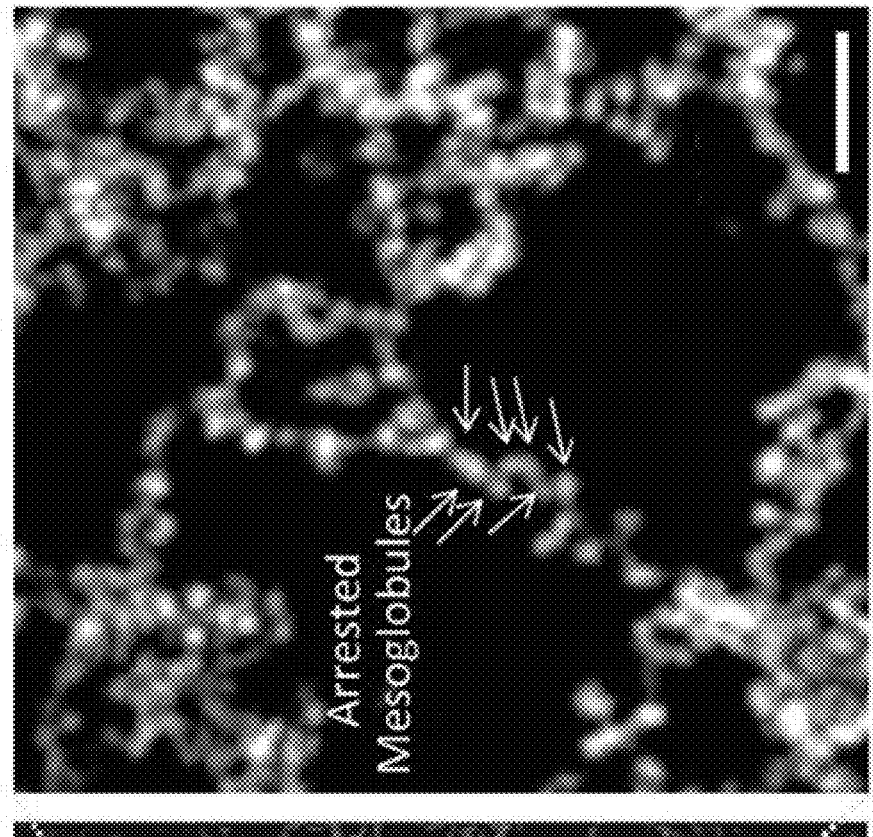
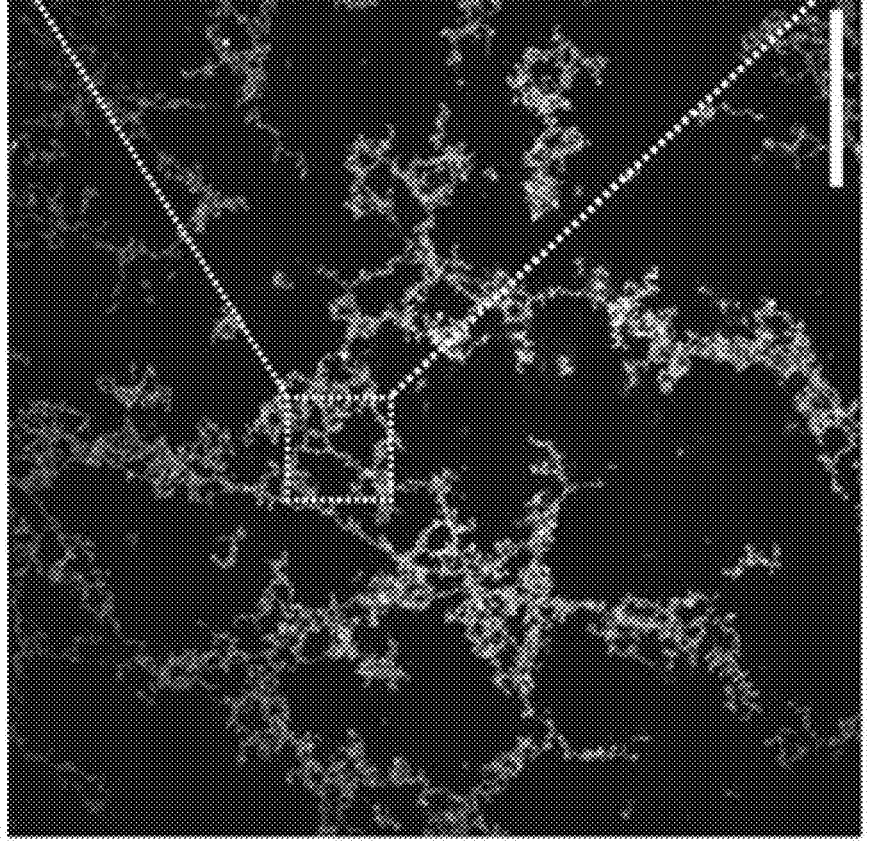
FIG. 4D

POP Day 10 - Internal Cross-section

| Polymer | Lane |
|---|---|
| (E1)80 | 1 |
| (E2)80 | 2 |
| (E3)80 | 3 |
| E1-H1-7.25% | 4 |
| E1-H1-12.5% | 5 |
| E1-H1-25% | 6 |
| E1-H2-12.5% | 7 |
| E1-H2-25% | 8 |
| E1-H2-50% | 9 |
| E1-H3-12.5% | 10 |
| E1-H3-25% | 11 |
| E1-H5-7.25% | 12 |
| E1-H5-12.5% | 13 |
| E1-H5-25% | 14 |
| E1-H5-25%-40mer | 15 |
| E1-H5-25%-120mer | 16 |
| E2-H5-25% | 17 |
| E3-H5-25% | 18 |

ELP

POP

Injections In vivo

Day 1 - 250uM

Day 3 - 250uM

Day 5 - 250uM

Day 10 - 250uM

Day 21 - 250uM

Day 1                    Day 3                    Day 5

Day 10                                    Day 21

FIG. 23D

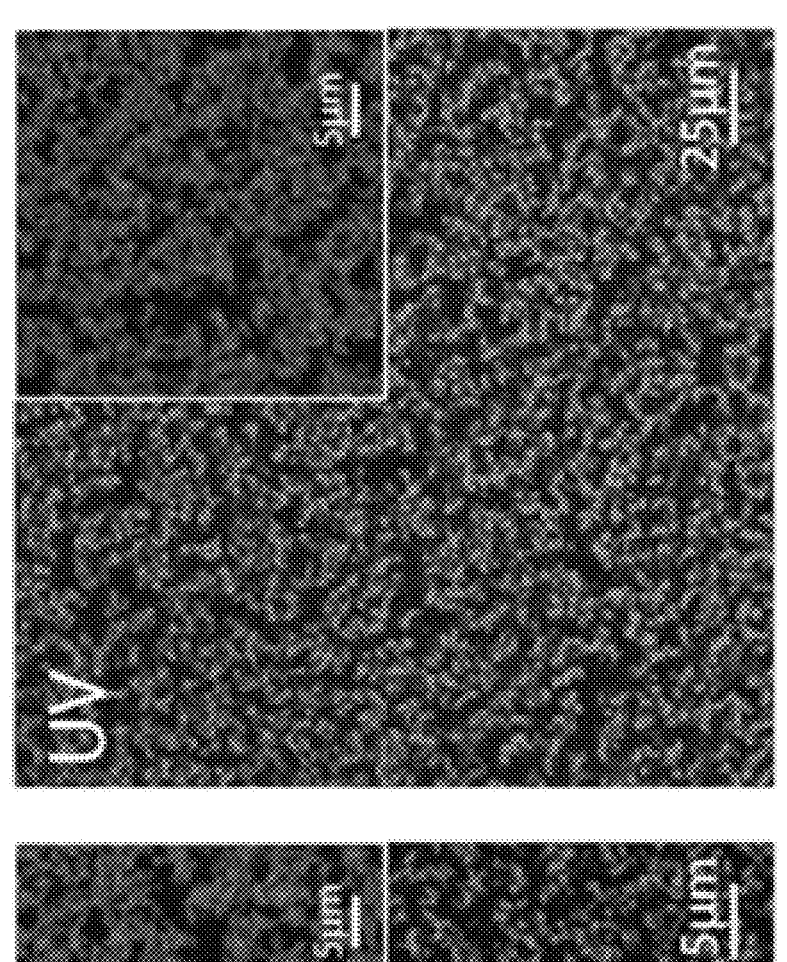
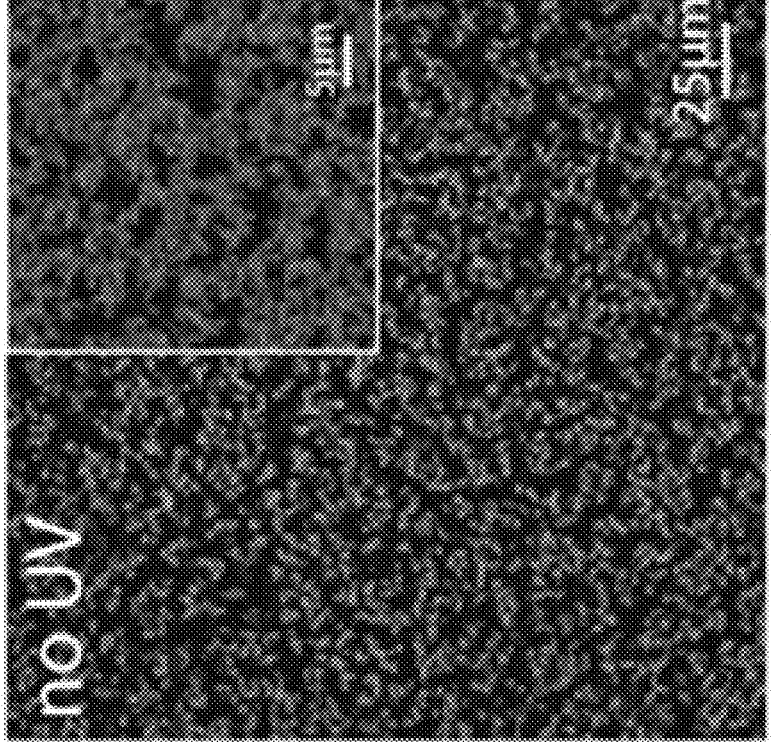
FIG. 24G

200µM

800μM

ORDER AND DISORDER AS A DESIGN PRINCIPLE FOR STIMULI-RESPONSIVE BIOPOLYMER NETWORKS

CROSS-REFERENCE TO RELATED APPLICATIONS

This application is a continuation of U.S. patent application Ser. No. 16/625,899, filed Dec. 23, 2019, which is the U.S. national stage entry, under 35 U.S.C. 371, of International Application No. PCT/US2018/040409, filed Jun. 29, 2018, which claims priority to U.S. Provisional Patent Application No. 62/527,836, filed Jun. 30, 2017; and U.S. Provisional Patent Application No. 62/534,019, filed Jul. 18, 2017, the entire contents of each of which are hereby incorporated by reference.

STATEMENT REGARDING FEDERALLY SPONSORED RESEARCH

This invention was made with government support under grant GM061232 awarded by the National Institutes of Health, and grant NSF DMR-11-21107 awarded by the National Science Foundation. The government has certain rights in the invention.

SEQUENCE LISTING

The application includes a Sequence Listing which has been submitted electronically in XML format and is hereby incorporated by reference in its entirety. Said XML Sequence Listing, created on Aug. 9, 2023, is named 028193-9261-US04 Sequence Listing.xml, and is 29,441 bytes in size.

FIELD

This disclosure relates to polypeptides with phase transition behavior and their use as cellular scaffolds.

INTRODUCTION

Both purely crystalline and amorphous materials have been extensively studied for their interesting properties, but they comprise a very small portion of the total materials space. Most material properties are a consequence of the interplay between their ordered and disordered domains. This phenomenon is one of the hallmarks of biological materials. For example, silk fibers owe their extraordinary attributes to the interactions of ordered and disordered domains at the inter- and intra-molecular level. With the recent expansion of research on intrinsically disordered proteins (IDPs), the importance of disorder-order interactions has become further undeniable. To understand how this interplay creates macroscopic material properties, ordered and disordered nanoscale modules have to be synthesized with molecular precision. The emergence of genetically encoded synthesis of peptide polymers makes it possible to design building blocks with this level of control over sequence and structure. There is a need for advanced materials that can be rationally designed and precisely tuned.

SUMMARY

In an aspect, the disclosure relates to a partially ordered polypeptide (POP) including: a plurality of disordered domains; and a plurality of structured domains, wherein the POP exhibits phase transition behavior.

In some embodiments, the disordered domain includes at least one of: (i) an amino acid sequence of $[VPGXG]_m$ (SEQ ID NO:1), wherein X is any amino acid except proline and m is an integer greater than or equal to 1; (ii) a PG motif including an amino acid sequence selected from PG, $P(X)_nG$ (SEQ ID NO:2), and $(B)_mP(X)_nG(Z)_p$ (SEQ ID NO:3), or a combination thereof, wherein m, n, and p are independently an integer from 1 to 15, and wherein U, X, and Z are independently any amino acid; (iii) a non-repetitive polypeptide including a sequence of at least 60 amino acids, wherein at least about 10% of the amino acids are proline (P), and wherein at least about 20% of the amino acids are glycine (G); (iv) a non-repetitive polypeptide including a sequence of at least 60 amino acids, wherein at least about 40% of the amino acids are selected from the group consisting of valine (V), alanine (A), leucine (L), lysine (K), threonine (T), isoleucine (I), tyrosine (Y), serine (S), and phenylalanine (F); and (v) a non-repetitive polypeptide including a sequence of at least 60 amino acids, wherein the sequence does not contain three contiguous identical amino acids, wherein any 5-10 amino acid subsequence does not occur more than once in the non-repetitive polypeptide, and wherein when the non-repetitive polypeptide includes a subsequence starting and ending with proline (P), the subsequence further includes at least one glycine (G). In some embodiments, the disordered domain includes an amino acid sequence of $[VPGXG]_m$ (SEQ ID NO:1), wherein X is Val, or Ala, or mixture of Ala and Val, and wherein m is an integer from 1 to 50. In some embodiments, X is a mixture of Ala and Val in a ratio from 10:1 to 1:10 (Ala:Val). In some embodiments, X is a mixture of Ala and Val in a ratio of 1:1 or 1:4. In some embodiments, the structured domain includes at least one of: (i) a polyproline domain, each polyproline domain including at least 5 proline residues and having at least about 50% of the amino acids in a PPI polyproline helical conformation or a PPII polyproline helical conformation; and (ii) a polyalanine domain, each polyalanine domain including at least 5 alanine residues and having at least about 50% of the amino acids in an alpha-helical conformation. In some embodiments, the structured domain includes a polyalanine domain. In some embodiments, at least about 60% of the amino acids in each polyalanine domain are in an alpha-helical conformation. In some embodiments, the polyalanine domain includes an amino acid sequence of $[B_p(A)_qZ_r]_n$ (SEQ ID NO:4) or $[(BA_s)_tZ_r]_n$ (SEQ ID NO:5), wherein B is Lys, Arg, Asp, or Glu; A is Ala; Z is Lys, Arg, Asp, or Glu; n is an integer from 1 to 50; p is an integer from 0 to 2; q is an integer from 1 to 50; r is an integer from 0 to 2; s is an integer from 1 to 5; and t is an integer from 1 to 50. In some embodiments, the structured domain includes $(A)_{25}$ (SEQ ID NO:6), $K(A)_{25}K$ (SEQ ID NO:7), $(KAAAA)_5K$ (SEQ ID NO:8), or $D(A)_{25}K$ (SEQ ID NO:9), or a combination thereof. In some embodiments, the POP includes alternating disordered domains and structured domains. In some embodiments, about 4% to about 75% of the POP includes structured domains. In some embodiments, the POP is soluble below a lower critical solution temperature (LCST). In some embodiments, the POP has a transition temperature of heating (Tt-heating) and a transition temperature of cooling (Tt-cooling). In some embodiments, the transition temperature of heating (Tt-heating) and transition temperature of cooling (Tt-cooling) are identical. In some embodiments, the transition temperature of heating (Tt-heating) is greater than the transition temperature of cooling (Tt-cooling). In some embodiments, the transition temperature of heating (Tt-heating) is concentration-dependent. In some embodiments, the transition temperature of cooling (Tt-cooling) is concentration-independent. In some embodiments, the Tt-heating is primarily determined by the disordered domains, and wherein the Tt-cooling is primarily determined by the structured domains. In some embodiments, the POP forms an aggregate above the Tt-heating. In some embodiments, the aggregate resolubilizes when cooled to below the Tt-cooling. In some embodiments, the aggregate is a stable three-dimensional matrix. In some embodiments, the aggregate is fractal-like. In some embodiments, the aggregate is porous with a void volume. In some embodiments, the void volume is tunable.

In a further aspect, the disclosure relates to a scaffold including a plurality of the polypeptide as detailed herein at a temperature greater than the transition temperature, such that the polypeptide forms an aggregate. Another aspect of the disclosure provides a cellular scaffold including the scaffold as detailed herein and a plurality of cells.

In a further aspect, the disclosure relates to a method for forming a cellular scaffold, the method including: mixing cells with a plurality of the polypeptide as detailed herein at a first temperature less than the transition temperature of the polypeptide, such that the polypeptide does not form an aggregate; and incubating the polypeptides at a second temperature suitable for cellular growth and greater than the transition temperature, such that the polypeptides form an aggregate with the cells encapsulated within, to form the cellular scaffold. In some embodiments, the method further includes implanting the cellular scaffold into a subject.

In a further aspect, the disclosure relates to a method for forming a cellular scaffold, the method including: mixing cells with a plurality of the polypeptide as detailed herein to form a mixture, at a first temperature less than the transition temperature of the polypeptide, such that the polypeptide does not form an aggregate; and injecting the mixture at the first temperature into a subject, wherein the subject is at a second temperature greater than the transition temperature, such that the polypeptides form an aggregate with the cells encapsulated within, to form the cellular scaffold in the subject.

In a further aspect, the disclosure relates to a method for forming a scaffold, the method including: injecting into a subject a plurality of the polypeptide as detailed herein at a first temperature less than the transition temperature of the polypeptide, such that the polypeptide does not form an aggregate prior to injection, wherein the subject is at a second temperature greater than the transition temperature, such that the polypeptides form an aggregate to form the scaffold in the subject.

In some embodiments, the cells within the scaffold (e.g., injected along with the scaffold) integrate into the surrounding cells or tissues of the subject. In some embodiments, the cells of the subject surrounding the scaffold integrate into the scaffold. In some embodiments, the scaffold modifies the surrounding cells or tissues of the subject. In some embodiments, the cells within the scaffold, the cells integrating into the scaffold, or the cells modified by the scaffold form new vasculature. In some embodiments, the methods further include reducing the temperature to the first temperature, such that the aggregate/scaffold solubilizes; and separating the cells from the solubilized scaffold. In some embodiments, the separating step includes centrifugation. In some embodiments, the cells comprise stem cells, bacterial cells, or human tissue cells. In some embodiments, the scaffold has low immunogenicity or low antigenicity. In some embodiments, the scaffold promotes at least one of cell growth, recruitment, and differentiation.

In a further aspect, the disclosure relates to a drug delivery composition including: a plurality of POPs as detailed herein, self-assembled into an aggregate above the Tt-heating; and an agent encapsulated within the aggregate. In some embodiments, the drug delivery composition modifies the surrounding cells or tissues of the subject. In some embodiments, the drug delivery composition (and agent therein) recruits dendritic cells.

In a further aspect, the disclosure relates to a method of delivering an agent to a subject, the method including: encapsulating the agent in an aggregate, the aggregate including a plurality of POPs as detailed herein; and administering the aggregate to the subject.

In a further aspect, the disclosure relates to a method of treating a disease in a subject in need thereof, the method including administering the drug delivery composition as detailed herein to the subject. In some embodiments, administering the drug delivery composition results in the formation of new vasculature, wound healing, or a combination thereof in the subject.

In a further aspect, the disclosure relates to a method of increasing the maximum tolerated dose of an agent, the method including: encapsulating the agent in an aggregate of POPs as detailed herein; and administering the agent-encapsulated aggregate to a subject.

In some embodiments, the agent includes a small molecule, a polynucleotide, a polypeptide, a carbohydrate, or a combination thereof.

The disclosure provides for other aspects and embodiments that will be apparent in light of the following detailed description and accompanying figures.

BRIEF DESCRIPTION OF THE DRAWINGS

(FIG. 1A) Recombinant POPs were constructed with 3 ELP components and 4 polyalanine helices at amino acid percentages up to 50%. Ultraviolet (UV)-Circular dichroism (CD) reveals definitive helical peaks at 222 and 208 nm, with peak amplitudes minimally altered by (FIG. 1B) polyalanine domain and (FIG. 1C) ELP but highly dependent on (FIG. 1D) total alanine content (dynode voltage >500 at <200 nm; data not used for analysis). (FIG. 1E) This structural signature is consistent with helix-coil predictions (Agadir). (FIG. 1F) $^{15}$N-HSQC and (FIG. 1G) H(N)CO (residue labels are the associated C' of the previous residue) 2D solution NMR spectra for E1-H2-25% were used to more precisely quantify total structural content. Each polyalanine domain was determined to have an average helicity of 90%.

(FIG. 2A) Hysteresis scales as a function of total helical content. (FIG. 2B-FIG. 2D) For a given E(X), the composition of the alanine domain modulates the $T_t$-heating and $T_t$-cooling with greater hydrophilicity leading to increased temperatures. Hysteresis is also dependent on the composition (charge distribution) of the polyalanine domains with an increase in charge producing a decrease in hysteresis. The $T_t$-cooling is concentration independent and solely determined by the polyalanine domains. (FIG. 2E) Therefore, for a given H(X), the $T_t$-heating can be independently controlled with ELP composition, providing a method to orthogonally control $T_t$-heating and $T_t$-cooling. (FIG. 2F) Polymers can be cyclically heated and cooled with no change in thermal behavior. Optical density measurements were taken at 350 nm in PBS at 50 µM unless otherwise indicated. Heating and cooling rates were kept at 1° C./min. OD amplitudes are non-interpretable due to difference in aggregate formation and settling.

FIG. 3A-FIG. 3D: Proposed mechanism for hysteresis. Simulations of the hysteretic cycle were performed using a coarse-grained model. Heating and cooling were achieved by modulating the interaction strengths between ELP domains. (FIG. 3A) Snapshots extracted from a phenomenological simulation of POPs shown in the middle, surrounded by cartoon representations of the four states observed for POP during heating and cooling. Rod-like objects represent alanine domains and string-like tethers represent ELPs. The colors indicate their initial cluster with shading indicating different proteins in the same initial cluster. The one-sided arrows provide a pictorial summary of the expected rates for transitions between different states (fast for 2-3 and slow for 4-1). Within entangled aggregates we observe two types of morphologies viz., entangled spheres or entangled cylinders. There is a reversible spheres to cylinders transition at even higher temperatures. (FIG. 3B) A simplified representation of experimental data is annotated by the species populating each regime. The ordinate is labeled as a measure of optical density consistent with experimental work. (FIG. 3C-FIG. 3D) Enlarged snapshots from the cooling arm of panel (FIG. 3A) demonstrate that the highlighted POP is not able to isolate itself into a single cluster and that the decrease in aggregate density is limited by the presence of domain swapped proteins.

FIG. 4A-FIG. 4D: Arrested phase separation into fractal networks. (FIG. 4A) E1-H5-25% (2 mM, PBS) aggregation during a heating and cooling cycle shows a reversible transition from an optically translucent liquid to an opaque solid-like structure (passes inversion test) with syneresis observed at higher temperatures. (FIG. 4B) At the microscale, E1 and E1-H5-25% (400 µM, PBS) form liquid-like coacervates and fractal networks, respectively; scale bar 50 µm. (FIG. 4C) The intricacy of the network is more clearly seen with a 20 µm thick 3D reconstruction of E1-H5-25% (200 µM, PBS); scale bar 50 µM. (FIG. 4D) Network architecture at the meso scale is that of interconnected "beads on a string", as revealed by SIM; scale bars 10 µm (left) and 1 µm (right).

(FIG. 5A) As determined by the limited fluorescence recovery 25 min after bleaching, 12.5% and 25% networks have a high kinetic stability and limited liquid-like properties; Inset pictures are shown for E1-H5-25% at 400 µM. (FIG. 5B and FIG. 5C) Void volumes can be tuned from 60-90% by altering polymer concentration. Scale bars are 50 µm.

FIG. 6A-FIG. 6J: In vivo stability and tissue incorporation of POPs. (FIG. 6A) E1-H5-25% POP subcutaneous (s.c.) injections were significantly more stable than their E1 counterparts with just 5% of the injected dose degraded at 120 hrs; 200 µL 250 µM injections; p<0.05 for all data points after 0 hr. (FIG. 6B) Whereas ELPs diffuse into the s.c. space, POP depots were externally apparent, retaining the shape and volume of the initial injection up to dissection and ex vivo analysis. (FIG. 6C) Representative CT-SPECT images of the depots confirm increased diffusivity of ELPs and increased stability of POPs. (FIG. 6D) POPs were injected into BL/6 mice and explanted for analysis over 21 days. Representative images are shown with arrows pointing at externally evident vascularization of the biomaterial. (FIG. 6E) POPs rapidly integrated into the subcutaneous environment with sufficient strength to endure moderate extension less than 24 hours after injection. (FIG. 6F) There is a high initial cell incorporation with some change over the observed time periods; for *, p<0.05. (FIG. 6G and FIG. 6H) Flow cytometry for cells involved in the innate immune reveals subsequent spikes in neutrophils, inflammatory monocytes, and macrophages, with a loss in all hematopoietic cells (CD45+) by day 21; for *, p<0.05. (FIG. 6I) The loss in inflammation corresponds with an increase in vascularization, quantified by number of visible capillaries in histological sections (n=3 separate injections, with * p<0.05). (FIG. 6J) An example tissue slice 10 days post injection shows an area of particularly high vascularization density.

FIG. 7A-FIG. 7C: Purity of POPs. (FIG. 7A) All POPs, listed in (FIG. 7B), were purified to >95% as determined by SDS-PAGE gels. (FIG. 7C) The molecular weight (MW) of E1-H5-25% was confirmed by Matrix Assisted Laser Desorption/Ionization (MALDI) and is within 1.5% of the predicted MW. Small bands observed in the sodium dodecyl sulfate polyacrylamide gel electrophoresis (SDS-PAGE) are also confirmed to be truncation products of the longer polymer, likely the result of ribosomal pausing. The presence of small amounts of truncation product did not have discernable effects on the properties of POPs.

(FIG. 8A) 12.5% polymers show indicative peaks at 208 and 222 nm, with all polyalanine domains showing similar peak amplitudes at 222 nm. (FIG. 8B) Peak amplitudes scale appropriately with the inclusion of helical domains for E1-H1 polymers. (FIG. 8C) E1-H3-25%, which does not transition at low temperatures, shows the preservation of helical signature peaks at high temperatures with some loss in peak amplitudes. (Data not used for analysis when dynode voltage >500 V at <200 nm for all).

(FIG. 10A) 12.5% POPs also show variability in hysteresis due to helix composition as well as (FIG. 10B) concentration independence and a tunable $T_t$-heating. (FIG. 10C) $T_t$-heating can be tuned by changing molecular weight without changing the total percentage of helicity, though $T_t$-cooling remains unaltered. (FIG. 10D) Attachment of Alexa Fluor 488 to the lysines on POPs does not significantly alter their phase behavior. Raw optical density measurements for (FIG. 10E) E1-H(X)-12.5% polymers, (FIG. 10F) E1-H(X)-25% polymers and (FIG. 10G) E1-H5-25% of different molecular weights illustrate their sharp phase behavior and varying degrees of hysteresis. Optical density measurements were taken in PBS. Heating and cooling rates were kept at 1° C./min. OD amplitudes are non-interpretable due to difference in aggregate formation, settling, and detector saturation.

(FIG. 11C) Despite their hysteretic nature, polymers are capable of fully recovering from heating and cooling cycles. Ten cycles show no change in transition temperatures. (FIG. 11D) E1-H5-25% (50 µM, PBS) shows no recovery for 24 hours when heated and cooled to the hysteretic range above the $T_r$-cooling. Subsequent cooling after 24 hours shows rapid dissolution.

(FIG. 12A and FIG. 12B) E1-H1-25% shows a spectral shift consistent with distortions for helical peptides at the expected transition temperature. This polymer also shows an isodichroic point at 225 nm for both 12.5 and 25%. 10 μM, water, 1 mm path length for all experiments. Dynode voltage <500 for all.

Figure 13A:
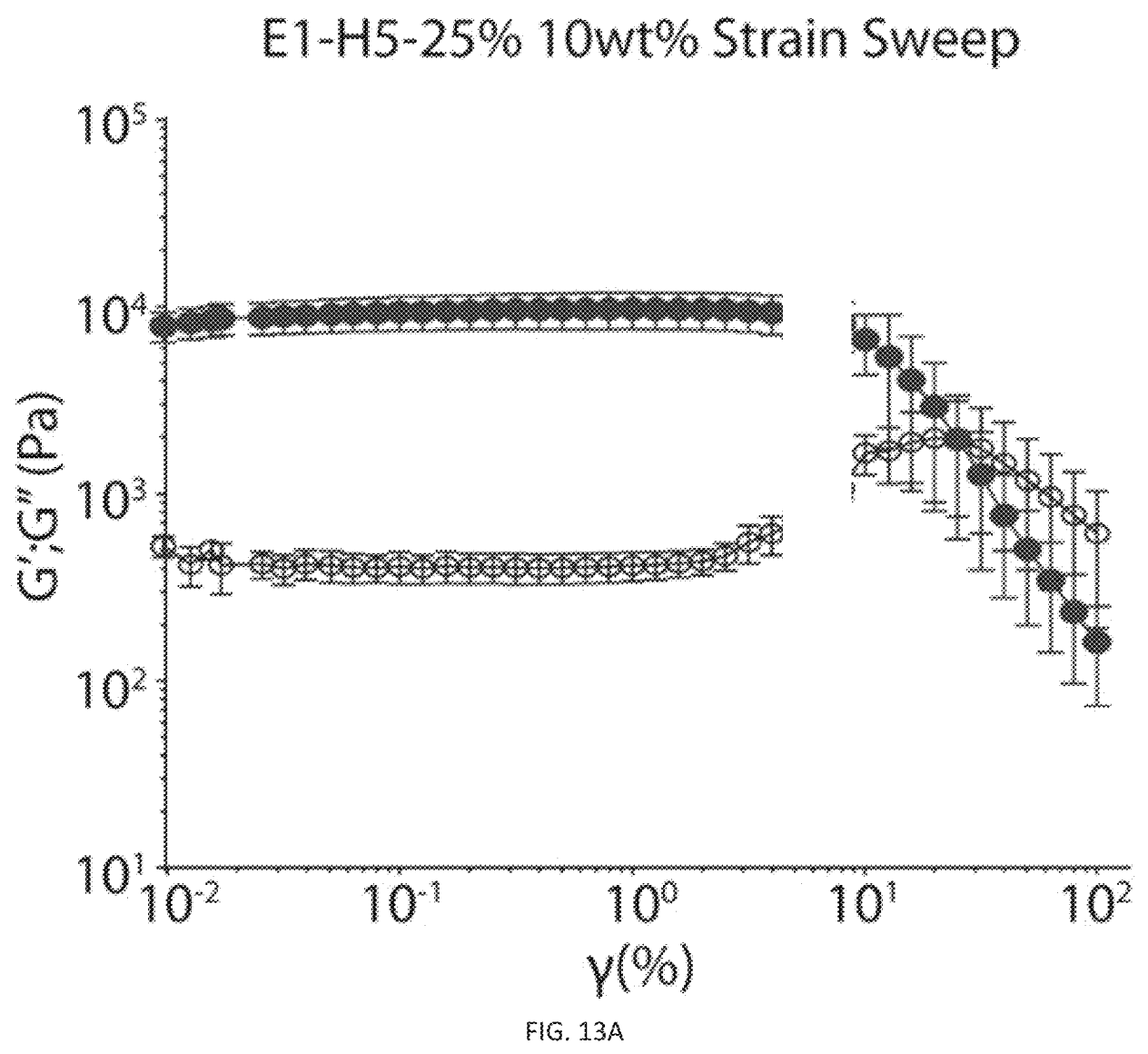

FIG. 13A-FIG. 13E: Rheology. (FIG. 13A) A strain sweep from 0.01 to 100% reveals the linear viscoelastic region (LVER) of POPs. (FIG. 13B) Frequency sweeps within the LVER (1% strain) reveal solid-like material properties for POPs which scale non-linearly with concentration. (FIG. 13C) ELPs show more liquid-like behavior (G">G') and decrease mechanical integrity compared to POPs. (FIG. 13D) POPs exhibit plastic, frequency dependent viscosity whereas ELPs behave as Newtonian fluids. (FIG. 13E) Temperature sweeps of E1-H5-25% show an increase in elastic moduli as the polymer aggregates. The G' plateau and drop-off after transition is likely due to aggregate shrinking and loss of contact with the plates. The change in normal force ($F_N$) (inset) reflects this loss of contact. All experiments in PBS after 30 min equilibration at 37° C.

(FIG. 14A) Single plane confocal images of E1-H5-25% in PBS were analyzed using a box counting algorithm in FracLac for ImageJ (FIG. 14B). The fractal dimension was determined graphically (FIG. 14C). Images for E1-H5-12.5% and 25% (n=3) revealed fractal dimensions ranging from 1.6 to 1.9 and varying with concentration.

(FIG. 15A) E1-H5-25% at 100 μM; (FIG. 15B) E1-H5-12.5% at 100 μM; and (FIG. 15C) E1-H5-25% at 500 μM.

(FIG. 16A) Body weight measures for all mice used are given along with the (FIG. 16B) dose of $^{125}$I for each group. Dosages were used for data normalization and differences in doses on reflect an increase in bound iodine for POPs which is not expected to be experimentally relevant. (FIG. 16C) Radiation measured for organs after 120 hrs reveals some small distribution differences for POPs and ELPs, but none expected to be harmful.

(FIG. 17A) SPECT-CT images are shown for three mice imaged for SPECT analysis following s.c. injection of ELP in their right hind flank. (FIG. 17B) SPECT-CT images are shown for three mice imaged for SPECT analysis following s.c. injection of POP in their right hind flank. Analysis of ELP vs POP following injection, (FIG. 17C) volume; (FIG. 17D) surface to volume ratio; (FIG. 17E) surface area; and (FIG. 17F): activity density.

(FIG. 18A) Mice did not significantly change body weight across time points (day 1 and 3 not collected). POP (E1-H5-25%-120) and Matrigel depots are shown (FIG. 18B) pre- and (FIG. 18C) post-excision from the subcutaneous right flank. Scale bars=5 mm.

(FIG. 19A) Gates for removing cell debris and isolating singlets and live cells are shown. (FIG. 19B-FIG. 19G) Flow cytometry gating procedures to isolate all cell types are shown with examples from each time point for 250 μM POP samples. Cell subtypes are described in more detail in the Examples.

(FIG. 21A) There was not significant change in the 250 μM POP (E1-H5-25%-120) subcutaneous injection sizes across all time points, though (FIG. 21B) total live cells did increase. (FIG. 21C) CD45+ subtypes for 250 μM POP show an initial spike in neutrophils, followed by monocytes and finally macrophages. (FIG. 21D) Epithelial cells and endothelial cells show little to no trend. (FIG. 21E) At day 5, the 250 μM and 750 μM POP groups were almost identical, with some slight change in the CD45+/− populations. * for p<0.05 for all plots. Isolated * notes significance to all other groups.

(FIG. 22A) Histological slices for explanted E1-H5-25%-120 injections were collected from the center of the depots and stained with Hematoxylin and Eosin (H&E). (FIG. 22B) Representative slices for days 1-5 show cells present in the depots from day 1 with a visible increase in density over time. Cells primarily migrate from surrounding tissue (also note in FIG. 22C), but some denser internal regions can also be seen by day 5. (FIG. 22C) H&E stained slices from day 10 and day 21 show a continued increase in cell density and the emergence of vasculature. Colored dots (and arrows) on the slices indicate the presence of blood vessels or capillaries. At day 10, the vasculature is denser around the edges, near surrounding tissue, but it becomes more uniformly distributed by day 21. Of note, chronic inflammatory markers such as foreign body giant cells and the formation of thick fibrin capsules were not observed in any of the stained sections.

Figure 23D:
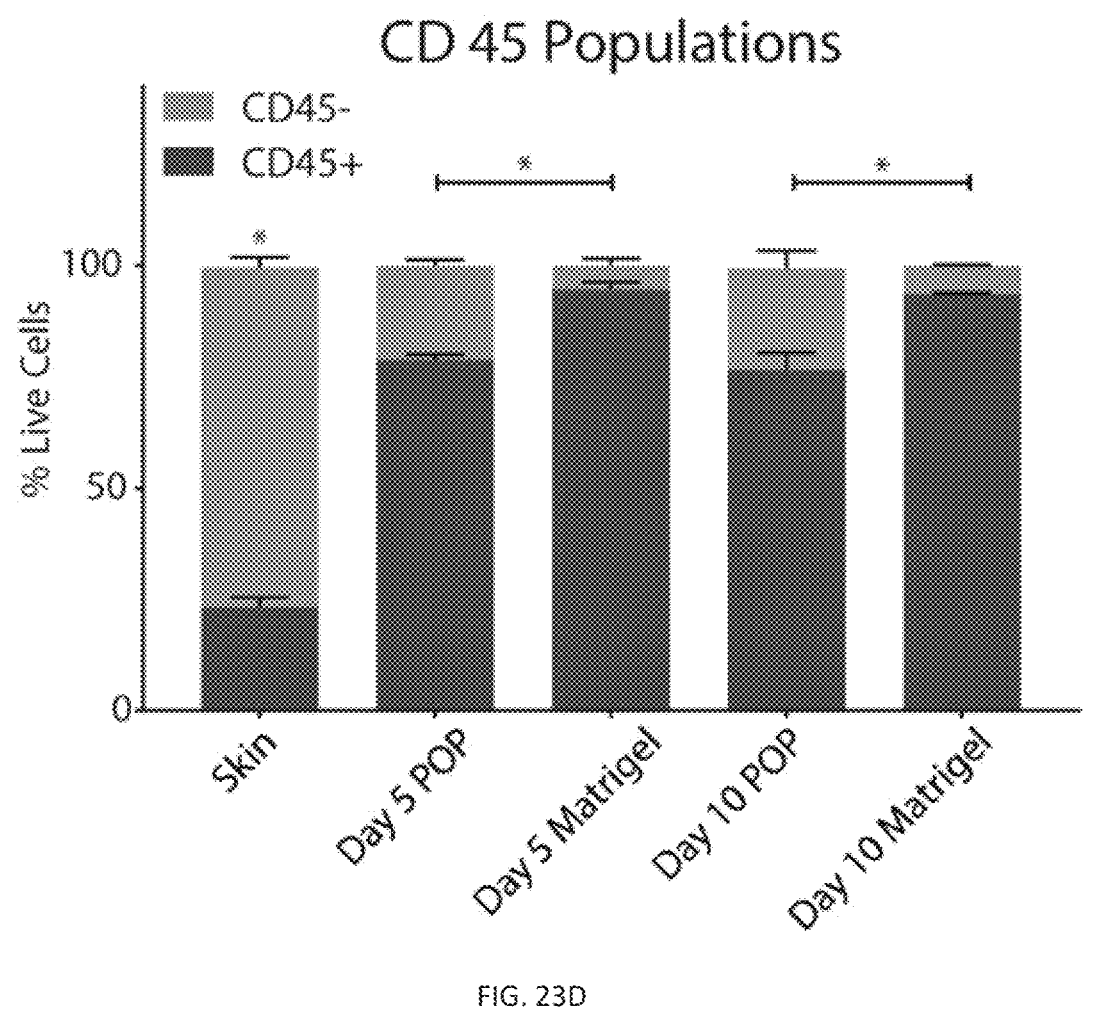

FIG. 23A-FIG. 23F: Comparison to Matrigel. (FIG. 23A) POPs recruit significantly more cells at day 5 and day 10. (FIG. 23B) An H&E stained Matrigel sample at Day 10 shows minimal cell recruitment and no vascularization. (FIG. 23C) POP shows significantly increase vascularization at day 10 (n=3). (FIG. 23D) POPs recruit more non-hematopoietic cells, (FIG. 23E) more neutrophils, fewer macrophages, and (FIG. 23F) more endothelial cells than Matrigel. * for p<0.05 for all plots.

FIG. 24A-FIG. 24G: Ultraviolet (UV) Crosslinkable POPs. (FIG. 24A) Through inclusion of the unnatural amino acid para-azidophenylalanine (pAzF), POPs can be made reactive in the presence of UV light. (FIG. 24B) The polymers tolerate the inclusion, retaining their thermal reversibility and hysteresis. (FIG. 24C) pAzF form nitrine groups under UV exposure capable of interacting non-specifically with protein chains. (FIG. 24D) As demonstrated by an SDS-page gel of the supernatant after reaction and centrifugation at 4° C., the reaction is rapid, with only 10 seconds of UV exposure required to fully remove all soluble components. (FIG. 24E) Fluorescent SDS-PAGE gel of POP made with and without the inclusion of pAzF in the production media. Az-POP contains pAzF residues that react with DBCO-Cy5, while the negative control is not fluorescently labeled via click chemistry. (FIG. 24F & FIG. 24G) Az-POP networks appear identical to POP networks without an Az component, and are not significantly different in void volume. Changes in concentration still allow tuning the void volume, as with non-Az-POPs.

(FIG. 25A) Increasing polymer molecular weight or (FIG. 25B) the total polymer helicity increases mechanical stiffness. (FIG. 25C) Helix composition has a significant effect on G', whereas the effect of (FIG. 25D) changing ELP composition is not as dramatic. (FIG. 25E) POP physical crosslinking can be combined with covalent, chemical crosslinking. The addition of a chemical crosslinker increases the elastic moduli. Using an ELP with equal and equivalently spaced lysines, we also show that chemical crosslinking increases ELP stability, though not to the same degree as POPs. (FIG. 25F) Matrigel also behaves as a solid, but soft gel. (FIG. 25G) The G' at 1% strain and 1 Hz were compared to E1-H5-25%, and all polymers showed statistically (p<0.05) different mechanical properties except the change in ELP composition. All polymers were tested at 5 wt % in PBS with 30 min equilibrations at 37° C. prior to oscillations.

(FIG. 28A) Similar porosities were observed for all tested polymer compositions (200 μM, PBS), though the inclusion of a chemical cross-linker did have a slight, significant effect (p<0.05 compared to E1-H5-25% control). (FIG. 28B) Representative z-stacks (20 μm thick) are shown for each tested composition. Scale bars=20 μm.

DETAILED DESCRIPTION

Figure 1A:
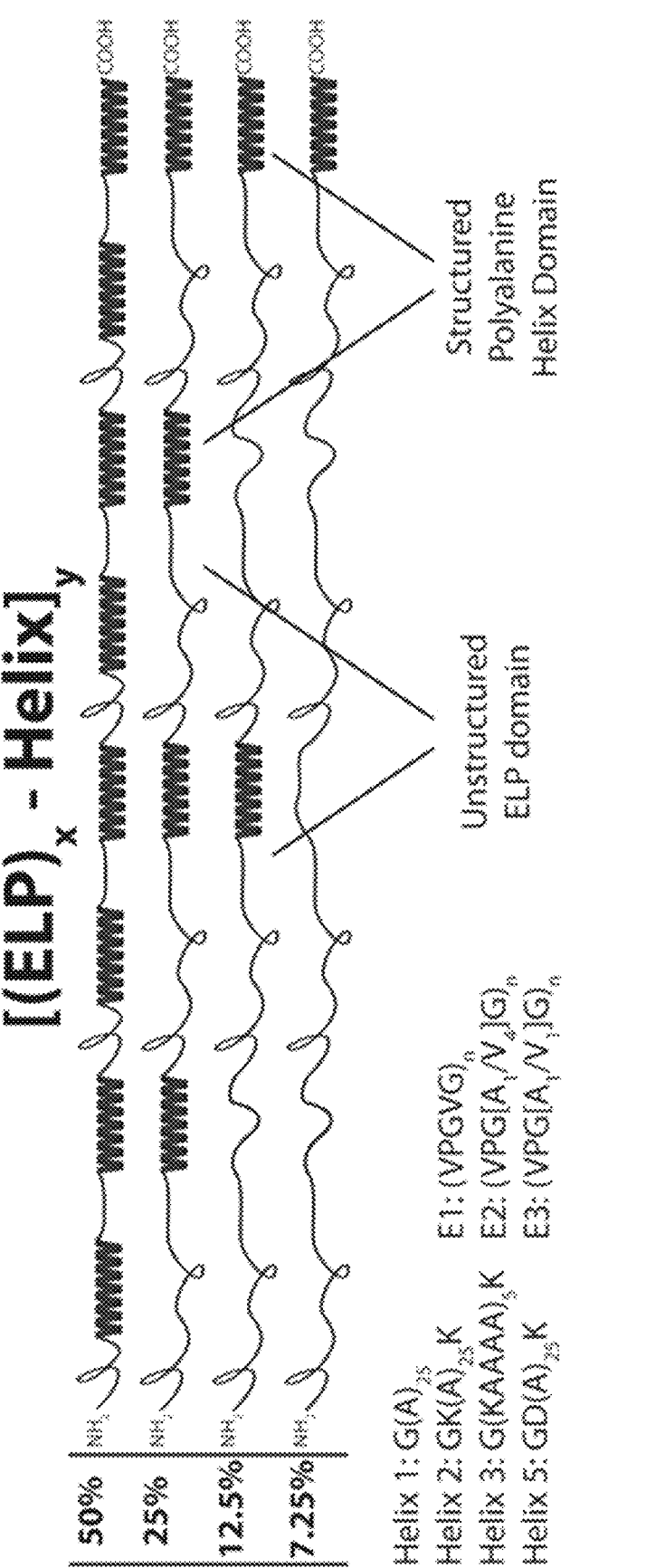
FIG. 1A-FIG. 1G: Partially ordered polymer library and structural characterization.
Figure 1B:
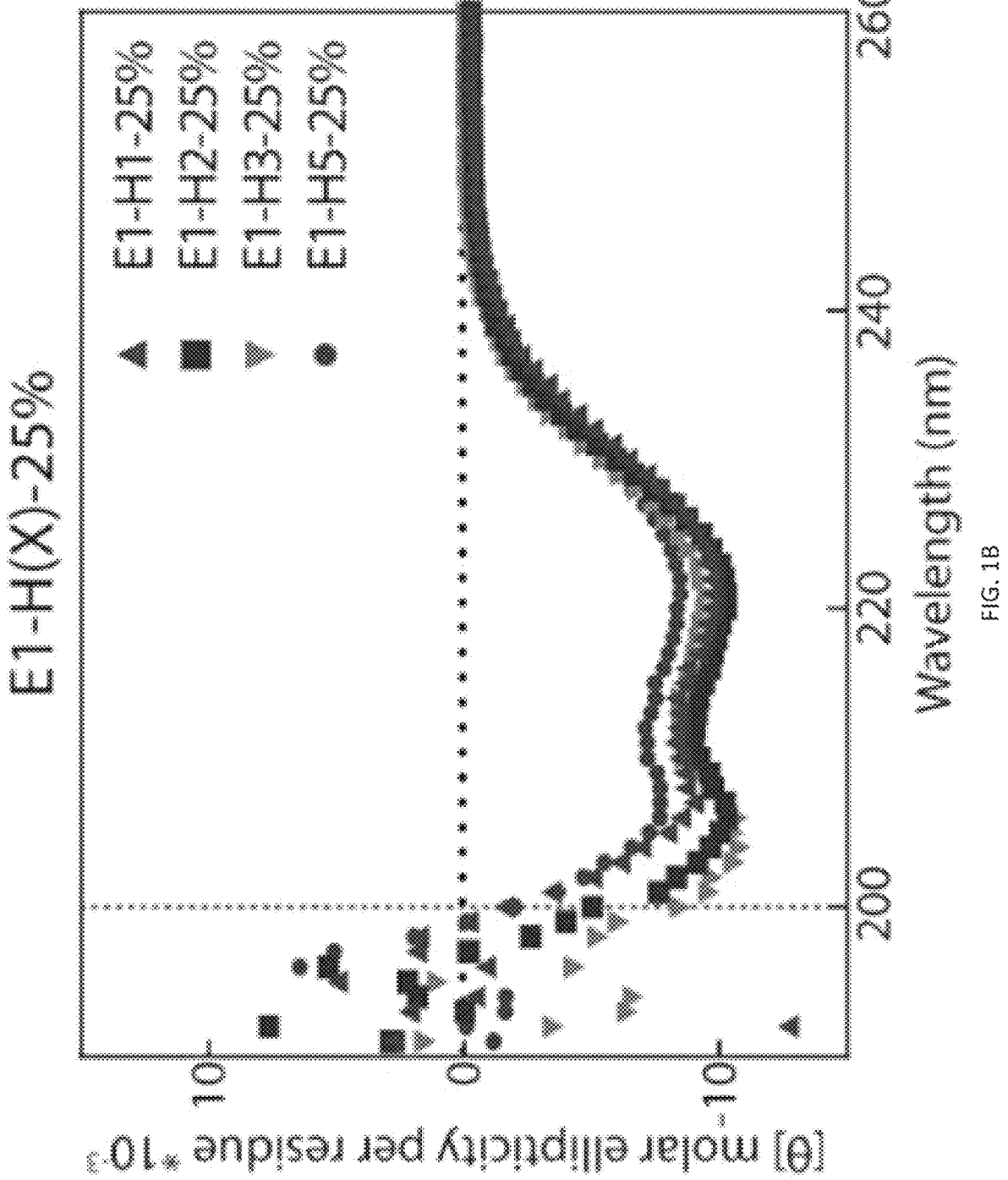
Figure 1C:
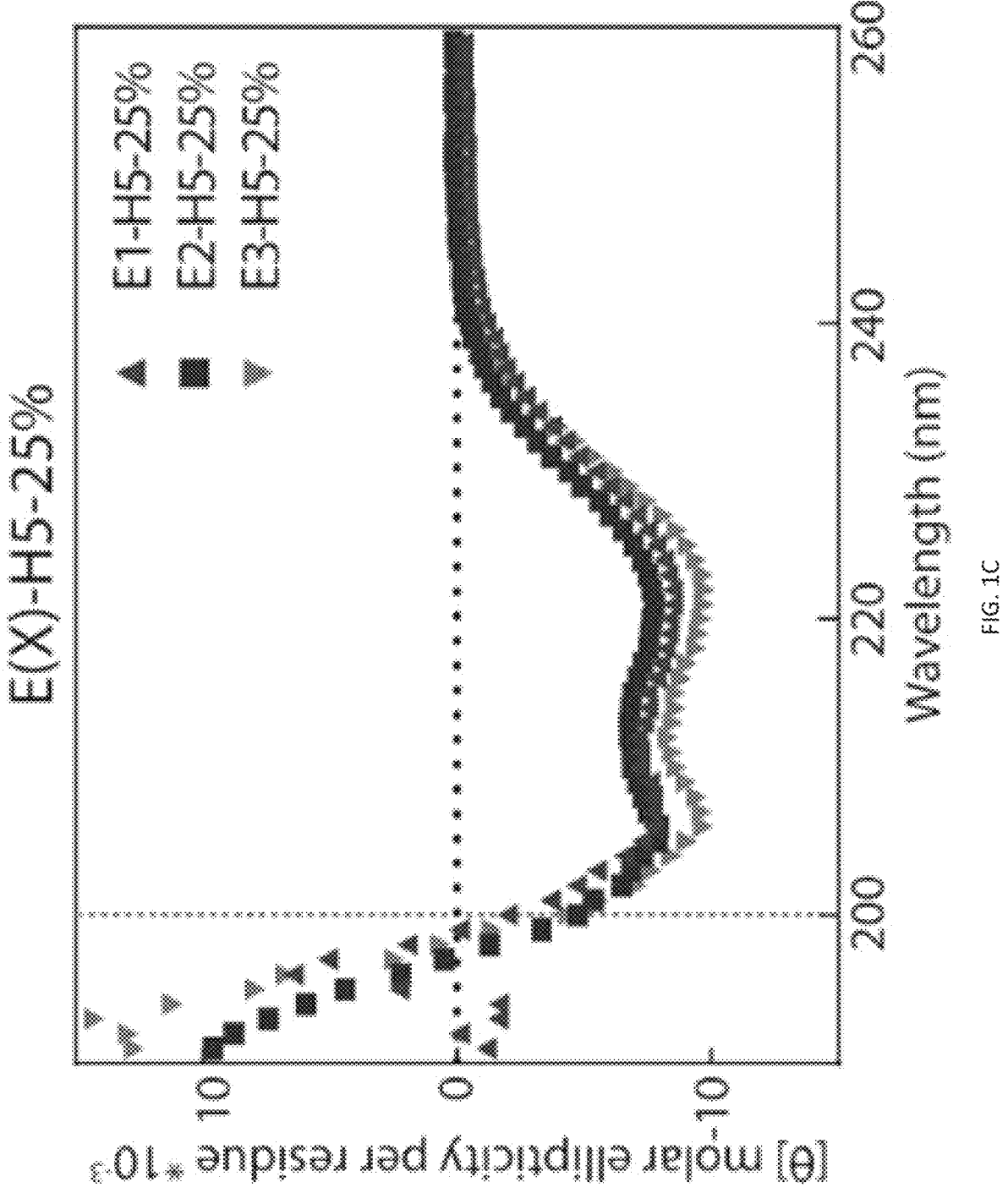
Figure 1D:
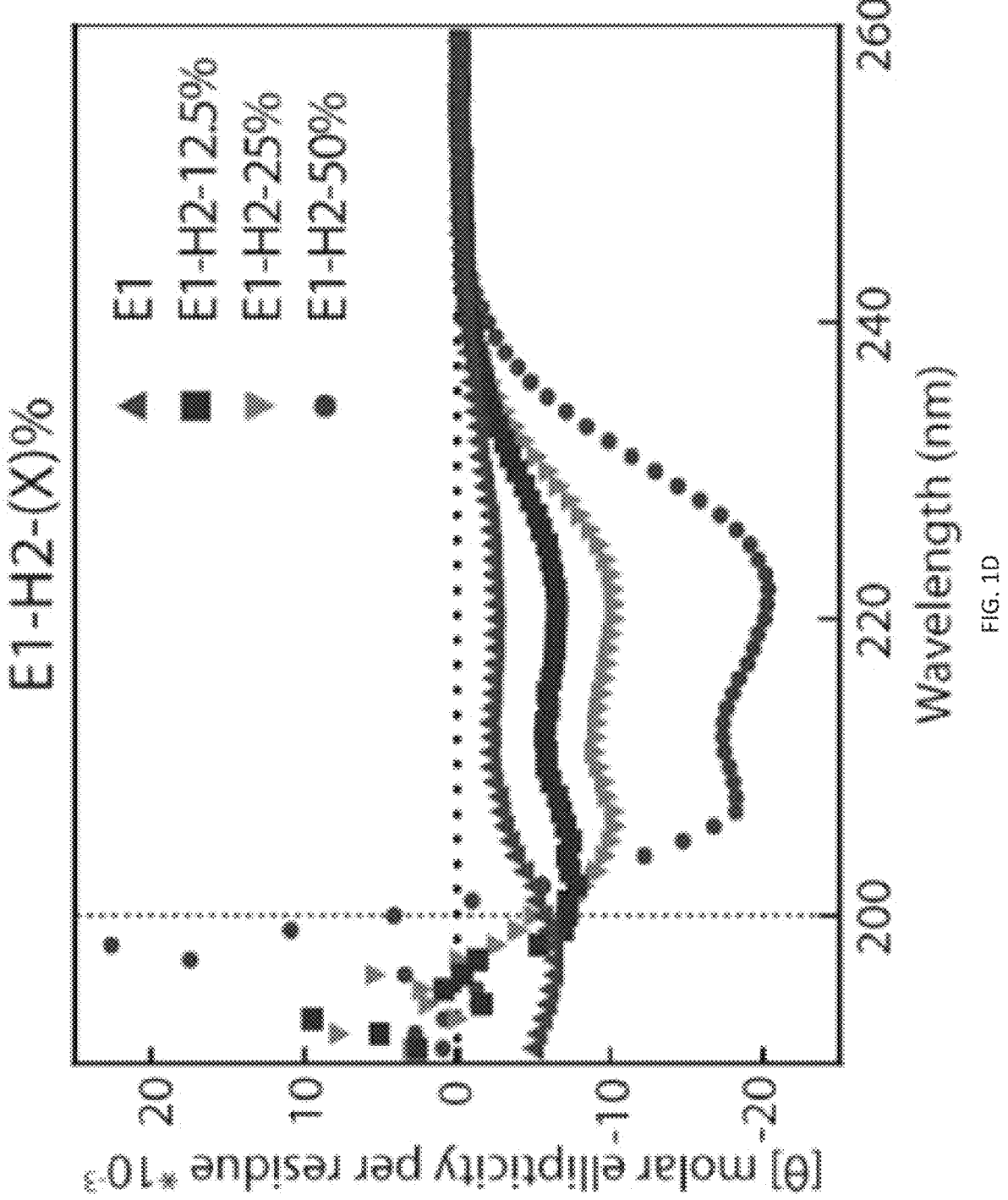

Described herein are partially ordered polypeptides (POPs). The polypeptides have phase transition behavior, and may be used to form aggregates with a variety of uses such as scaffolds for cell growth. The polypeptides include a combination of structured domains and disordered domains. The ratio and length of the structured and disordered domains may be varied, which may be used to tune the temperature at which the polypeptides change phase(s).

Many natural biomaterials derive their meso and microscale properties from the nanoscale interactions of ordered domains and disordered regions. To mimic this multiscale synergy, we designed a set of partially ordered polypeptides (POPs) in which we precisely tune nanoscale order and disorder through design of amino acid sequences. The stimuli-responsiveness of the disordered components including an elastin-like polypeptide (ELP), and the structural stability of the ordered domains including polyalanine helices, combine to produce materials with emergent properties that are not realized in materials that include each sequence block alone. The resultant materials are thermally-responsive, fractal protein networks with tunable thermal stability. We have further explored the mechanisms driving these interactions using molecular dynamics simulations and have demonstrated their ability to support cell penetration and growth in vivo.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Antigen" refers to a molecule capable of being bound by an antibody or a T cell receptor. The term "antigen", as used herein, also encompasses T-cell epitopes. An antigen is additionally capable of being recognized by the immune system and/or being capable of inducing a humoral immune response and/or cellular immune response leading to the activation of B-lymphocytes and/or T-lymphocytes. In some embodiments, the antigen contains or is linked to a Th cell epitope. An antigen can have one or more epitopes (B-epitopes and T-epitopes). Antigens may include polypeptides, polynucleotides, carbohydrates, lipids, small molecules, and combinations thereof. Antigens may also be mixtures of several individual antigens. "Antigenicity" refers to the ability of an antigen to specifically bind to a T cell receptor or antibody and includes the reactivity of an antigen toward pre-existing antibodies in a subject. "Immunogenicity" refers to the ability of any antigen to induce an immune response and includes the intrinsic ability of an antigen to generate antibodies in a subject. As used herein, the terms "antigenicity" and "immunogenicity" are different and not interchangeable.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for a protein activity may be defined in accordance with standard practice. A control may be an agent or cell without a POP. A control may be a molecule, or sample comprising a molecule, with a polypeptide or polymer, that is different from a POP as detailed herein, conjugated thereto or encapsulated within. A control may be a subject, or a sample therefrom, whose disease state is known. The subject, or sample therefrom, may be healthy, diseased, diseased prior to treatment, diseased during treatment, or diseased after treatment, or a combination thereof. The control may include, for example, an agent or cell alone or by itself.

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli.*

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target is to be detected or determined or any sample comprising an agent, cell, or POP as described herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described conjugates. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. PARTIALLY ORDERED POLYPEPTIDE (POP)

Described herein are partially ordered polypeptides (POPs). Each POP may include a plurality of disordered domains, and a plurality of structured domains. The POP may exhibit phase transition behavior by changing solubility and aggregate dissolution/formation with temperature.

The disordered domains and the structured domains of the POP can be arranged in any number of possible ways. In some embodiments, one or more disordered domains are positioned between at least two adjacent structured domains of the POP. In some embodiments, the POP includes a plurality of structured domains repeated in tandem and a plurality of disordered domains repeated in tandem. In some embodiments, the plurality of structured domains repeated in tandem are positioned C-terminal to the plurality of disordered domains repeated in tandem. In some embodiments, the plurality of structured domains repeated in tandem are positioned N-terminal to the plurality of disordered domains repeated in tandem. In some embodiments, the POP is arranged as [disordered domain]$_q$-[structured domain]$_r$-[disordered domain]$_s$-[structured domain]$_t$, wherein q, r, s, and t are independently an integer from 0 to 100, such as from 1 to 100, from 2 to 100, from 1 to 50 or from 2 to 50. In some embodiments, the POP is arranged as [disordered domain]$_q$-[structured domain]$_r$, wherein q and r are independently an integer from 1 to 100. In some embodiments, q, r, s, and t are independently an integer from 0 to 10, from 0 to 20, from 0 to 30, from 0 to 40, from 0 to 50, from 0 to 60, from 0 to 70, from 0 to 80, from 0 to 90, from 0 to 100, from 1 to 10, from 1 to 20, from 1 to 30, from 1 to 40, from 1 to 150, from 1 to 60, from 1 to 70, from 1 to 80, from 1 to 90 or from 1 to 100.

a. Disordered Domain

The POP may include a plurality of disordered domains. The disordered domain may comprise any polypeptide that has minimal or no secondary structure as observed by CD, and have phase transition behavior. The disordered domain may include an amino acid sequence of repeated amino acids, non-repeated amino acids, or a combination thereof.

In some embodiments, about 20% to about 99%, such as about 25% to about 97%, about 35% to about 95% or about 50% to about 94% of the POP comprises disordered domains. At least about 2%, 3%, 4%, 5%, 10%, 15%, 20%, 25%, 30%, 35%, 40%, 45%, 50%, 55%, 60%, 65%, 70%, 75%, 80%, 85%, 90%, or 95% of the POP may comprise disordered domains.

In some embodiments, the disordered domain comprises an amino acid sequence of [VPGXG]$_m$ (SEQ ID NO:1), wherein X is any amino acid and m is an integer greater than or equal to 1. In some embodiments, m is an integer from 1 to 500. In some embodiments, m is at least, at most, or exactly 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195,200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m may be less than 500, less than 400, less than 300, less than 200, or less than 100. In some embodiments, m is from 1 to 500, from 1 to 400, from 1 to 300, from 1 to 200, or from 60 to 180. In some embodiments, m is 60, 120, or 180. In some embodiments, X is any amino acid except proline. In some embodiments, X is Val, or Ala, or a mixture of Ala and Val. In some embodiments, X is Val. In some embodiments, X is Ala. In some embodiments, X is a mixture of Ala and Val. In some embodiments, X is a mixture of Ala and Val in a ratio of 1:1, 1:2, 1:3, 1:4, 1:5, 1:6, 1:7, 1:8, 1:9, 1:10, 2:1, 3:1, 4:1, 5:1, 6:1, 7:1, 8:1, 9:1, or 10:1. In some embodiments, X is a mixture of Ala and Val in a ratio of 1:1 or 1:4. In some embodiments, X is a mixture of Ala and Val in a ratio from 10:1 to 1:10 (Ala:Val), such as from 5:1 to 1:5 or from 1:1 to 1:4.

In some embodiments, the disordered domain comprises a PG motif. The PG motif may include an amino acid sequence selected from PG, P(X)$_n$G (SEQ ID NO:2), and (B)$_m$P(X)$_n$G(Z)$_p$ (SEQ ID NO:3), or a combination thereof, wherein m, n, and p are independently an integer from 1 to 15, and wherein U, X, and Z are independently any amino acid. In some embodiments, m, n, and p are independently an integer less than 2, 3, 4, 5, 6, 7, 8, 9, 10, 11, 12, 13, 14, or 15. In some embodiments, m, n, and p are independently an integer greater than or equal to 1, 2, 3, 4, 5, 6, 7, 8, 9, 10, 11, 12, 13, 14, or 15. P(X)$_n$G (SEQ ID NO:2) may include PXG, PXXG (SEQ ID NO:10), PXXXG (SEQ ID NO:11), PXXXXG (SEQ ID NO:12), PXXXXXG (SEQ ID NO:13), PXXXXXXG (SEQ ID NO:14), PXXXXXXXG (SEQ ID NO:15), PXXXXXXXXG (SEQ ID NO:16), PXXXXXXXXXG (SEQ ID NO:17), PXXXXXXXXXXG (SEQ ID NO:18), PXXXXXXXXXXXG (SEQ ID NO:19), PXXXXXXXXXXXXG (SEQ ID NO:20), PXXXXXXXXXXXXXG (SEQ ID NO:21), PXXXXXXXXXXXXXXG (SEQ ID NO:22), or PXXXXXXXXXXXXXXXG (SEQ ID NO:23), or a combination thereof. The disordered domain may further include additional amino acids at the C-terminal and/or N-terminal end of the PG motif. These amino acids surrounding the PG motif may also be part of the overall repeated motif. The amino acids that surround the PG motif may balance the overall hydrophobicity and/or charge so as to control the phase transition behavior of the disordered domain.

In some embodiments, the disordered domain comprises a non-repetitive polypeptide. The non-repetitive polypeptide may include a sequence of at least 60 amino acids, wherein at least about 10% of the amino acids are proline (P), and wherein at least about 20% of the amino acids are glycine (G). The non-repetitive polypeptide may include a sequence of at least 60 amino acids, wherein at least about 40% of the amino acids are selected from the group consisting of valine (V), alanine (A), leucine (L), lysine (K), threonine (T), isoleucine (I), tyrosine (Y), serine (S), and phenylalanine (F). The non-repetitive polypeptide may include a sequence of at least 60 amino acids, wherein the sequence does not contain three contiguous identical amino acids, wherein any 5-10 amino acid subsequence does not occur more than once in the non-repetitive polypeptide, and wherein when the non-repetitive polypeptide comprises a subsequence starting and ending with proline (P), the subsequence further comprises at least one glycine (G). The non-repetitive polypeptide may include less than about 50, 100, 200, 300, or 400 amino acids. The non-repetitive polypeptide may include at least about 50, 60, 70, 80, 90, or 100 amino acids.

b. Structured Domain

The POP may include a plurality of structured domains. The structured domain may have a secondary structure as observed by CD, such as, for example, an alpha helix. The structured domain may comprise at least one of a polyproline domain and a polyalanine domain. In some embodiments, the POP comprises alternating disordered domains and structured domains. In some embodiments, the structured domain comprises only polyalanine domains. In some embodiments, the structured domain comprises only polyproline domains.

In some embodiments, about 4% to about 75%, such as about 5% to about 70%, about 6% to about 60% or about 7% to about 50% of the POP comprises structured domains. At least about 2%, 3%, 4%, 5%, 10%, 15%, 20%, 25%, 30%, 35%, 40%, 45%, 50%, 55%, 60%, 65%, 70%, 75%, 80%, 85%, 90%, or 95% of the POP may comprise structured domains.

i) Polyalanine

In some embodiments, the structured domain comprises a polyalanine domain. Each polyalanine domain may include at least 5 alanine residues. Each polyalanine domain may have at least about 50% of the amino acids in an alpha-helical conformation. In some embodiments, the polyalanine domain comprises an amino acid sequence of [B$_p$(A)$_q$Z$_r$]$_n$ (SEQ ID NO:4) or [(BA$_s$)$_t$Z$_r$]$_n$ (SEQ ID NO:5), or a combination thereof, wherein B is Lys, Arg, Asp, or Glu; A is Ala; Z is Lys, Arg, Asp, or Glu; n is an integer from 1 to 50; p is an integer from 0 to 2; q is an integer from 1 to 50; r is an integer from 0 to 2; s is an integer from 1 to 5; and t is an integer from 1 to 50. In some embodiments, the structured domain comprises (A)$_{25}$ (SEQ ID NO:6), K(A)$_{25}$K (SEQ ID NO:7), (KAAAA)$_5$K (SEQ ID NO:8), or D(A)$_{25}$K (SEQ ID NO:9), or a combination thereof.

ii) Polyproline

In some embodiments, the structured domain comprises a polyproline domain. Each polyproline domain may include at least 5 proline resides. Each polyproline domain may have at least about 50% of the amino acids in a Polyproline Helix I (PPI) polyproline helical conformation or a Polyproline Helix II (PPII) polyproline helical conformation, or a combination thereof. PPI includes a helical conformation with backbone dihedral angles of roughly [−75,160] and having cis isomers of the peptide bonds. PPII includes a helical conformation with backbone dihedral angles of roughly [−75,150] and having trans isomers of the peptide bonds. At least about 50%, 55%, 60%, 65%, 70%, 75%, 80%, 85%, 90%, or 95% of the amino acids in each polyproline domain may be in a helical conformation. In some embodiments, about 50% to about 95% of the amino acids in each polyproline domain are in helical conformation.

c. UV Crosslinkable Amino Acid Derivative

The POP may also include amino acid derivatives that are not naturally occurring, such as a UV crosslinkable amino acid derivative. The non-native amino acid derivative can be used to introduce covalent crosslinks between different POPs and within the same POP. For example, POPs that include the UV crosslinkable amino acid derivative can be exposed to UV light, which can result in covalent crosslinks being formed between the amino acid derivative and a side chain of an amino acid of another POP or with a side chain of an amino acid of the same POP (having the amino acid derivative). The UV crosslinkable amino acid derivative may be any amino acid that has been functionalized with an azide group. In some embodiments, the amino acid derivative is para-azidophenylalanine.

The UV crosslinkable amino acid derivative may be included at varying amounts without affecting the POP's ability to transition at different temperatures. For example, the UV crosslinkable amino acid derivative may be included within the POP from about 0.1% to about 20% (of the POP), such as from about 0.5% to about 15% or from about 1% to about 10% (of the POP).

d. Transition Behavior

The POP may demonstrate phase transition behavior by changing solubility and aggregate formation with temperature. The phase transition behavior of the POP may derive from the phase transition behavior of the disordered domains of the POP. "Phase transition" or "transition" may refer to the aggregation of a polypeptide, which occurs sharply at a specific temperature. The phase transition may be reversible, although the specific temperature of dissolution may be the same or different from the specific temperature of aggregation.

In some embodiments, the POP is soluble below a lower critical solution temperature (LCST). LCST is the temperature below which the polypeptide is miscible.

A transition temperature (Tt) is a temperature at which the POP changes from one state to another. States may include, for example, soluble polypeptides, gels, and aggregates of varying sizes and dimensions. The POP may have a transition temperature of heating (Tt-heating) and a transition temperature of cooling (Tt-cooling). In some embodiments, the transition temperature heating (Tt-heating) is concentration-dependent. In some embodiments, the transition temperature cooling (Tt-cooling) is concentration-independent. The Tt-heating may be primarily determined by the disordered domains. The Tt-cooling may be primarily determined by the structured domains.

Below the transition temperature (LCST or Tt), the POP may be highly soluble. Upon heating above the transition temperature, the POP may hydrophobically collapse and aggregate, forming a separate phase.

The POP may phase transition at a variety of temperatures. The POP may have a transition temperature from about 0° C. to about 100° C., from about 10° C. to about 50° C., or from about 20° C. to about 42° C. The transition temperature of heating (Tt-heating) and transition temperature of cooling (Tt-cooling) may be identical. As used herein, temperatures may be "identical" when the temperatures are within 2.0° C., 1.0° C., 0.5° C., or 0.1° C. of each other. In some embodiments, the transition temperature of heating (Tt-heating) is greater than the transition temperature of cooling (Tt-cooling). In embodiments where the POP has a Tt-heating greater than the Tt-cooling, the difference between the two transition temperatures may be referred to as a hysteresis. In some embodiments, the POP has a hysteresis of about 5° C. to about 70° C., such as about 5° C. to about 60° C. or about 10° C. to about 50° C.

The phase transition behavior of the POP may be utilized in purification of the POP according to a method referred to as "inverse transition cycling," in which the POP's reversible phase transition behavior is used to cycle the solution through soluble and insoluble phases, thereby removing contaminants. Phase transition may also be triggered using kosmotropic salts, such as, for example, ammonium sulfate or sodium chloride. The kosmotropic salt may be added to a solution comprising the POP, with the kosmotropic salt being added until the POP forms aggregates or is precipitated out of solution. The aggregates may be pelleted by centrifugation and resuspended in a second solution or buffer. Aggregates of the POP may re-solubilize into solution once cooled below their Tt or when the kosmotropic salt is removed from the solution. In some embodiments, the POP is purified without any chromatographic purification. In some embodiments, the POP is generated recombinantly and purified from bacterial culture, such as, for example, from *E. coli*.

i) Aggregate

The POP may form an aggregate when the temperature is greater than the Tt-heating. The aggregate may resolubilize when cooled to below a temperature less than the Tt-cooling.

The aggregate formed by a plurality of POPs may have advantageous properties that can arise from the structure of the POPs. For example, the aggregate may have physical, non-covalent crosslinks. These physical, non-covalent crosslinks may arise from helical bundling of the structured domain(s) interacting with each other. The aggregate may also have covalent crosslinks (e.g., chemical crosslinks) in addition to physical, non-covalent crosslinks. Covalent crosslinks can be included in the aggregate in order to increase their mechanical stability without altering their porous architecture. In some embodiments, the aggregate can be formed from a plurality of POPs and can then be further stabilized by covalent crosslinking (after the formation of the aggregate). Covalent crosslinks can be introduced via a UV crosslinkable amino acid derivative having an azide functionality as described herein. Further examples of crosslinks that can be incorporated into the aggregate include, but are not limited to, small molecule crosslinks and cysteine disulfide bridges. An example of a chemical, small molecule crosslink is tetrakis(hydroxymethyl)phosphonium chloride (THPC), which can crosslink lysines within POPs.

In addition, the aggregate formed by a plurality of POPs may have solid-like properties that distinguish it from liquid-like coacervate structures. For example, the aggregate may have a storage modulus (G') that is greater than its loss modulus (G"), such as having a G' 2× greater, 5× greater, 10× greater, 15× greater, 20× greater, 25× greater, 30× greater, 35× greater, 50× greater or 100× greater than its G". In some embodiments, the aggregate has a G' from 2× greater to 100× greater than its G", such as from 10× greater to 50× greater or from 20× greater to 35× greater than its G".

The aggregate formed from a plurality of POPs may be a variety of sizes and dimensions. In some embodiments, the aggregate is a stable three-dimensional matrix. In some embodiments, the aggregate is fractal-like. In some embodiments, the aggregate is gel-like. In some embodiments, the aggregate is porous with a void volume, e.g., the non-protein rich phase of the aggregate. In some embodiments, the void volume is tunable. For example, the aggregate may have a void volume from about 60% to about 90% (of the volume of the aggregate). In addition, the aggregate may comprise pores having a diameter of about 1 μm to about 100 μm, such as about 1 μm to about 10 μm, about 3 μm to about 5 μm, about 25 μm to about 60 μm, about 30 μm to about 50 μm, or about 3 μm to about 50 μm.

3. POLYNUCLEOTIDES

Further provided are polynucleotides encoding the POPs detailed herein. A vector may include the polynucleotide encoding the POPs detailed herein. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further provided is a host cell transformed or transfected with an expression vector comprising a polynucleotide encoding a POP as detailed herein. Bacterial expression systems for expressing the protein are available in, e.g., *E. coli, Bacillus* sp., and *Salmonella* (Paiva et al., *Gene* 1983, 22, 229-235; Mosbach et al., *Nature* 1983, 302, 543-545). Kits for such expression systems are commercially available. Eukaryotic expression systems for mammalian cells, yeast, and insect cells are well known in the art and are also commercially available. Retroviral expression systems can be used in the present invention.

The POP may be expressed recombinantly in a host cell according to one of skill in the art. The POP may be purified by any means known to one of skill in the art. For example, the POP may be purified using chromatography, such as liquid chromatography, size exclusion chromatography, or affinity chromatography, or a combination thereof. In some embodiments, the POP is purified without chromatography. In some embodiments, the POP is purified using inverse transition cycling.

4. SCAFFOLD

Further provided herein is a scaffold comprising a plurality of POPs. The scaffold may be formed at a temperature greater than the transition temperature of the POP, such that the polypeptide forms an aggregate. The scaffold may be injectable.

Further provided herein is a cellular scaffold. A cellular scaffold includes the scaffold and a plurality of cells. The cells may include a variety of types. In some embodiments, the cells comprise stem cells, bacterial cells, or human tissue cells, or a combination thereof.

The scaffold may have low immunogenicity or low antigenicity or both. The scaffold may promote at least one of cell growth, cell recruitment, and cell differentiation, or a combination thereof. The scaffold, or cellular scaffold, may be suitable for cell transplantation, tissue regeneration, cell culture, and cell-based in vitro assays. In addition, the scaffold and/or cellular scaffold may promote the formation of vasculature, wound healing, or a combination thereof.

5. DRUG DELIVERY COMPOSITION

Further provided herein is a drug delivery composition. The drug delivery composition may include a plurality of POPs as detailed herein, self-assembled into an aggregate above the Tt-heating, and an agent encapsulated within the aggregate.

a. Agent

The agent may be a therapeutic. In some embodiments, the agent is selected from a small molecule, nucleotide, polynucleotide, protein, polypeptide, carbohydrate, lipid, and a combination thereof. In some embodiments, the agent comprises a small molecule. In some embodiments, the agent comprises a protein. In some embodiments, the agent comprises a cancer therapeutic. In some embodiments, the agent recruits cells, such as, for example, dendritic cells. In some embodiments, the drug delivery composition recruits dendritic cells.

6. ADMINISTRATION

The POPs as detailed above can be formulated into a composition in accordance with standard techniques well known to those skilled in the pharmaceutical art. Accordingly, a composition may comprise the POP or aggregate thereof. The composition may be prepared for administration to a subject. Such compositions comprising a POP can be administered in dosages and by techniques well known to those skilled in the medical arts taking into consideration such factors as the age, sex, weight, and condition of the particular subject, and the route of administration.

The POP, aggregate thereof, or composition thereof can be administered prophylactically or therapeutically. In prophylactic administration, the POP can be administered in an amount sufficient to induce a response. In therapeutic applications, the POPs are administered to a subject in need thereof in an amount sufficient to elicit a therapeutic effect. An amount adequate to accomplish this is defined as "therapeutically effective dose." Amounts effective for this use will depend on, e.g., the particular composition of the POP regimen administered, the manner of administration, the stage and severity of the disease, the general state of health of the patient, and the judgment of the prescribing physician. In some embodiments, the POP may be co-administered with an agent, cells, or a combination thereof.

The POP can be administered by methods well known in the art as described in Donnelly et al. (Ann. Rev. Immunol. 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The POP can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The POPs can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the POP is administered intravenously, intraarterially, or intraperitoneally to the subject.

7. METHODS a. Methods for Forming a Cellular Scaffold

Provided herein are methods for forming a cellular scaffold. In some embodiments, the methods include mixing cells with a plurality of POPs at a first temperature less than the transition temperature of the polypeptide, such that the polypeptide does not form an aggregate, and incubating the POPs at a second temperature suitable for cellular growth and greater than the transition temperature, such that the polypeptides form an aggregate with the cells encapsulated within, to form the cellular scaffold. In some embodiments, the methods further include implanting the pre-formed cellular scaffold into a subject.

In some embodiments, the methods include mixing cells with a plurality of POPs to form a mixture, at a first temperature less than the transition temperature of the polypeptide, such that the polypeptide does not form an aggregate, and injecting the mixture at the first temperature into a subject, wherein the subject is at a second temperature greater than the transition temperature, such that the polypeptides form an aggregate with the cells encapsulated within, to form the cellular scaffold in the subject.

In some embodiments, the methods include injecting into a subject a plurality of POPs at a first temperature less than the transition temperature of the polypeptide, such that the polypeptide does not form an aggregate prior to injection, wherein the subject is at a second temperature greater than the transition temperature, such that the polypeptides form an aggregate to form the scaffold in the subject.

In some embodiments, the methods further include reducing the temperature to the first temperature, such that the aggregate/scaffold solubilizes, and separating the cells from the solubilized scaffold. The first temperature may be the $T_t$-cooling. In some embodiments, the separating step comprises centrifugation.

In some embodiments, the cells within the scaffold integrate into the surrounding cells or tissues of the subject. In some embodiments, the cells of the subject surrounding the scaffold integrate into the scaffold. In some embodiments, the cells within the scaffold modify the surrounding cells or tissues of the subject.

In some embodiments, the cells within the scaffold, the cells integrating into the scaffold, or the cells modified by the scaffold form new vasculature. The new vasculature may be formed within about 10 days of administration. In some embodiments, the newly created vasculature comprises capillaries or vasculature having capillary-like characteristics. In some embodiments, the newly created vasculature comprises arterioles or vasculature having arteriole-like characteristics. In some embodiments, the newly created vasculature comprises capillaries, arterioles or a combination thereof.

b. Methods of Delivering an Agent to a Subject

Provided herein are methods of delivering an agent to a subject. The methods may include encapsulating the agent in an aggregate, the aggregate comprising a plurality of POPs as detailed herein, and administering the aggregate to the subject.

c. Methods of Treating a Disease in a Subject

Provided herein are methods of treating a disease in a subject. The methods may include administering a drug delivery composition, scaffold, and/or cellular scaffold as detailed herein to the subject.

In some embodiments, the methods may include treating a disease where new vascularization is needed at a site of injury (e.g., vascular tissue engineering). The methods may include administering a drug delivery composition, scaffold, and/or cellular scaffold as described herein to a site of injury, e.g., a site of injury that needs creation of new vasculature. The methods of creating new vasculature for treating a disease may form the new vasculature within about 10 days of administration of the drug delivery composition, scaffold, and/or cellular scaffold. In some embodiments, the newly created vasculature comprises capillaries or vasculature having capillary-like characteristics. In some embodiments, the newly created vasculature comprises arterioles or vasculature having arteriole-like characteristics. In some embodiments, the newly created vasculature comprises capillaries, arterioles or a combination thereof. Further description on vascular tissue engineering can be found in Serbo et al., Stem Cell Res. Ther., 2013 Jan. 24; 4(1):8 and Lovett et al., Tissue Eng. Part B Rev., 2009 Sep.; 15(3):353-70, both of which are incorporated by reference herein in their entirety.

In some embodiments, the methods may include treating a disease where the administration of the drug delivery composition, scaffold, and/or cellular scaffold disclosed herein results in wound healing. For example, the methods may include administering a drug delivery composition, scaffold, and/or cellular scaffold as described herein to a site of injury, e.g., a site of injury in need of wound healing. The site of injury can be an acute injury or a chronic injury. An example of an acute injury includes, but is not limited to, a deep cut. Examples of a chronic injury include, but are not limited to, diabetic foot ulcers, pressure ulcers, and venous leg ulcers. In some embodiments, the disease in need of wound healing is diabetes mellitus and the site of injury in need of wound healing is a diabetic ulcer. Further description on wound healing can be found in W. International. Acellular Matrices for the Treatment of Wounds (2011); W. International. Best Practice Guidelines: Wound Management in Diabetic Foot Ulcers (2013); and Jarbrink, K. et al. Prevalence and incidence of chronic wounds and related complications: a protocol for a systematic review. Syst Rev 5, 152; all of which are incorporated by reference herein in their entirety.

d. Methods of Increasing the Maximum Tolerated Dose of an Agent

Provided herein are methods of increasing the maximum tolerated dose of an agent. The methods may include encapsulating the agent in an aggregate of POPs as detailed herein, and administering the agent-encapsulated aggregate to a subject.

8. EXAMPLES

Example 1

Materials and Methods

Synthesis of polymer genes. All polymers were cloned into a modified pet24 vector using a previously described process known as recursive directional ligation by plasmid reconstruction (PRe-RDL)(McDaniel, J. R., et al. *Biomacromolecules* 2010, 11, 944-952). Briefly, single stranded oligomers encoding the desired sequences were annealed into cassettes with CC and GG overhangs. The overhangs enabled their concatemerization and ligation (Quick Ligase, NEB, Ipswich, MA) into the pet24 vector. Using this process, we created a library of elastin-like polypeptide and polyalanine cassettes which could be pieced together through multiple cycles of PRe-RDL to form the final partially ordered polymers. All of the base oligomer cassettes used for polymer construction can be found below. Plasmids were transfected into chemically competent Eb5a (EdgeBio, Gaithersburg, MD) cells for cloning and BL21 (DE3) (EdgeBio, Gaithersburg, MD) cells for protein expression. Sequences are shown in TABLE 4.

TABLE 4

DNA Cassettes for Pre-RDL.

| E1 | Forward | TGTGGGTGTTCCGGGCGTAGGTGTCCCAGGTGTGGGCGTACC GGGCGTTGGTGTTCCTGGTGTCGGCGTGCCGGG (SEQ ID NO: 24) |
|----|---------|---|
|    | Reverse | CGGCACGCCGACACCAGGAACACCAACGCCCGGTACGCCCAC ACCTGGGACACCTACGCCCGGAACACCCACACC (SEQ ID NO: 25) |
| E2 | Forward | CGTGGGTGTTCCGGGCGTAGGTGTCCCAGGTGCGGGCGTACC GGGCGTTGGTGTTCCTGGTGTCGGCGTGCCGGG (SEQ ID NO: 26) |
|    | Reverse | CGGCACGCCGACACCAGGAACACCAACGCCCGGTACGCCCG CACCTGGGACACCTACGCCCGGAACACCCACGCC (SEQ ID NO: 27) |
| E3 | Forward | CGCCGGAGTGCCAGGCGTGGGTGTTCCAGGAGCAGGCGTTC CAGGTGTGGGTGTTCCTGG (SEQ ID NO: 28) |
|    | Reverse | AGGAACACCCACACCTGGAACGCCTGCTCCTGGAACACCCAC GCCTGGCACTCCGGCGCC (SEQ ID NO: 29) |
| H1 | Forward | TGCGGCCGCAGCTGCGGCGGCAGCCGCGGCTGCCGCGGCTG CAGCGGCAGCCGCGGCTGCGGCGGCCGCAGCTGCGGG (SEQ ID NO: 30) |
|    | Reverse | CGCAGCTGCGGCCGCCGCAGCCGCGGCTGCCGCTGCAGCCG CGGCAGCCGCGGCTGCCGCCGCAGCTGCGGCCGCACC (SEQ ID NO: 31) |
| H2 | Forward | TAAAGCGGCCGCAGCTGCGGCGGCAGCCGCGGCTGCCGCGG CTGCAGCGGCAGCCGCGGCTGCGGCGGCCGCAGCTGCGAAA GG (SEQ ID NO: 32) |
|    | Reverse | TTTCGCAGCTGCGGCCGCCGCAGCCGCGGCTGCCGCTGCAG CCGCGGCAGCCGCGGCTGCCGCCGCAGCTGCGGCCGCTTTA CC (SEQ ID NO: 33) |
| H3 | Forward | TAAAGCGGCCGCAGCTAAAGCCGCGGCAGCGAAAGCAGCCGC GGCGAAAGCCGCAGCTGCGAAAGCGGCAGCCGCGAAGGG (SEQ ID NO: 34) |
|    | Reverse | CTTCGCGGCTGCCGCTTTCGCAGCTGCGGCTTTCGCCGCGGC TGCTTTCGCTGCCGCGGCTTTAGCTGCGGCCGCTTTACC (SEQ ID NO: 35) |
| H5 | Forward | TGATGCGGCCGCAGCTGCGGCGGCAGCCGCGGCTGCCGCGG CTGCAGCGGCAGCCGCGGCTGCGGCGGCCGCAGCTGCGAAA GG (SEQ ID NO: 36) |
|    | Reverse | TTTCGCAGCTGCGGCCGCCGCAGCCGCGGCTGCCGCTGCAG CCGCGGCAGCCGCGGCTGCCGCCGCAGCTGCGGCCGCATCA CC (SEQ ID NO: 37) |

Expression and purification of POPs. For protein expression, 5 mL starter cultures were grown overnight from −80° C. DMSO stocks. Cells were then pelleted, resuspended in 1 mL of terrific broth, and used, along with 1 mL 100 μg mL⁻¹ of kanamycin (EMD Millipore, Billerica, MA) to inoculate 1 L of media. Cells were shaken at 200 rpm for 8 hrs at 25° C. before induction. For induction of protein expression, 1 mL of 1 M isopropyl β-D-1-thiogalactopyranoside (Goldbio, St. Louis, MO) was added to the flask and cultures were placed at 16° C. and 200 rpm overnight. Expression at lower temperature was necessary to prevent the formation of truncation products at ELP-polyalanine junctions. Cells were then pelleted and resuspended in 10 mL of 1×PBS for every 1 L of culture grown. Pulse sonication on ice, with a total active time of 3 minutes, was used to lyse cells. Cell lysates were treated with 10% PEI (MP Biomedical, Santa Ana, CA) (2 mL L⁻¹ culture) to remove contaminating DNA and centrifuged at 14 k rpm for 10 min at 4° C. Polymer was purified from the resulting soluble fraction using a modified version of inverse thermal cycling (Meyer, D. E. et al. *Nat. Biotechnol.* 1999, 17, 1112-1115). The fraction was heated to 65° C. or until a phase separation was observed. For more hydrophilic polymers, this often required the addition of 1-2 M NaCl to depress the transition temperature. Once aggregated, the polymer solutions were centrifuged at 14 k rpm for 10 min at 35° C., and the resulting pellet was resuspended in 5-10 mL PBS. The heating and cooling centrifugation cycles were repeated 2-3 more times until a purity of 95% was achieved, as analyzed by SDS-PAGE. Pure polymers were dialyzed at 4° C. with frequent water changes for 2 days and lyophilized for storage.

Secondary structure characterization. Circular dichroism experiments were carried using an Aviv Model 202 instrument and 1 mm quartz cells (Hellma USA, Plainview, NY). Unless otherwise noted, scans were carried out in PBS (pH=7.4) with a polymer concentration of 10 μM. Polymers were scanned in triplicate from 260 nm to 185 nm in 1 nm steps with a 1 s averaging time. Data points with a dynode voltage above 500V were ignored for analysis. All measurements were done at 20° C. unless otherwise specified. Temperature ramping was done in 5° C./min increments with a 1 min equilibration at each step.

For NMR, polymers were grown in M9 minimal media with $^{15}$N—NH$_4$Cl and $^{13}$C-Glucose (Cambridge Isotopes, Tewksbury, MA) as the only nitrogen and carbon sources to ensure protein labelling. Samples were prepared in PBS (pH=7.4) unless otherwise noted. All NMR spectra were collected on an INOVA 600 (Varian Instruments, Palo Alto, CA) spectrometer with a triple resonance cryoprobe equipped with a z-field gradient coil. Resonance assignments were made using a set of triple resonance experiments including HNCO, HN(CA)CO, HN(CO)CA, HNCA, HCAN, and HCA(CO)N. The NMR spectra were processed using NMRpipe (Delaglio, F. et al. *Journal of Biomolecular NMR* 1995, 6), and were analyzed using NMRviewJ. Chemical shifts in the proton dimension were referenced relative to TMSP (trimethylsilylpropanoic acid) as 0 ppm. Quantification of helicity was accomplished using the identified alanine peaks of the H(N)CO spectra for E1-H2-25%. Chemical shift positions were placed on a spectrum of values ranging from fully disordered (177.19 ppm) to fully helical (180.78 ppm), as determined Vendruscolo et al. (De Simone, A., et al. *J. Am. Chem. Soc.* 2009, 131, 16332-16333; Camilloni, C., et al. *Biochemistry* 2012, 51, 2224-2231) and the central alanine peak of the 15° C. H(N)CO respectively, producing the values in TABLE 2. The method to calculate helicity was adapted from δ2D algorithm developed by Vendruscolo et al. (Camilloni, C., et al. *Biochemistry* 2012, 51, 2224-2231). Alanines corresponding to carbon chemical shifts of peaks 2-7 were designated as fringe amino acids at the edges of the helix. This designation is consistent with our helix-coil transition theory prediction in which 6 alanines occur at values lower than the core set. All other alanines were assumed to be in the helix core. A subsequent averaging of the helicity values produces a helicity for each H2 polyalanine domain of 91%.

TABLE 2

| | | CD Structural Analysis. | | |
|---|---|---|---|---|
| Polymers | Helix (%) | Beta Sheet (%) | Turn (%) | Disorder (%) |
| (ELP1)$_{80}$ | 1.6 | 23.9 | 14.8 | 59.7 |
| ELP1-H1-25% | 47 | 13.7 | 6.1 | 33.2 |
| ELP1-H2-25% | 35.8 | 34.5 | 0.3 | 29.4 |
| ELP1-H3-25% | 27.5 | 44.9 | 0 | 27.6 |
| ELP1-H4-25% | 40.1 | 16.8 | 6.5 | 36.6 |
| ELP1-H5-12.5% | 19.4 | 32.1 | 4.4 | 44.1 |

Temperature-dependent turbidity. The transition temperature (Tt) of each sample was determined by monitoring the optical density at 350 nm as a function of temperature on a UV-vis spectrophotometer (Cary 300 Bio; Varian Instruments, Palo Alto, CA) equipped with a multicell thermoelectric temperature controller. The Tt was defined as the point of greatest inflection (maximum of the first derivative) for the optical density. Unless otherwise stated, all samples were heated and cooled at 1° C. min$^{-1}$ in PBS at concentrations between 10 and 1000 μm.

Molecular dynamics simulations. The phenomenological simulations were designed to test the role of having two energy scales on the coarse structural features. We chose the interaction strengths of the ELP beads such that this range would span from highly soluble to aggregating polymers. This was quantified by running simulations with a range of energies and after equilibrating for 100 ns, decreasing these interaction strengths by 0.05 kcal/mol every 25 ns. We then quantified the number of polymers in the largest cluster, where two proteins were considered interacting if two beads were within 8 Angstroms, as a proxy for aggregation versus solubility in our simulations. These polymers were strongly aggregating with an interaction strength of 0.35 kcal/mol and readily disaggregated when that interaction dropped to 0.25 kcal/mol. As such, we used a range of interactions strengths for the ELPs that spanned at least 0.05 kcal/mol to 0.40 kcal/mol. This range of interaction strengths is our simulation equivalent to increasing the temperature of the system from below the LCST to above the LCST. Unfortunately, without any further constraints, we cannot be more quantitative in the scaling between the strength of our interactions and the experimental equivalent temperatures. We used a similar technique to parameterize the alanine domain bead interaction strength. Here our constraint in choosing an interaction strength is based on being strong enough to push it significantly into the aggregation prone regime. As such, we used interaction strengths of at least 1 kcal/mol for the alanine beads.

To test for effects related to hysteresis we utilized two different schemes for initial conditions. The first scheme, denoted the dimer initial conditions, was designed to create states that we think are representative of the pathway that the system will pass through as it approaches the LCST from below. Simulations of two proteins were equilibrated for 100 ns in a simulation box of 250A. This allowed the alanine domains in these dimers to pre-aggregate into a core. 25 different conformations of these dimers were then randomly placed in the simulations for the full system. At high ELP interaction strengths these simulations docked together. This means that the ELPs that are exposed around the alanine cores find each other. There is some degree of alanine cores merging together into larger cores that converge toward their thermodynamically favorable radius.

The second scheme, denoted the coil initial conditions, was designed to create a thermodynamically equilibrated aggregated state that we think the dimer initial condition simulations would eventually converge toward. We started the simulation with each polymer generated randomly. The only correction was to prevent steric clashes. These simulations showed a rapid initial collapse as the alanine domains found other alanine domains, and, if the ELP domains were above the LCST, the collapse of ELP domains as well. These simulations converged toward conformations with clusters of alanine domains that were well connected. After equilibrating for 100 ns, the interaction strength of the ELPs were decreased by 0.10 kcal/mol every 25 ns to model crossing from above the LCST to below the LCST. These simulations showed swelling as the ELPs no longer favored being in a high density but the connectivity of alanine domains between the two domains prevented the system from separating.

Fluorescence imaging and analysis. POPs were fluorescently labeled using Alexa Fluor 488 NHS Ester (Thermo Fisher, Waltham, MA) with a reaction efficiency of 20%. Excess dye was removed with dialysis and polymers were lyophilized for storage. For all experiments, the dyed polymers were diluted into an undyed stock such that no more than 5% of POPs in solution were labelled. Confocal images were taken on a Zeiss 710 inverted microscope with temperature controlled incubation. To prevent dehydration, 50

μL of sample solution was added to 384 well #1.5 glass bottom plates (Cellvis, Mountain View, CA) for imaging. Solutions were added below the $T_t$ and allowed to transition and equilibrated for 5 minutes on the microscope stage. For FRAP experiments, samples (n=3 for each group) were equilibrated for 30 min to prevent thermal movement of the focusing stage, and fluorescence intensity analysis was done using Zen software (ZEISS Microscopy, Jena, Germany). For void volume analysis, 20 μm image stacks (n=3 for each concentration) were taken with a pinhole size of 1 Airy unit and vertical slice intervals of 230 nm. Three dimensional reconstructions of the resultant networks and quantification of their void volume was done in IMARIS 8 (Bitplane. Belfast, Ireland). Surface renders were constructed with a minimum object detail of 200 nm and local background thresholding with the diameter of the largest sphere that fits into the object set a 1 μm. A consistent minimum threshold of 1000 FU was used across samples. Concentrations beyond 800 μM were not evaluated, as quantification using our methodology was not possible as the feature size approached the spatial resolution of the confocal fluorescence microscope. Network fractal dimensions were determined using the 2D box counting algorithm from the FracLac plugin for ImagJ (Schneider, C. A., et al. *Nature Methods* 2012, 9, 671-675; Karperien, A. FracLac for Image J, version 2.5. Structured illumination microscopy images were taken with assistance from Dr. Kai Wang using an in-house microscope constructed at Janelia Farm in the lab of Dr. Eric Betzig. Technical details and the experimental setup have been previously published (Shao, L., et al. *Nat. Methods* 2011, 8, 1044-1046). Because the SIM was an upright microscope, polymer was compressed between a glass slide and a coverslip before imaging. All other sample preparation was identical to that for confocal microscopy. Image stacks of 8-12 μm were taken and maximum intensity projections were created and analyzed in ImageJ.

Pharmacokinetic and SPECT analysis. All constructs were endotoxin purified to <1 EU/mL and prepared at 500 μM in sterilized PBS and reacted with [125]Iodine (Perkin Elmer, Boston MA) in Pierce® pre-coated IODOGEN tubes (Fisher Scientific, Hampton, NH)(Wood, W. G., et al. *J. Clin. Chem. Clin. Bio.* 1981, 19, 1051-1056). The product was centrifugally purified through 40K MWCO Zeba Spin Desalting Columns (Thermo Scientific, Rockford, IL) at 2500 rpm for 3 min at 4° C. to remove unreacted radioiodine from the conjugate. After labeling, each construct was diluted down to a final biopolymer concentration of 250 μM. The resulting activity dose for the POP was 1.18 mCi mL-1, while the ELP dose was 1.37 mCi mL-1.

Female athymic nude mice were purchased from Charles River and housed in a centralized animal facility at Duke University. All procedures were approved by the Duke University Institutional Animal Care and Use Committee and were in compliance with the NIH Guide for the Care and Use of Laboratory Animals. 50 μL of the POP was prepared in an Eppendorf tube at 63 μCi to provide a reference imaging standard. Prior to either the depot injection, blood draw, or single-photon emission computed tomography (SPECT) imaging, each mouse was anesthetized using a 1.6% isoflurane vaporizer feed at an $O_2$ flow rate of 0.6 L min⁻¹. For depot injections, each mouse received a soluble 200 μL injection of their respective solution at 250 μM into the subcutaneous space on the right hind flank. The whole body activity of the mouse was then measured in an Atom-Lab 400 dose calibrator (Biodex, Shirley, NY). A total of 12 athymic nude mice (n=6 for each group) were used for pharmacokinetic analysis of depot stability and distribution.

An initial 10 μL blood sample was drawn and pipetted into 1000 mg mL⁻¹ heparin with subsequent blood draws at time points of 45 min, 4 h, 8 h, 24 h, 48 h, 72 h, 96 H, and 120 h to determine the release profile for the depots. 6 total athylmic nude mice also were imaged using SPECT at time points of 0, 48, and 120 hrs. Mice were then transferred under anesthesia to the bed of the U-SPECT-II/CT for imaging using a 0.350 collimator (MILabs B.V., Utrecht, Netherlands) courtesy of G. Al Johnson in the Duke CIVM. Anesthesia was maintained with a 1.6% isoflurane feed at an $O_2$ flow rate of 0.6 L min⁻¹. SPECT acquisition was conducted over a time frame of 15 minutes in 'list-mode' and at a 'fine' step-mode. Upon completion, a subsequent CT scan was carried out at a current of 615 μA and a voltage of 65 kV. Mice were then returned to their cages. Post-imaging SPECT reconstruction was carried out using MILabs proprietary software without decay correction and centered on the $^{125}$I photon range of 15-45 keV. All images were reconstructed at a voxel size of 0.2 mm. Reconstructed SPECT images were then registered with their corresponding CT scans to provide spatial alignment for anatomical reference.

Upon completion of the study, all mice were euthanized and dissected. The subcutaneous depots were excised and visually examined for physical differences. In addition, the heart, thyroid, lungs, liver, kidneys, spleen, skin, muscle and pancreas were collected and analyzed using a Wallac 1282 Gamma Counter (Perkin Elmer, Boston, MA) to determine the relative biodistribution of the different constructs. All blood samples and the set of PK standards were similarly analyzed using the gamma counter. The counts per minute detected for each sample were converted to their corresponding activity. Blood samples were then scaled to determine the total amount in circulation according to the formula Total=CPM/0.01*BW*72 mL/kg (Diehl, K. H. et al. *J. Appl. Toxicol.* 2001, 21, 15-23). Depot retention was analyzed by measuring the total photon intensity of the depot SPECT image in ImageJ. Measured photon intensity was converted to total depot activity using a calibration factor determined from the imaging standard. This calibration was determined by performing a linear regression of the known activities of the standard over time against the corresponding SPECT intensity measurements. The factor was applied to each depot and the calculated activity compared against the original whole body injected dose at 0 h to determine its percent retention.

Cell Recruitment. Female C57BL/6 mice were purchased from Charles River and housed in a centralized animal facility at Duke University. All procedures were approved by the Duke University Institutional Animal Care and Use Committee and were in compliance with the NIH Guide for the Care and Use of Laboratory Animals. For analysis of POP persistence and cell recruitment, female C57BL/6 mice (used for their complete immune system over the nude mice used in the previous study for easier depot observation) received soluble injections in the subcutaneous space of the right and left hind flanks. Mice were injected with either 200 μL of 250 μM E1-H5-25%-120 (19), 200 μL of 750 μM E1-H5-25%-120 (4), or Matrigel (Standard Formulation, Corning, Tewksbury, MA) (7). Matrigel was chosen for comparison since fully disordered ELPs were shown to dissipate too quickly for long term analysis of cell recruitment. POPs were endotoxin purified to <1 EU/mL and sterile filtered prior to injection. At respective time points, mice were euthanized and dissected. Left hind injections were excised and placed in 10% neutral buffered formalin (Sigma, St. Louis, MO) for histological analysis (n=3 for all groups). Fixed depots were embedded in paraffin, and 5 um slices from the center of each depot were stained with Hematoxylin and Eosin (H&E). H&E stained slides were imaged using an Axio 506 color camera mounted on a Zeiss Axio Imager Widfield microscope. Images at 200× magnification were stitched and exported for analysis. Blood vessels and capillaries were manually counted in ImageJ (n=3). For changes in depot size, images of excised depots were taken at a controlled distance and imported into ImageJ for quantification.

For flow cytometry, excised right hind injections (n=3-4) were transferred to 2 mL PBS and digested with 0.5 mg/ml Collagenase IV (Sigma, St. Louis, MO) and 50 units of DNase I (Sigma, St. Louis, MO) at 37° C. for 45 min. Digested tissue was filtered through a 70 μm cell strainer and repeatedly washed with sterile 2% FBS (Thermo Fisher, Waltham, MA) in PBS. After ACK (Thermo Fisher, Waltham, MA) lysis, cells were counted using a hemocytometer. Cells were stained as previously described (Chen, J. et al. *Biomaterials* 2013, 34, 8776-8785). Briefly, cells were blocked with 2.4 G2 antibody (BD Biosciences, San Jose, CA) and stained with anti-mouse CD45-BV-510 (30-F11, BD Biosciences, San Jose, CA), F4/80-PerCP-Cy5.5 (BM8, Biolegend, San Diego, CA), CD11b-APC (M1/70, Biolegend, San Diego, CA), Ly6C-FITC (AL-21 Biolegend, San Diego, CA), Ly6G-PE (IA8, Biolegend, San Diego, CA), CD31-PE-Cy7 (390, Biolegend, San Diego, CA), CD326-APC-Cy7 (G8.8, Biolegend, San Diego, CA), and DAPI (Biolegend, San Diego, CA). Cell subtypes were defined as: neutrophils (CD45+CD11b+Ly6C+Ly6G+F4/80−), inflammatory monocytes (CD45+, CD11b+F4/80+Ly6C+Ly6G−), tissue macrophages (CD45+CD11b+F4/80+Ly6C−Ly6G−), endothelial cells (CD45−CD31+CD326−), and epithelial cells (CD45−CD326+CD31−). Cell type analysis was done on a FACSCANTO II (BD Biosciences, San Jose, CA) with a minimum of 50000 live cells analyzed for each sample. AbC anti-rat antibody control beads (Thermo Fisher, Waltham, MA) were used as compensation controls for all antibody dyes, and a 1:1 mixture of live and dead cells was used as a compensation control for DAPI. Gating procedures are shown in FIG. 19. Flow cytometry data was gated and quantified with FlowJo (FlowJo LLC, Portland, Oregon) and exported for analysis.

Statistical Analysis. All statistical analysis was carried out using Prism 6 (Graphpad Inc, La Jolla, CA). When comparing individual groups, two-tailed t-tests were used to determine statistical significance. ANOVA was used to evaluate significance among three or more groups and the Tukey-Kramer method was used as a post hoc test for comparisons between groups. Experimental group sizes are given within the descriptions of each experiment.

Example 2

Polymer Library Design

We chose elastin-like polypeptides (ELPs), a family of repetitive polypeptides based on a consensus (VPGXG) pentapeptide repeat derived from the disordered regions of tropoelastin and that exhibit a tunable lower critical solution temperature (LCST) phase behavior (McDaniel, J. R., et al. *Biomacromolecules* 2013, 14, 2866-2872; Li, N. K., et al. *Biomacromolecules* 2014, 15, 3522-3530; Meyer, D. E. & Chilkoti, A. *Biomacromolecules* 2004, 5, 846-851; Roberts, S., et al. *FEBS Lett.* 2015, 589, 2477-2486) as our disordered component. ELPs have been characterized as models of elastomeric disorder and their intrinsic disorder is thought to be at least partially responsible for their LCST behavior. They are biocompatible polymers with numerous applications including protein purification, drug delivery, and tissue engineering. Polyalanine helices are also an important element of tropoelastin where they combine with disordered domains to produce the elasticity and resilience that make elastin an important component of the extracellular matrix. In aqueous solutions, alanine-rich sequences are known to have high intrinsic alpha-helical propensity, and they can drive self-association through intermolecular interactions either via helical bundling or the formation of beta-sheet rich fibrils. Accordingly, we selected polyalanine as the scaffold for the ordered domains. We hypothesized that recombinant polymers composed of polyalanine domains doped into an ELP scaffold, thus mimicking the exon composition and organization of tropoelastin, would produce biomaterials with unique, tunable properties.

Figure 7A:
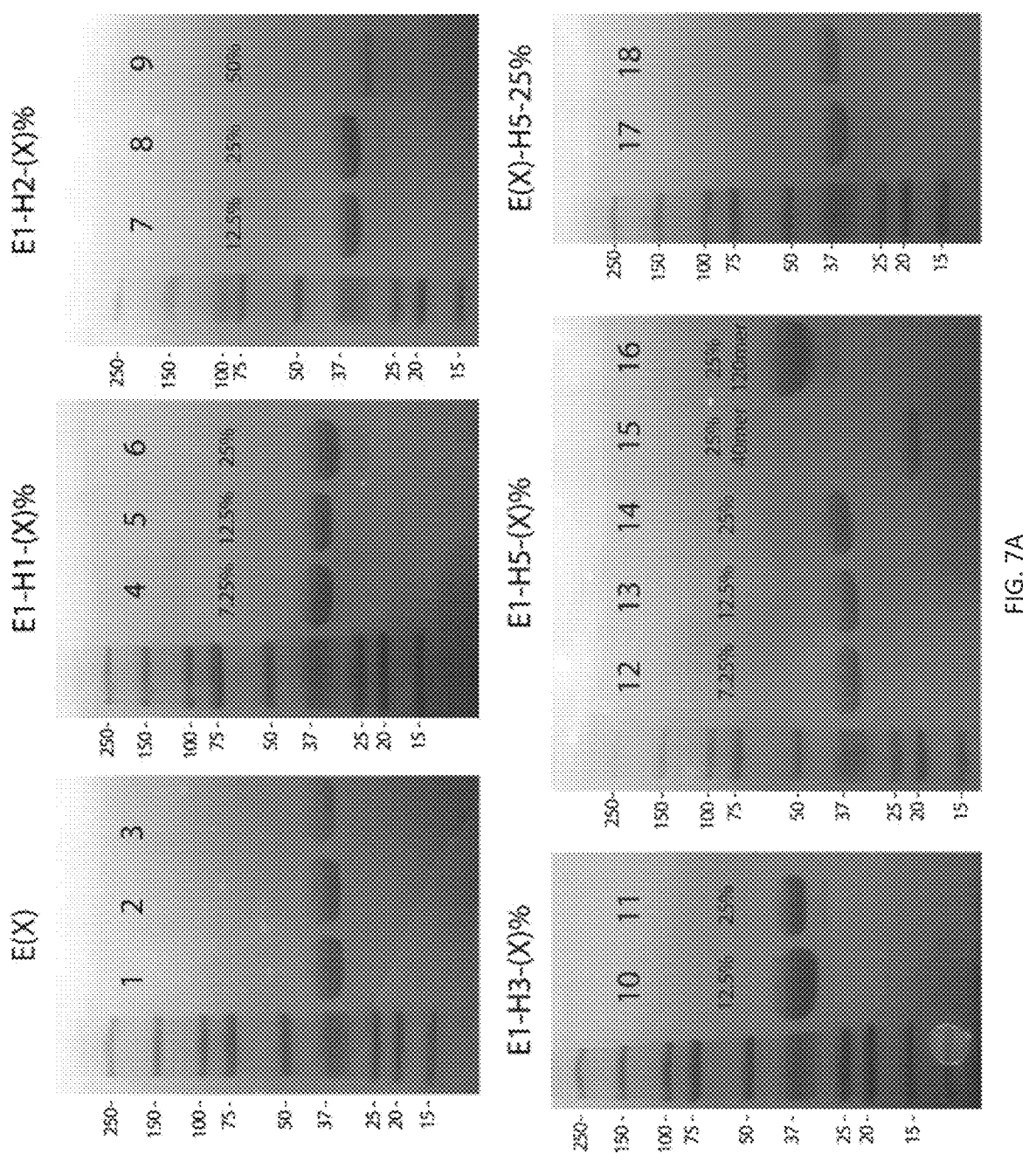
Figure 7C:
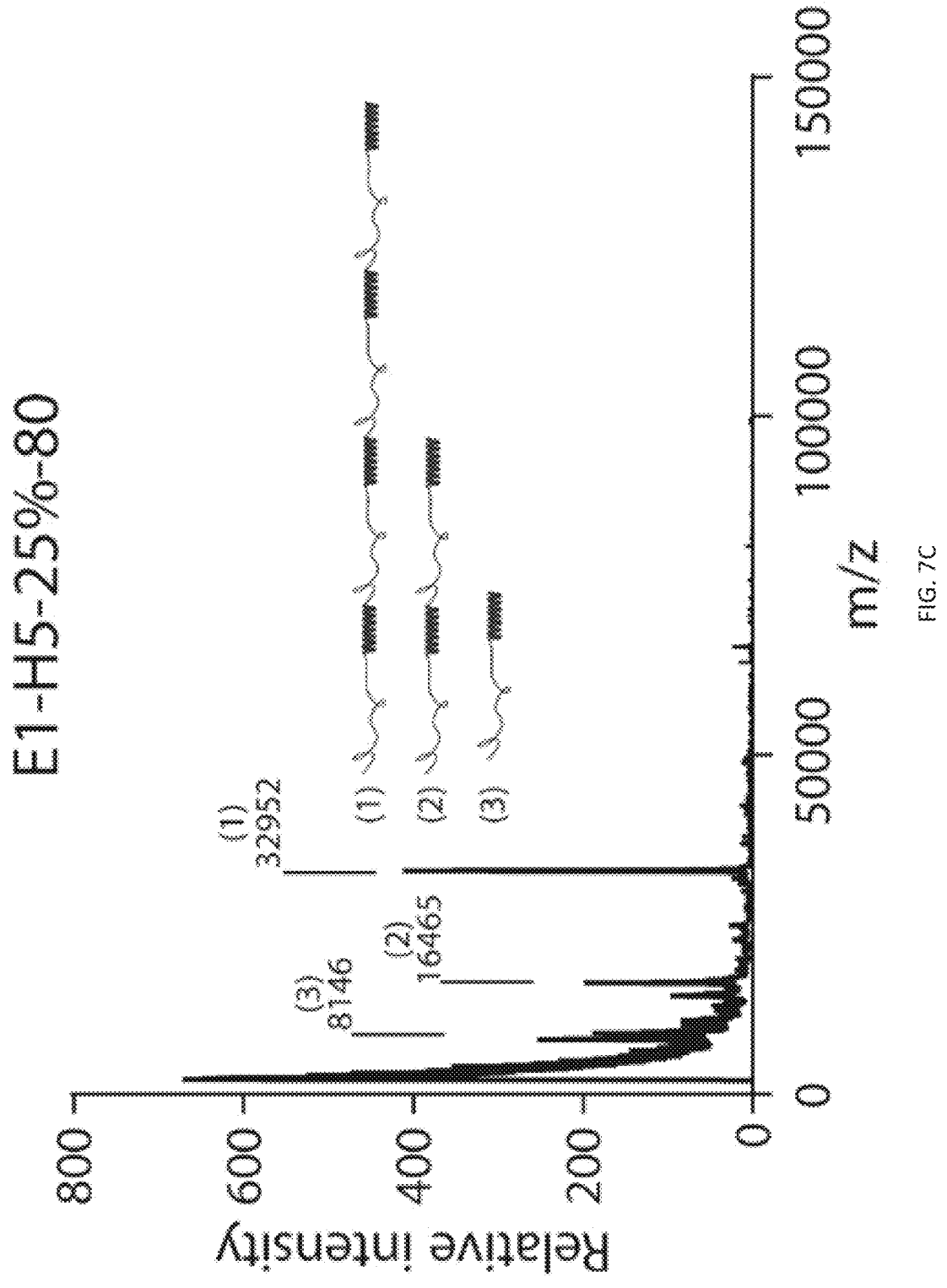

Four polyalanine helices (H1, 2, 3, and 5) with different charge distributions were incorporated into three ELPs (E1-3) of varying side chain hydrophobicities at either 7.25%, 12.5%, 25%, or 50% of the total amino acid number (FIG. 1A). Polyalanine domain compositions were chosen to maximize helicity while controlling hydrophilicity through charge-charge interactions. ELP compositions were chosen to span a range of LCSTs suitable for in vivo injection. The naming convention for our partially ordered polymers (POPs) specifies the ELP (EX), the helix (HY), and the percent helicity (Z %): EX-HY-Z %. The molecular weights (MW) for all polymers are in TABLE 1. All POPs and ELP controls were recombinantly expressed from plasmid-borne synthetic genes in *E. coli* and purified to >95% by inverse transition cycling (Meyer, D. E. & Chilkoti, A. *Nat. Biotechnol.* 1999, 17, 1112-1115). POP purity and homogeneity was verified by sodium dodecyl sulfate polyacrylamide gel electrophoresis (SDS-PAGE) (FIG. 7), and their MWs were verified by matrix assisted laser desorption ionization mass spectrometry (MALDI-MS); in all cases, the experimentally determined MWs agreed with their theoretical MWs within 2%.

TABLE 1

Polymer lengths and molecular weights.

| Polymer | AA Number | MW (kDa) |
|---|---|---|
| (E1)80 | 404 | 33.2 |
| (E2)80 | 404 | 32.8 |
| (E3)80 | 404 | 32.1 |
| E1-H1-7.25% | 405 | 33.0 |
| E1-H1-12.5% | 406 | 32.8 |
| E1-H1-25% | 408 | 32.4 |
| E1-H2-12.5% | 410 | 33.3 |
| E1-H2-25% | 416 | 33.4 |
| E1-H2-50% | 428 | 33.6 |
| E1-H3-12.5% | 408 | 33.6 |
| E1-H3-25% | 412 | 34.0 |
| E1-H5-7.25% | 407 | 33.2 |
| E1-H5-12.5% | 410 | 33.3 |
| E1-H5-25% | 416 | 33.4 |
| E1-H5-25%-40mer | 210 | 16.9 |
| E1-H5-25%-120mer | 622 | 49.8 |
| E2-H5-25% | 416 | 33.0 |
| E3-H5-25% | 436 | 34.1 |

*Met leader and Gly-Try-Pro trailer for all polymers

Example 3

Structural Characterization

Figure 1E:
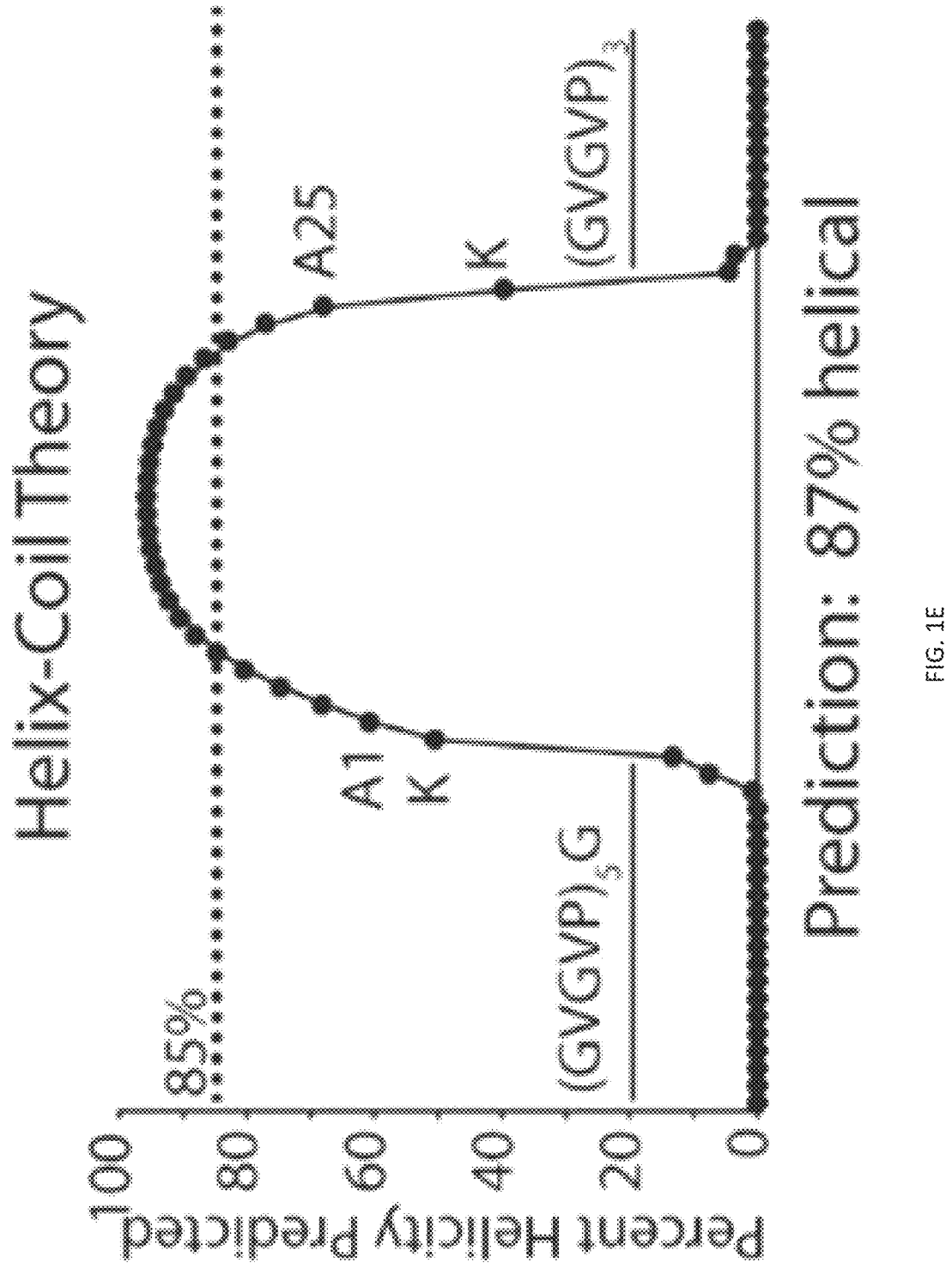
Figure 1F:
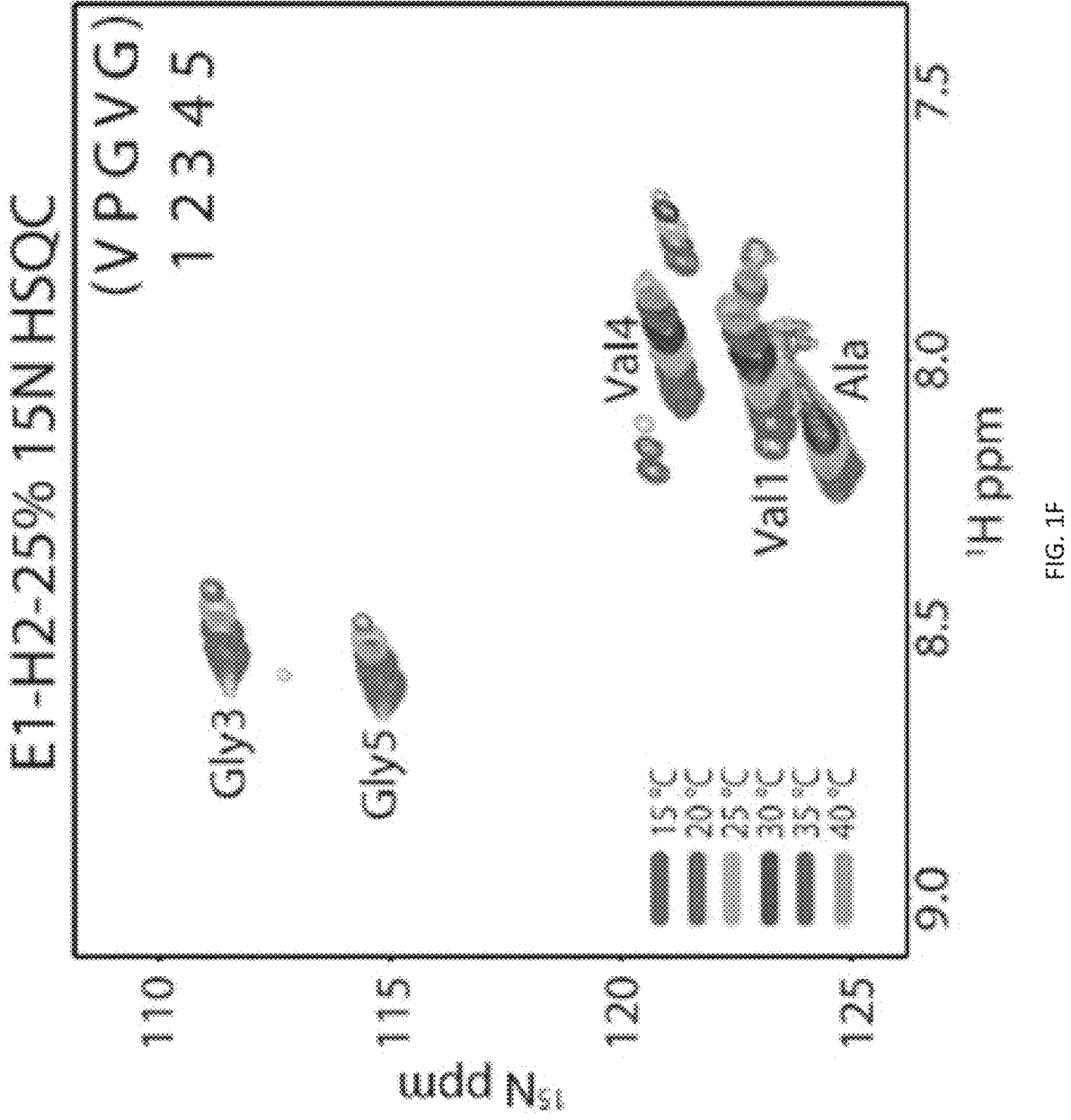
Figure 1G:
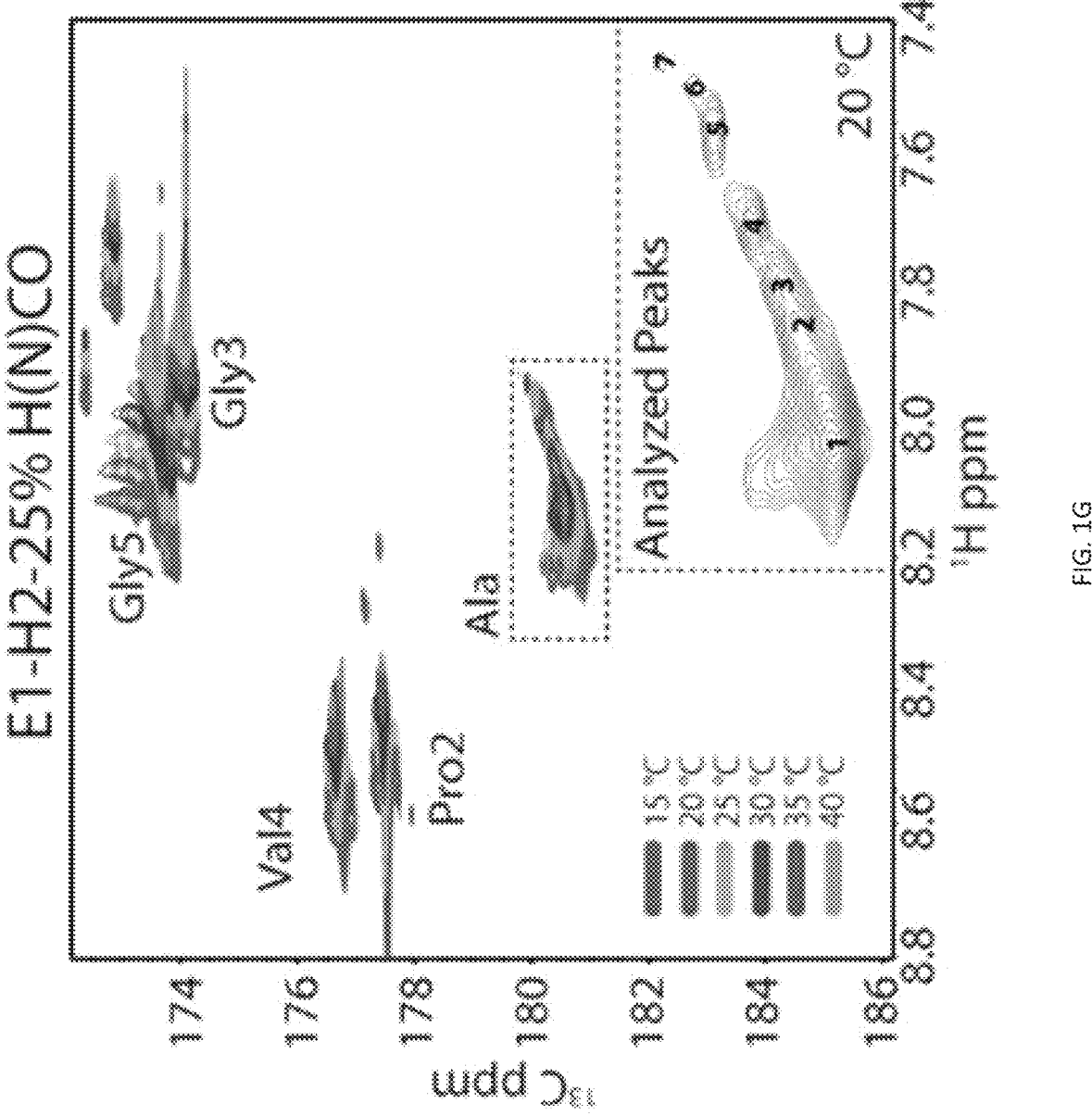
Figure 8A:
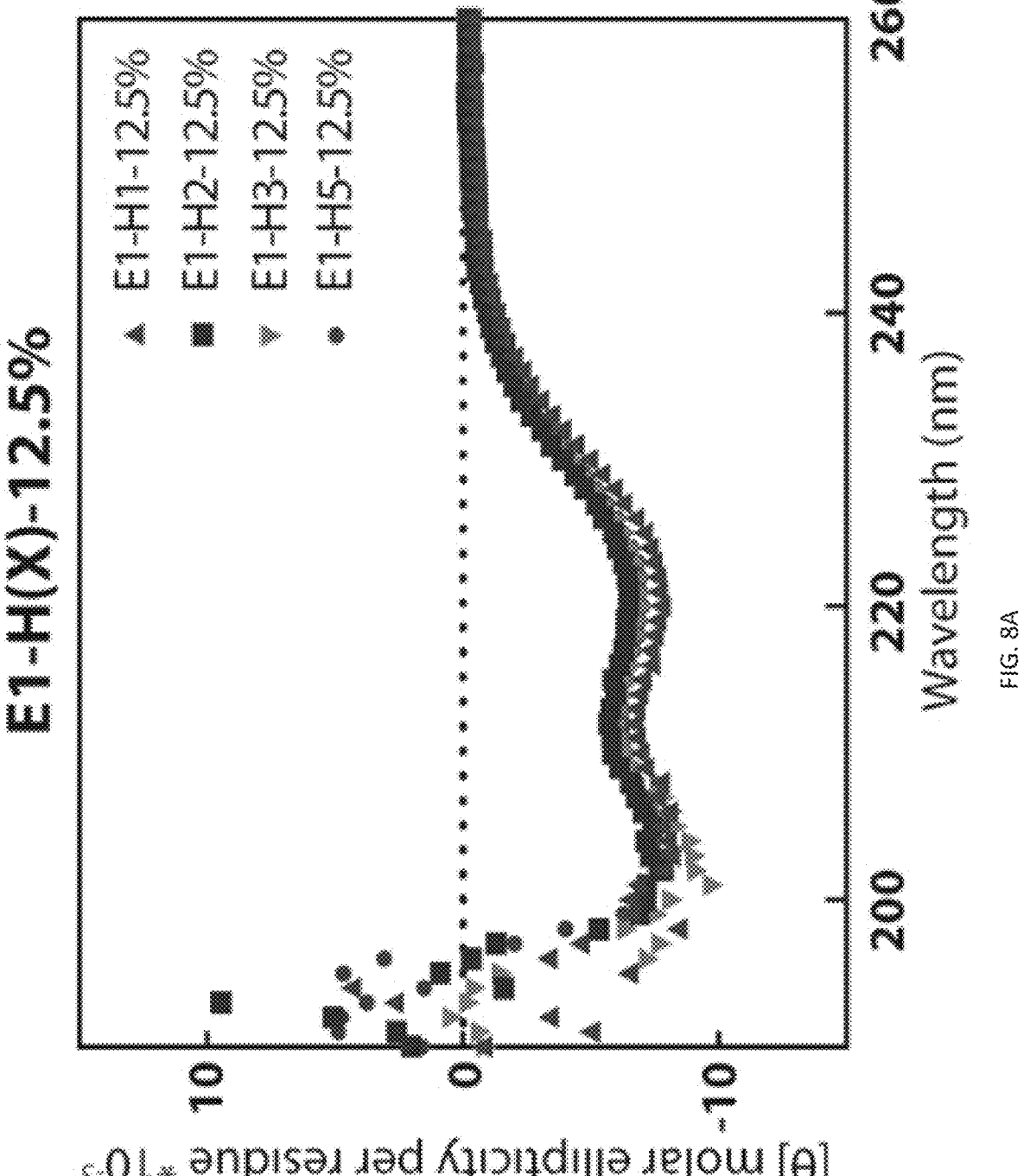
FIG. 8A-FIG. 8C: Additional structural characterization.
Figure 8B:
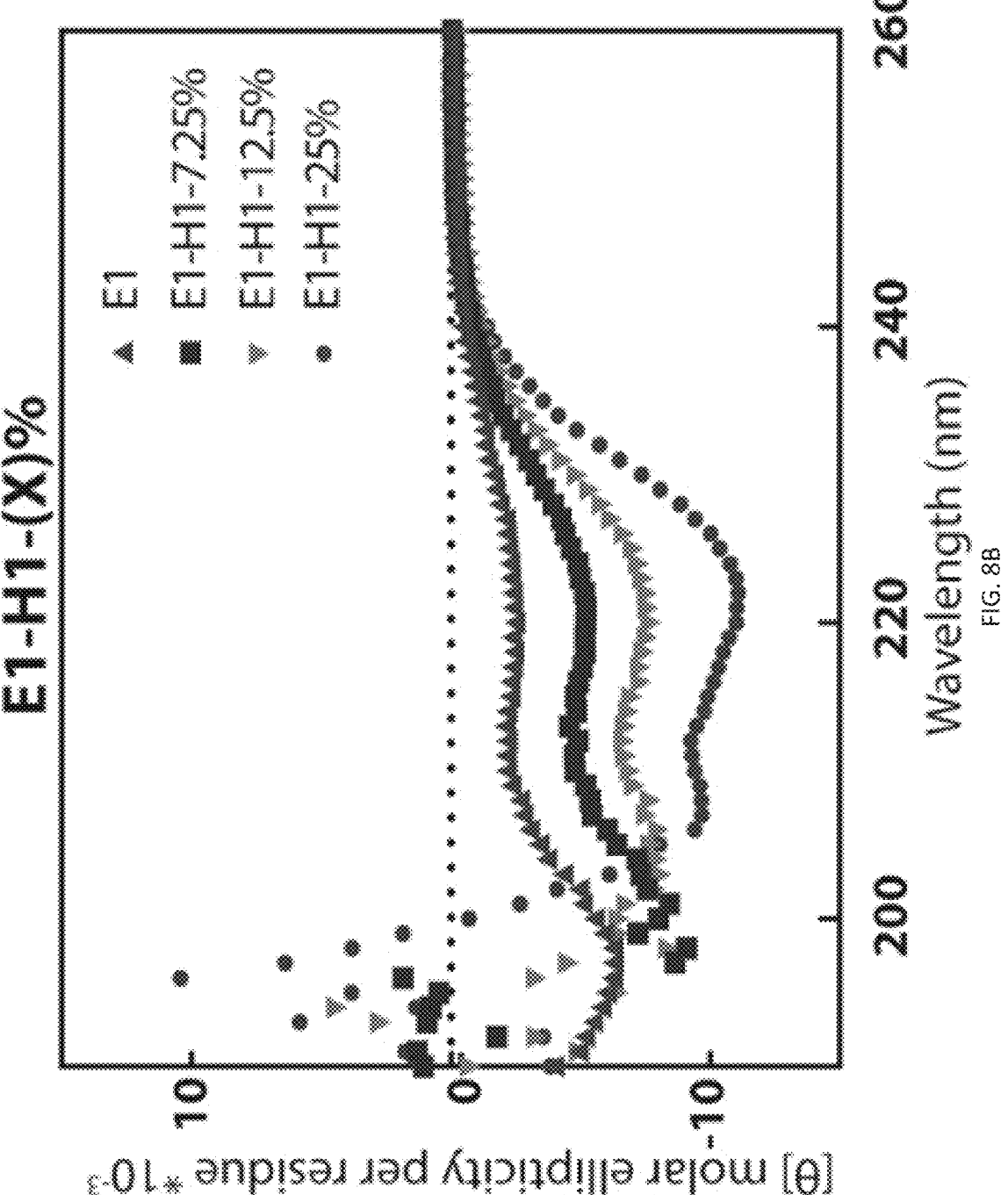
Figure 8C:
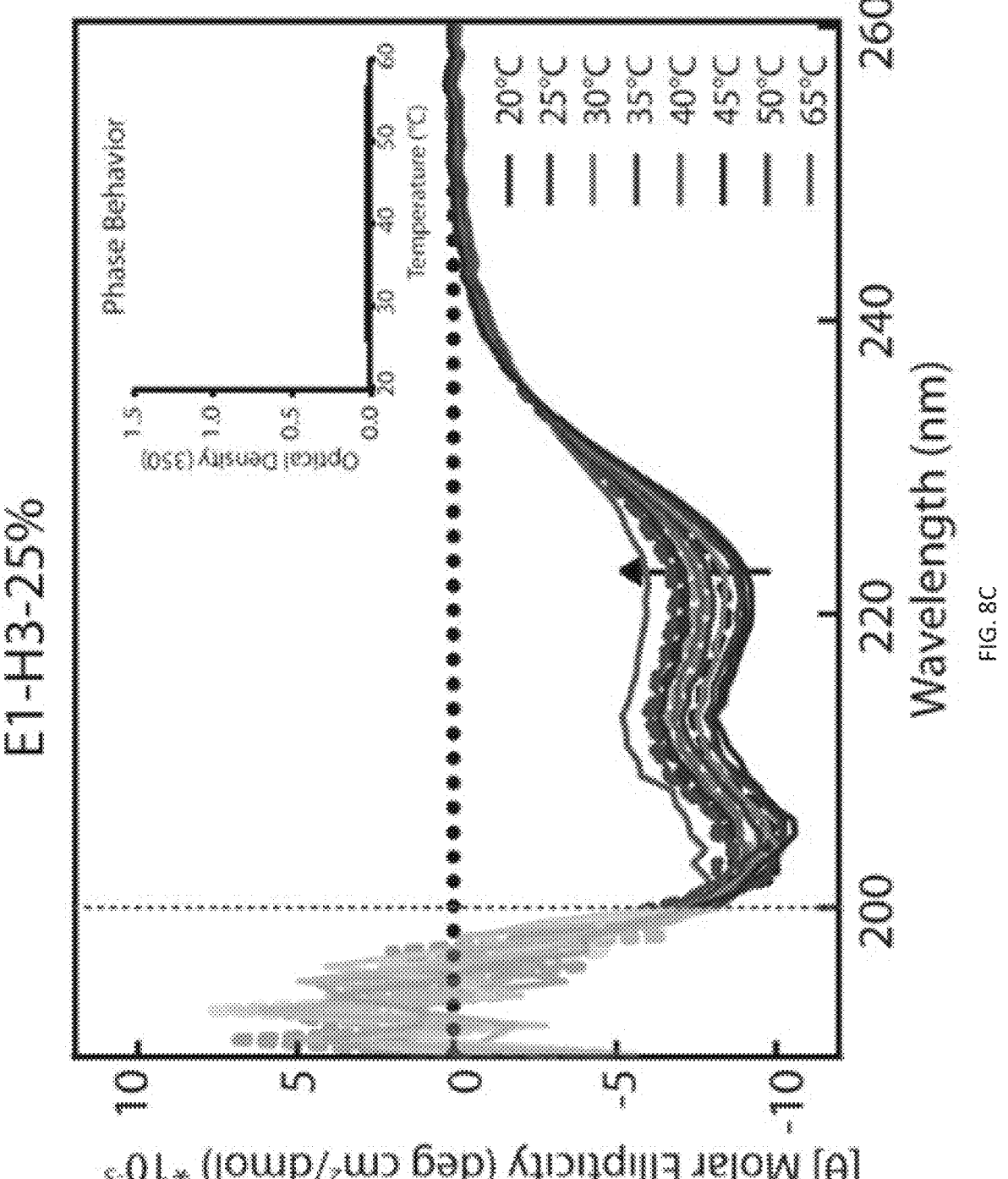
Figure 9A:
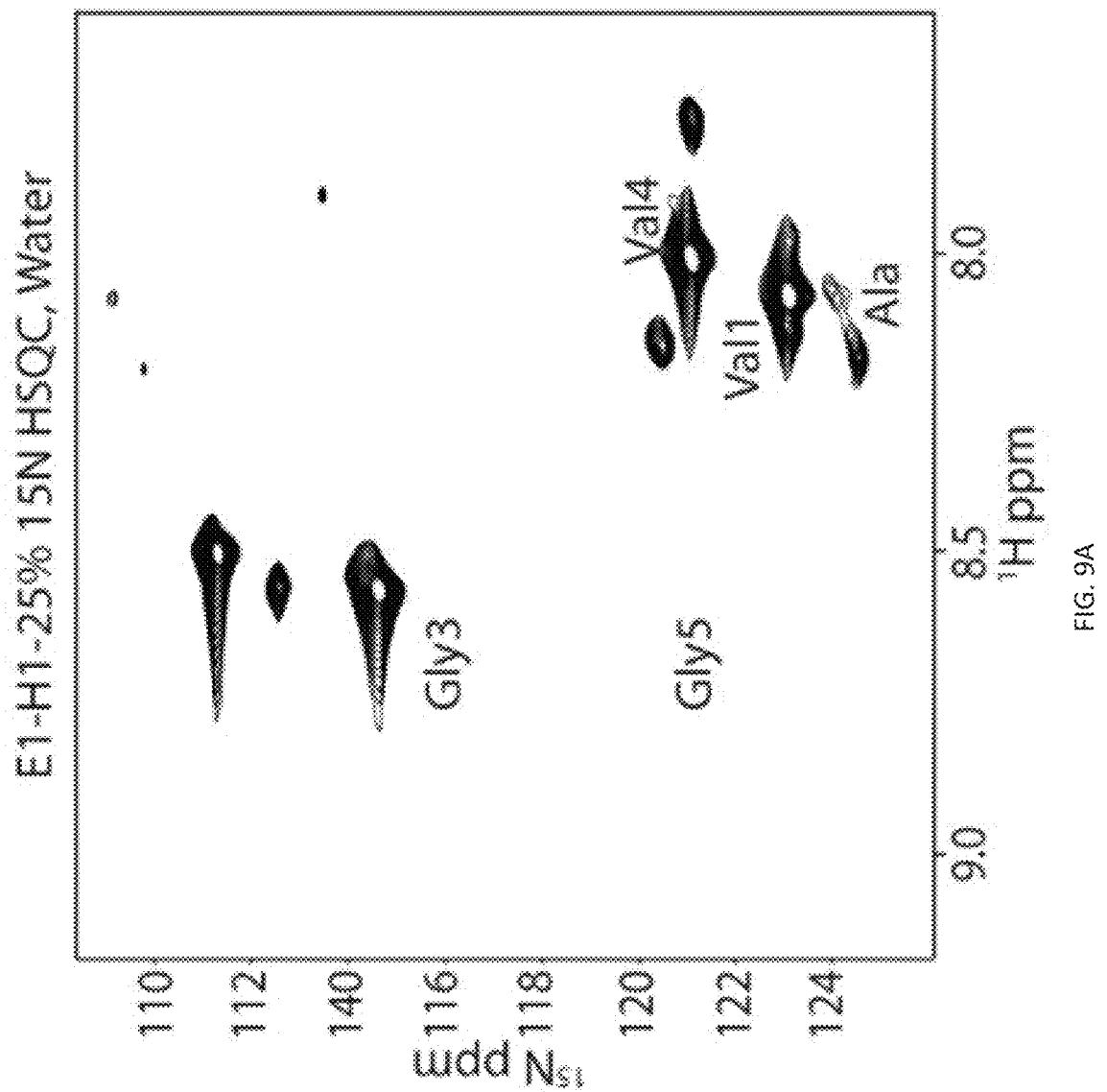
FIG. 9A-FIG. 9C: Additional NMR analysis. The 15N-HSQC spectrum for E1-H1-25% (FIG. 9A) and E1-H2-25% (FIG. 9C) and the 13C-HSQC spectrum for E1-H2-25% (FIG. 9B) show the identifiable amino acid peaks despite the repetitiveness of the polymers. The addition salts in PBS does not appreciably alter the chemical shift positions for the polymers.
Figure 9B:
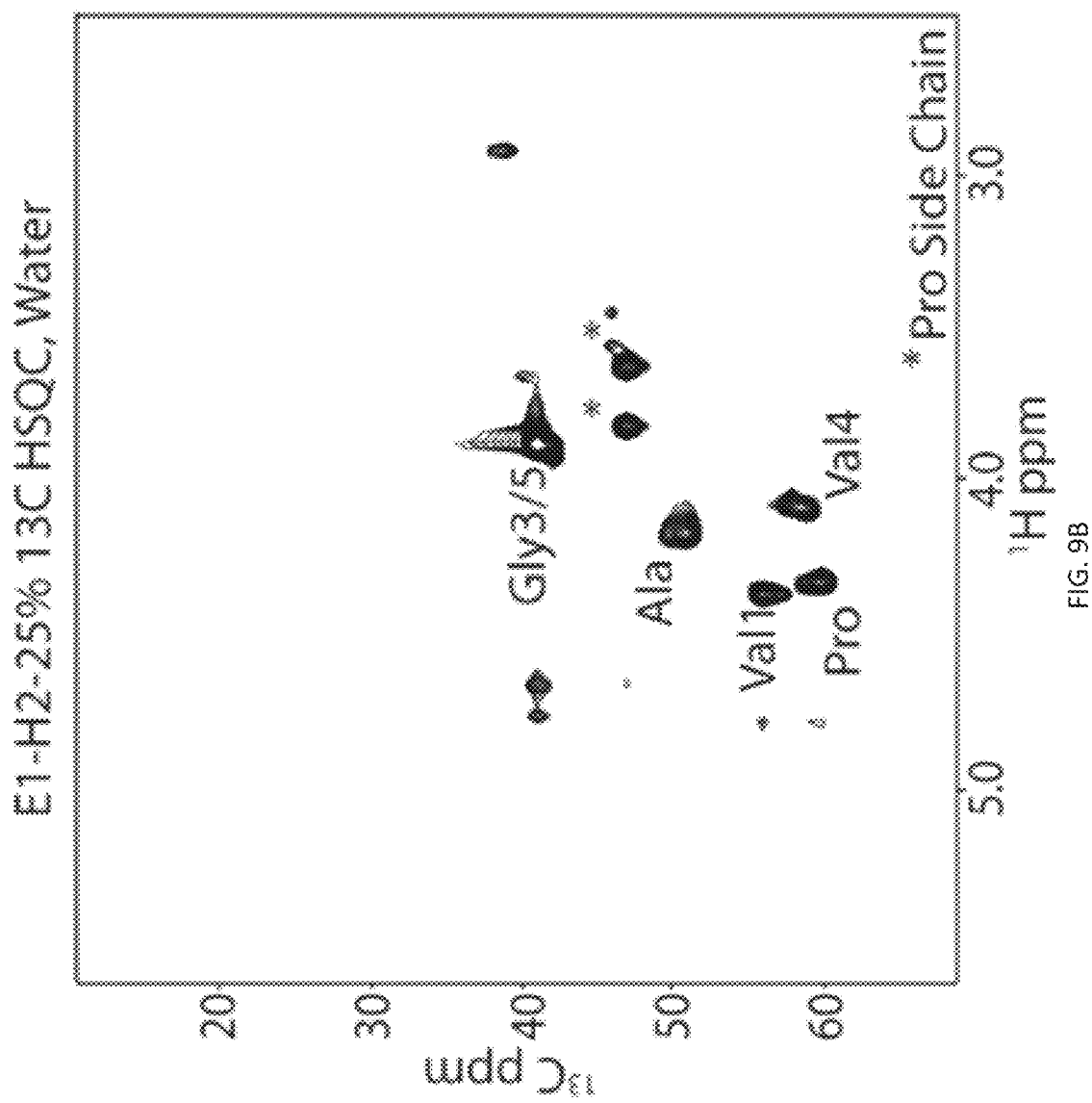
Figure 9C:
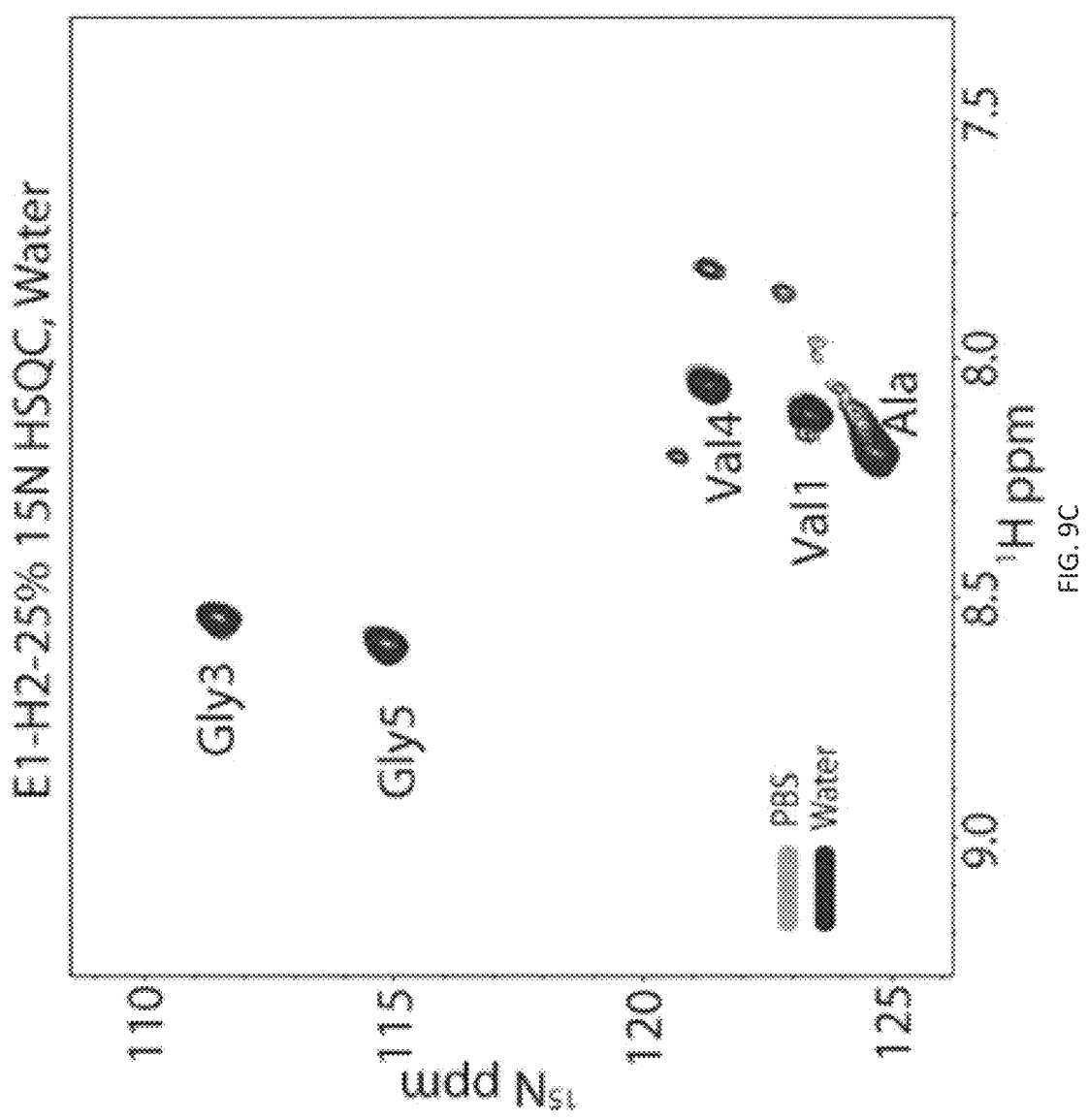
Figure 10A:
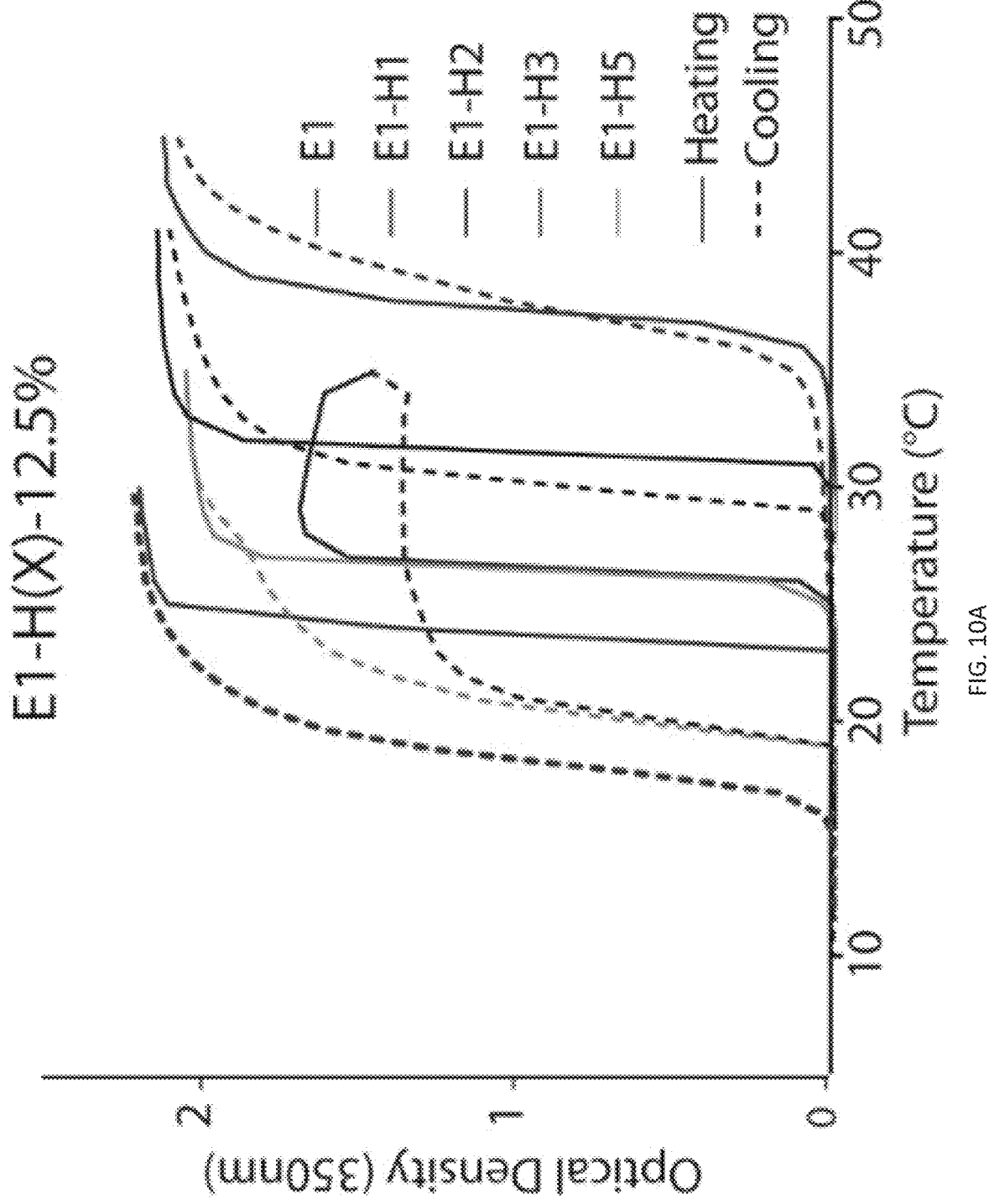
FIG. 10A-FIG. 10G: Additional turbidity data.
Figure 10B:
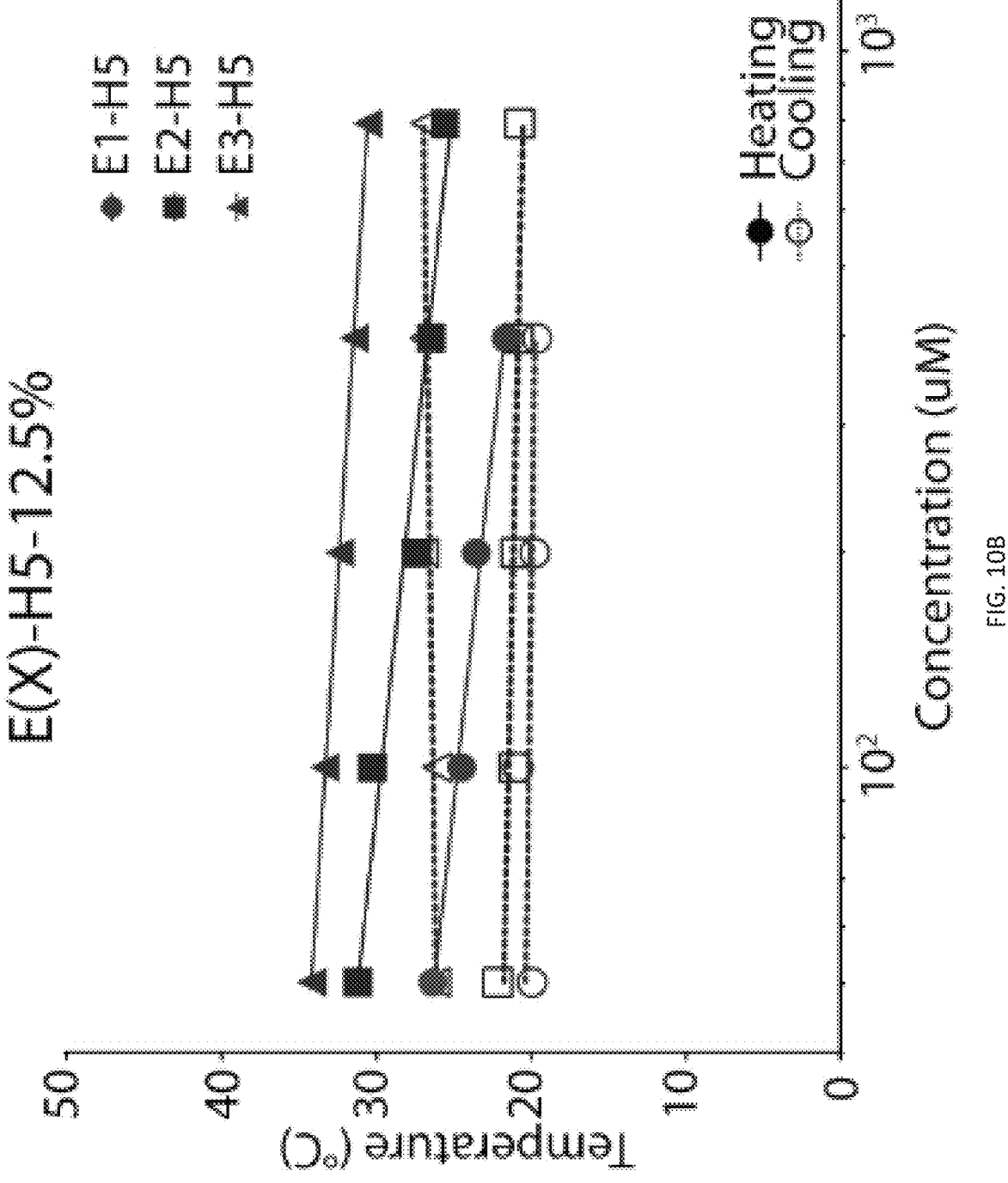
Figure 10C:
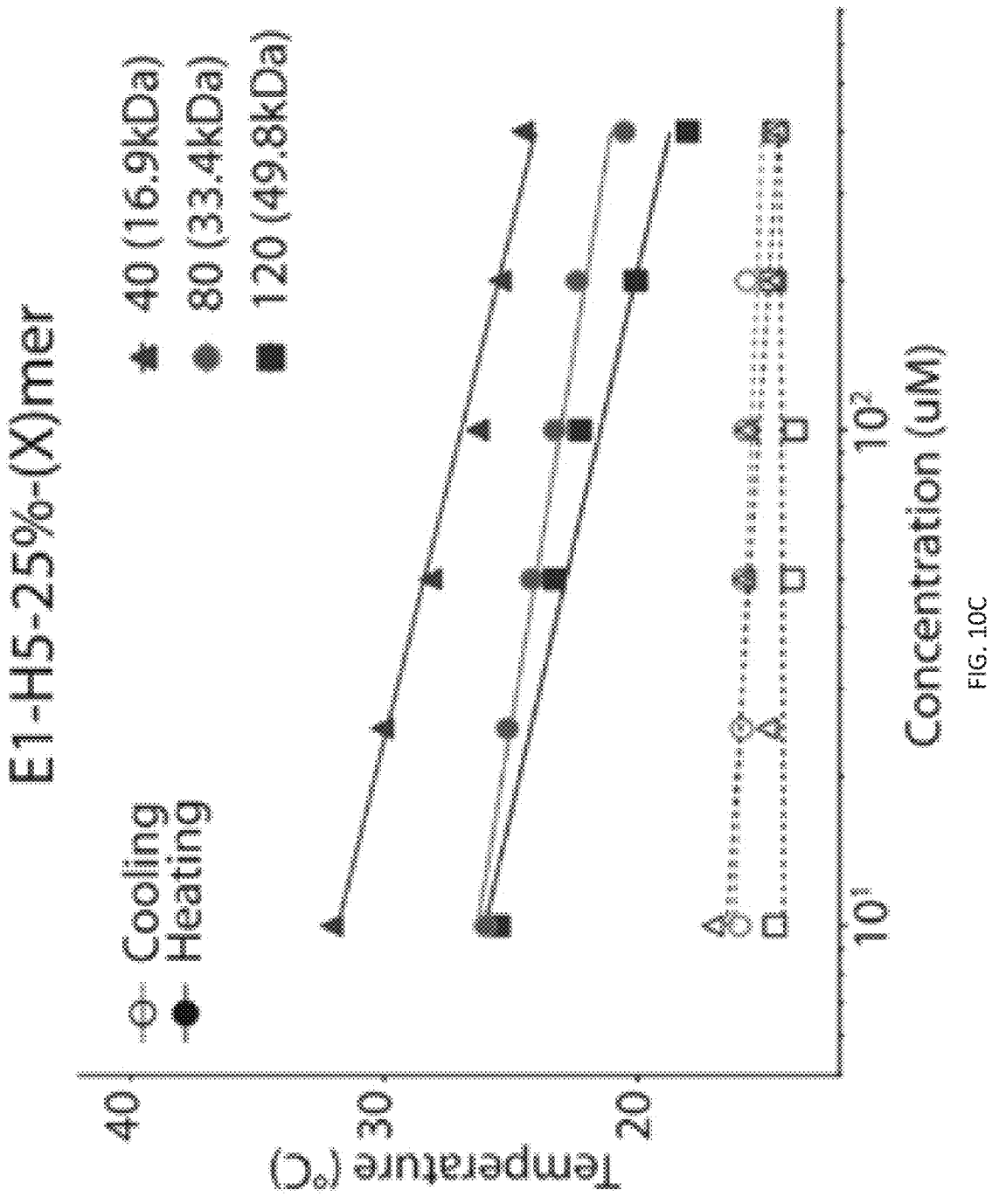
Figure 10D:
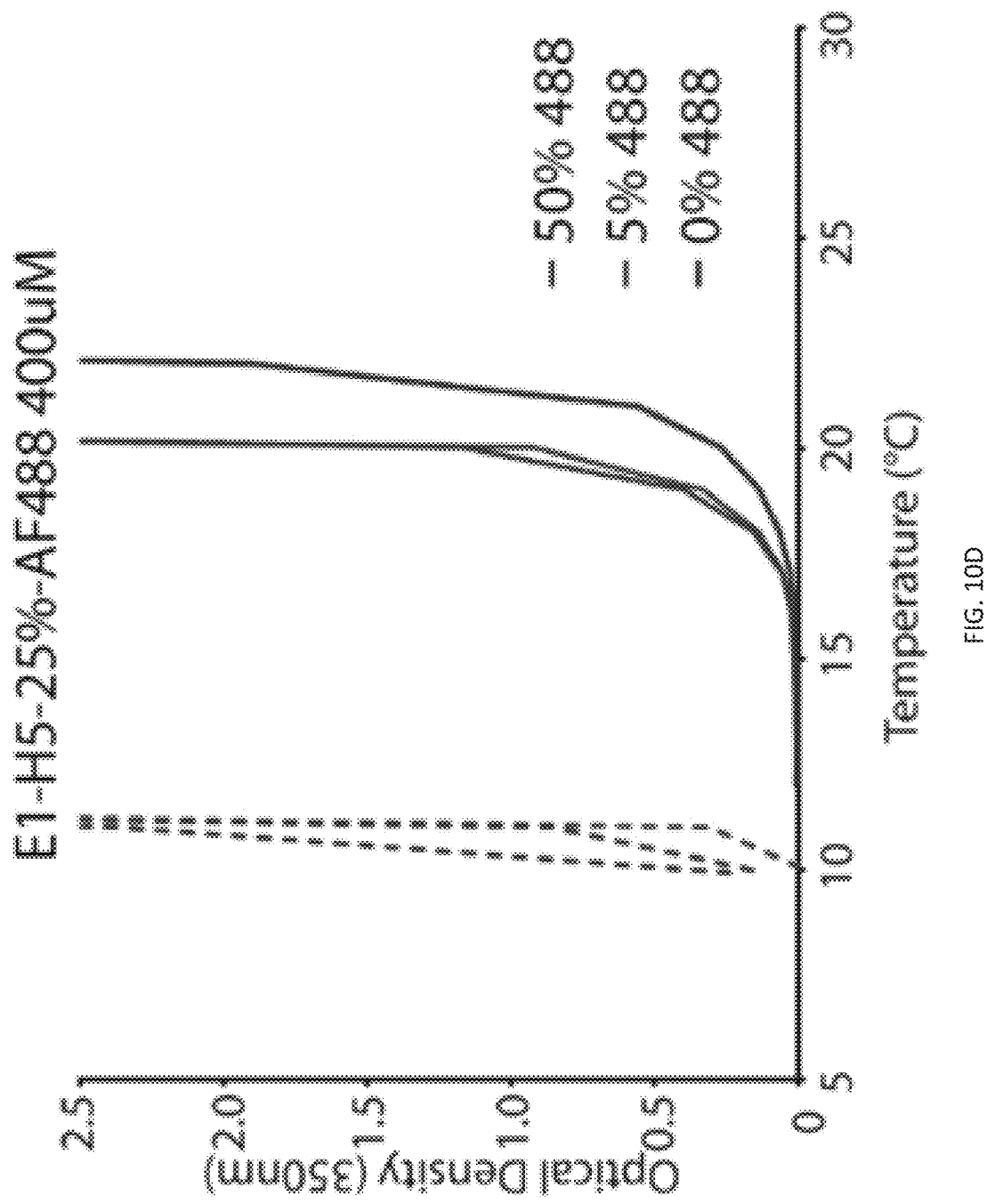
Figure 10E:
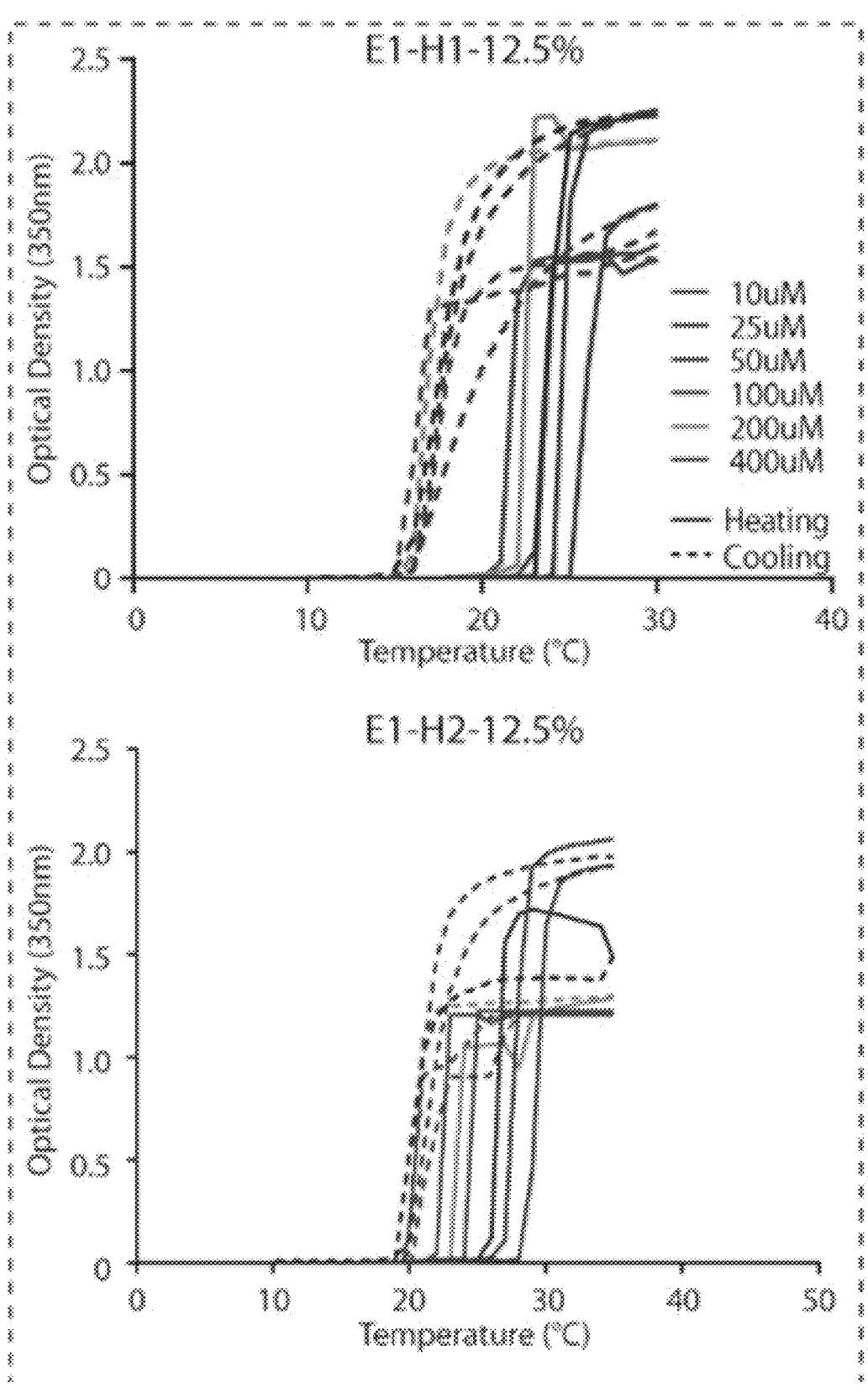
Figure 10E:
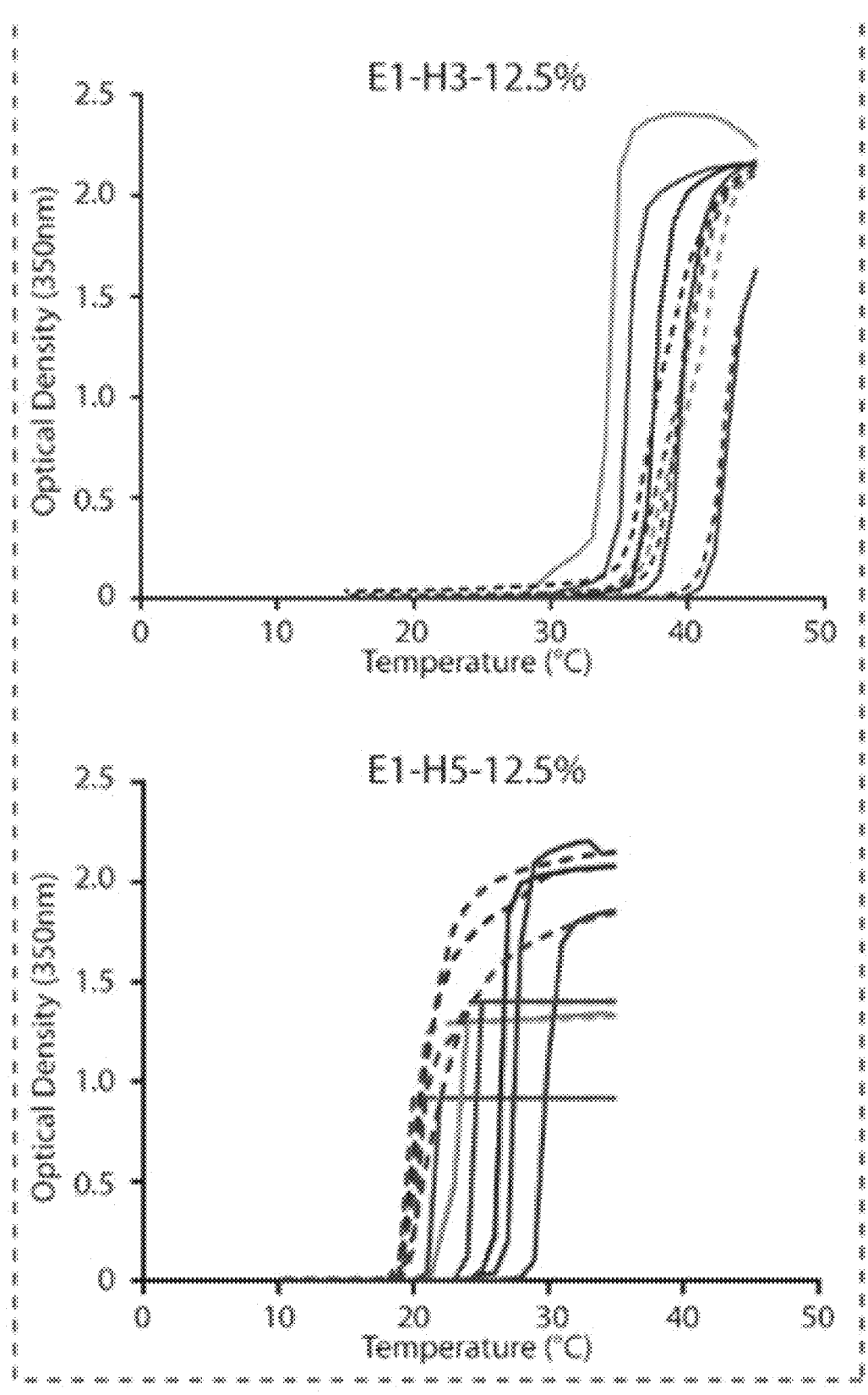
Figure 10F:
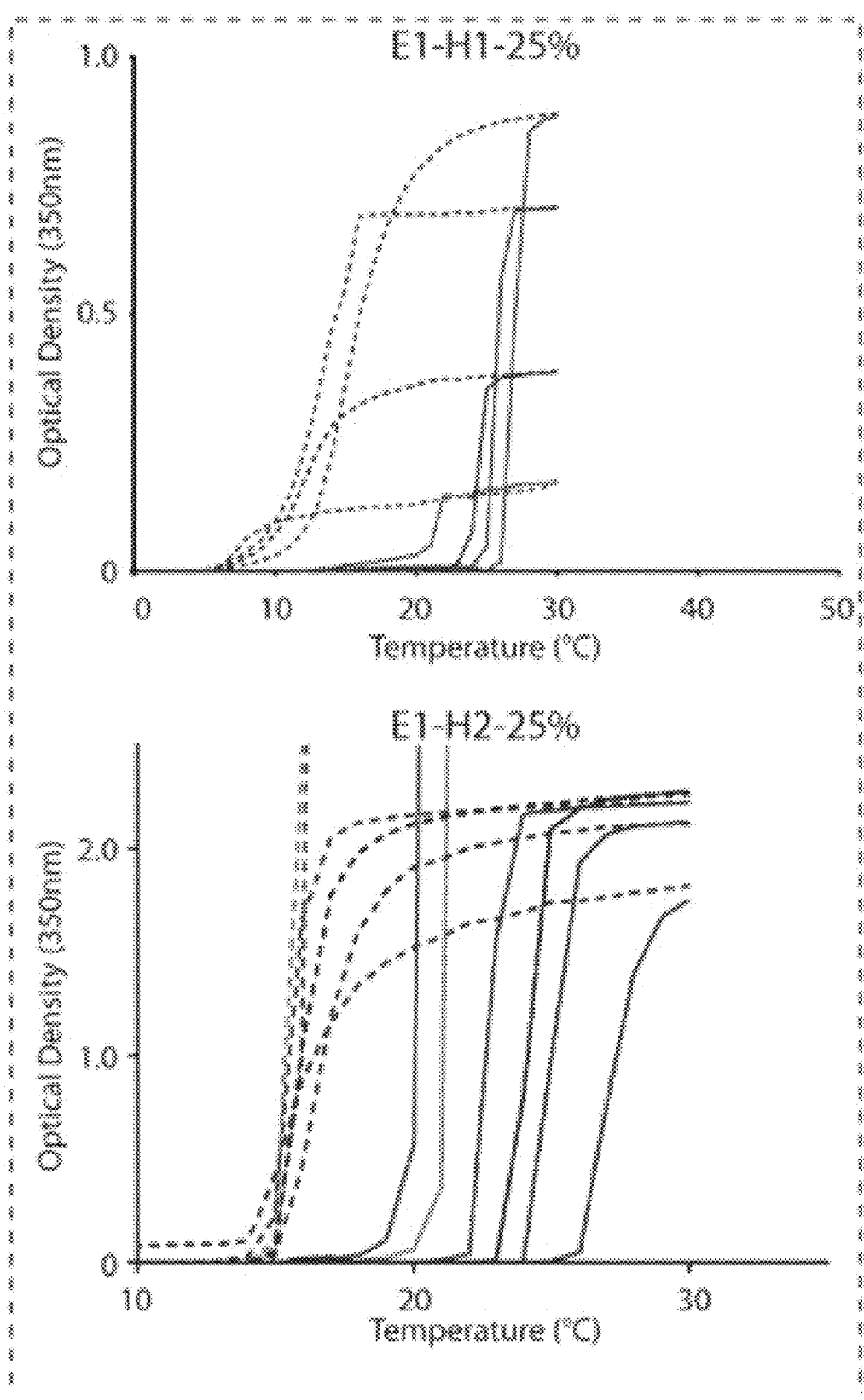
Figure 10F:
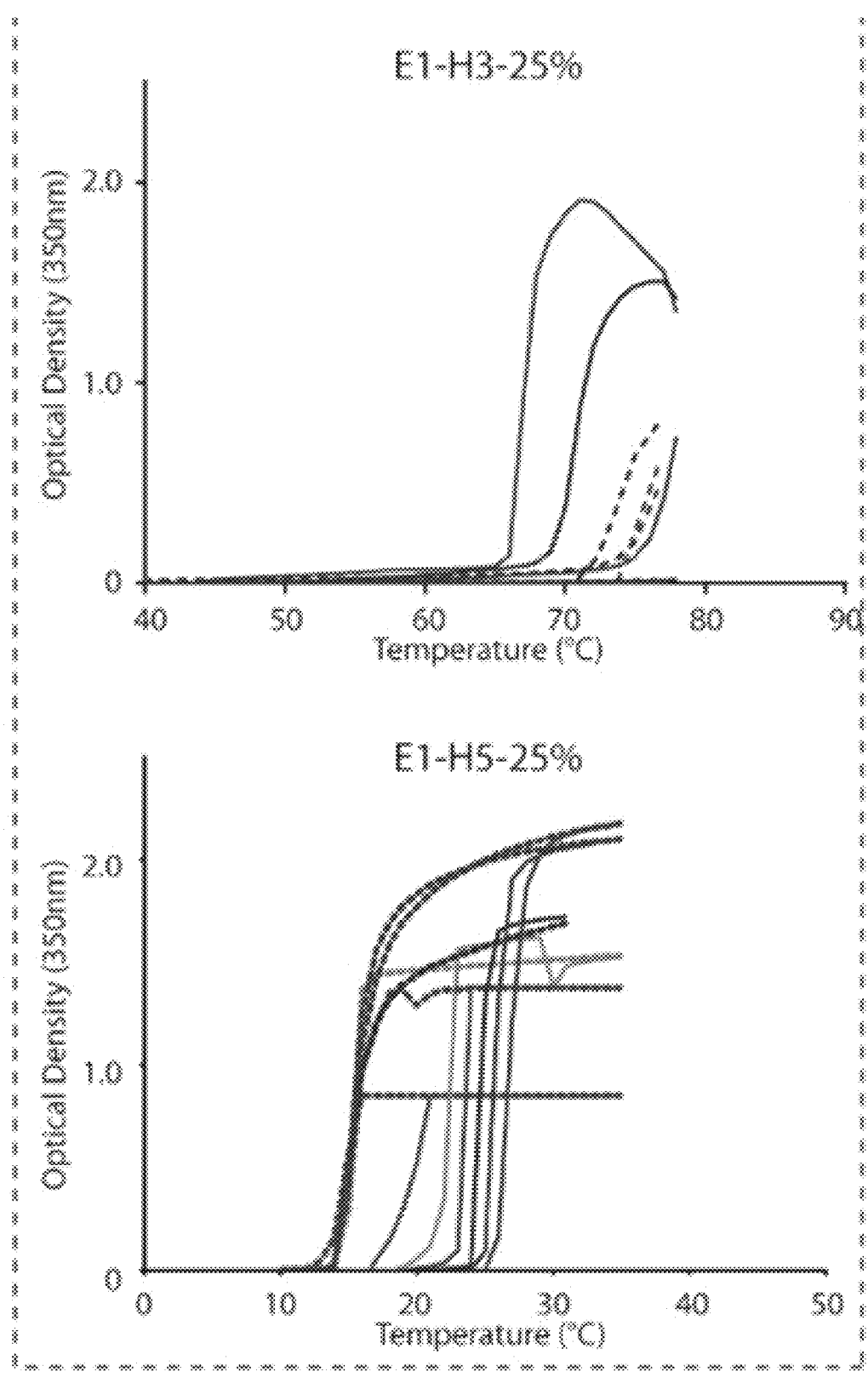
Figure 10G:
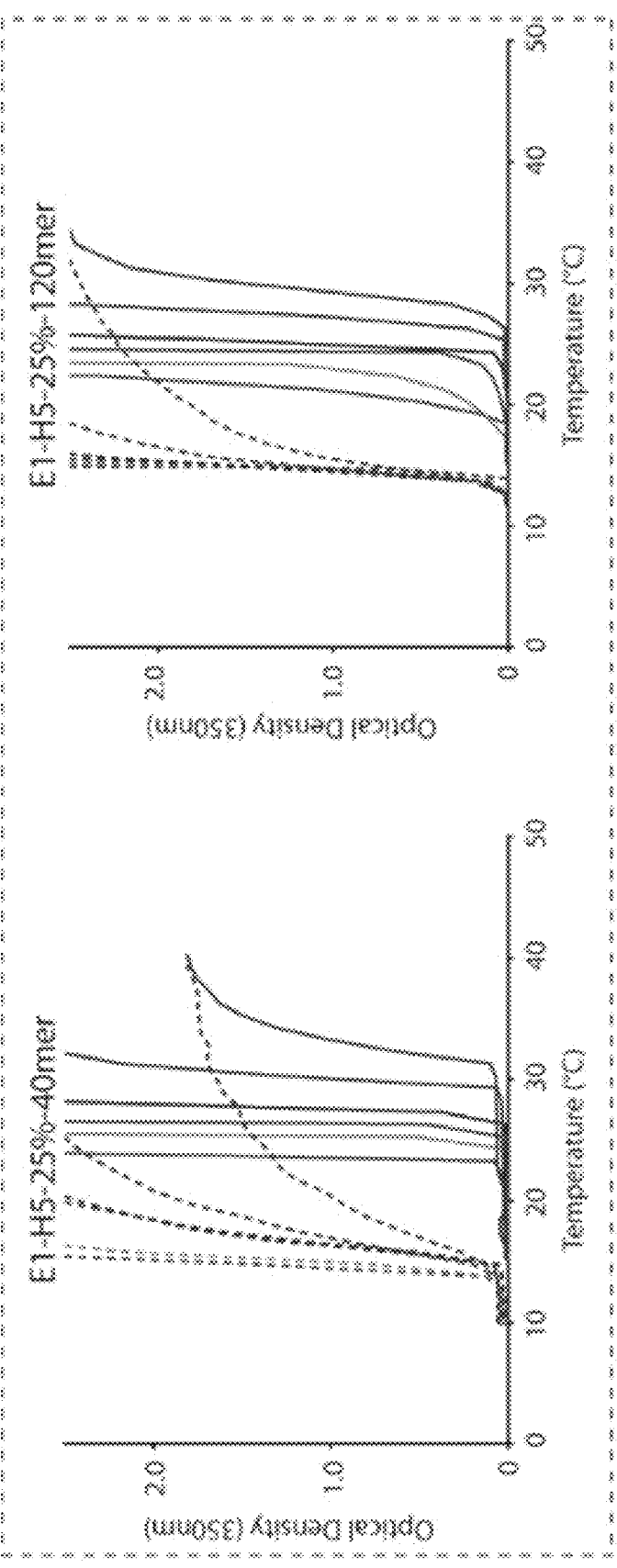
Figure 11A:
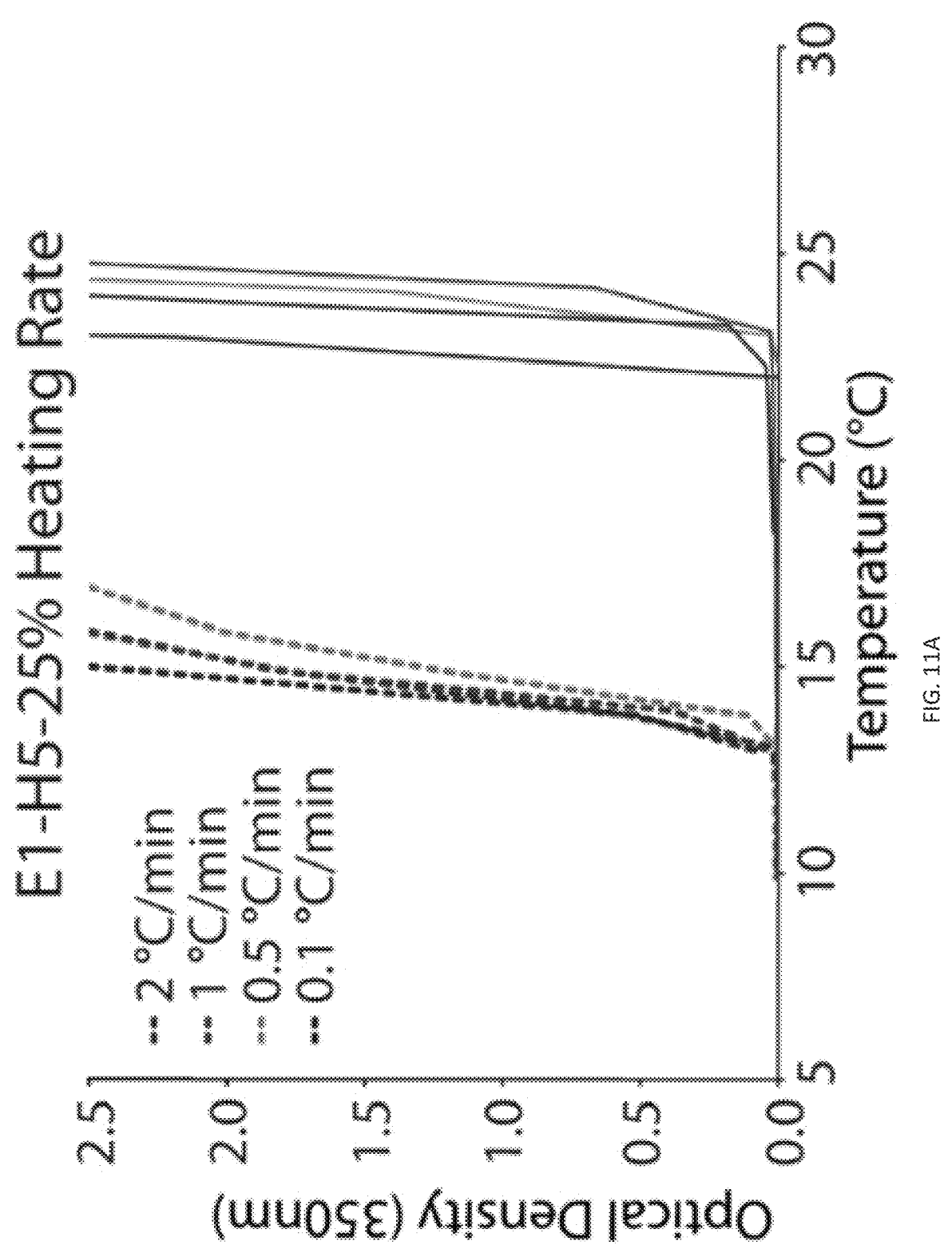
FIG. 11A-FIG. 11D: Kinetics of hysteresis. Altering the (FIG. 11A) heating rates and (FIG. 11B) cooling rates also does not change the phase behavior, though some settling occurs at slower cooling rates.
Figure 11B:
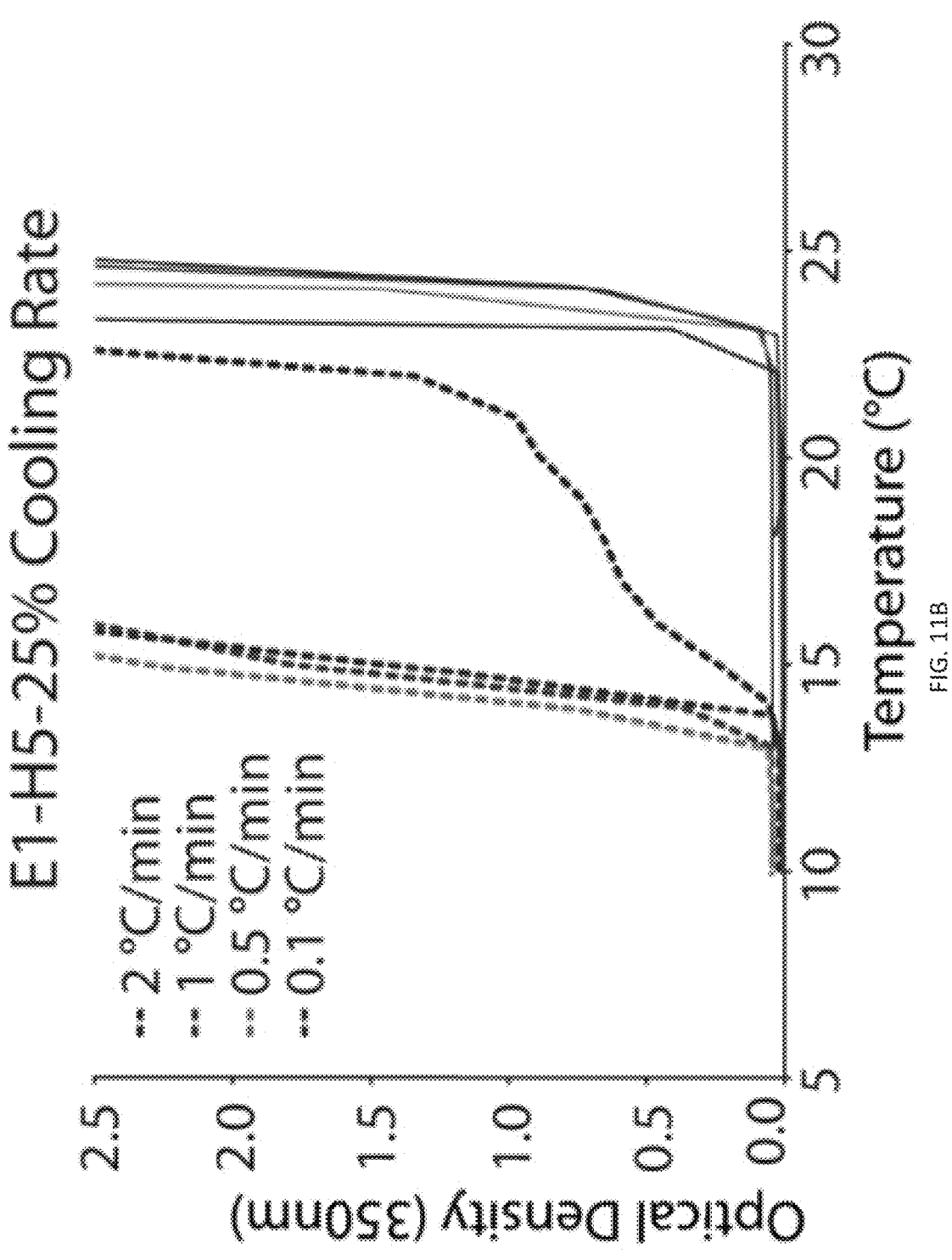
Figure 11C:
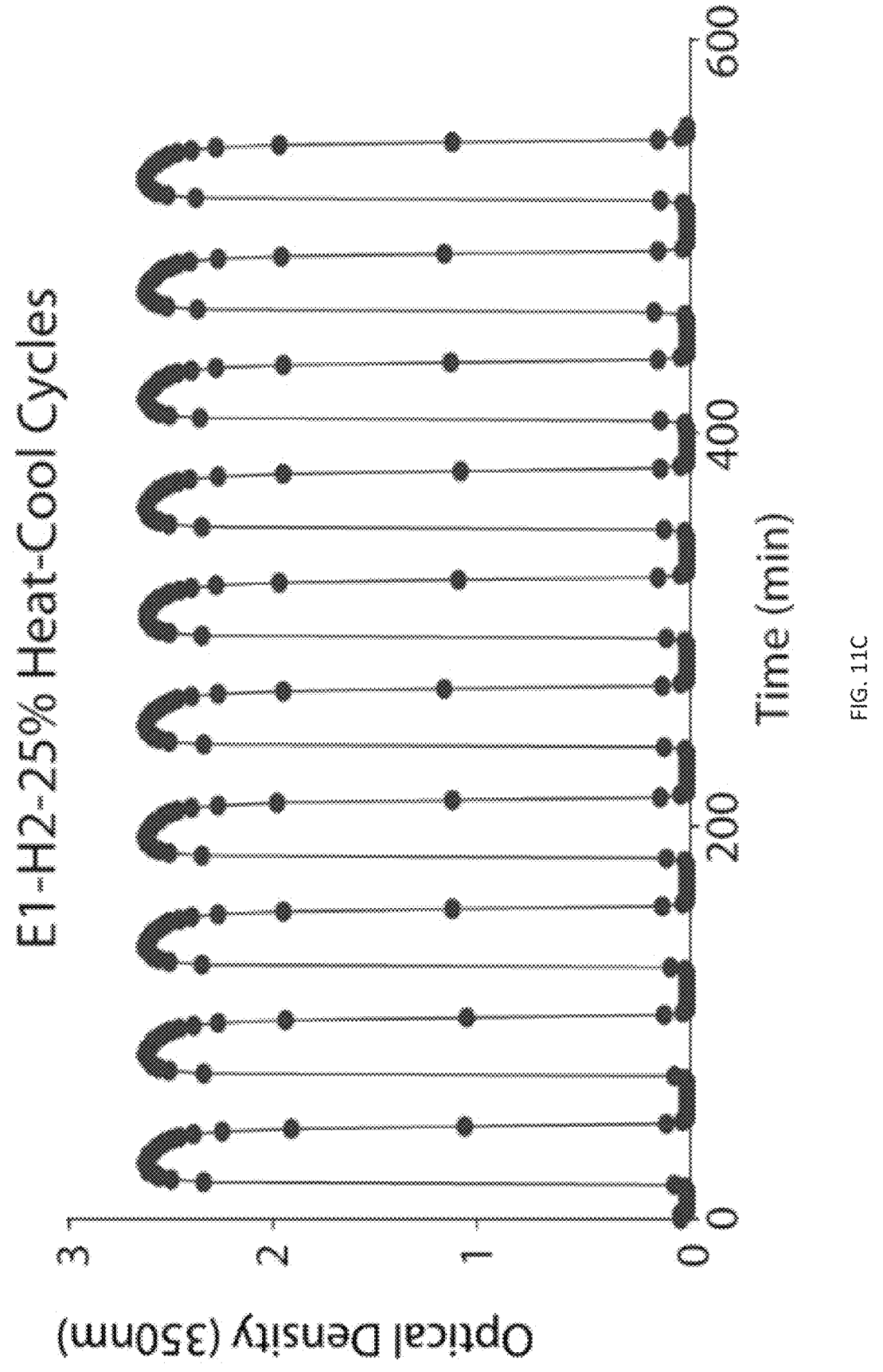
Figure 11D:
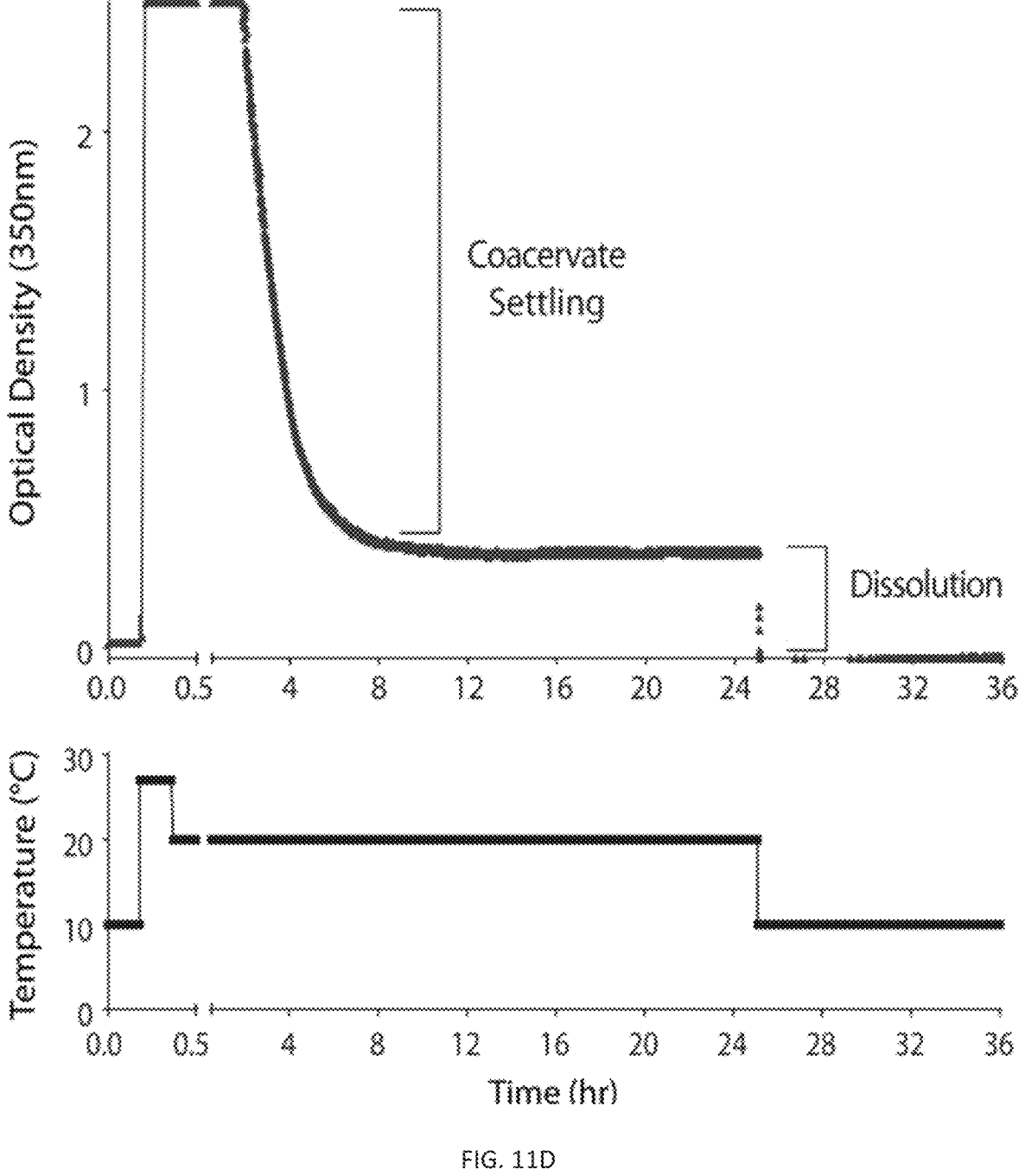

We used ultraviolet circular dichroism (UV-CD) to verify the secondary structure of POPs. All POPs show the negative ellipticity peaks at 222 nm and 208 nm (FIG. 1B-FIG. 1D and FIG. 8). These bands are characteristic of α-helices. Peak magnitudes are largely independent of polyalanine and ELP composition but are highly dependent on total polyalanine percentage. The helices are thermally stable with minimal melting at temperatures of up to 65° C. (FIG. 8). Helicity was quantified using BeStSel (TABLE 2)(Micsonai, A. et al. *Proc. Natl. Acad. Sci. U.S.A.* 2015, 112, E3095-3103); however, because quantitative analysis of UV-CD data for disordered proteins can be inaccurate, we also used 2D-solution NMR to determine POP helicity. Though the repetitive and proline rich nature of POPs increases the complexity of resonance assignments, identifying key amino acids was still feasible using combinations of triple resonance NMR spectra (FIG. 1F-FIG. 1G and FIG. 9). Based on the backbone carbonyl carbon chemical shifts of the alanine peaks in the H(N)CO spectrum—a particularly sensitive spectral signature for secondary structure changes—90% of the residues within each polyalanine domain (H2) were found to be in a helical conformation at 20° C. This result is supported by predictions from helix-coil transition theory (FIG. 1E) (Muñoz, V. & Serrano, L. *Nature Structural Biology* 1994, 1, 399-409; Munoz, V. & Serrano, L. *Journal of Molecular Biology* 1995, 245, 275-296; Munoz, V. & Serrano, L. *J. Mol. Biol.* 1995, 245, 297-308) and the temperature dependent change of the chemical shifts of backbone carbonyl carbons (TABLE 3). Given the similarity in UV-CD structural signatures (FIG. 1B), the remaining helical compositions can be confidently approximated to a similar degree of structure.

TABLE 3

NMR peak predicted helicity and temperature shift coefficients.

| Peak | Helicity* | Coefficient (ppb/K)** |
|------|-----------|------------------------|
| 1 | 93.0% | −19.6 |
| 2 | 91.9% | −20.8 |
| 3 | 90.9% | −20.7 |
| 4 | 89.4% | −24.2 |
| 5 | 86.0% | −25.7 |
| 6 | 84.1% | −29.1 |
| 7 | 79.7% | −30.3 |

*determined for H2 at 20° C. based on chemical shifts at 20° C.
**$^{13}$C in H(N)CO spectra Example 4

Sharp Phase Behavior and Tunable Hysteresis

ELPs exhibit thermally reversible LCST behavior, cycling between clear solutions and turbid states. We measured the thermal phase transition of our POPs by monitoring their optical turbidity as a function of temperature. Remarkably, all proteins demonstrate very sharp phase transitions that occur over a 1-2° C. range, even when composed of 50% α-helix (FIG. 2 and FIG. 10). These transition temperatures vary depending on the specific ELP and helix composition due to differences in their hydrophilicity and charge, but all POPs exhibit the sharp phase behavior characteristic of fully disordered ELPs.

Figure 2A:
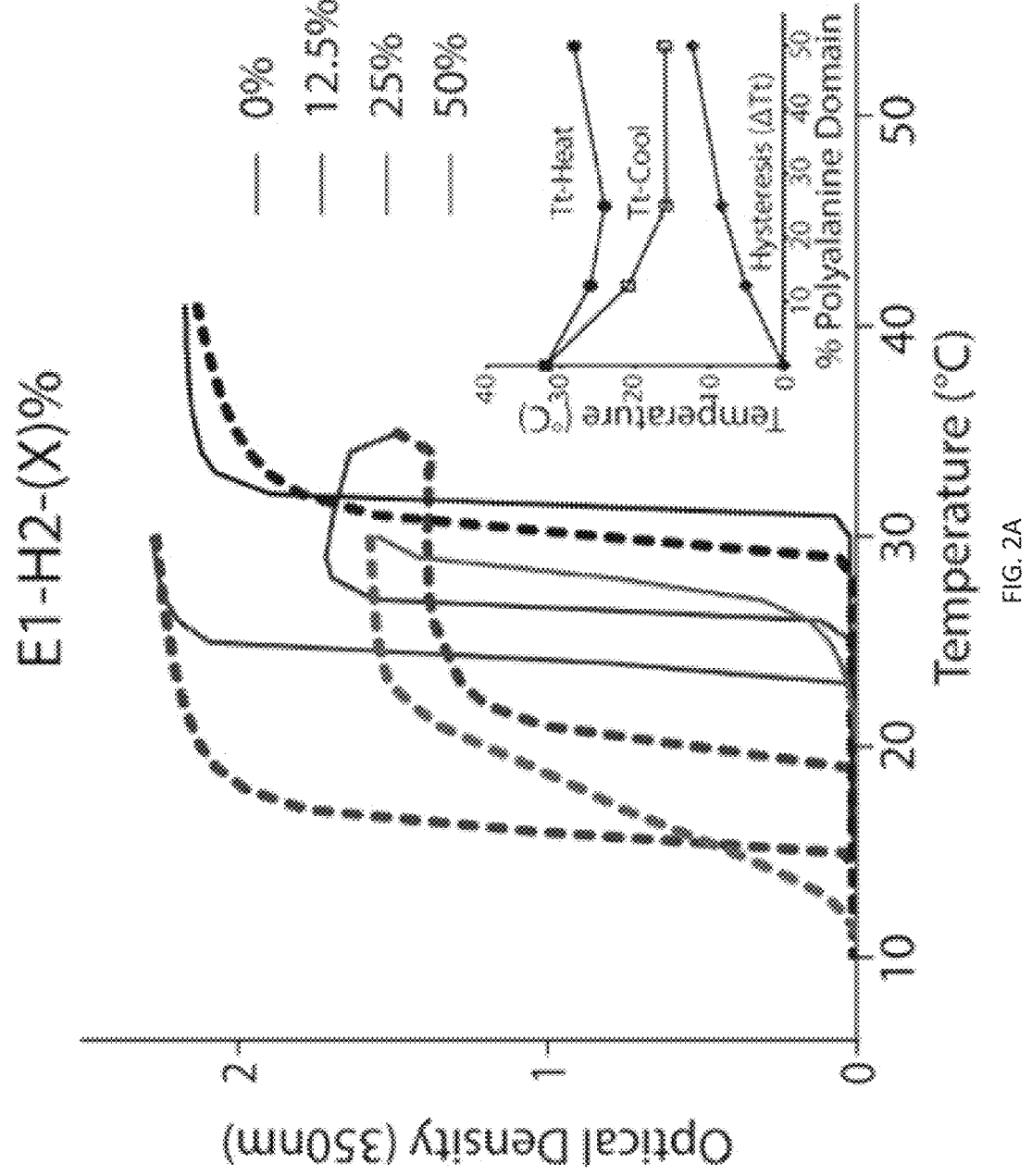
FIG. 2A-FIG. 2F: Turbidity and hysteresis. OD measurements as a function of temperature show sharp, reversible phase behavior and hysteresis for POPs.
Figure 2B:
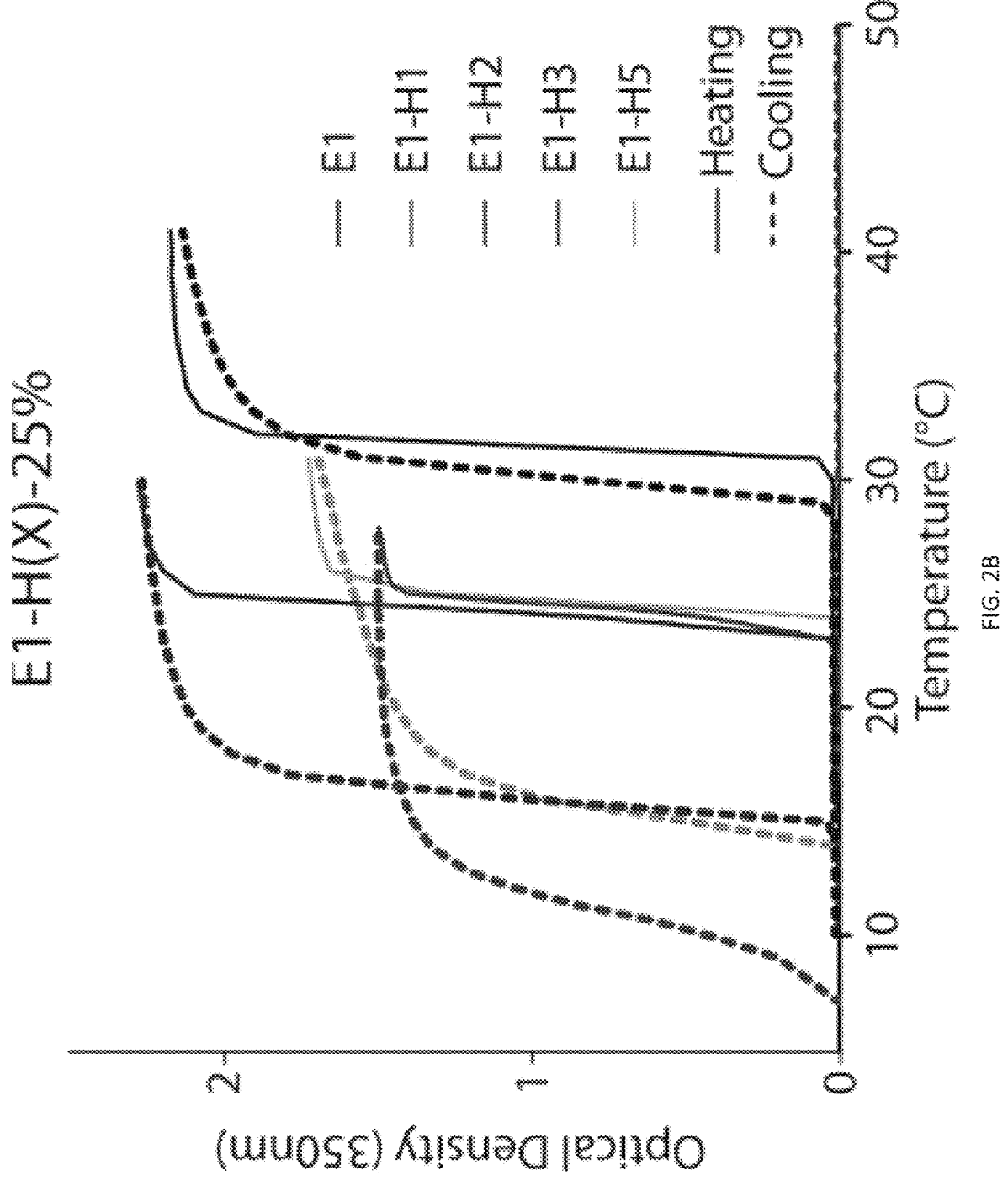
Figure 2C:
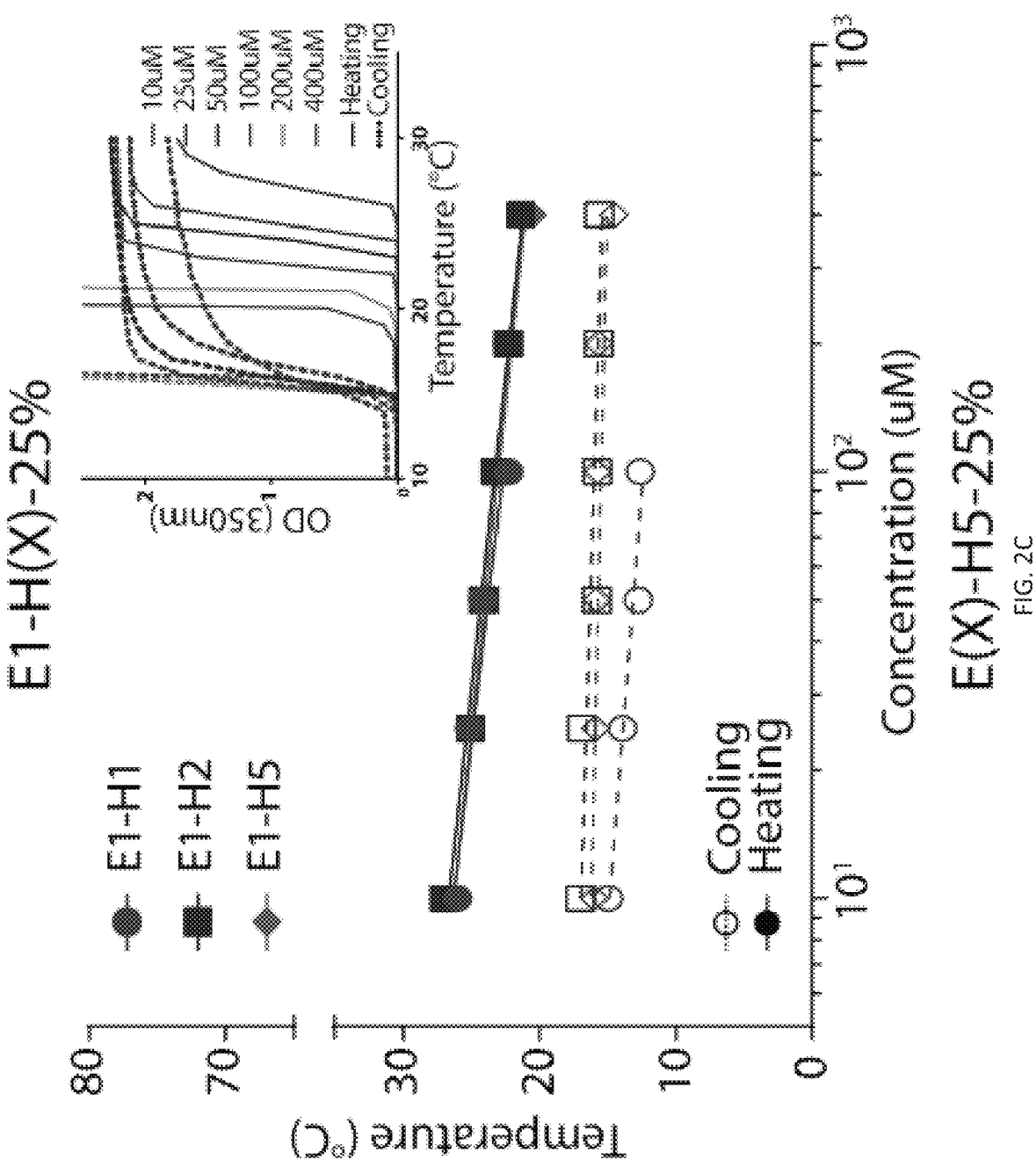
Figure 2D:
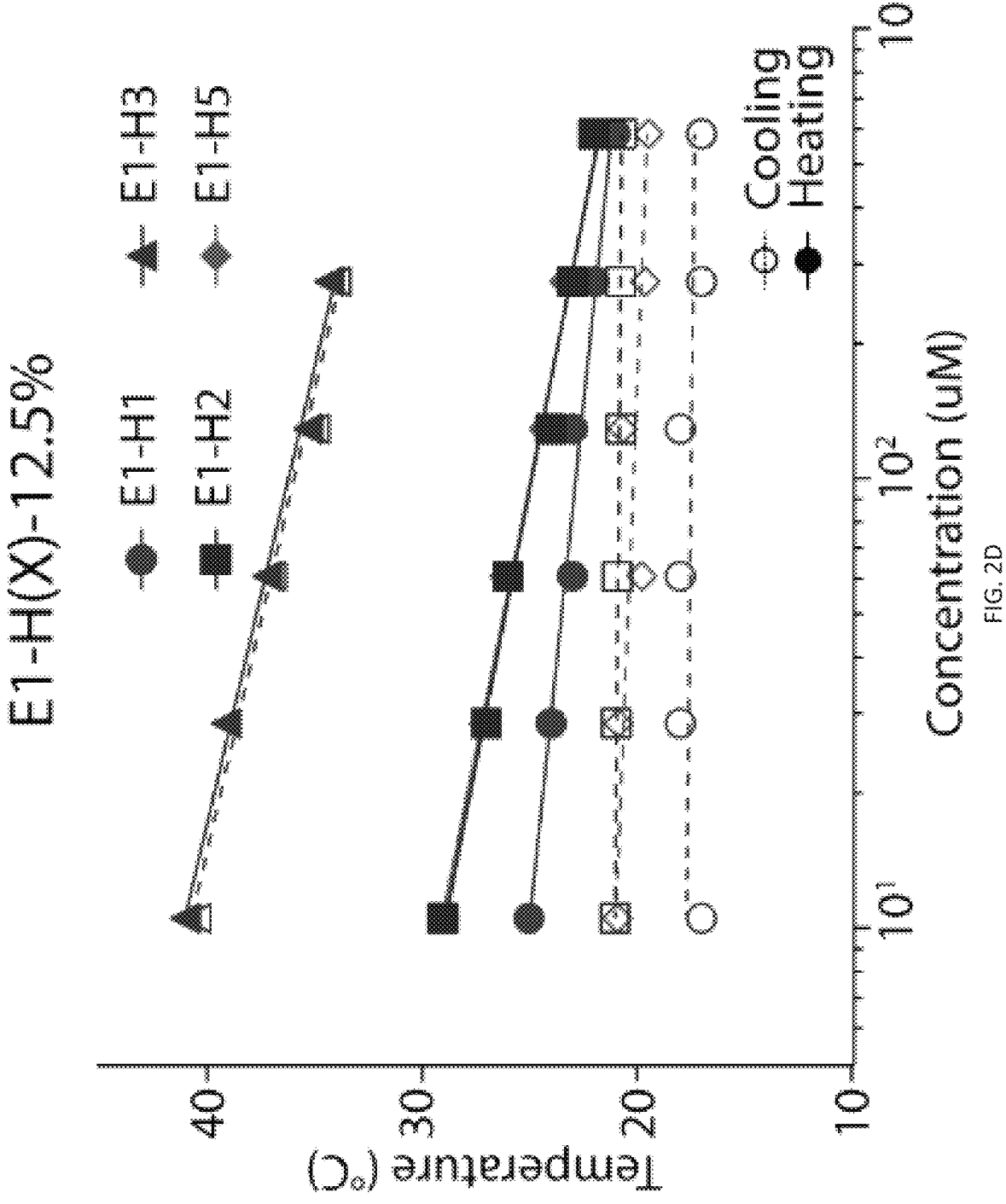
Figure 2E:
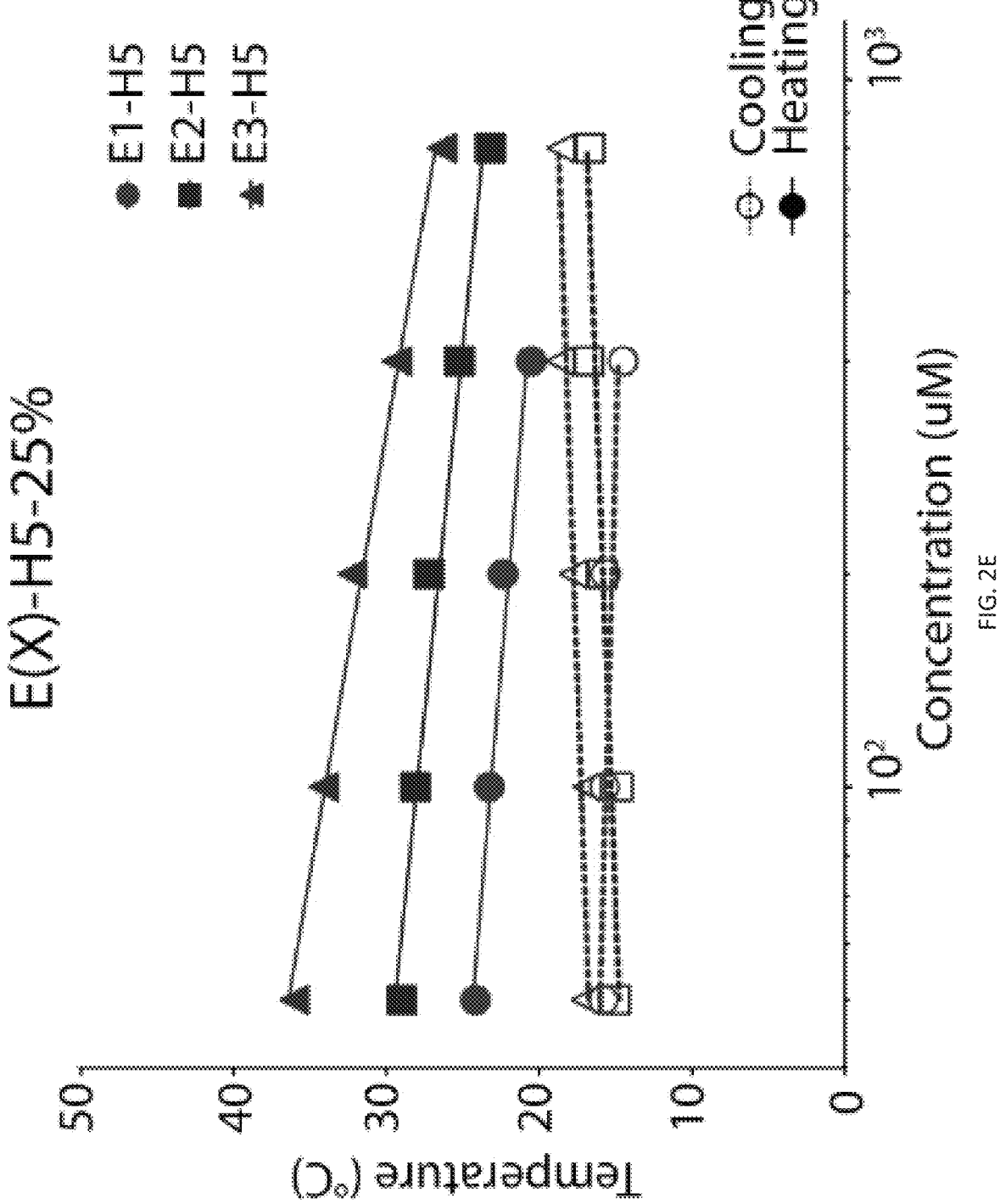
Figure 2F:
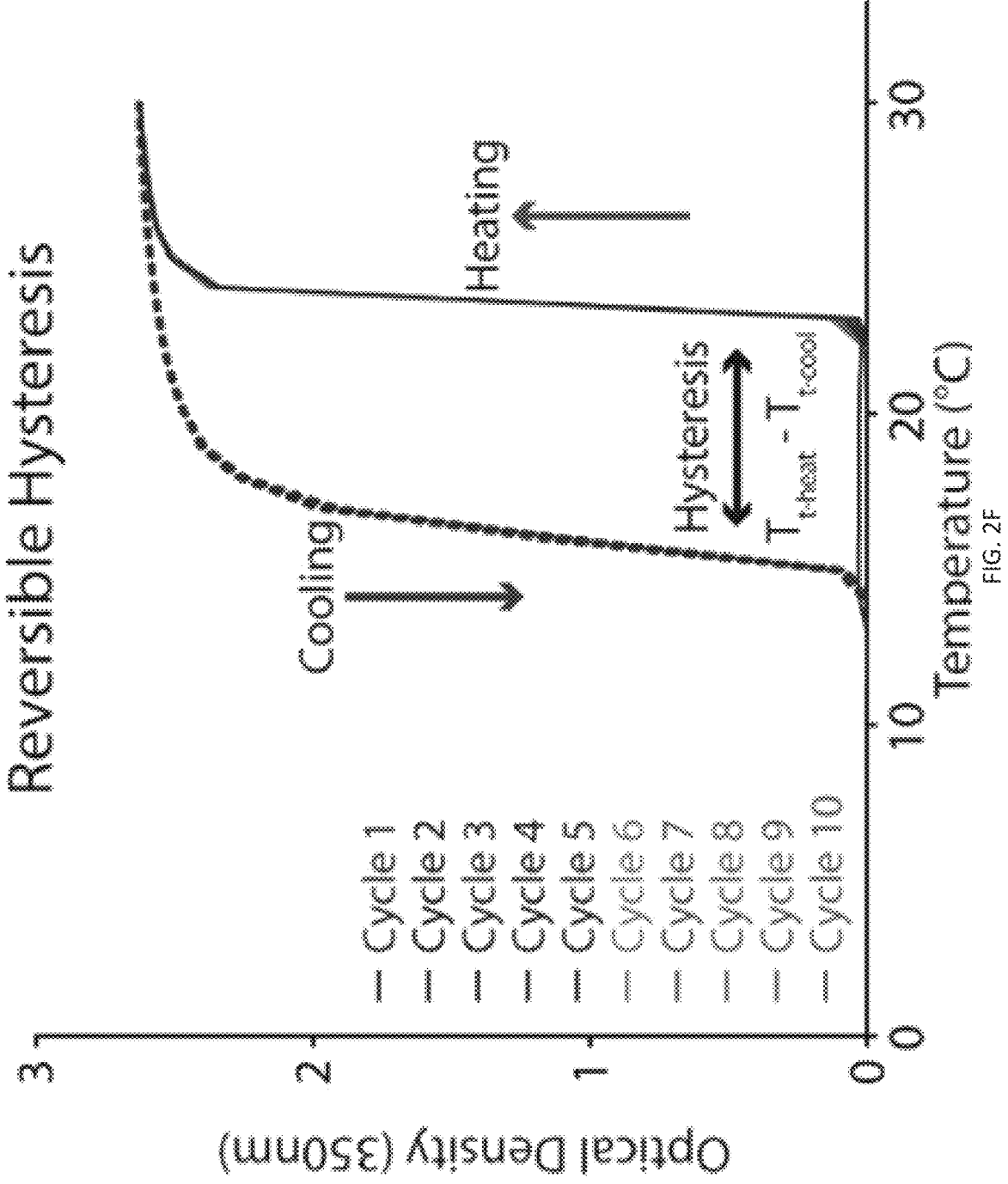

When turbid POP solutions are cooled, they form clear solutions; however, one aspect their behavior was of particular interest—the marked downshift in the $T_t$-cooling from the original $T_t$-heating. This thermal hysteresis, defined as the difference between $T_t$-heating and $T_t$-cooling ($\Delta T_t$), is not observed in ELPs although it has been advantageous in other recombinant polymers for the development of hyper-stable nano/micro-particles and for stabilizing protein scaffolds. However, the inability to tune the temperature range over which hysteresis occurs in these systems has severely impeded their application. In contrast, the thermal hysteresis in POPs can be precisely controlled as it directly correlates with polymer helicity (FIG. 2A) and inversely correlates with the amount of charge on the helix side chains (FIG. 2B-FIG. 2D and FIG. 10). Importantly, once fully solvated, POPs return to their original state and can be cyclically heated and cooled with no permanent alterations (FIG. 2F). By incorporating helices with sufficient charge repulsion, such as H3, hysteresis can be eliminated altogether. Hysteresis is independent of both heating and cooling rates, and polymers heated and then cooled to their hysteretic range remain aggregated after 24 h (FIG. 11). Subsequent cooling below the $T_t$-cooling after 24 h causes rapid dissolution.

For POPs, The $T_t$-heating scales logarithmically with polymer concentration, in accordance with ELP behavior. However, $T_t$-cooling is independent of concentration (FIG. 2C-FIG. 2E). Altering the ELP composition adjusts the $T_t$-heating appropriately, but does not change the $T_t$-cooling (FIG. 2E). These observations indicate that the $T_t$-heating is controlled by the composition and chain length of the ELP segment, while the helix composition is the primary determinant for $T_t$-cooling. Tuning these two apparently orthogonal parameters—composition of the ELP segment and fraction of helical residues in the POP—at the sequence level provides a dial to tune the temperature for the onset of thermal hysteresis and the temperature range of hysteresis at the sequence level. These attributes are likely to be useful for specific applications that require hysteresis to encode memory effects.

Example 5

A Model for the Mechanism of Hysteresis

Figure 12A:
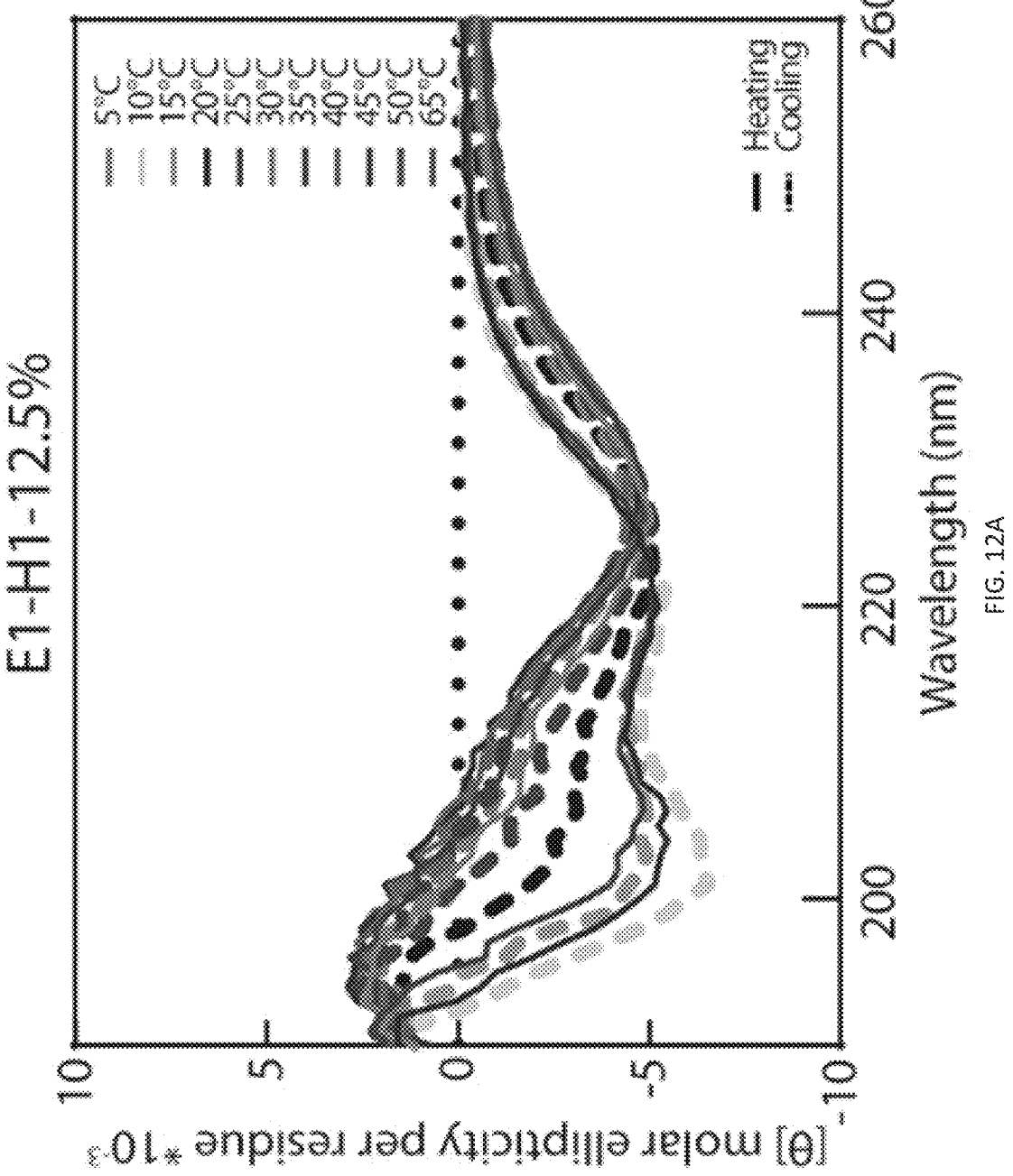
FIG. 12A and FIG. 12B: Temperature dependent CD.
Figure 12B:
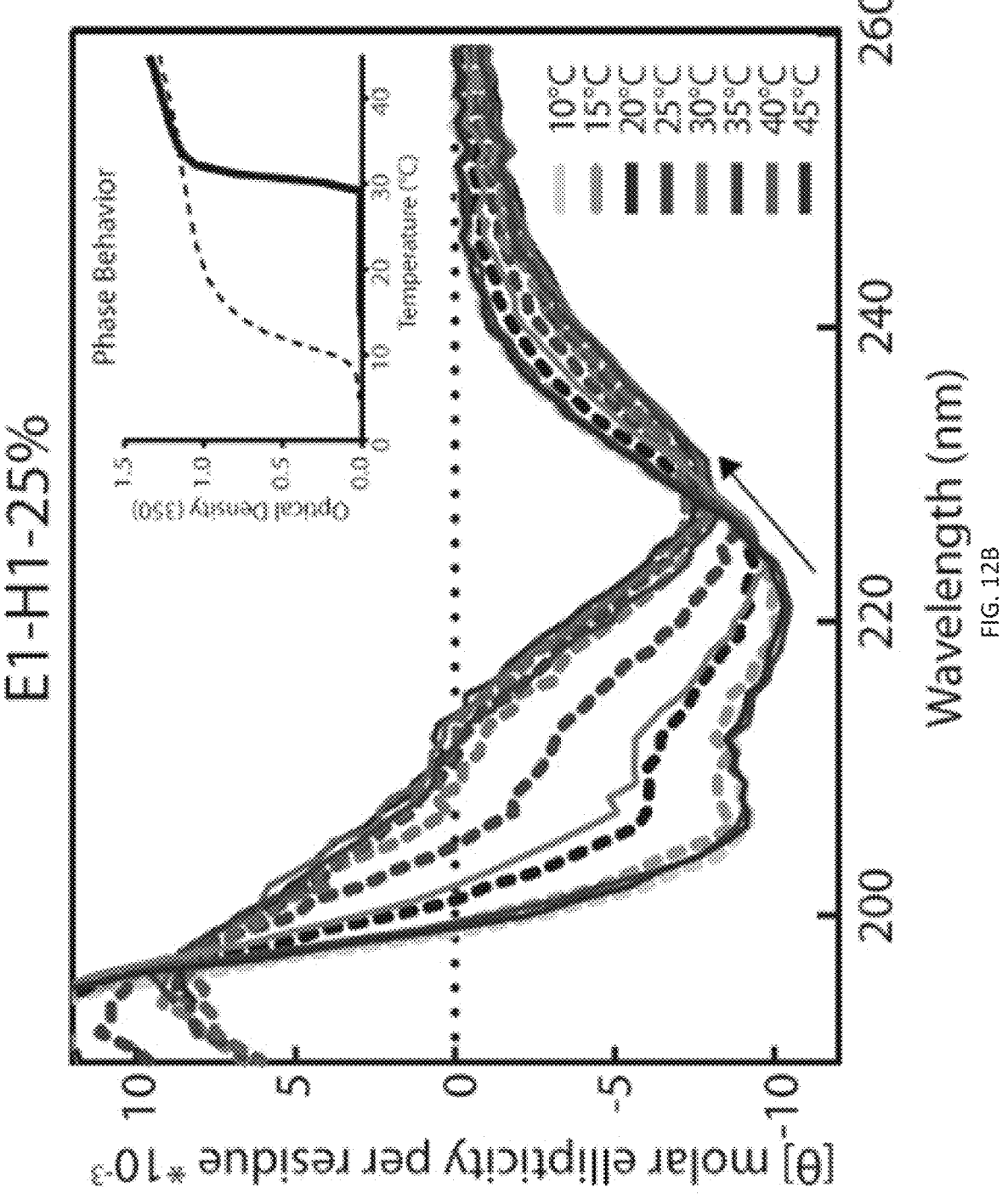
Figure 13B:
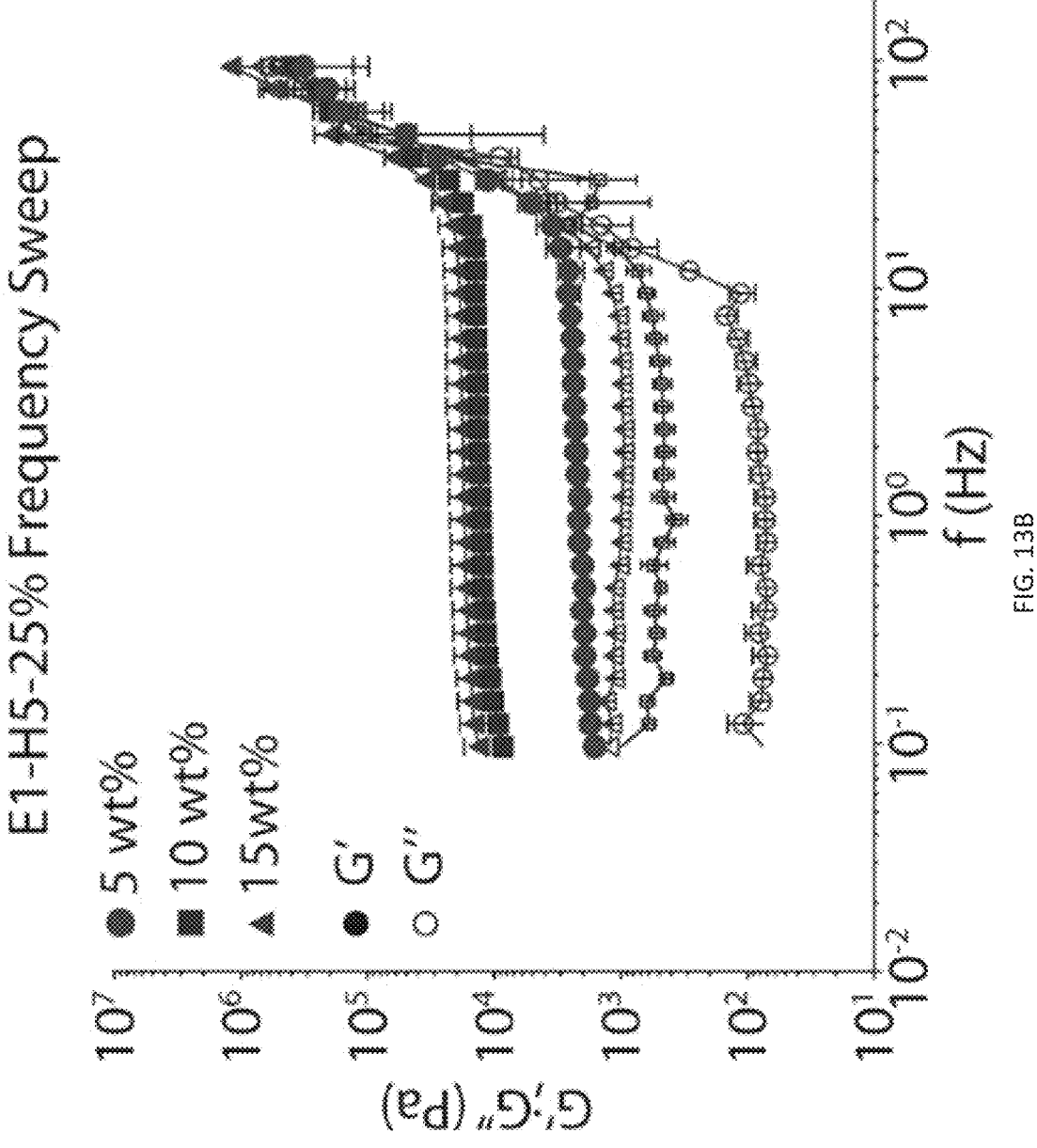
Figure 13C:
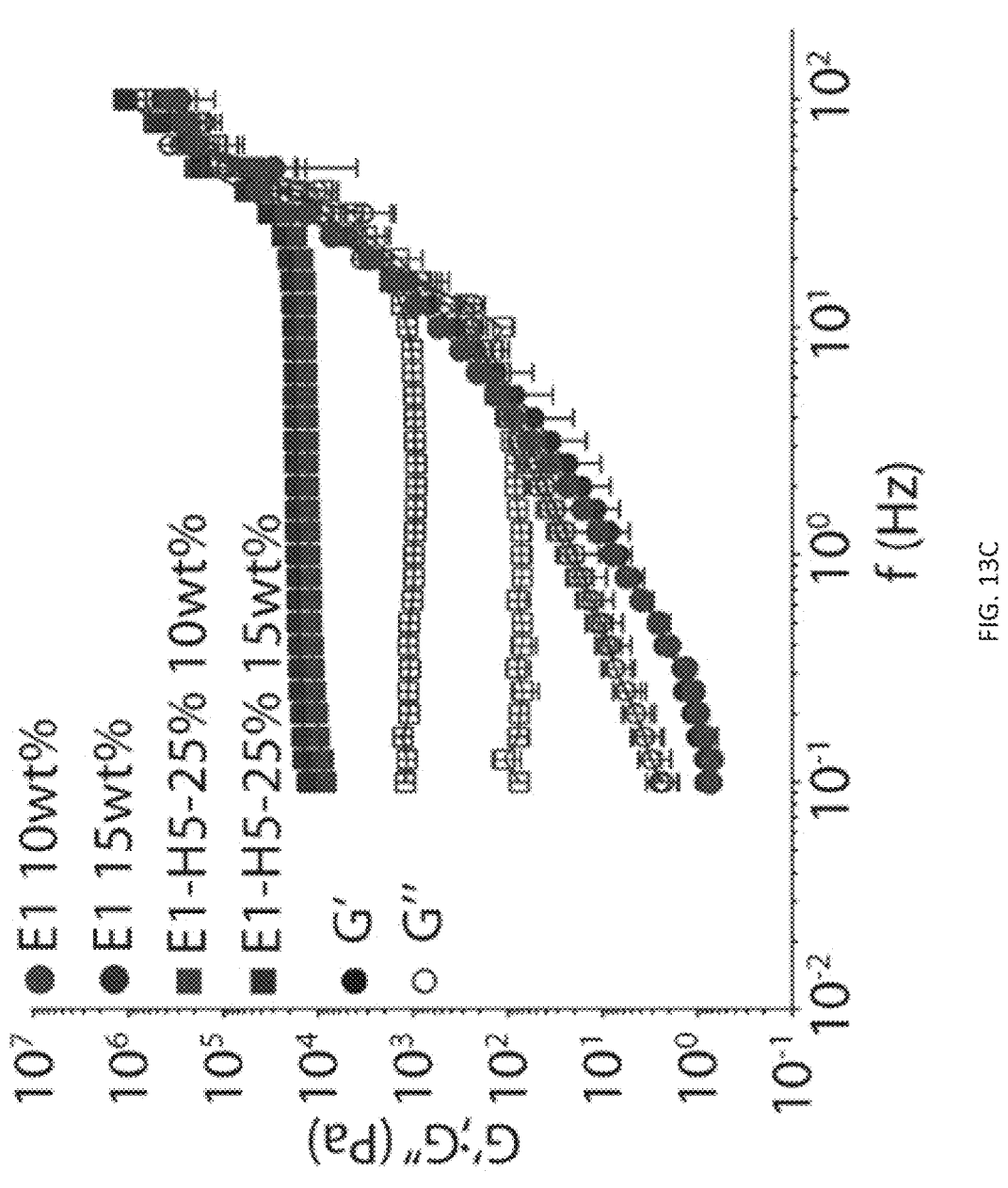
Figure 13D:
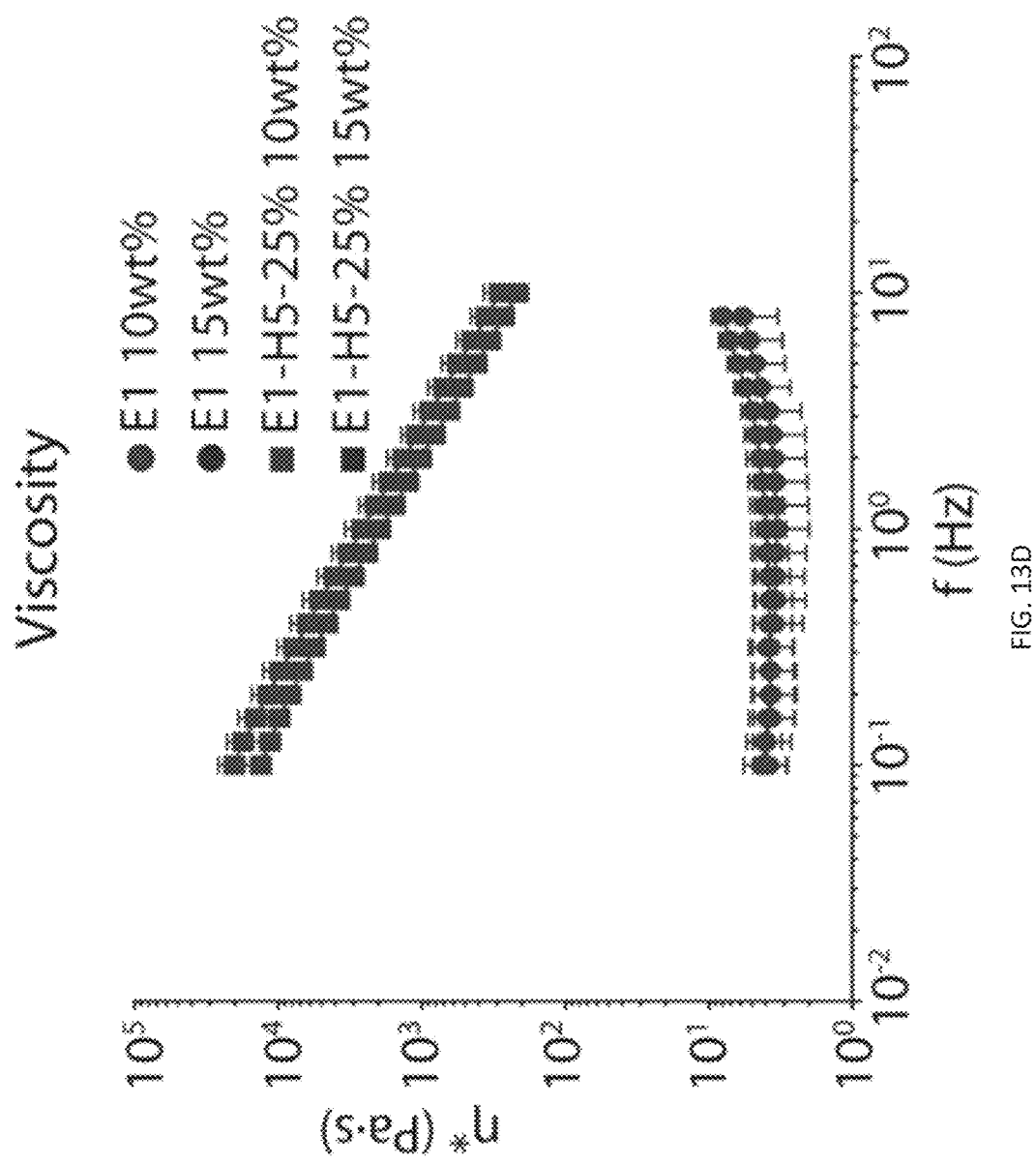
Figure 13E:
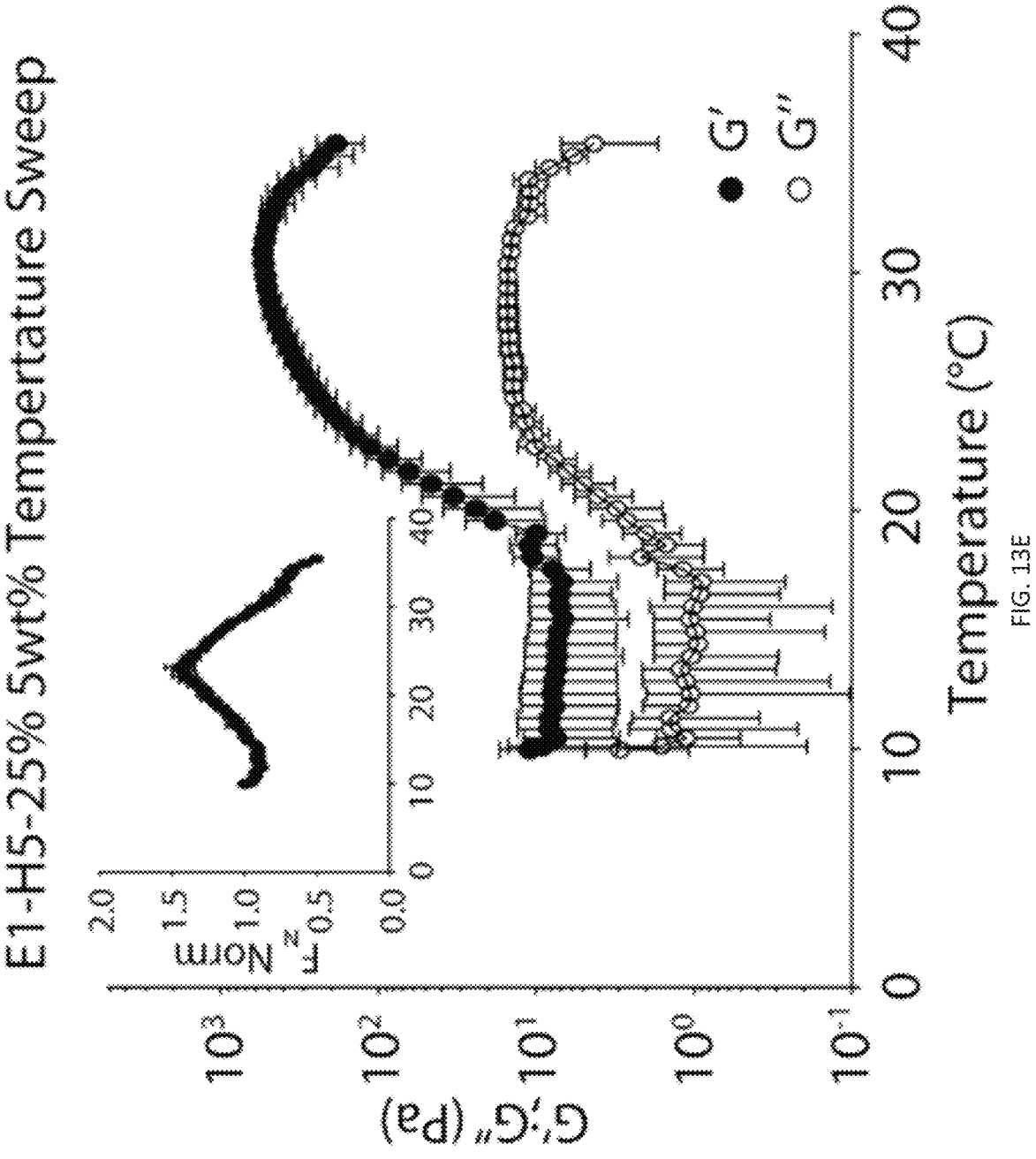

Thermal hysteresis is commonly attributed to changes in secondary structure. Because polyalanine can adopt coil, helical, and beta configurations (Ding, F., et al. *Proteins* 2003, 53, 220-228), we first analyzed POPs to determine if a secondary structure shift upon aggregation was driving this behavior. UV-CD spectra of a hydrophilic POP (E1-H3-25%) indicate that, in the absence of self-associations, the polymers retain a high degree of helicity up to 65° C. (FIG. 8). POPs that do phase separate show distortions in the UV-CD spectra that are consistent (FIG. 12) with those observed for proposed helical bundles of tropoelastin. These spectral shifts suggest the presence of bundled helices within the POP assemblies. This observation is consistent with the proposed coacervation of tropoelastin, in which polyalanine domains retain their structural integrity during coacervation to stabilize side-chain interactions for crosslinking.

Figure 3B:
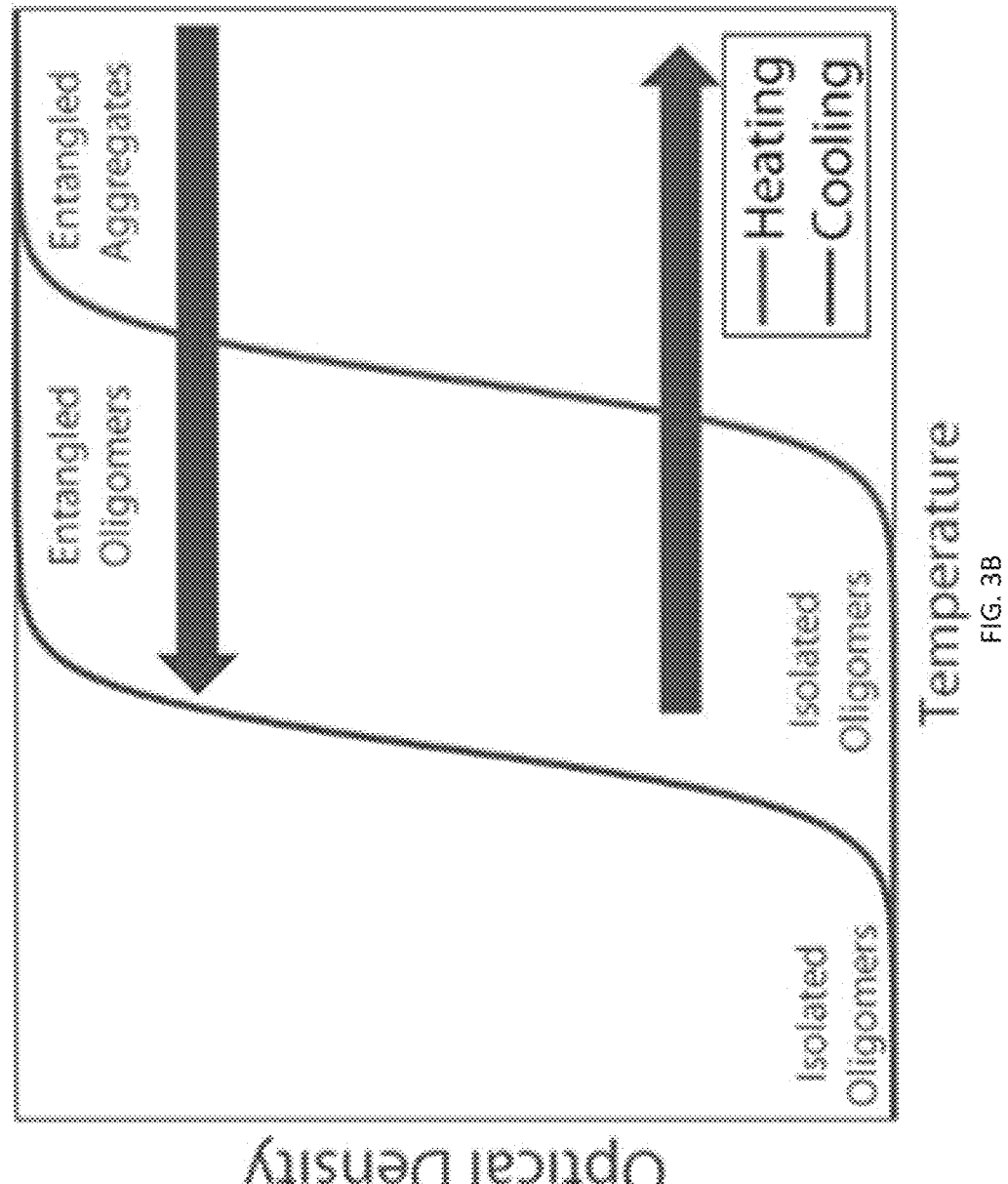
Figure 3C:
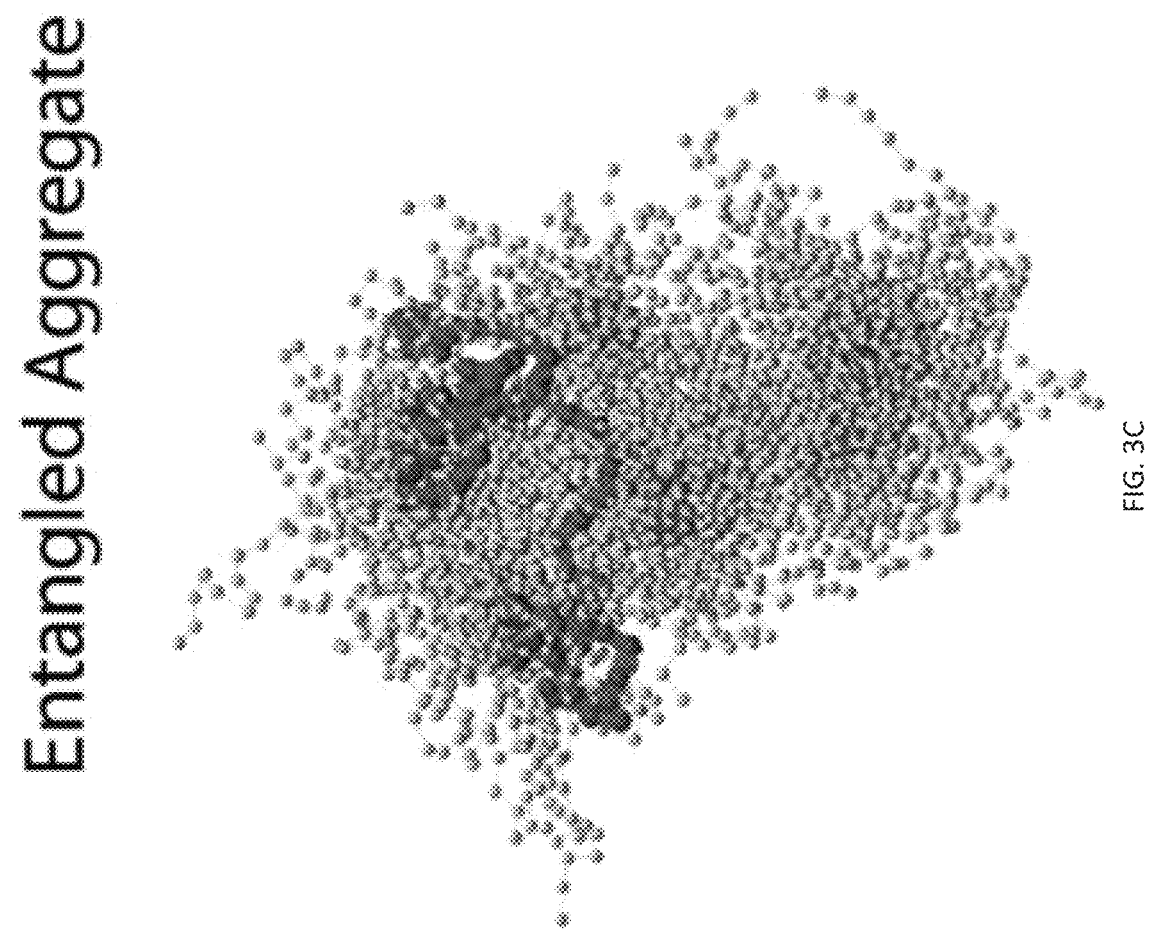
Figure 3D:
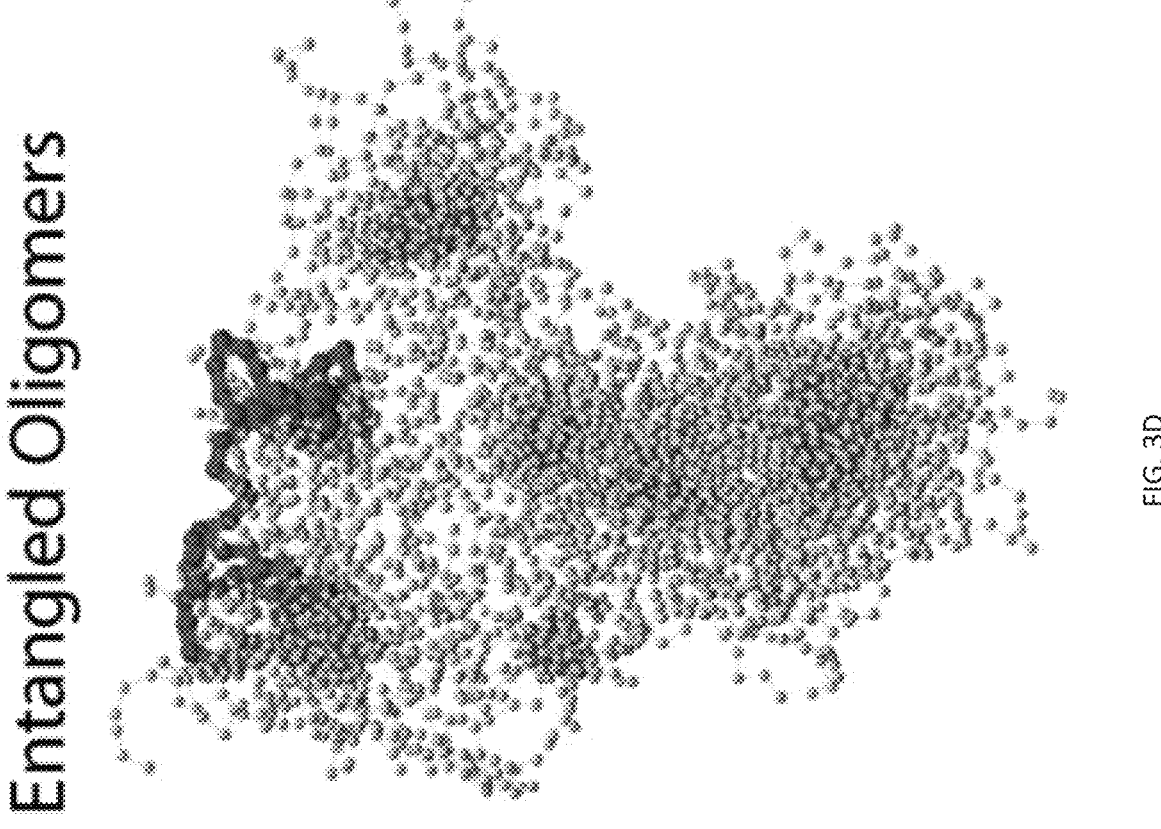

Given the intrinsic tendency of polyalanine to form helical bundles (Bernacki, J. P. & Murphy, R. M. *Biochemistry* 2011, 50, 9200-9211; Miller, J. S., et al. *Journal of the American Chemical Society* 2002, 124, 945-962) and the persistence of helices within POP aggregates, we propose helical bundling is a significant contributor to hysteresis. To test this proposal, we performed proof-of-concept assessments using coarse grain molecular dynamics simulations. We used a phenomenological model that separates the protein domains into two categories of pentapeptide "beads": polyalanine (AAAAA) (SEQ ID NO:38) and ELP (VPGVG) (SEQ ID NO:39). Polyalanine interaction energies ($E_{AA}$) are always preferred because this promotes polyalanine self-associations; ELP interaction energies ($E_{EE}$) change with temperature, increasing in strength above the $T_t$-heating. ELP-polyalanine interactions ($E_{EA}$) were always unfavorable. We simulated a hysteretic cycle for 50 polymers of 25% helicity (E1-H1-25%) in a 25 nm radius spherical box. The results (FIG. 3) suggest that POPs move through four stages during a thermal cycle. (1) Below their $T_t$-heating, POPs are isolated oligomers with local helical clusters that are solvated by ELPs. (2) Above the $T_t$-heating, localized clusters dock due to the increased favorability of ELP hydrophobic interactions. (3) Given sufficient time, the alanine domains exchange with neighboring clusters such that single POPs span multiple clusters, entangling them into a percolated network. Swapping helices between clusters is feasible because of the high density in the docked state and is thermodynamically favored through the entropy of mixing. As the temperature increases further and the ELP repulsive term further decreases, a second reversible transition becomes favored where docked spherical clusters convert into denser, less dynamic linear aggregates. (4) Once cooled below the $T_t$-heating, aggregate entanglement prevents dissolution of the ELP domains, producing entangled oligomers. Unlike the fast and irreversible transition from docked aggregates to entangled aggregates (2-3), transitions between entangled oligomers and isolated oligomers are slow. A sufficient drop in ELP interaction energy (below $T_t$-cooling) leads to eventual solvation of the POPs, diluting the clusters and returning them to their original state.

Example 6

Formation of Solid-Like, Fractal Networks

Figure 4A:
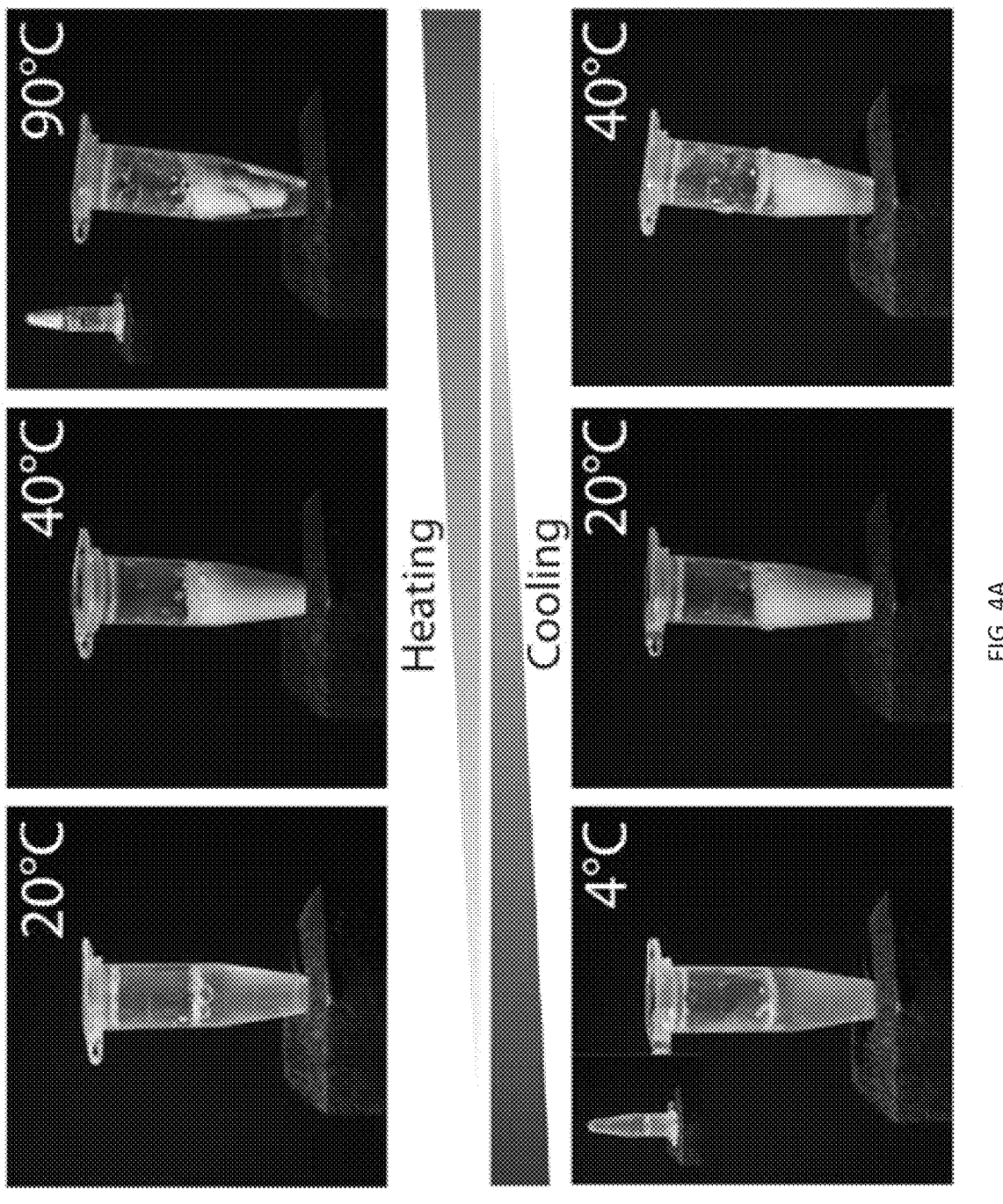

The macroscopic properties of POP aggregates also indicate a mechanism for aggregation distinct from the liquid coacervation of disordered ELPs. Rather than a turbid suspension, POPs transition into mechanically stable, opaque aggregates. These aggregates undergo syneresis at high temperatures, cracking and shrinking as temperatures increase beyond the $T_t$-heating (FIG. 4A). Syneresis suggests percolated crosslinking interactions among polymers, likely due to network formation from the helical clustering that is predicted by our simulations.

We performed oscillatory rheology on POPs and ELP controls to characterize the mechanical properties of the POP networks and compared them to an ELP control (FIG. 13A-FIG. 13E). Prior to performing oscillatory shear rheology, samples were prepared in PBS and allowed to equilibrate at 4° C. Measurements were taken on a Kinexus Pro (Malvern, Westborough, MA) using a Peltier heating element and a 10 mm parallel plate geometry. Samples were enclosed in a humidified environment to prevent drying during heating, equilibration, and oscillation. Soluble polymer samples were loaded onto the lower portion of the geometry set at 4° C. The upper portion of the geometry was lowered to 0.5 mm, and the instrument was subsequently heated to the experimental temperature (37° C. unless otherwise specified) and allowed to equilibrate for 30 min. To account for volume contraction in ELP and POP gels, samples were run with a normal force control of 0.1N—determined to be the optimal normal force to maintain geometry contact without sample deformation. Uncrosslinked ELP gels were too soft for adequate normal force control, and were instead run with a gap control set to the average gap of their corresponding POP concentration. Each polymer condition was repeated in triplicate. For comparison to chemical crosslinking, an additional ELP (E1$_{80}$DK)

was produced which matched the aspartic acid and lysine distribution of E1-H5-25%, with otherwise identical composition to E1$_{30}$. Tetrakis(hydroxymethyl)phosphonium chloride (THPC) was used to crosslink available lysines, and, unless otherwise stated, crosslinker was mixed in a 1:1 molar ratio with polymer lysines (a 4:1 molar ratio with polymer). THPC was added to the polymer solution at 4° C. prior heating and equilibration.

Frequency sweeps in the linear viscoelastic region of ELPs above their $T_t$ show the loss modulus (G") (23 Pa, 1 Hz, 10 mg/mL) to be greater than the storage modulus (G') (8.0 Pa, 1 Hz, 10 mg/mL) and both to be proportional to frequency. This behavior is consistent with liquid-like coacervates. In contrast, POPs exhibit a G' (12.2 kPa, 1 Hz, 10 mg/mL) that is much greater than G" (0.36 kPa, 1 Hz, 10 mg/mL) and independent of frequency. This behavior is typical of more solid-like materials. The measured values of G' were found to be four orders of magnitude greater for POPs when compared to ELPs at equivalent concentrations. POPs also display high viscosity with plastic, shear-thinning flow, while ELPs behave as Newtonian fluids. The shear thinning slope for POPs was unusually high (−0.95) for long-chain, polymers indicative of some network rupture, and this observation is consistent with reported values for tropoelastin networks.

Importantly, POP mechanical properties can be altered with polymer composition (FIG. 25A-FIG. 25G). Material stiffness correlated with MW and helical percentage but is unaffected by the composition of the disordered region. Though POP aggregate stability is driven by physical crosslinking, other crosslinking mechanisms may also be utilized to further modulate mechanical properties. Indeed, POP aggregates chemically crosslinked with Tetrakis(hydroxymethyl)phosphonium chloride (THPC), show a 2-fold increase in stiffness. We also note that chemically crosslinking E1(DK)$_{80}$, an ELP with identical lysine spacing compared to POP, also increases in stiffness, though their G' remains an order of magnitude lower than both the chemically crosslinked and POPs lacking chemical crosslinks (FIG. 25A-FIG. 25G). As previous work has shown that fully disordered polymers can achieve similarly high stiffness with sufficient chemical crosslinking densities, even stiffer POPs are likely achievable should the disordered domain be substituted for one with a high density of chemical crosslinking sites.

Figure 4B:
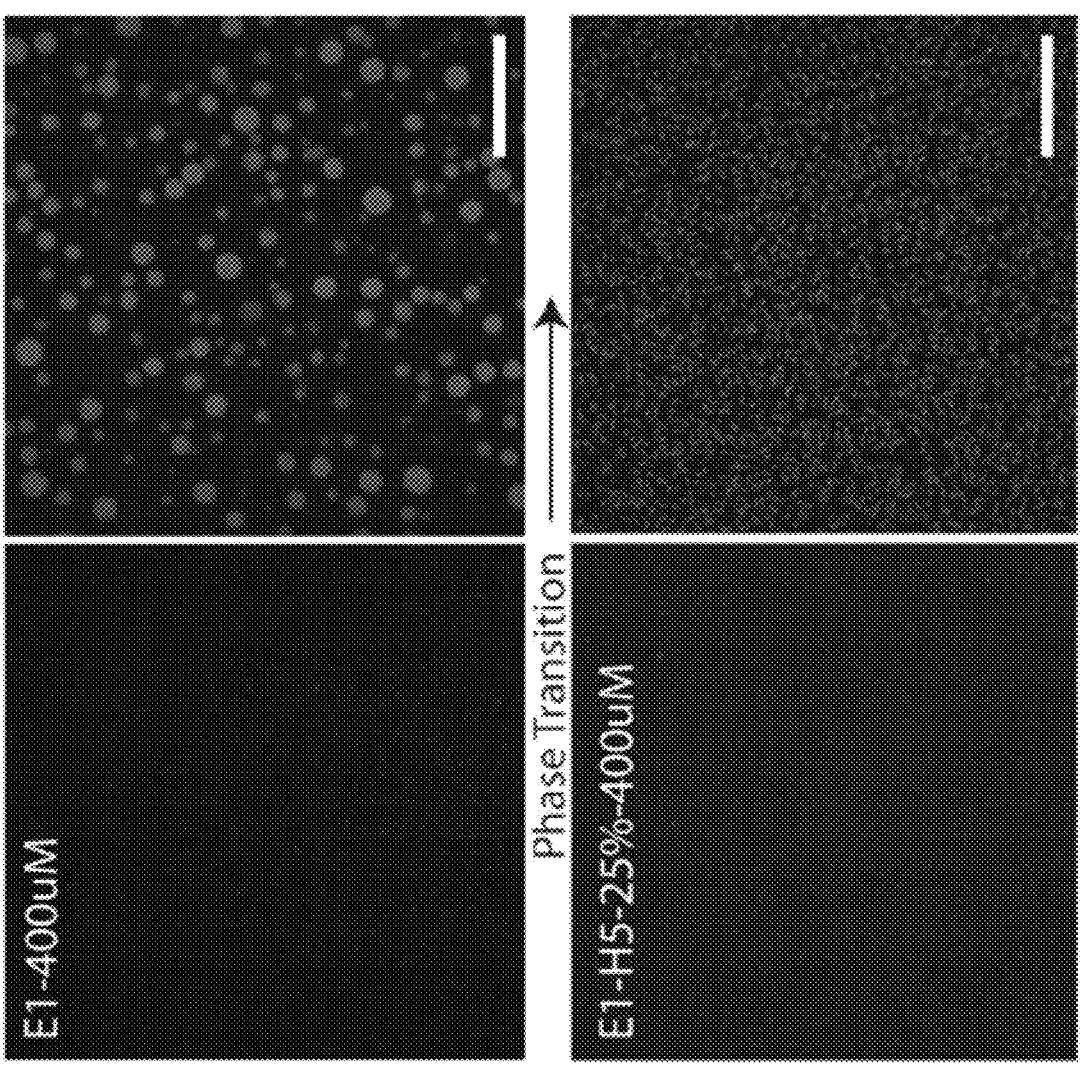
Figure 4C:
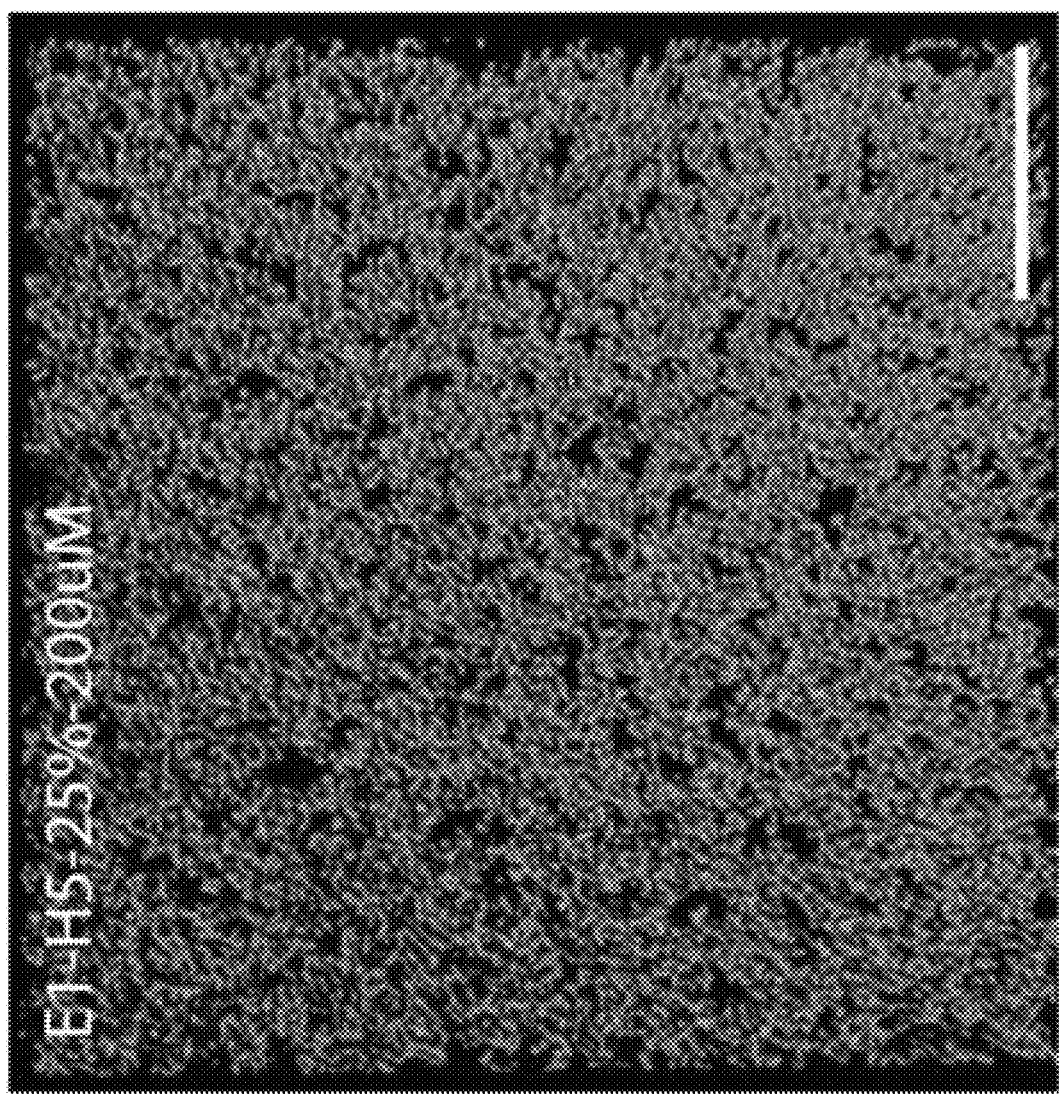
Figure 14A:
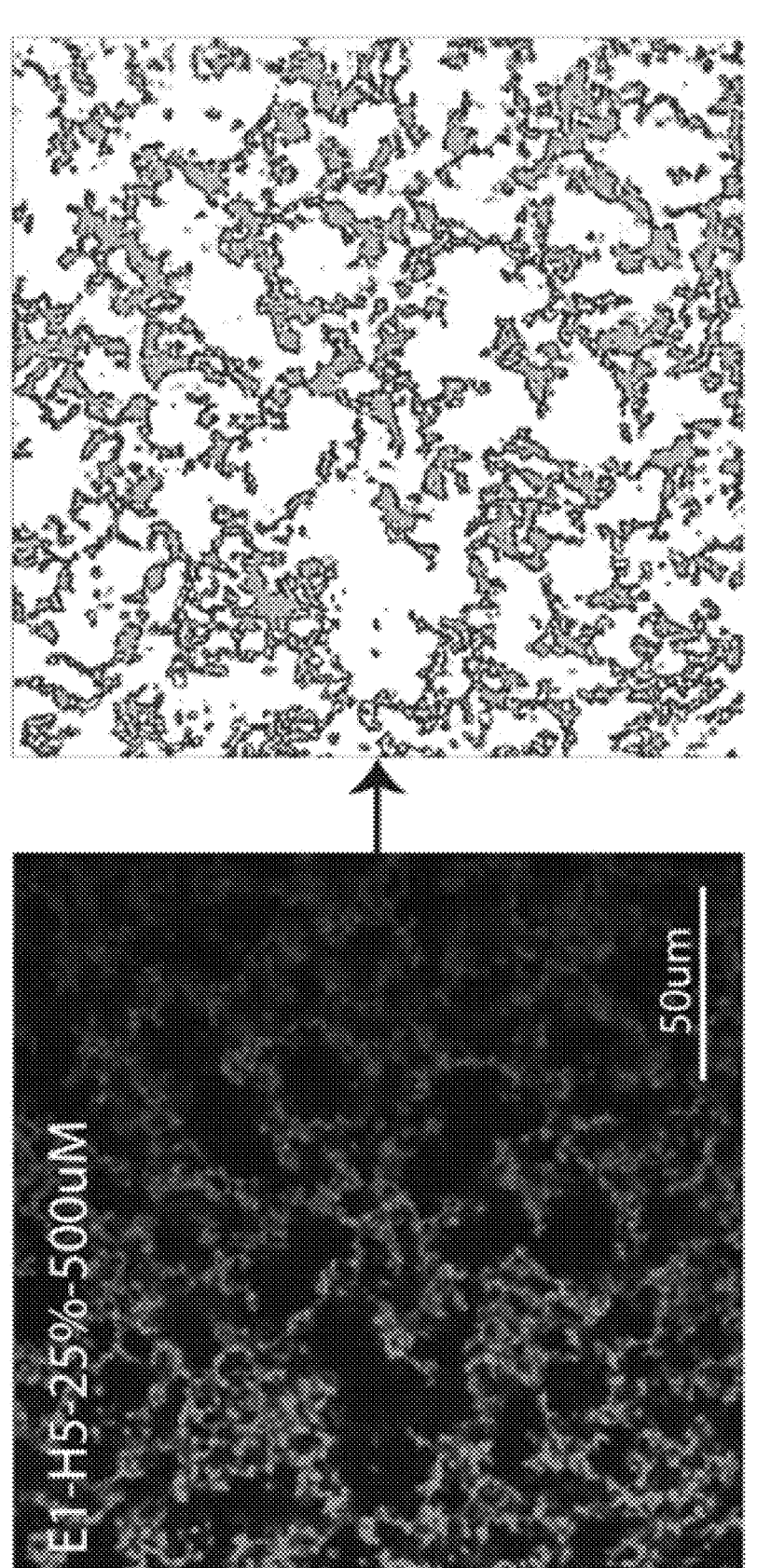
FIG. 14A-FIG. 14C: Fractal Dimensions of POP Networks.
Figure 14B:
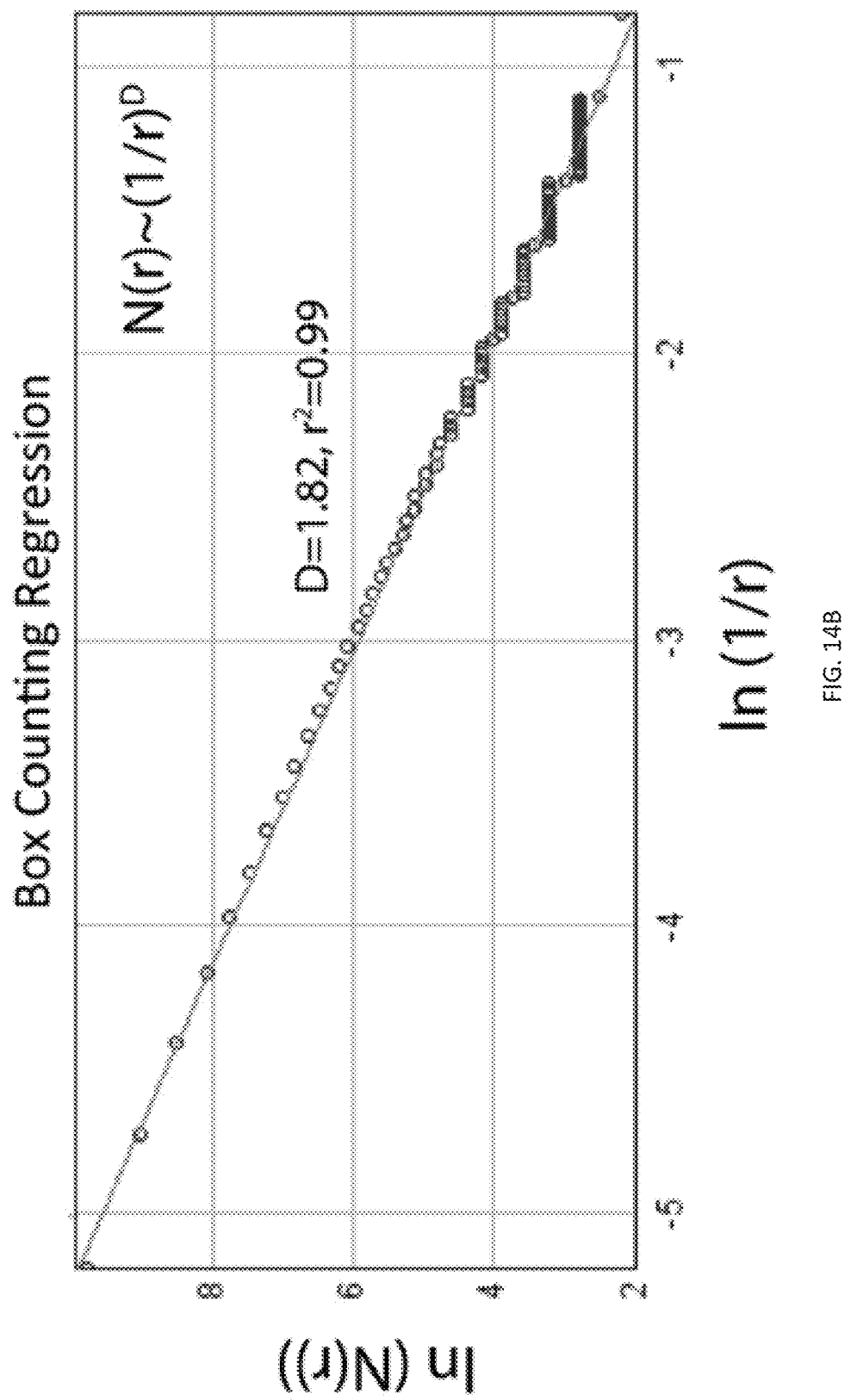
Figure 14C:
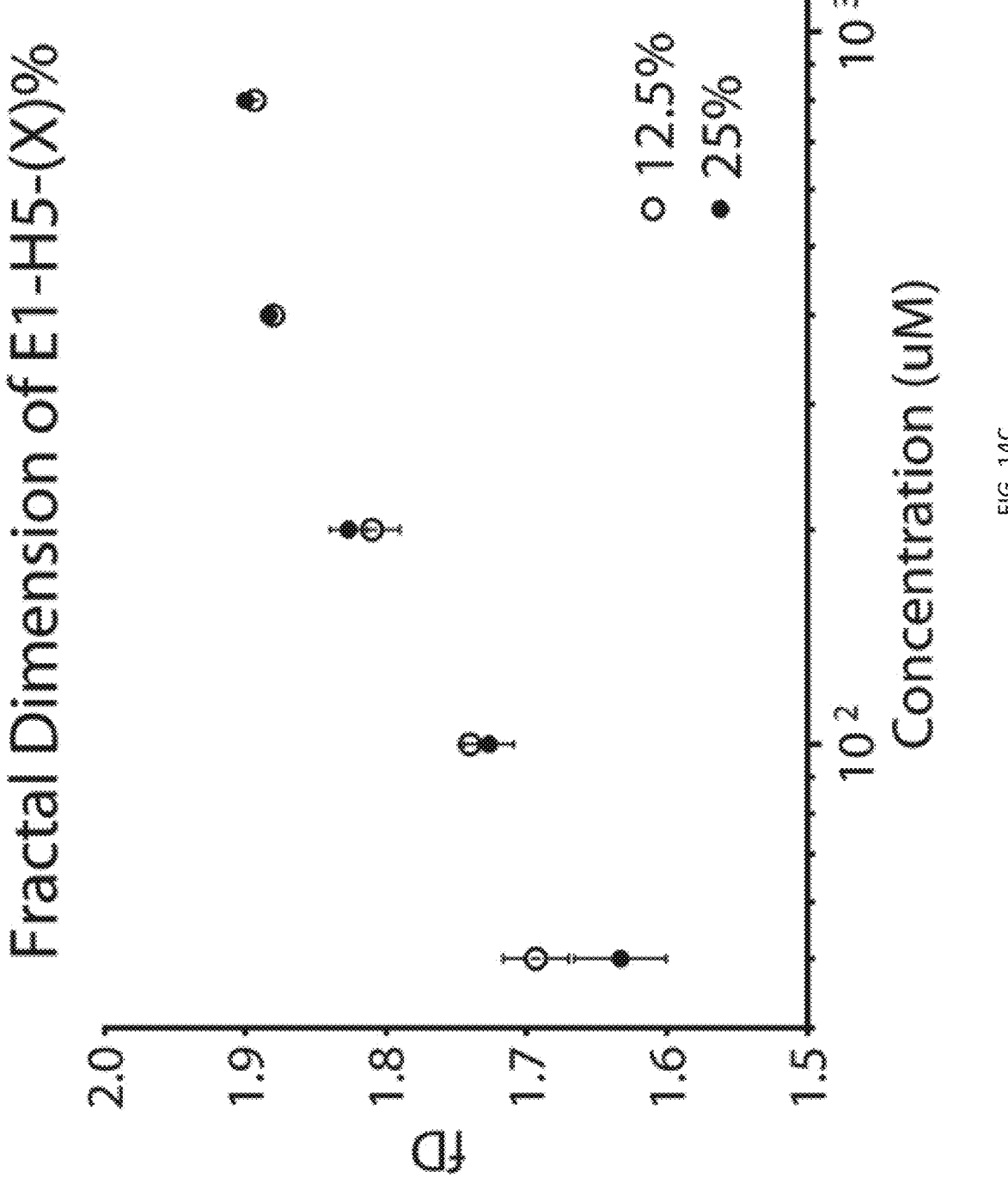
Figure 26:
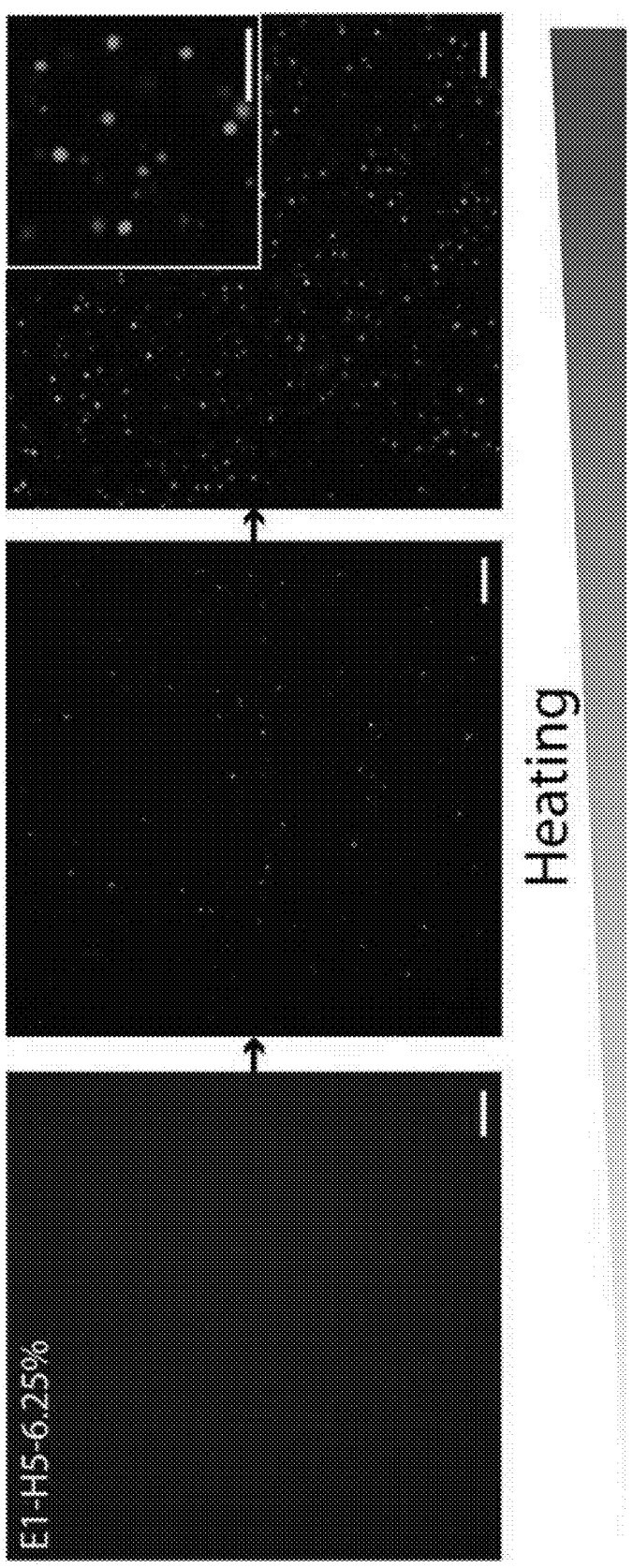
FIG. 26: Single Helix Polymer Coacervates. E1-H5-6.25% (200 μM, PBS), which contains only one helical domain per polymer, does not form a fractal network; rather, the polymer forms a colloidal suspension of coacervates, similar to that of ELP. Scale bars=20 μm, 10 μm for insert. Images from left to right show increase of heating.

The incorporation of helical domains in POPs also affects microscale phase separation (FIG. 4B-FIG. 4C). While ELPs form micron-sized aggregates that mature and coalesce, forming a colloidal suspension of liquid-like droplets, POPs undergo arrested phase separation into porous networks. POPs with only a single helix form coacervates similar to fully disordered ELPs (FIG. 26), indicating that physical crosslinks between helical domains from separate POP chains are important for network formation. These networks have a fractal-like architecture, with E1-H5-12.5% and E1-H5-25% POP networks having fractal dimensions between 1.6 and 1.9 that are dependent on POP concentration (FIG. 14). This fractal dimension is comparable to that observed for native elastin networks. We highlight the fractal-nature of POP networks as an intriguing observation because fractals are ubiquitous in nature yet difficult to artificially recreate.

Figures 15A, 15B, 15C:
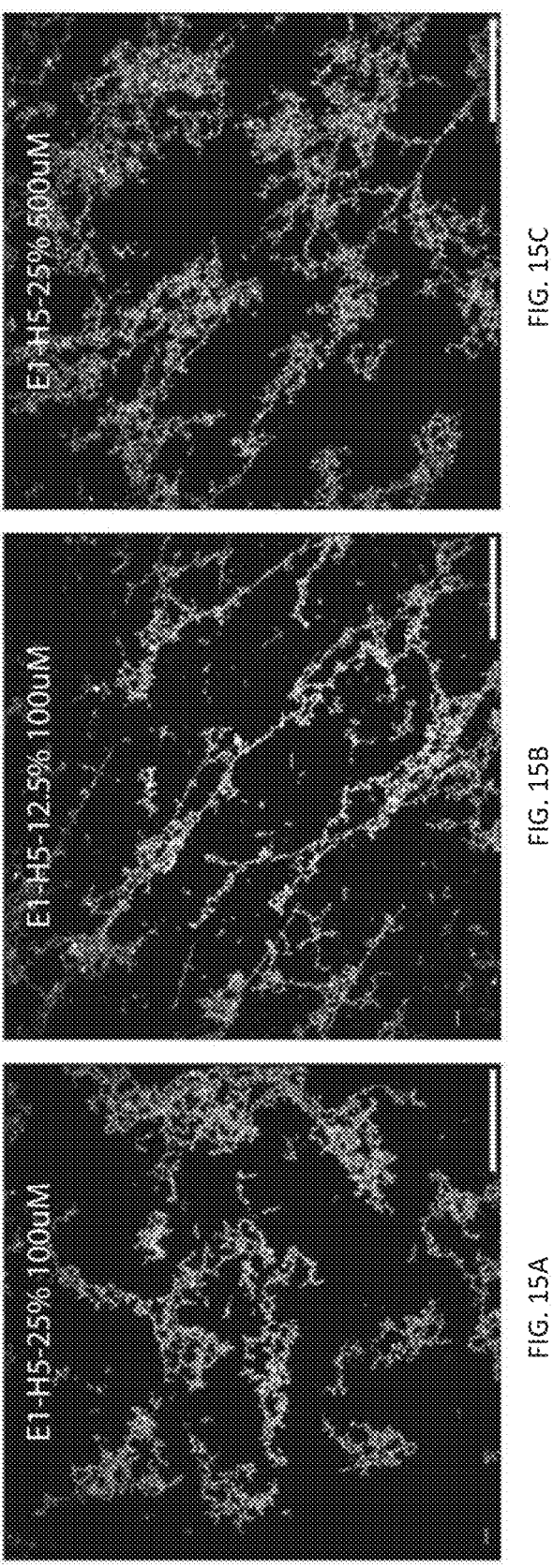
FIG. 15A-FIG. 15C: Additional Structured Illumination Microscopy (SIM) images. The "beads-on-a-string" mesoscale architecture is consistent across concentrations and helical percentages; scale bar 10 μm.

We next used structured illumination microscopy (SIM), a super-resolution microscopy technique (Gustafsson, M. G. L. SHORT COMMUNICATION. Journal of Microscopy 2000, 198, 82-87; Gustafsson, M. G. Proc. Natl. Acad. Sci. U.S.A. 2005, 102, 13081-13086), to better characterize network architecture. SIM revealed the presence of mesoscale polymer globules no larger than 200 nm interconnected with a "pearl-necklace" like architecture (FIG. 4D). This architecture is consistent across multiple polymer compositions (FIG. 15A-FIG. 15C) and is suggestive of a two-stage aggregation process. The polymers initially nucleate like their disordered counterparts ($T_t$-heating driven by the disordered domains). Rather than coalesce, however, the aggregates rapidly link, forming fractal networks. Indeed, our coarse-grain simulations also predict a two-stage process on the nanoscale (aggregate docking and entanglement), and we propose that similar entanglements must also occur on a meso to micro-scale. This type of aggregation is mirrored in tropoelastin, which also undergoes a multistage aggregation process. This process includes an initial hydrophobic coacervation into spherical droplets and subsequent maturation into networks or fibers due to interactions between crosslinking domains.

Figure 5A:
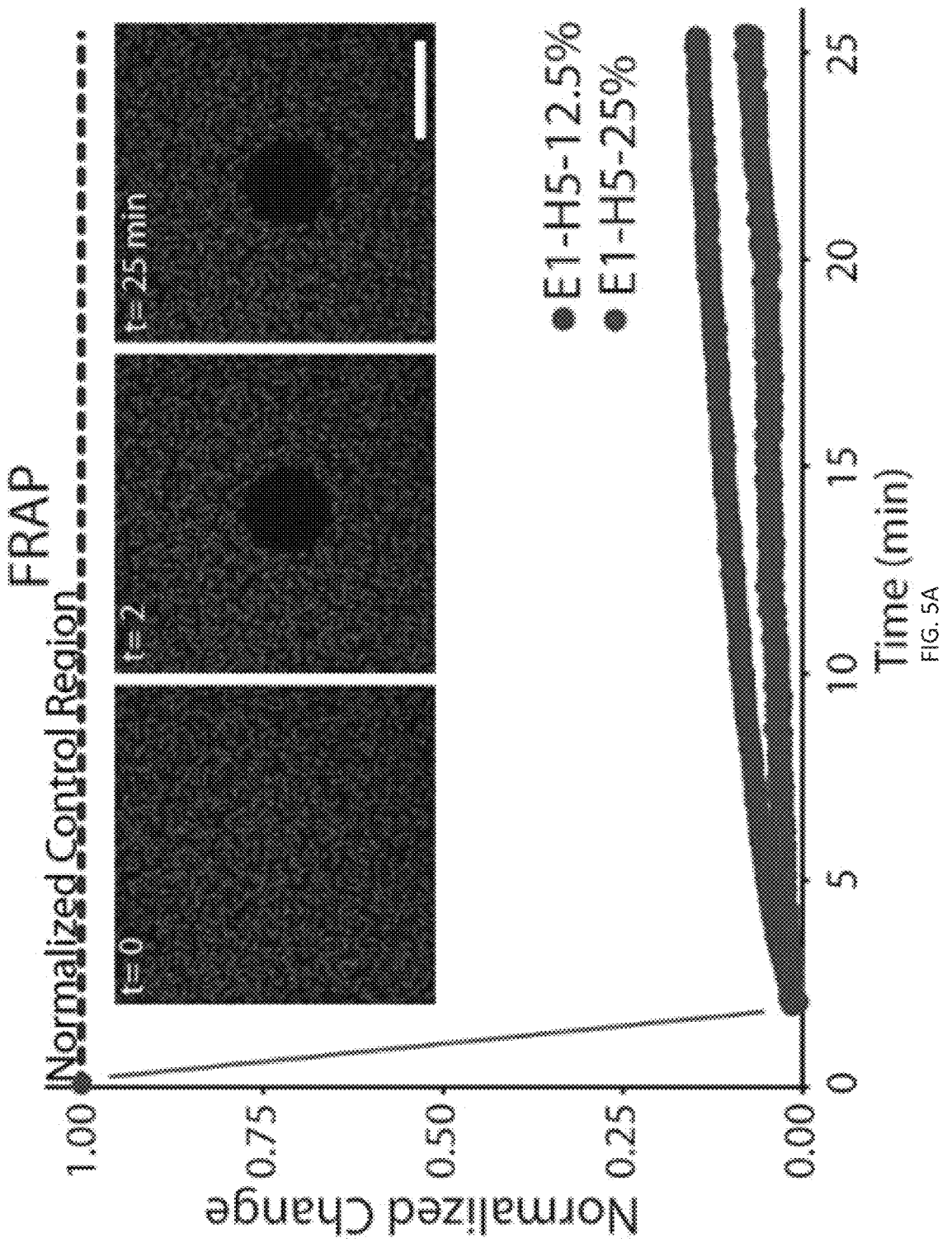
FIG. 5A-FIG. 5C: Network stability and void volume.
Figure 5B:
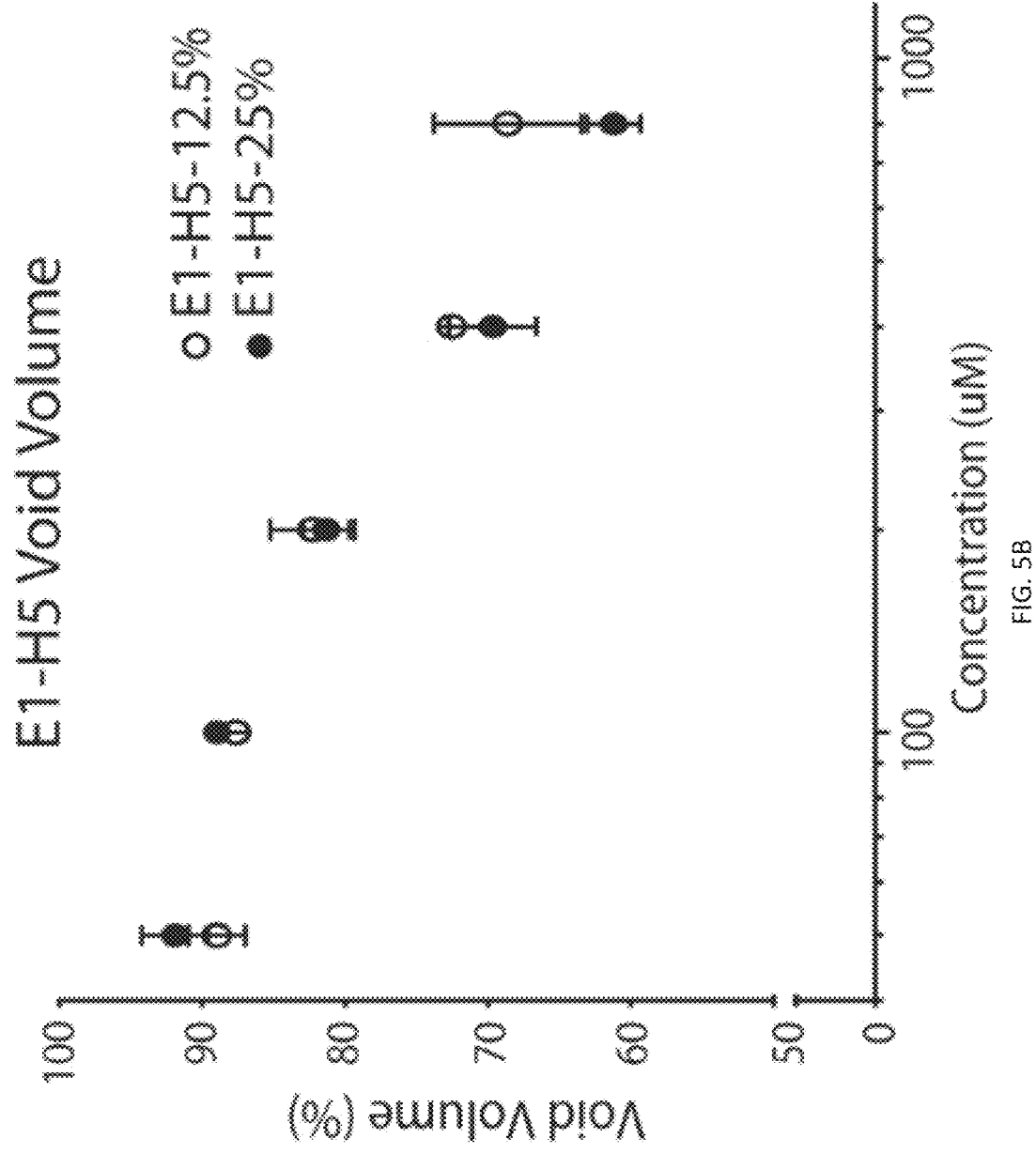
Figure 5C:
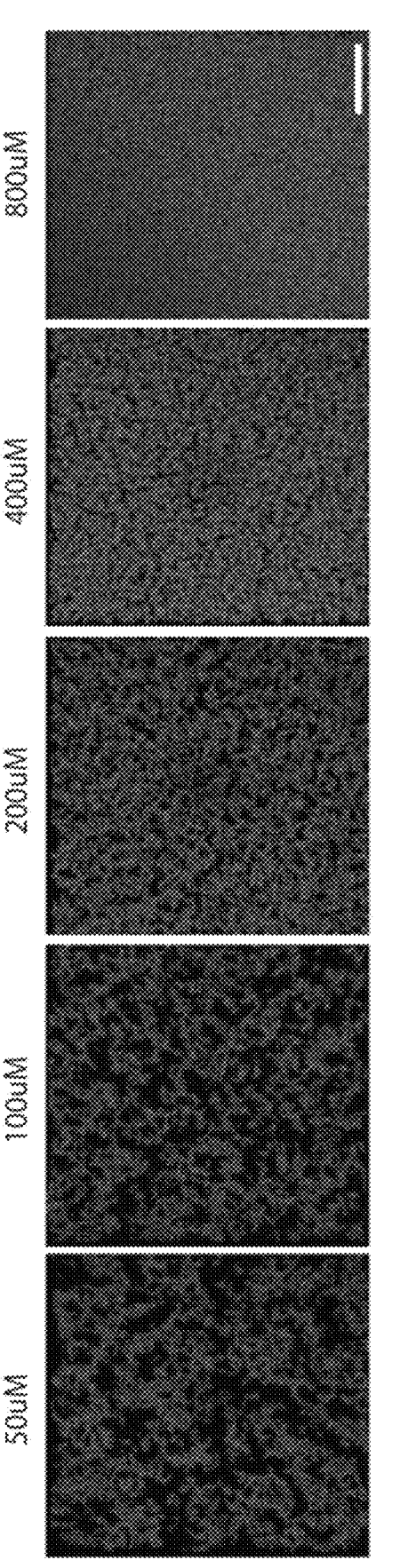
Figure 27A:
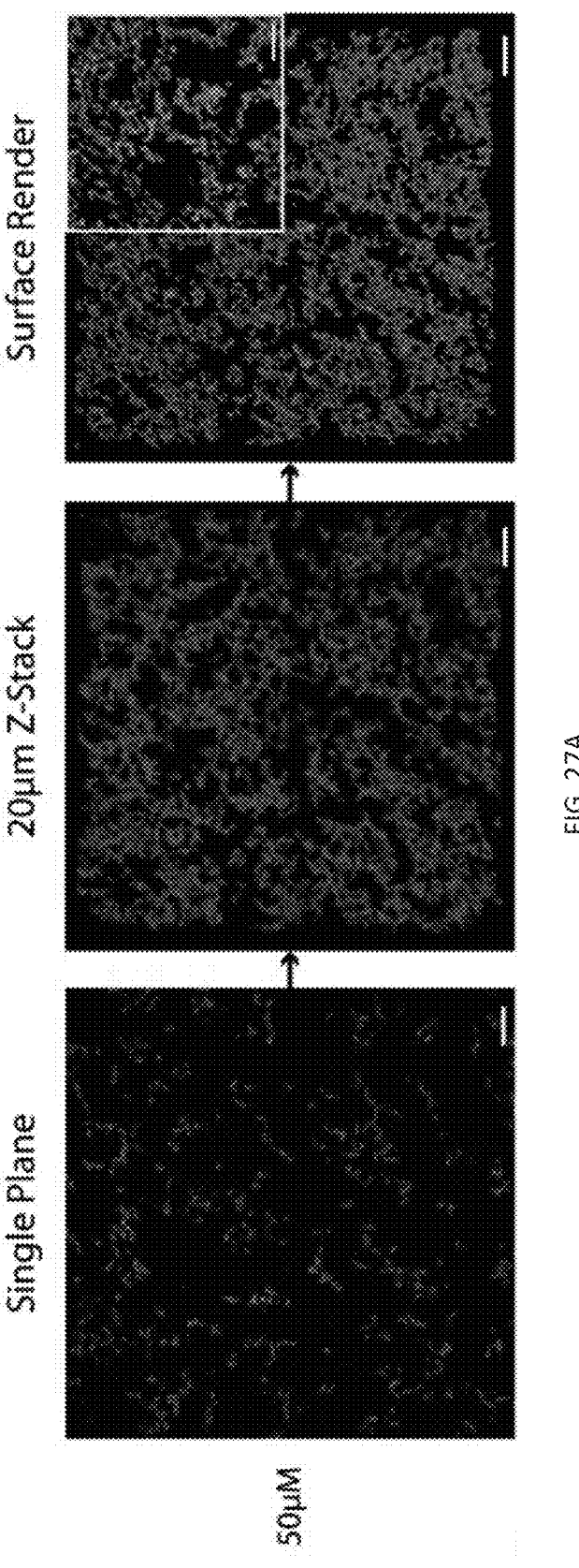
FIG. 27A-FIG. 27C: Confocal microscopy analysis of POPs. Representative single z-slices, 20 μm z-stacks, and Imaris surface renders of z-stacks (including magnified insets) for E1-H5-25% at (FIG. 27A) 50 μM, (FIG. 27B) 200 μM, and (FIG. 27C) 800 μM. Scale bars=2 μm; scale bars in insets=10 μm.
Figure 27B:
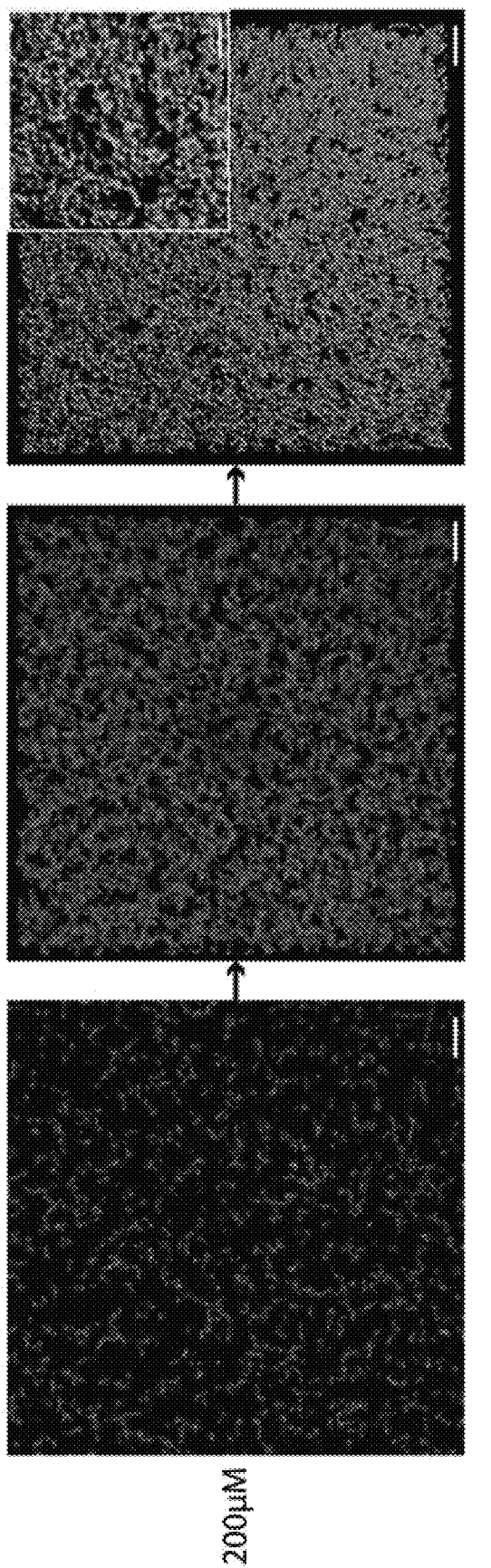
Figure 27C:
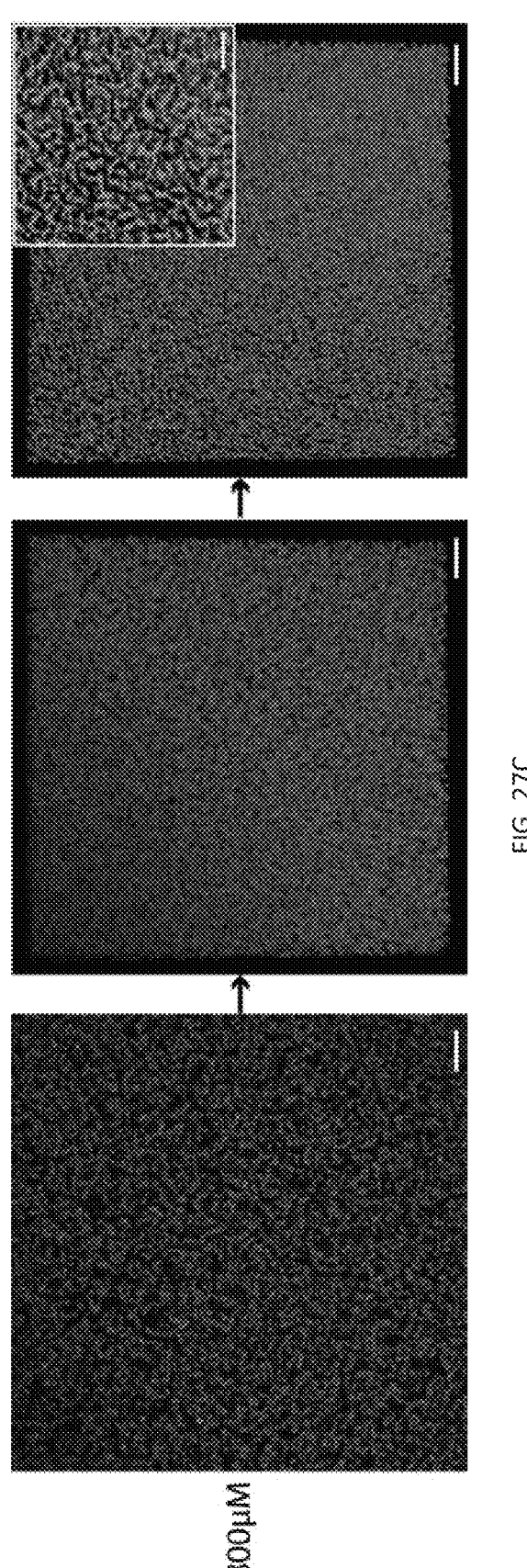
Figure 28A:
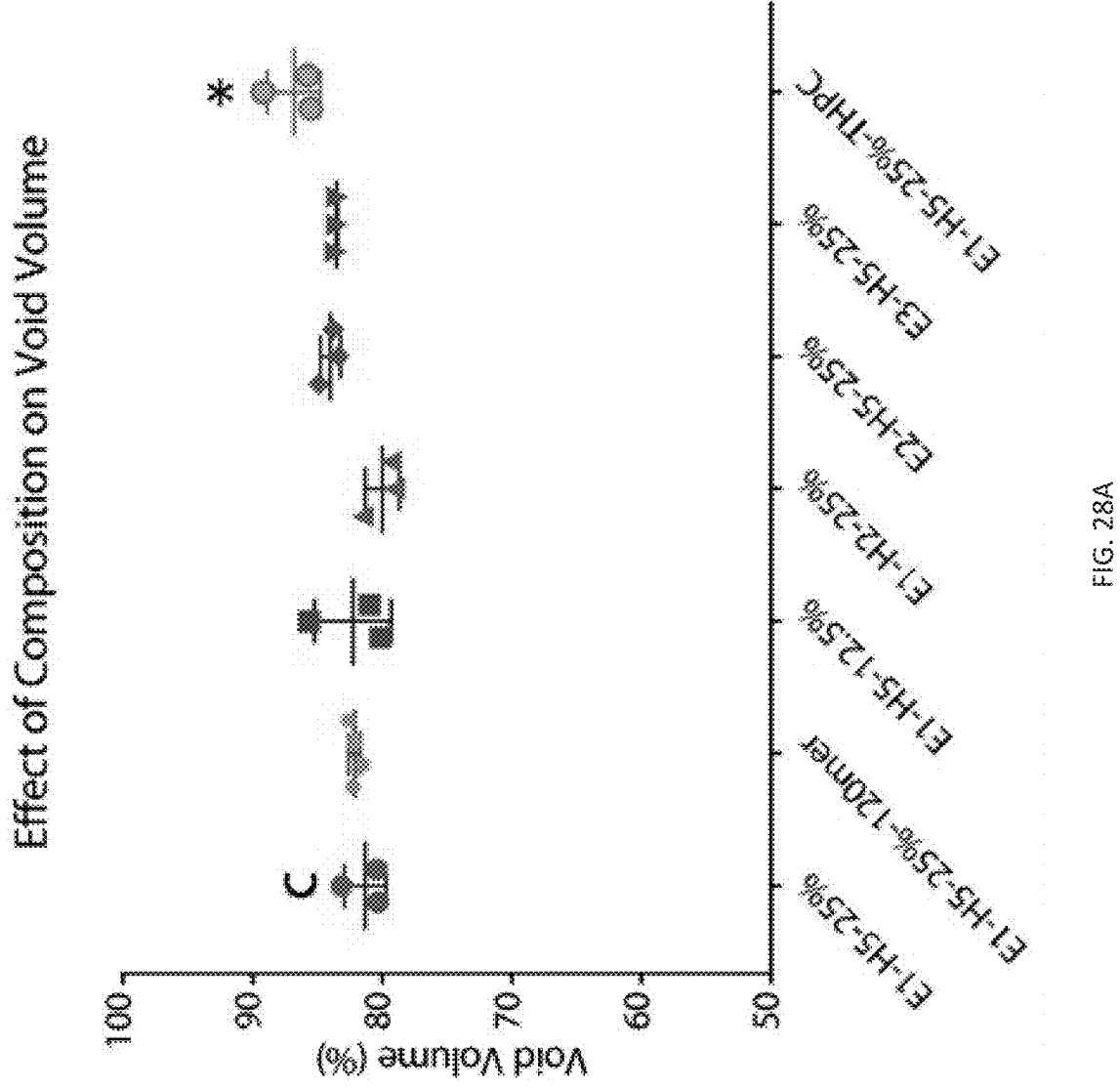
FIG. 28A-FIG. 28B: Void volume and Composition.
Figure 28B:
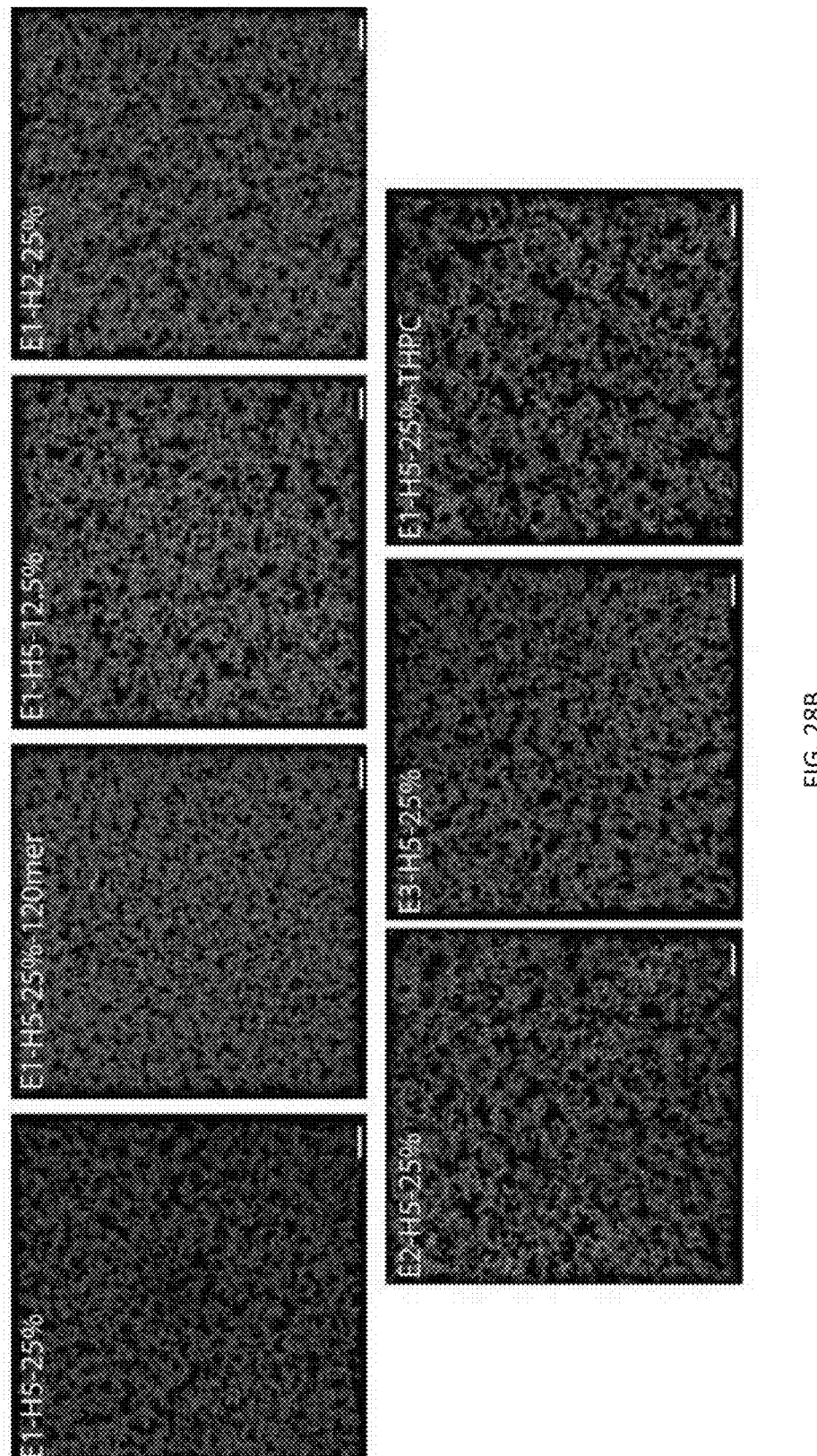

We also measured the internal mobility of POP networks prepared from 12.5 and 25% wt. % POP solutions, by monitoring their fluorescence recovery after photobleaching (FRAP). Minimal recovery was observed after 30 min, suggesting that POP networks are kinetically stable (FIG. 5A). This kinetic stability is likely due to physical crosslinking from helical bundling within the network. There is slightly more recovery for 12.5% networks, but the unrecovered fraction remains high (86%). We can also control network porosity by modulating polymer concentration. Using three-dimensional reconstructions from confocal microscopy, we evaluated the effects of concentration and polymer composition on total void volume, defined as the non-protein rich phase of the network. Within a range of 50 μM (1.6 mg/ml) to 800 μM (25.6 mg/ml) for E1-H5-(X) %, the void volume can be tuned between 90% (~30-50 μm pores) and 60% (~3-5 μm pores), with no significant difference in void volume observed between the POPs with 12.5% and 25% helical content over all tested concentrations (FIG. 5B, FIG. 5C and FIG. 27). We also measured the void volume for a variety of POP compositions and found that polymer composition—including changes to MW, helical percentage, helix sequence, and ELP sequence—had no measurable impact on void volume (FIG. 28). This finding allows us to tune porosity of the POP network independently of other network properties. Having porosity as an independently tunable parameter provides a stepwise means to tailor POP networks to specific applications. Toward this end, we envisage the following protocol to orthogonally tune POP properties: (1) choose the desired porosity with concentration; (2) choose other physical properties (mechanical properties or $T_t$-cool) with MW, helix sequence and percentage; (3) finally, choose aggregation temperature ($T_t$-heating) with ELP composition. The ability to tailor POP networks in this manner, and their ability to span 2-3 orders of magnitude in elastic moduli ranging from several hundred Pa to >10 kPa, could be useful, for example, in guiding stem cell differentiation, which are known to be very sensitive to the mechanical properties of the 3-D matrix they are cultured in, but which also require control of the diffusivity of the matrix to enable transport of nutrients and biological signaling factors to cells from the surrounding growth medium.

Our work departs in significant ways from previous studies on block copolymers of bioactive or mechanically active folded protein domains with disordered sequences such as ELPs. Hydrogels and fibers have been produced with ordered segments such as coiled-coils and leucine-zippers to alter their self-assembly; however, these studies have focused on the specific impact of more complicated structural peptides rather than the modular incorporation of ordered versus disordered regions. Likewise, copolymers of disordered domains have produced gels and nanostructures, but these too lack the interplay of order and disorder as a design principle to encode higher order structure. Recombinant combinations of peptide sequences derived from structural proteins such as collagen and silk with elastin are more closely related to this study, although neither the precise and tunable control over thermal hysteresis nor the emergence of an interconnected thermally reversible fractal network architecture has been reported in these studies.

Combinations of order and disorder have also been explored in the field of synthetic polymers. Ratios of atactic (disordered) and isotactic (ordered) polymer blocks have been used as a means to control gelation and thermoresponsive phase transitions. Although synthetic polymers and recombinant peptide polymers each have their own advantages, peptide polymers are attractive for biotechnology and biomedical applications because of their biocompatibility and our ability to design absolute molecular levels through recombinant synthesis. This makes them better suited for tuning material properties via precise—genetically encodable—changes of their amino acid sequence.

Example 7

In Situ Network Stability and Cell Penetration

POPs designed to transition below the body temperature (37° C.) are advantageous for forming depots in vivo since they can be handled and injected as liquids, yet rapidly form viscoelastic materials when injected in vivo. Although injectable ELP depots have been similarly used for controlled drug delivery, the homogenous liquid nature of ELP coacervates has limited their applications in tissue engineering. Without chemical crosslinking, ELP coacervates are not mechanically stable enough to support cell growth, and their lack of porosity inhibits cell migration. Research has also shown that porous materials more favorably interact with the immune system, preventing foreign body response and inducing the migration of regenerative immune cells. Polypeptides that exhibit thermally triggered hierarchical self-assembly into stable porous networks can expand the scope of applications for recombinant biomaterials.

Figure 6A:
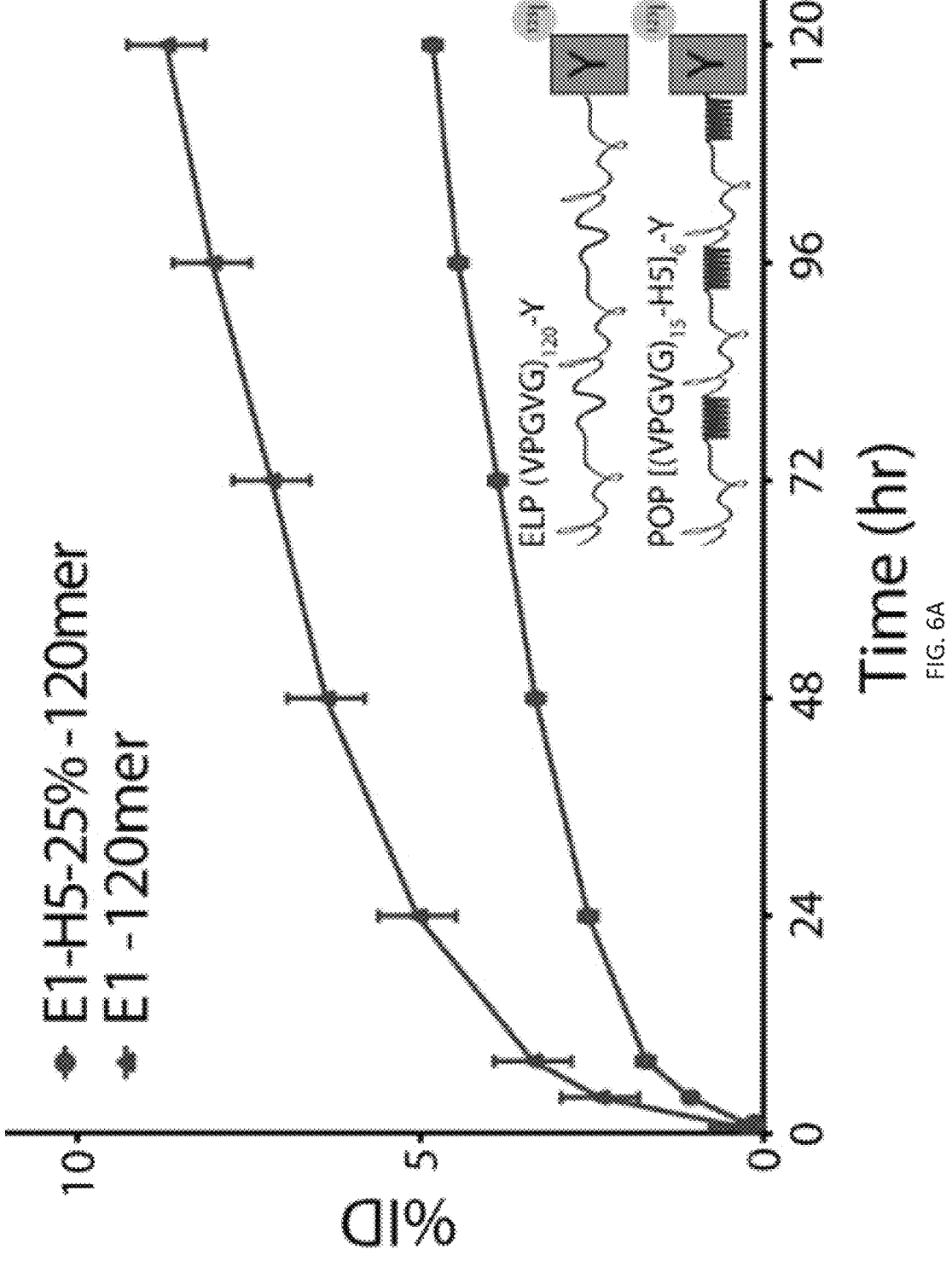
Figure 6B:
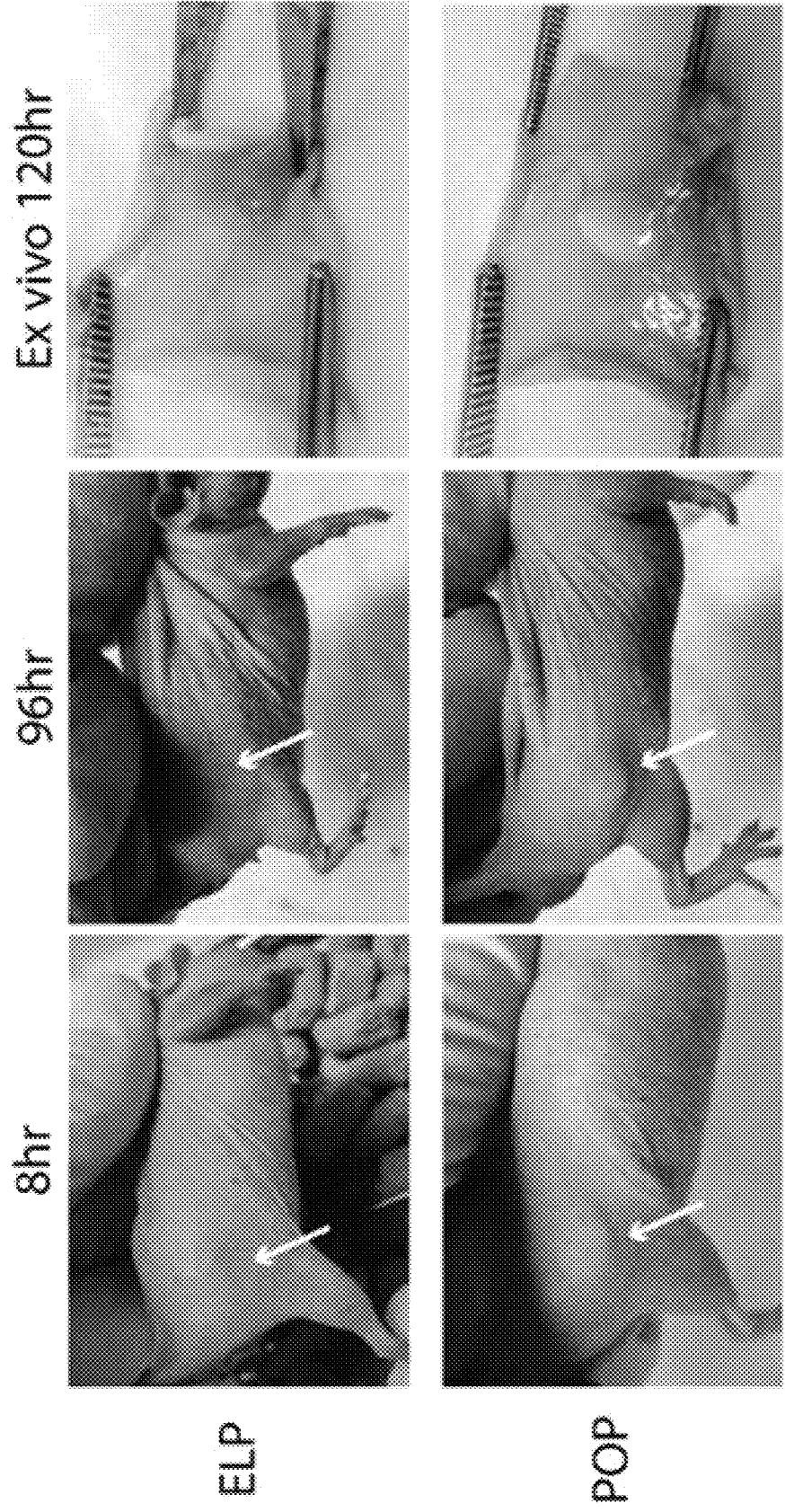
Figure 6C:
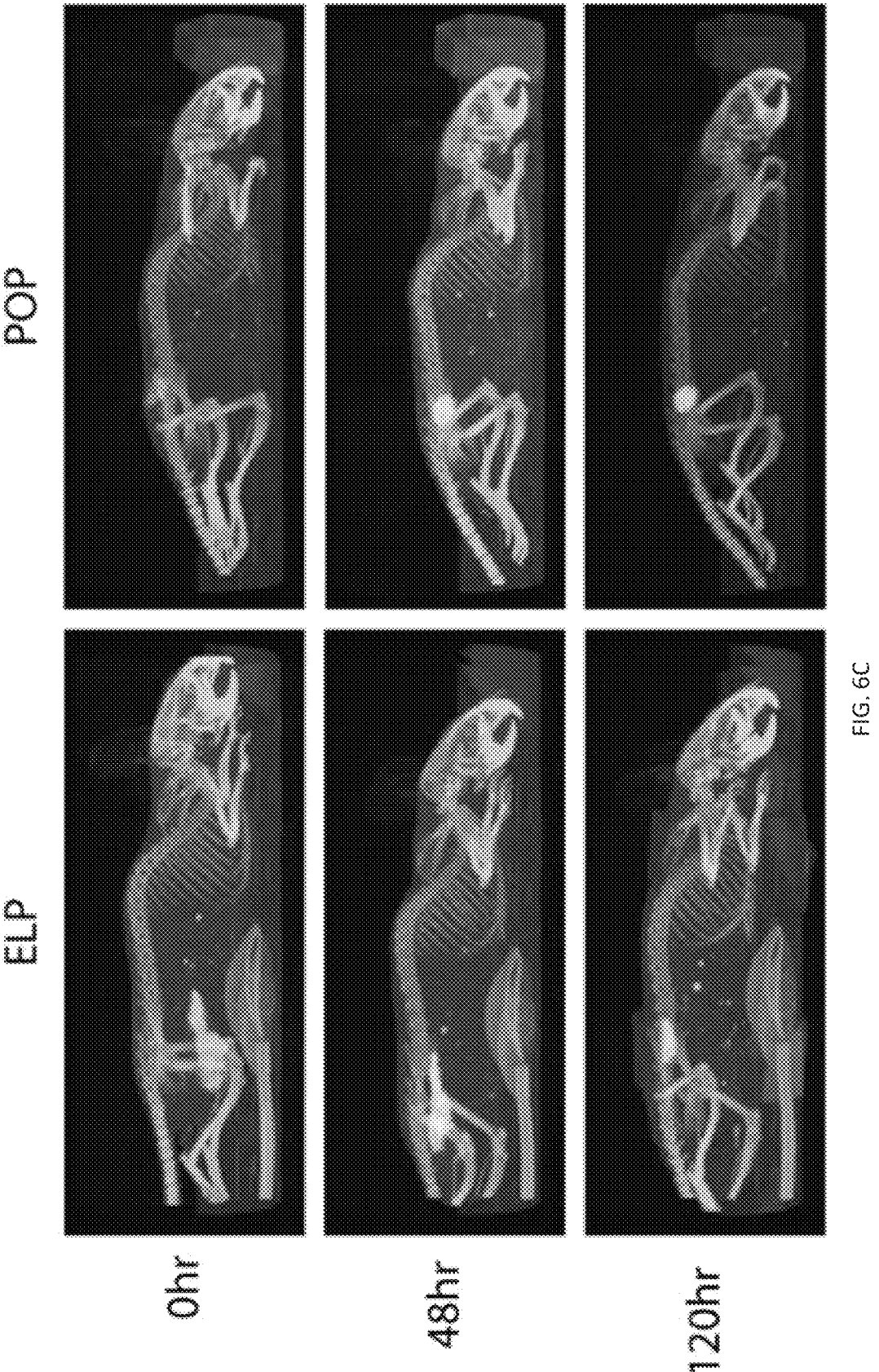
Figures 16A, 16B:
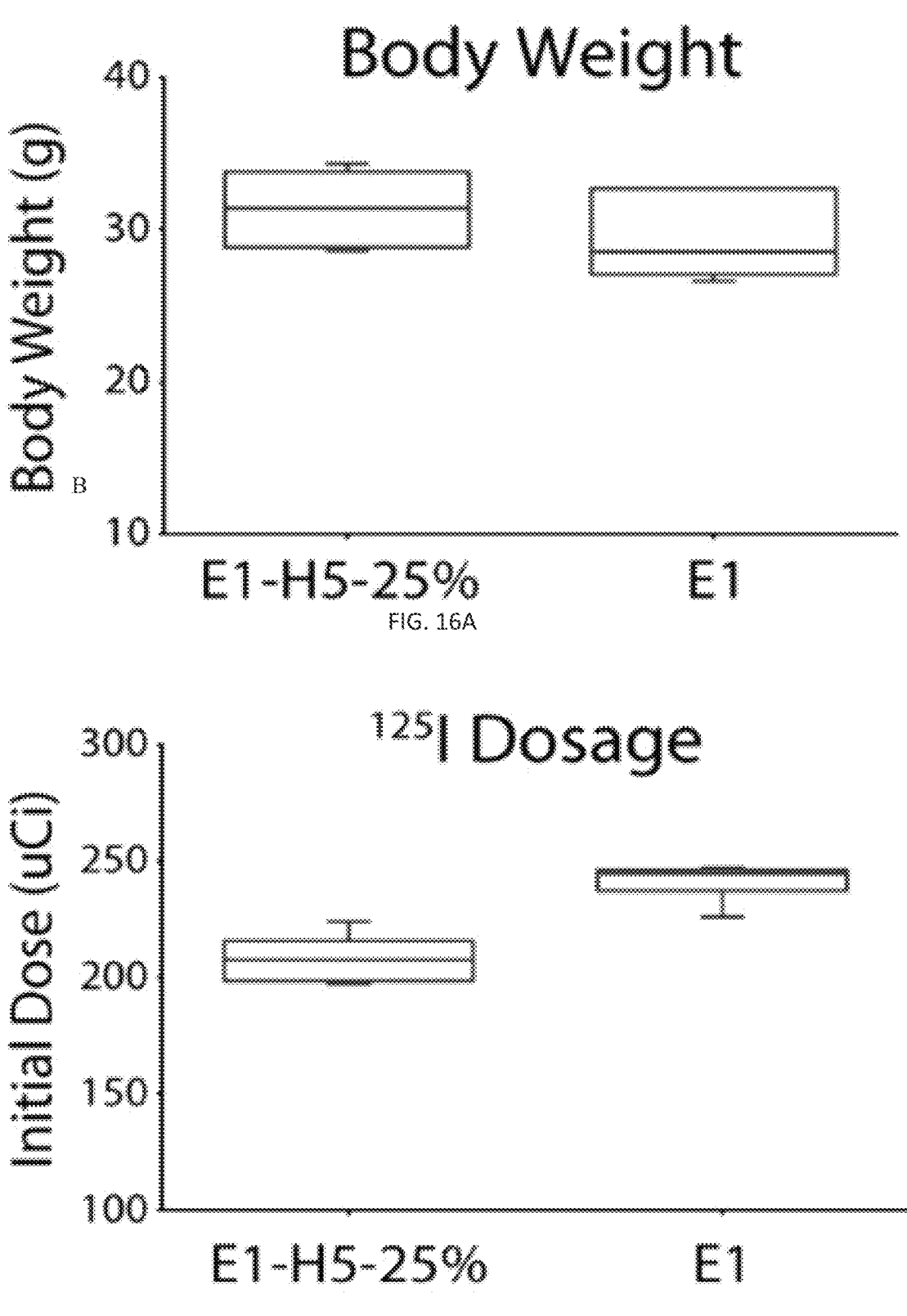
FIG. 16A-FIG. 16C: Biodistribution of POPs.
Figure 16C:
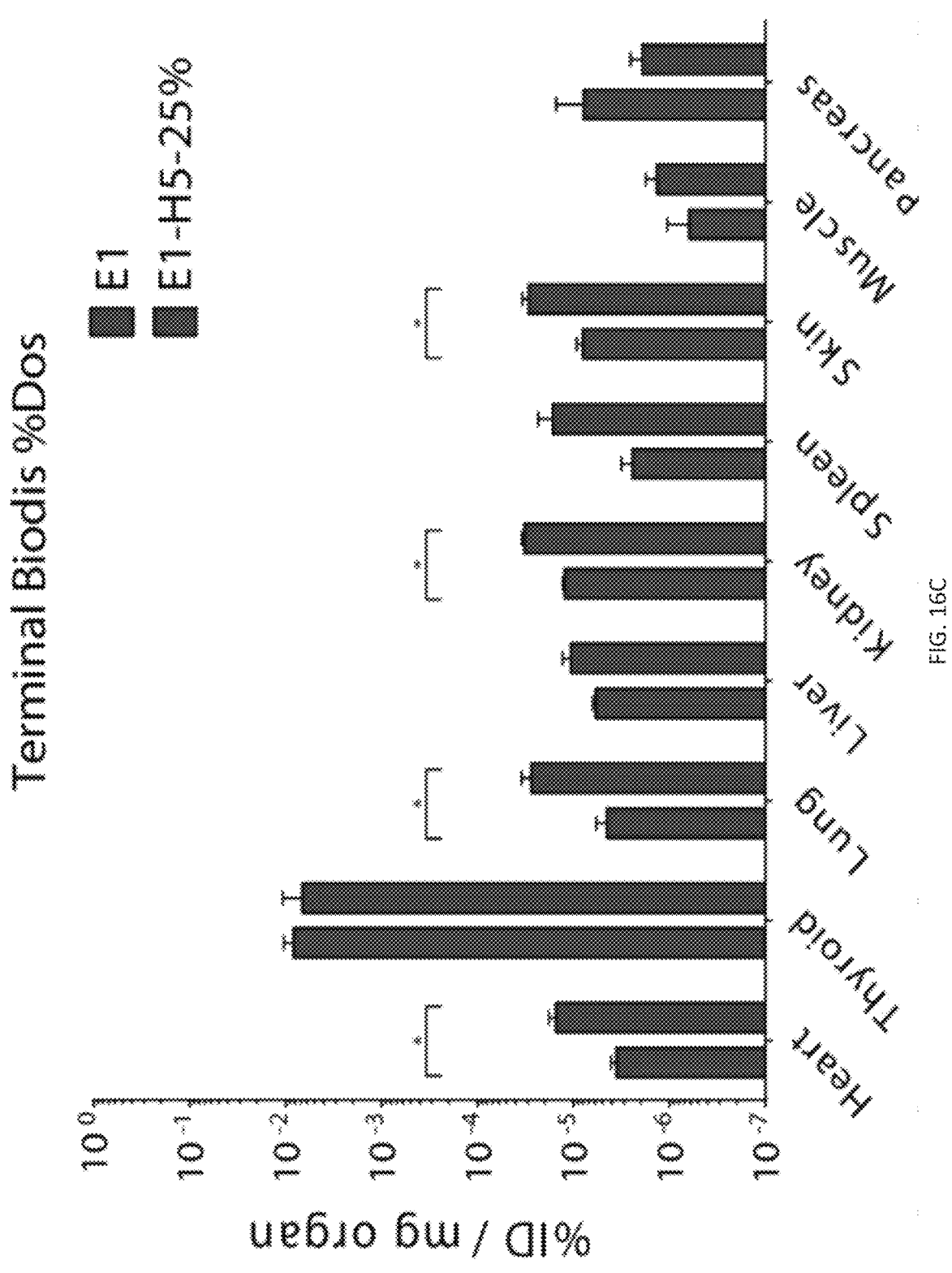
Figure 17A:
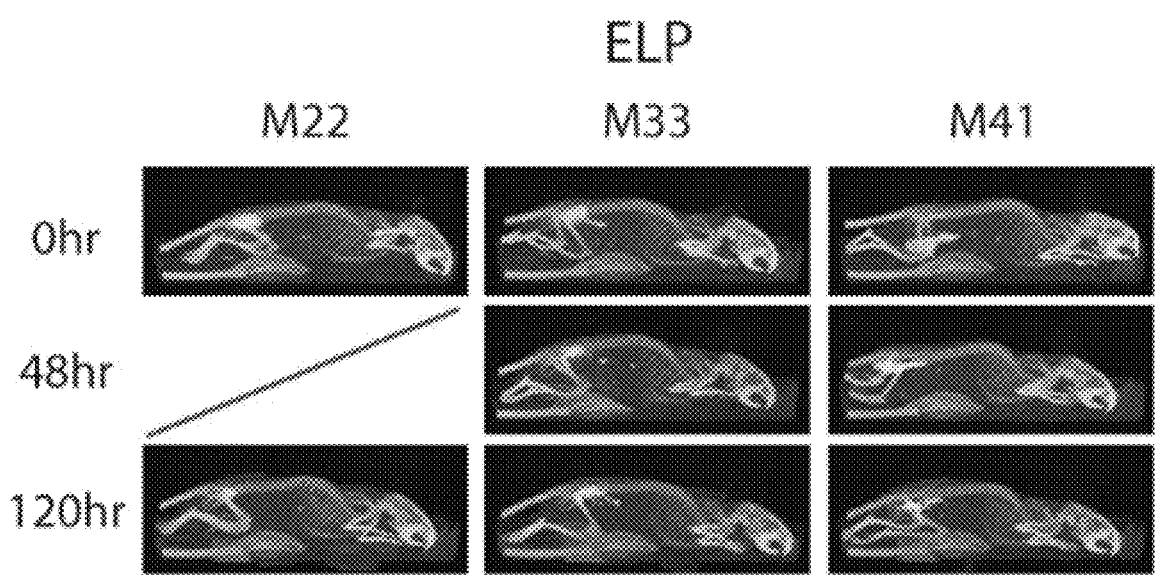
FIG. 17A-FIG. 17F: Single photon emission computed tomography (SPECT)-Computed tomography (CT) analysis.
Figure 17B:
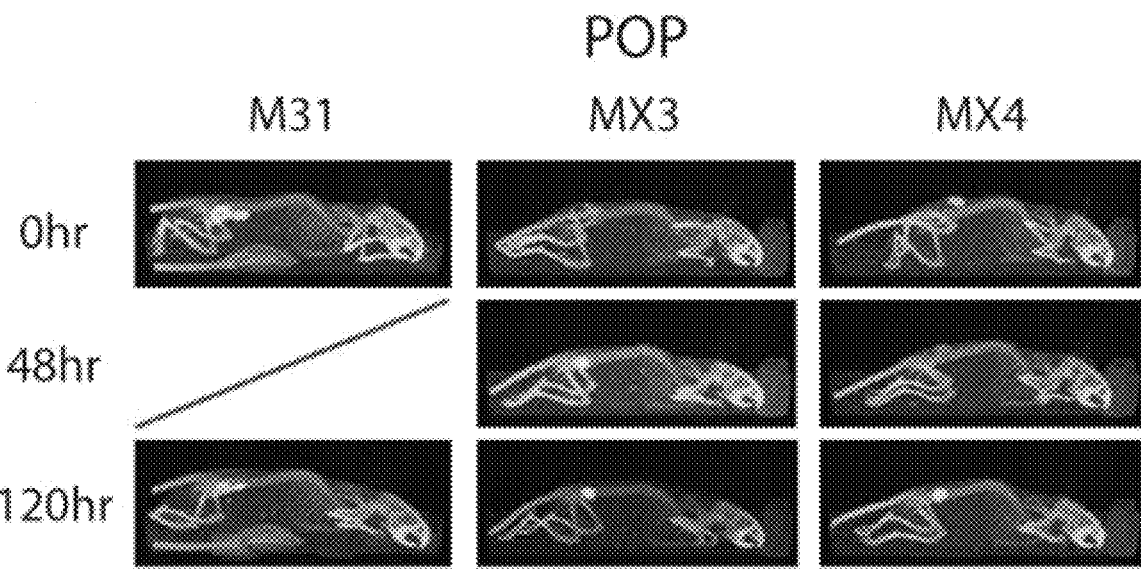
Figure 17C:
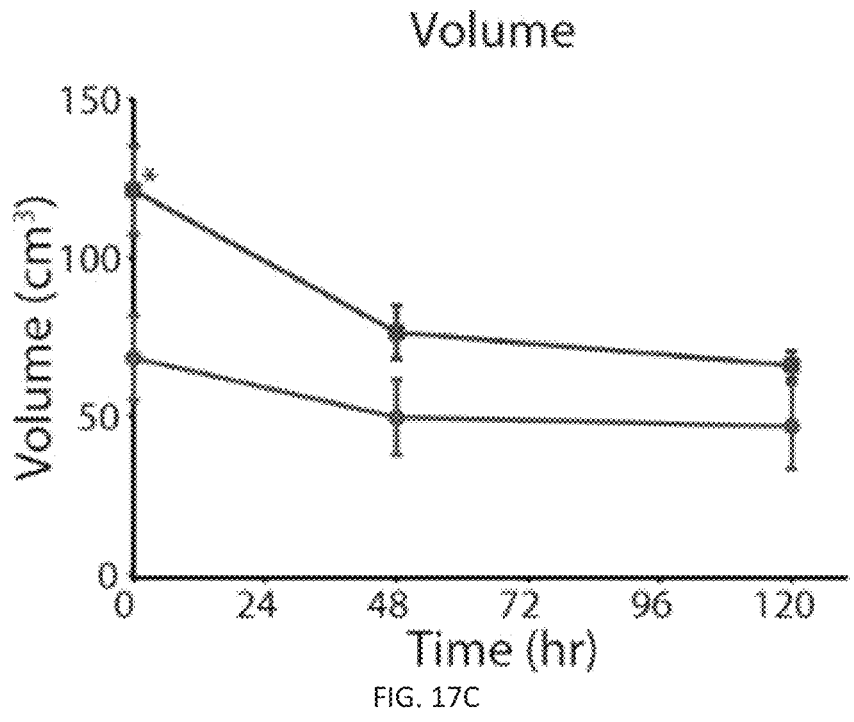
Figure 17D:
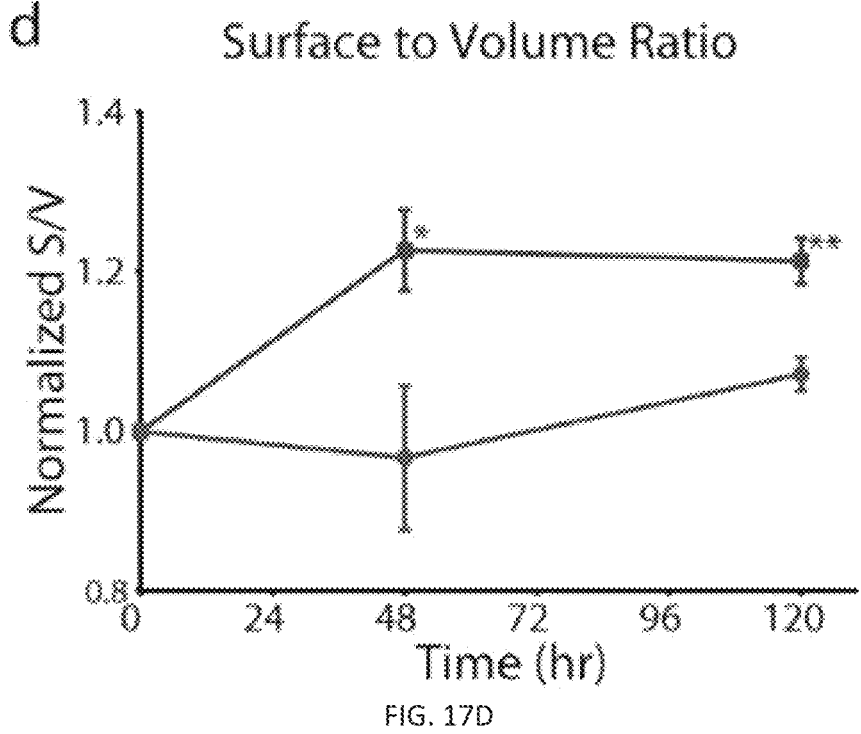
Figure 17E:
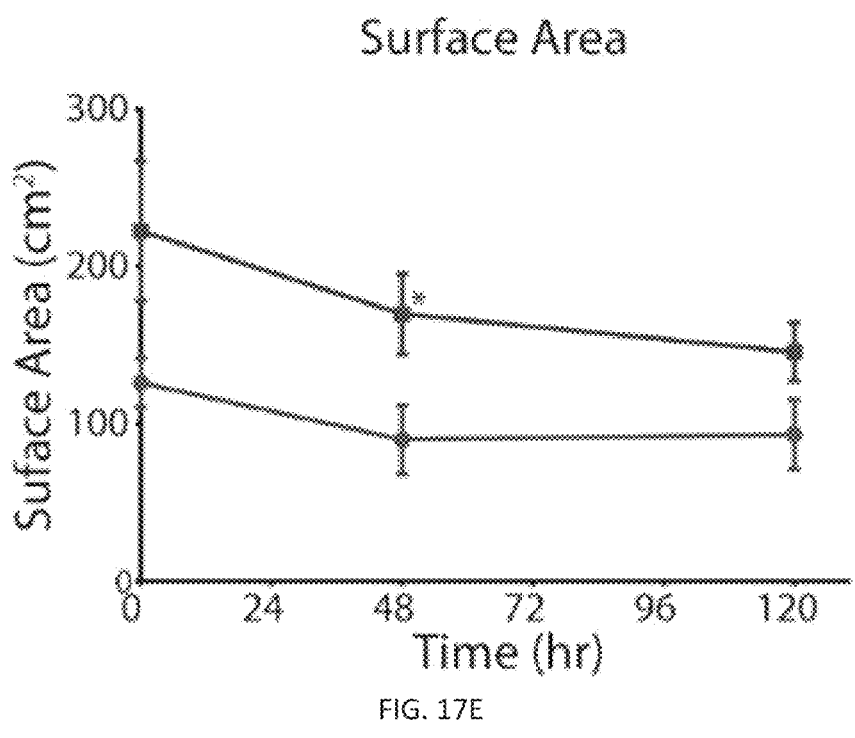
Figure 17F:
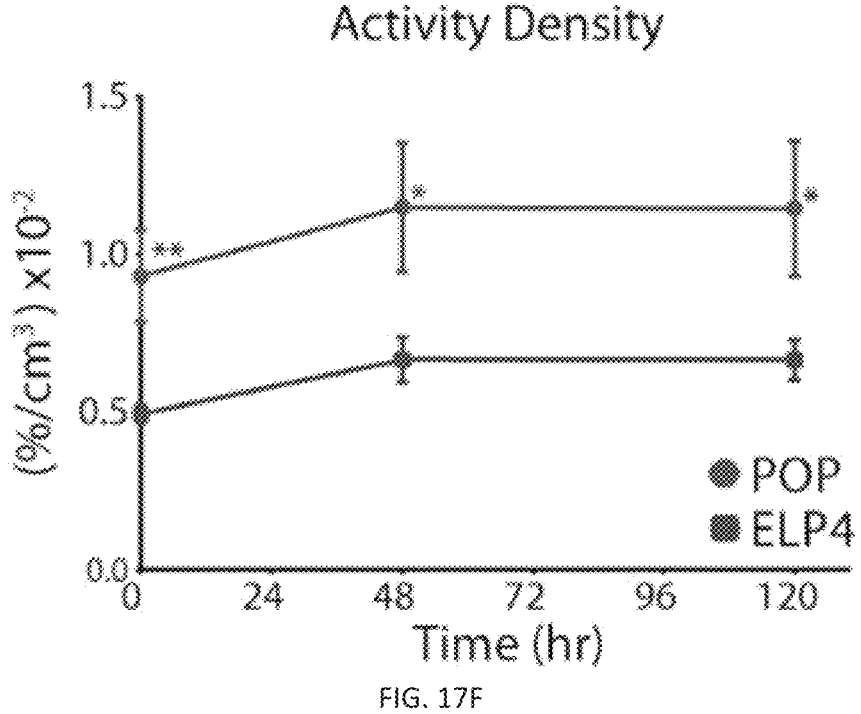
Figure 18A:
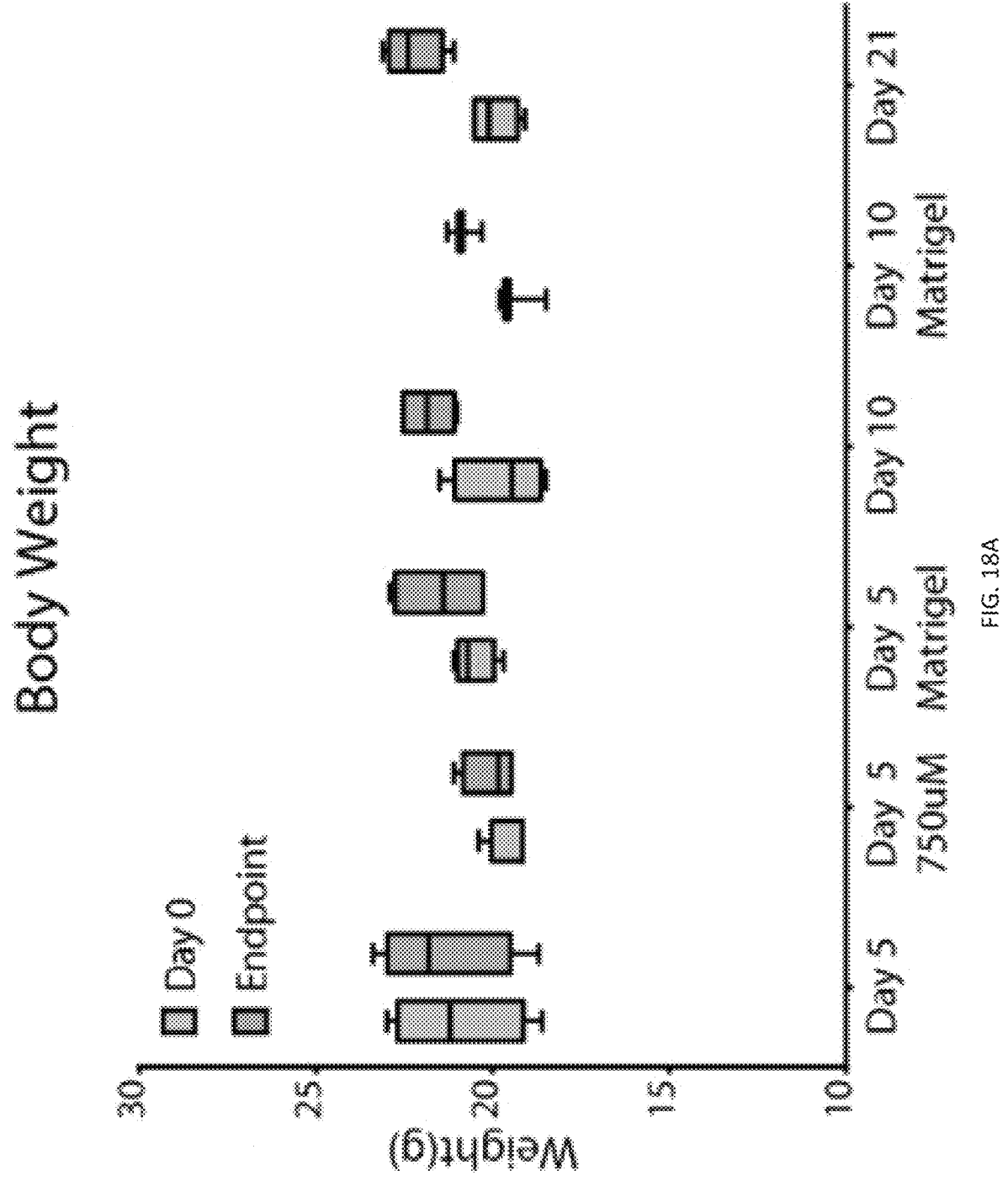
FIG. 18A-FIG. 18C: Excised depots.
Figure 18B:
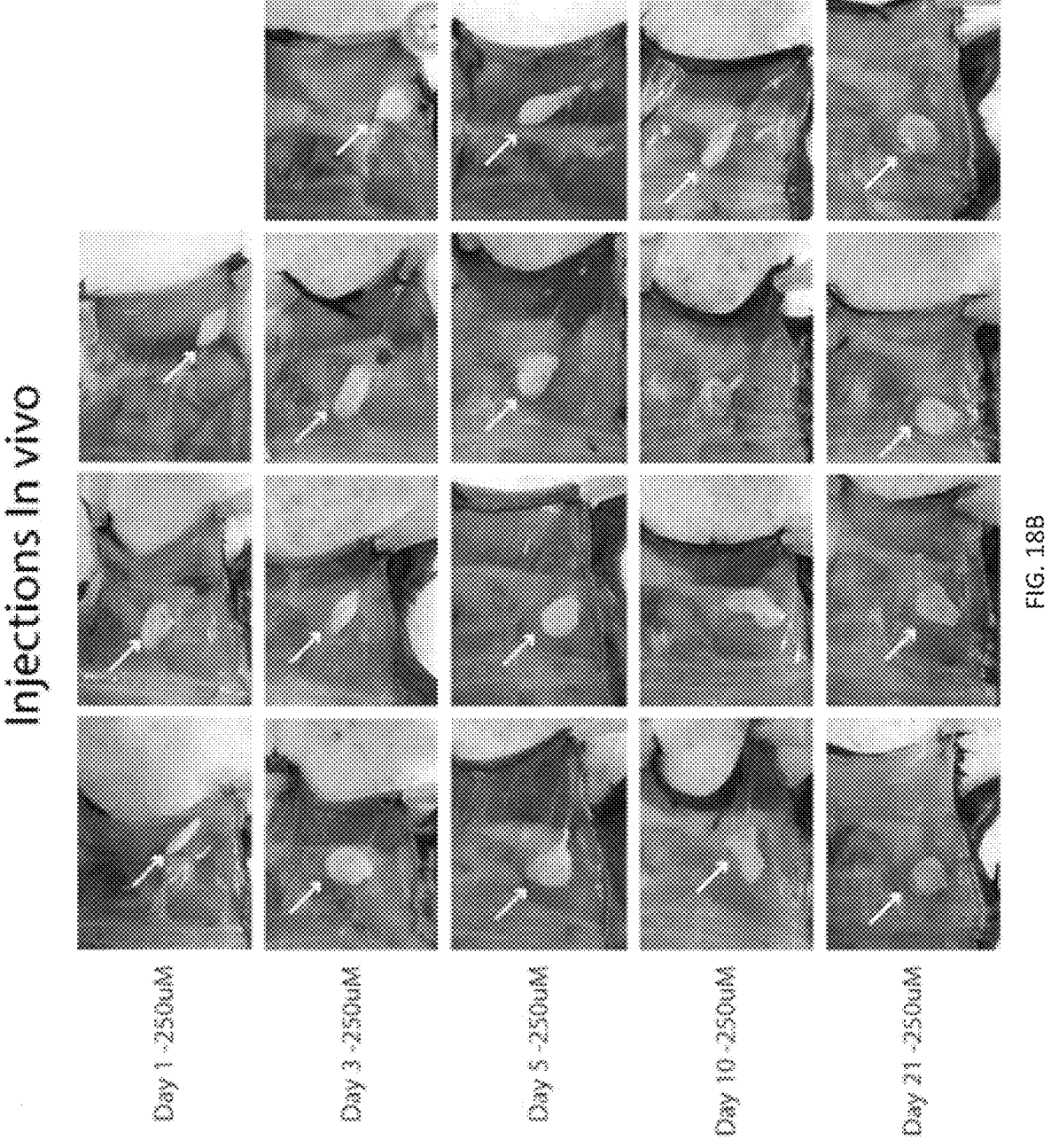
Figure 18B:
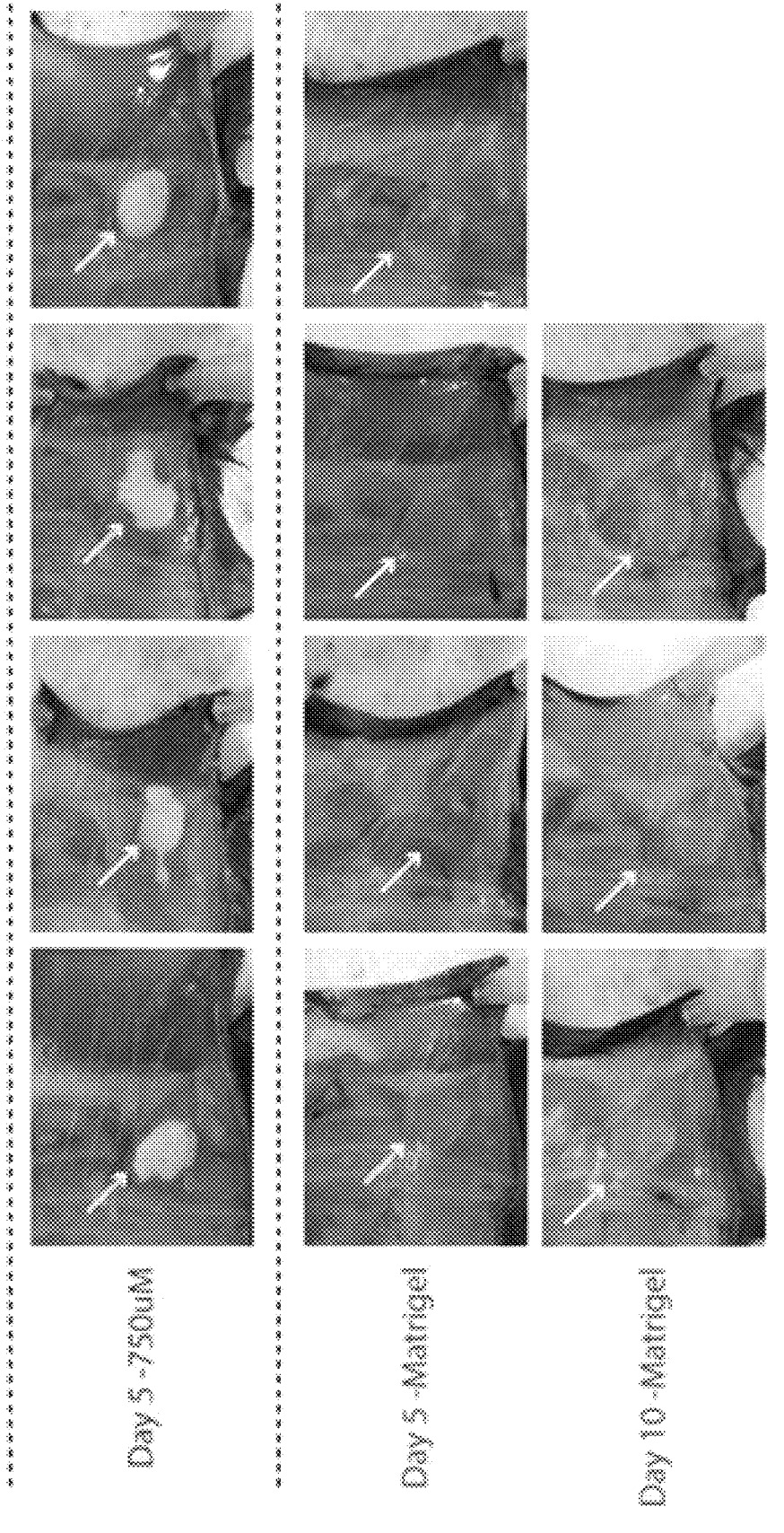
Figure 18C:
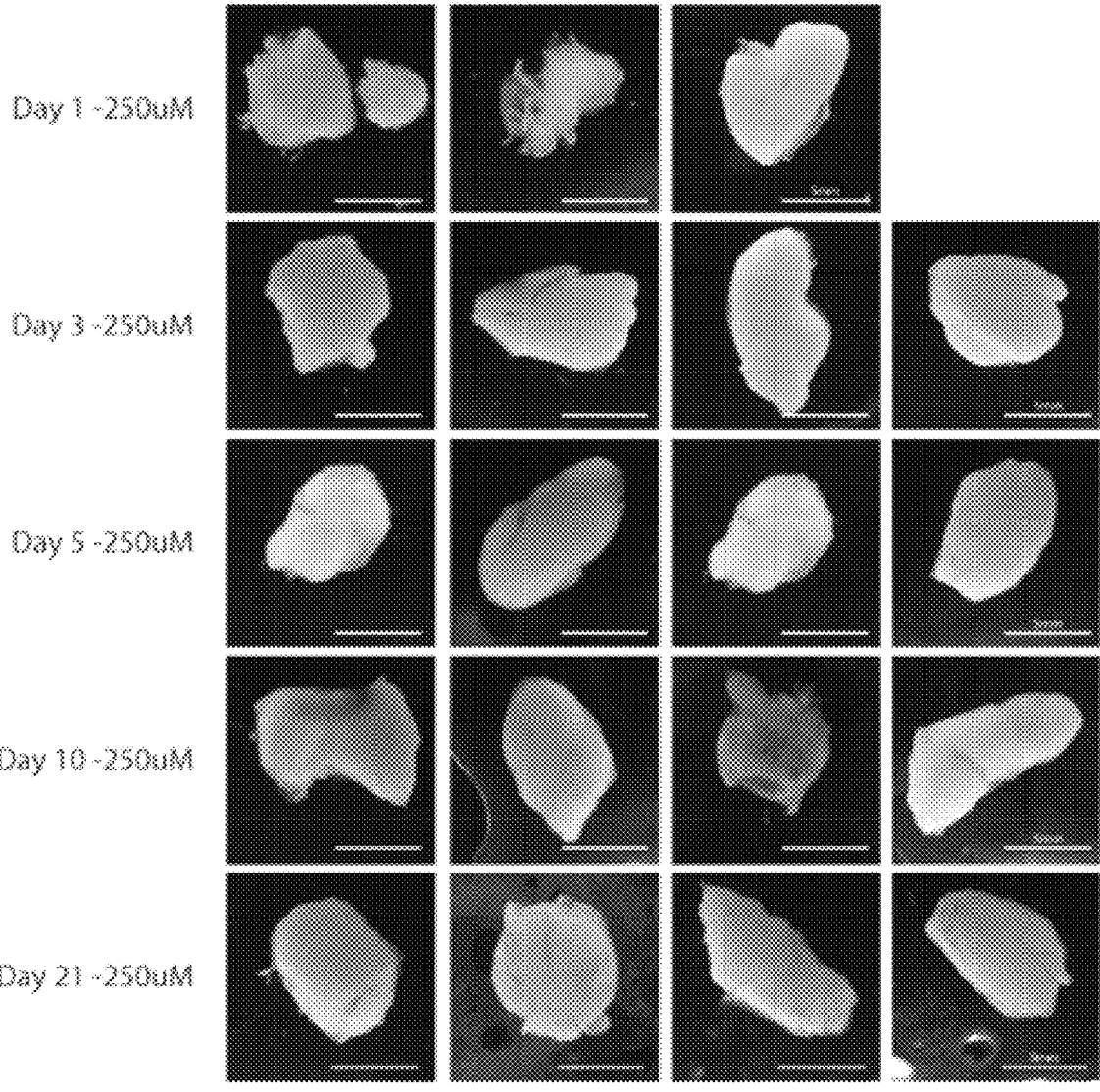
Figure 18C:
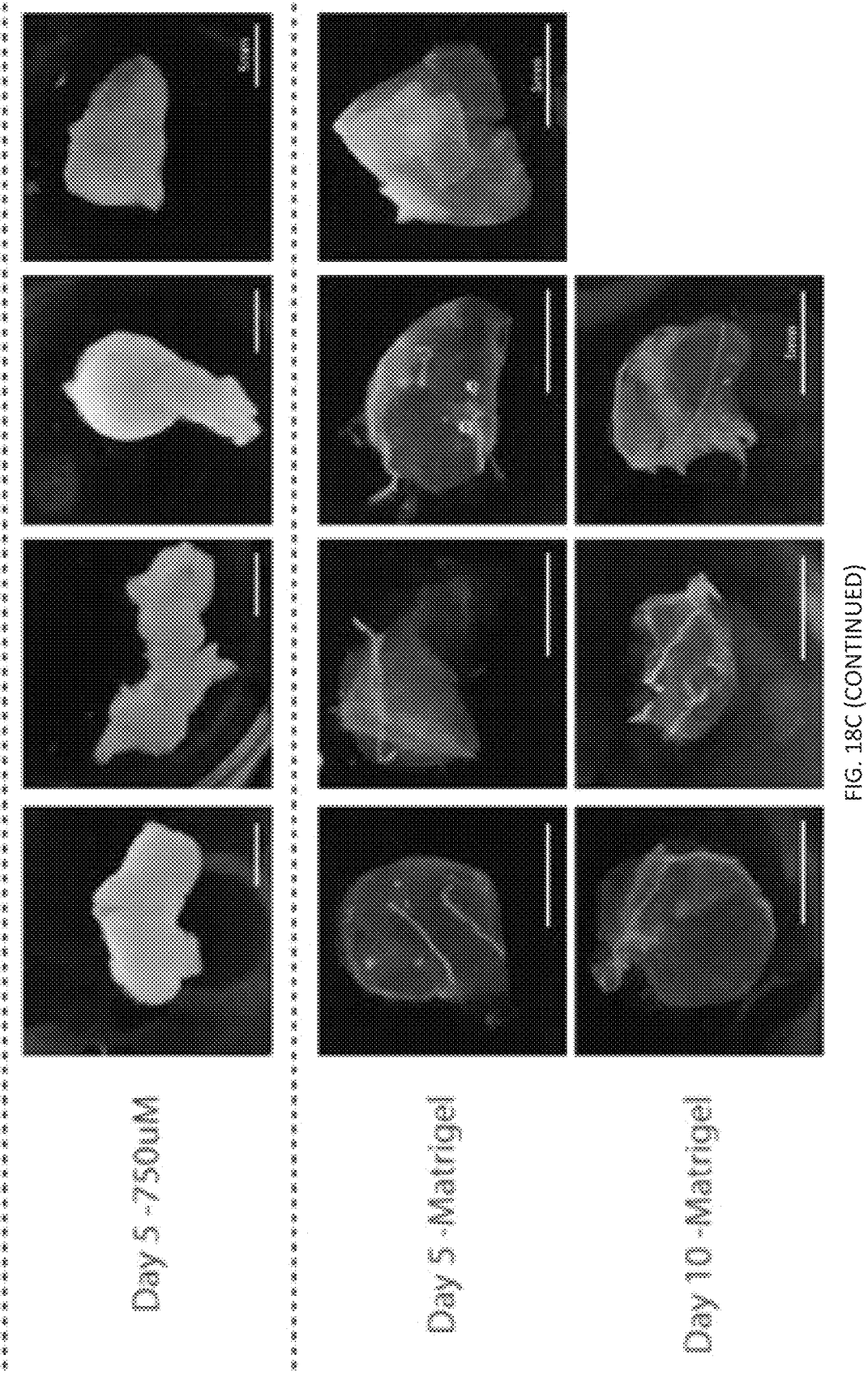
Figure 19A:
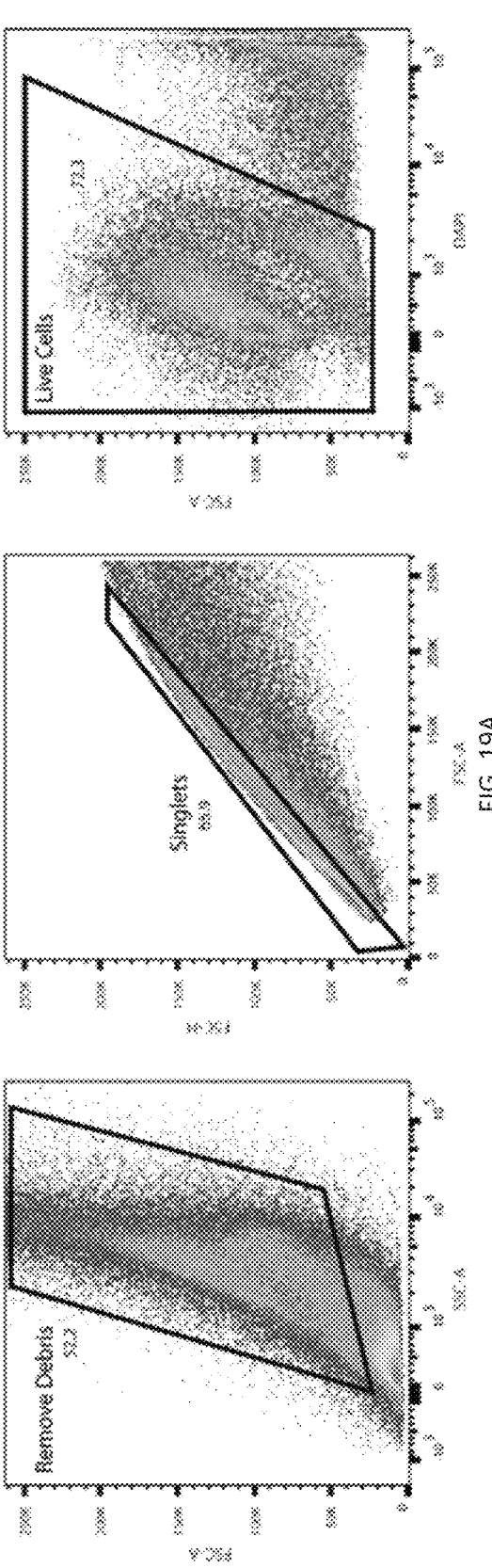
FIG. 19A-FIG. 19G: Flow cytometry gates for 250 μM POP.
Figure 19B:
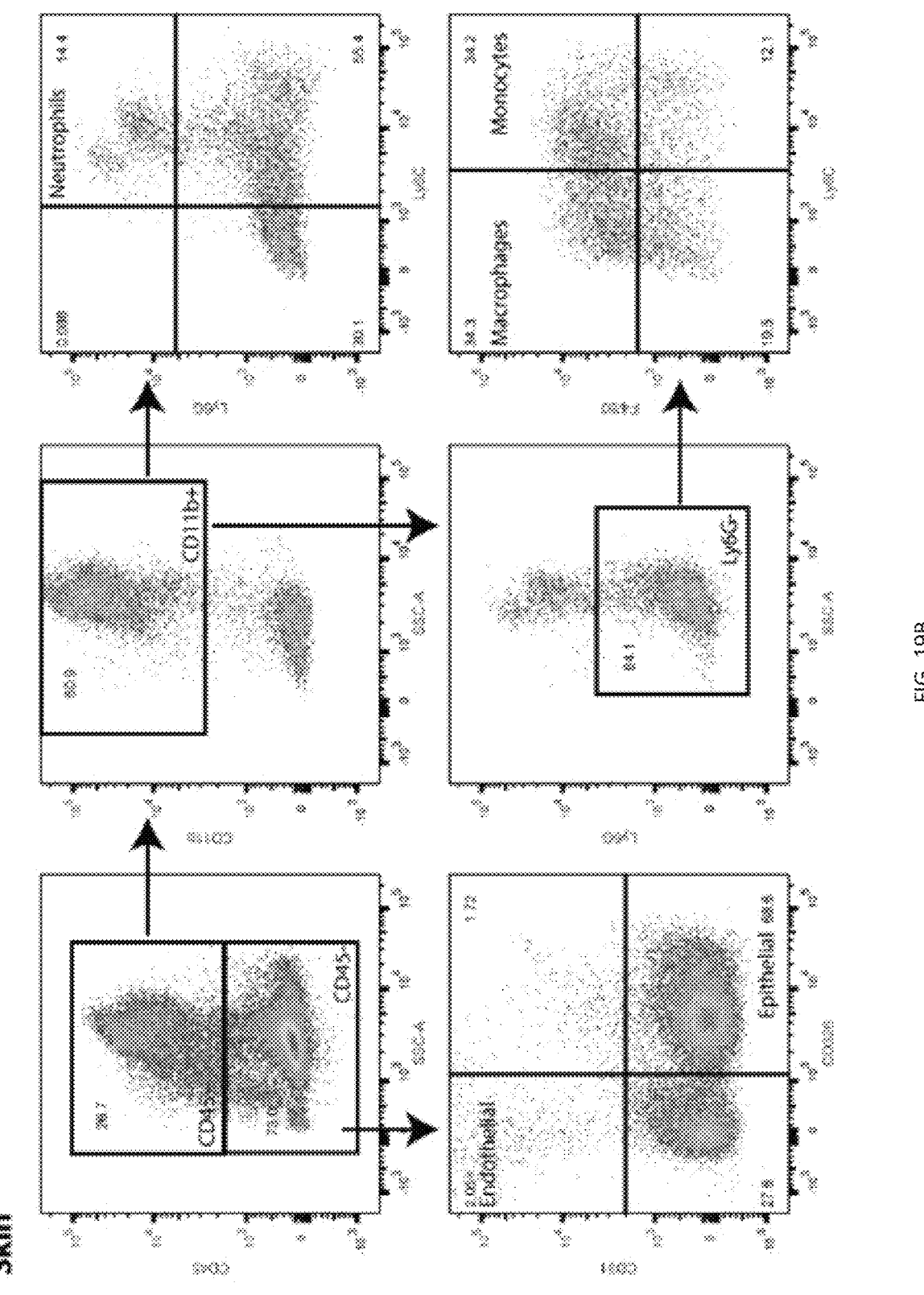
Figure 19C:
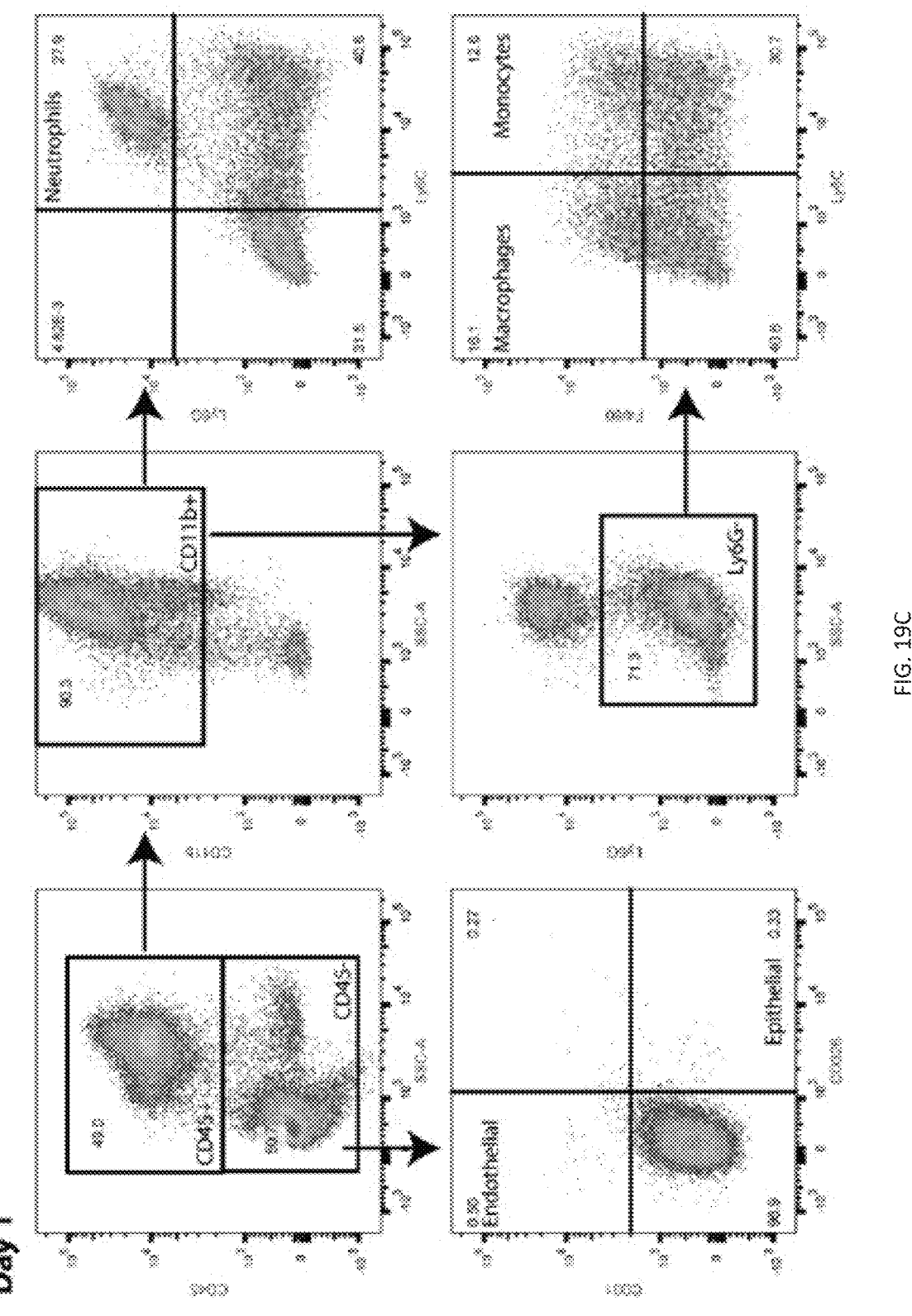
Figure 19D:
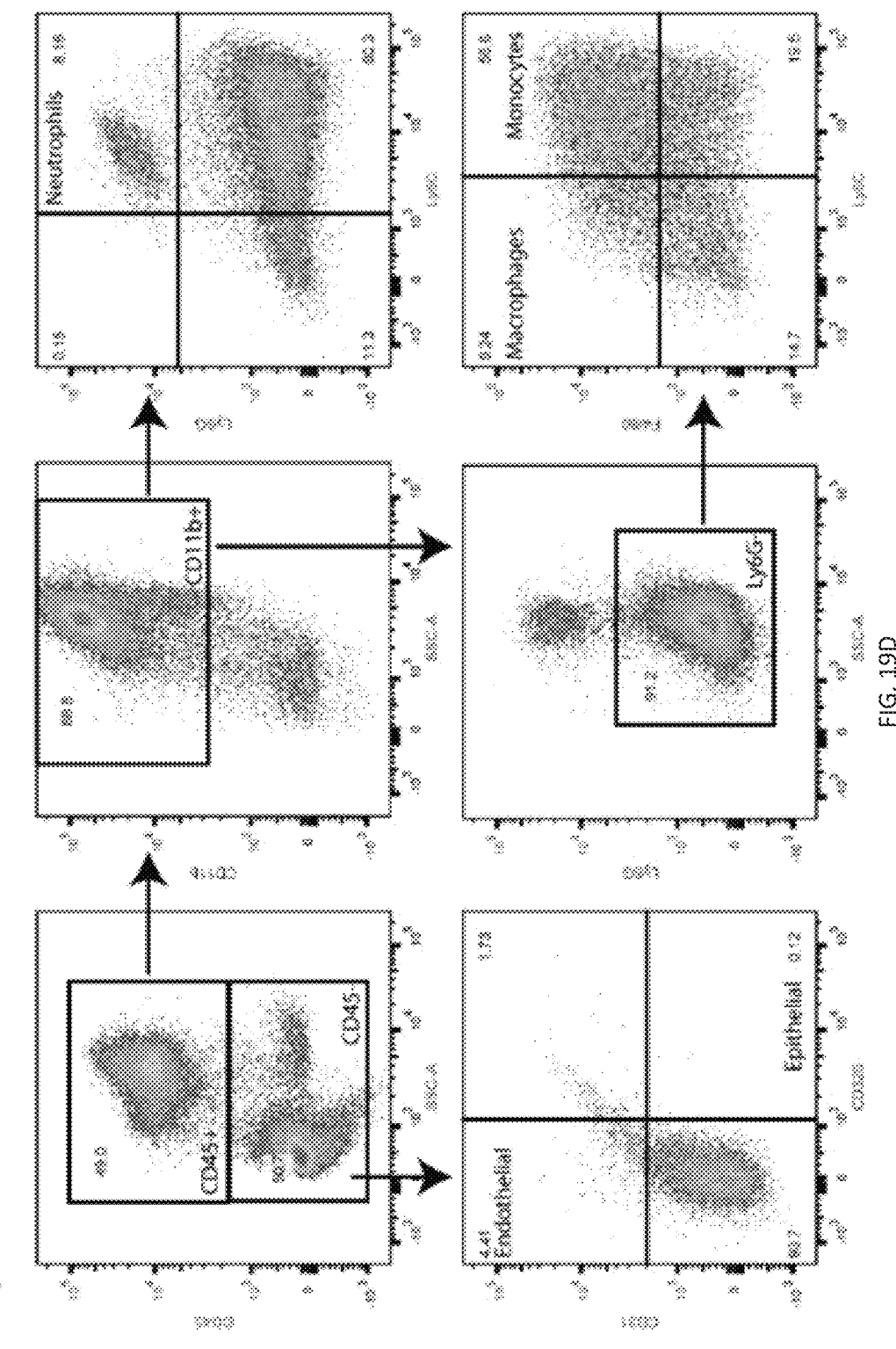
Figure 19E:
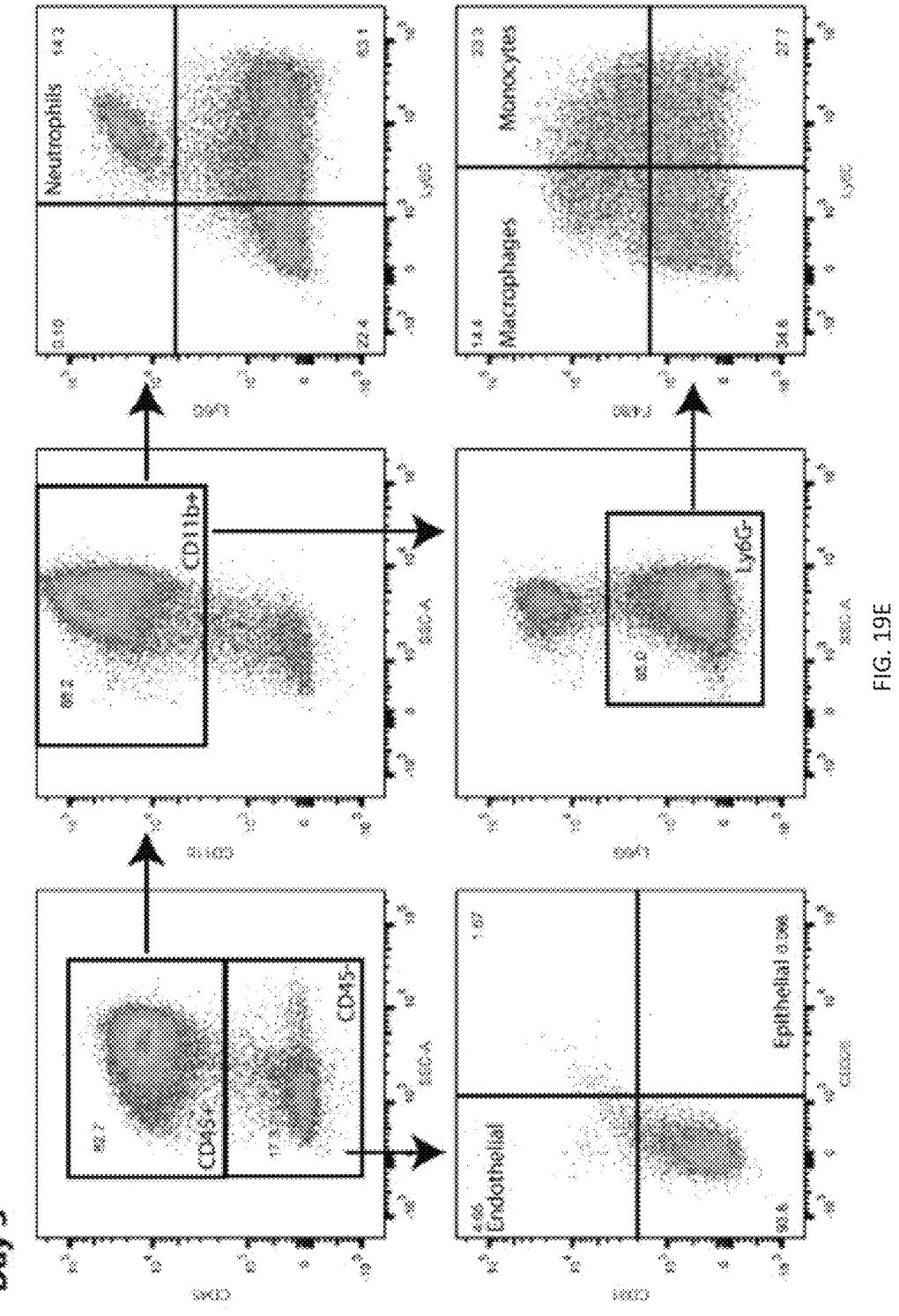
Figure 19F:
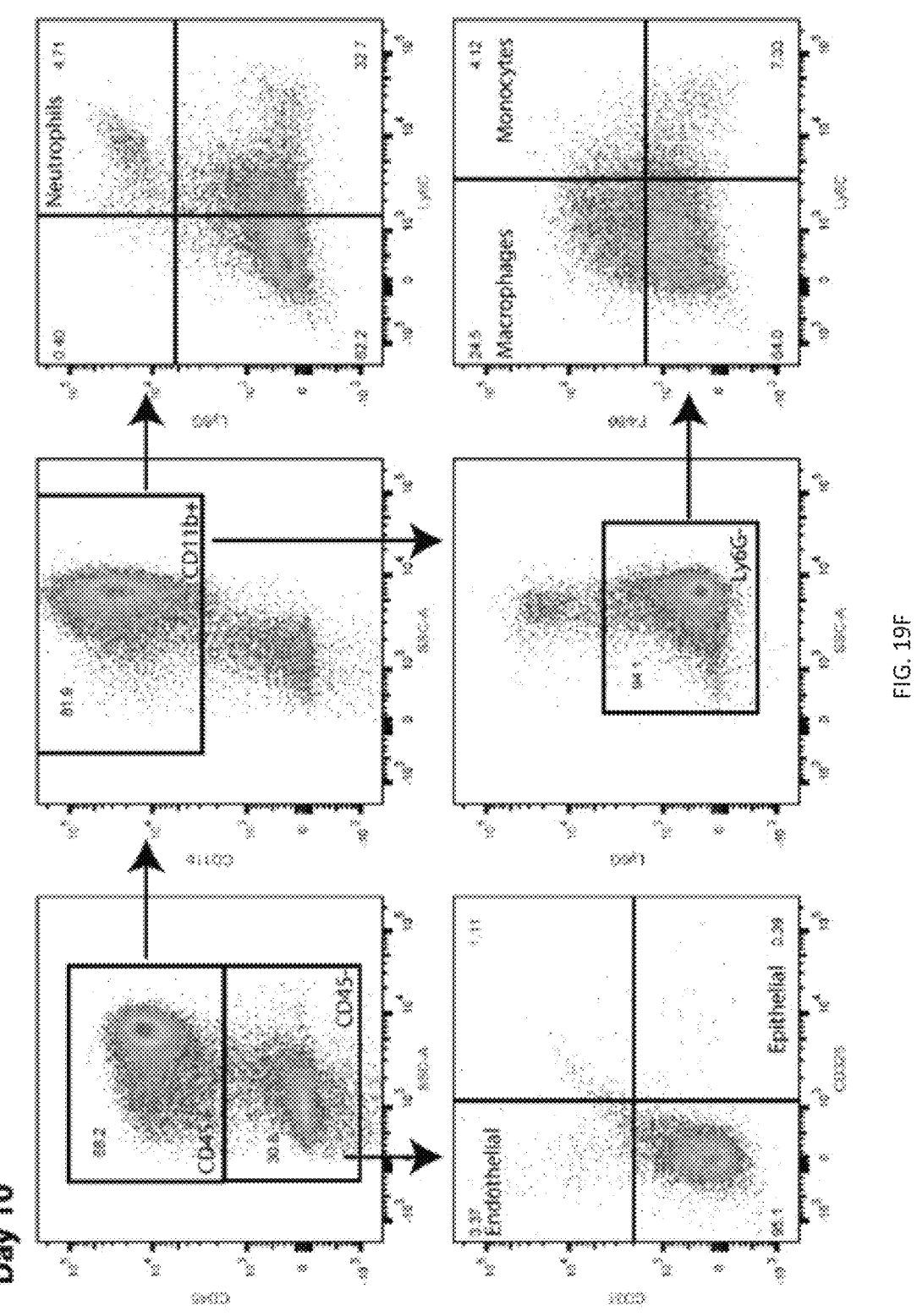
Figure 19G:
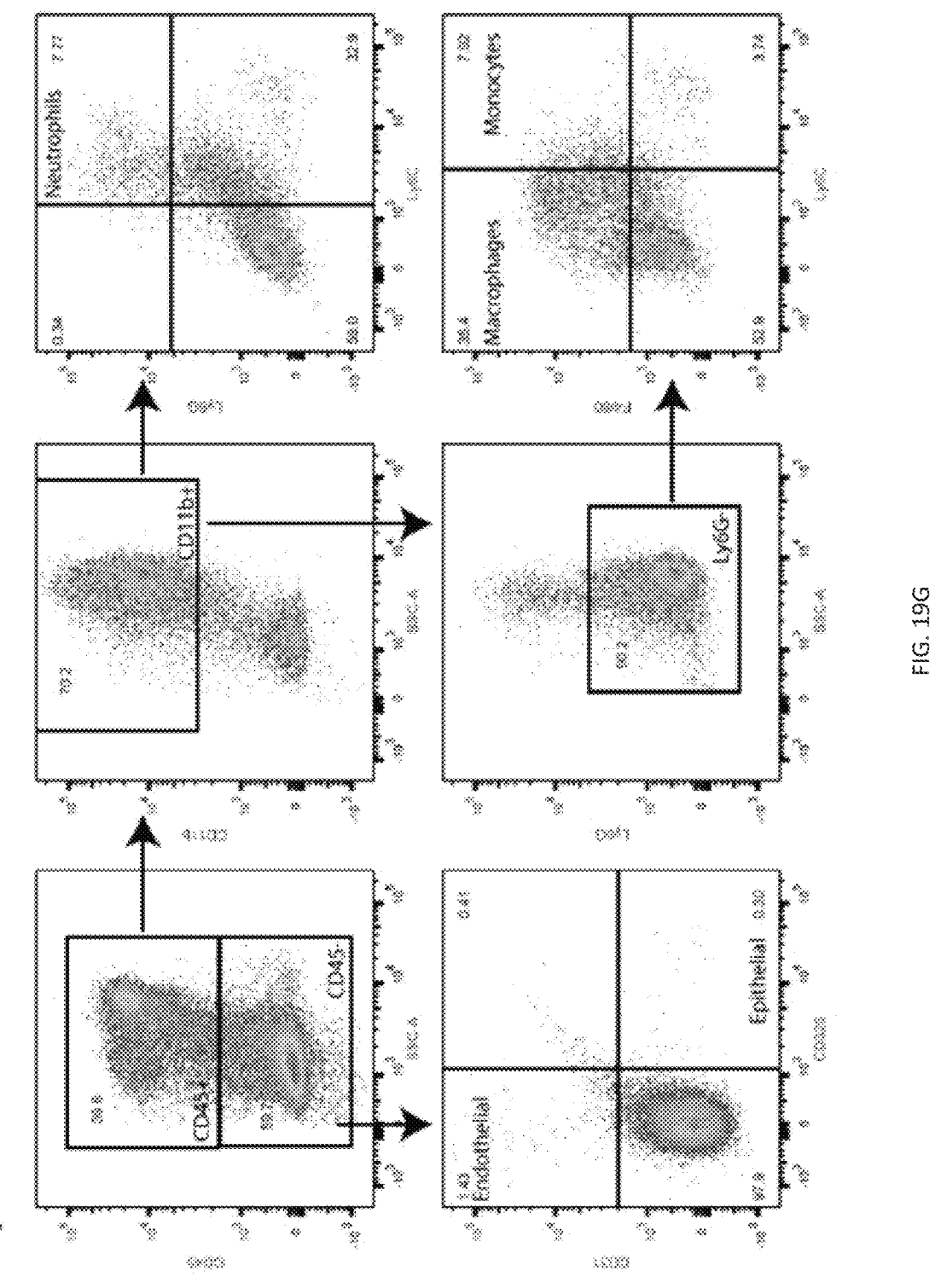

To assess the in vivo behavior of injected POP networks, we injected E1-H5-25%-120 (200 μL at 250 μM, 50 kDa) as subcutaneous (s.c.) depots and compared their pharmacokinetic (PK) properties to fully disordered ELPs of the same base sequence. POP depots, labeled with $^{125}$I, showed significantly less polymer release (4.8% of initial dose) than their pure ELP counterparts (8.7%) after 120 hours despite their increased porosity and greater surface area (FIG. 6A). Terminal bio-distribution also revealed no critical accumulation in vital organs (FIG. 16). Upon injection, ELPs diffuse in the s.c. space until they are not externally apparent whereas POPs form large, depots that are easily visible through the skin (FIG. 6B). Single-photon emission computed tomography (SPECT) confirms that ELP depots are more diffuse than POP depots with higher surface-to-volume ratios and lower polymer densities (FIG. 6C and FIG. 17).

Figure 6D:
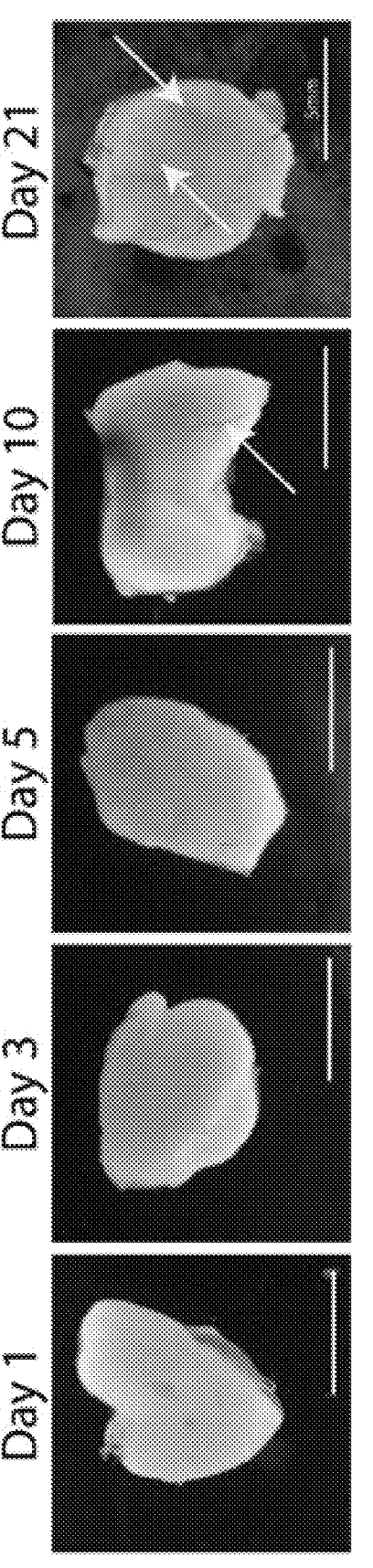
Figure 6E:
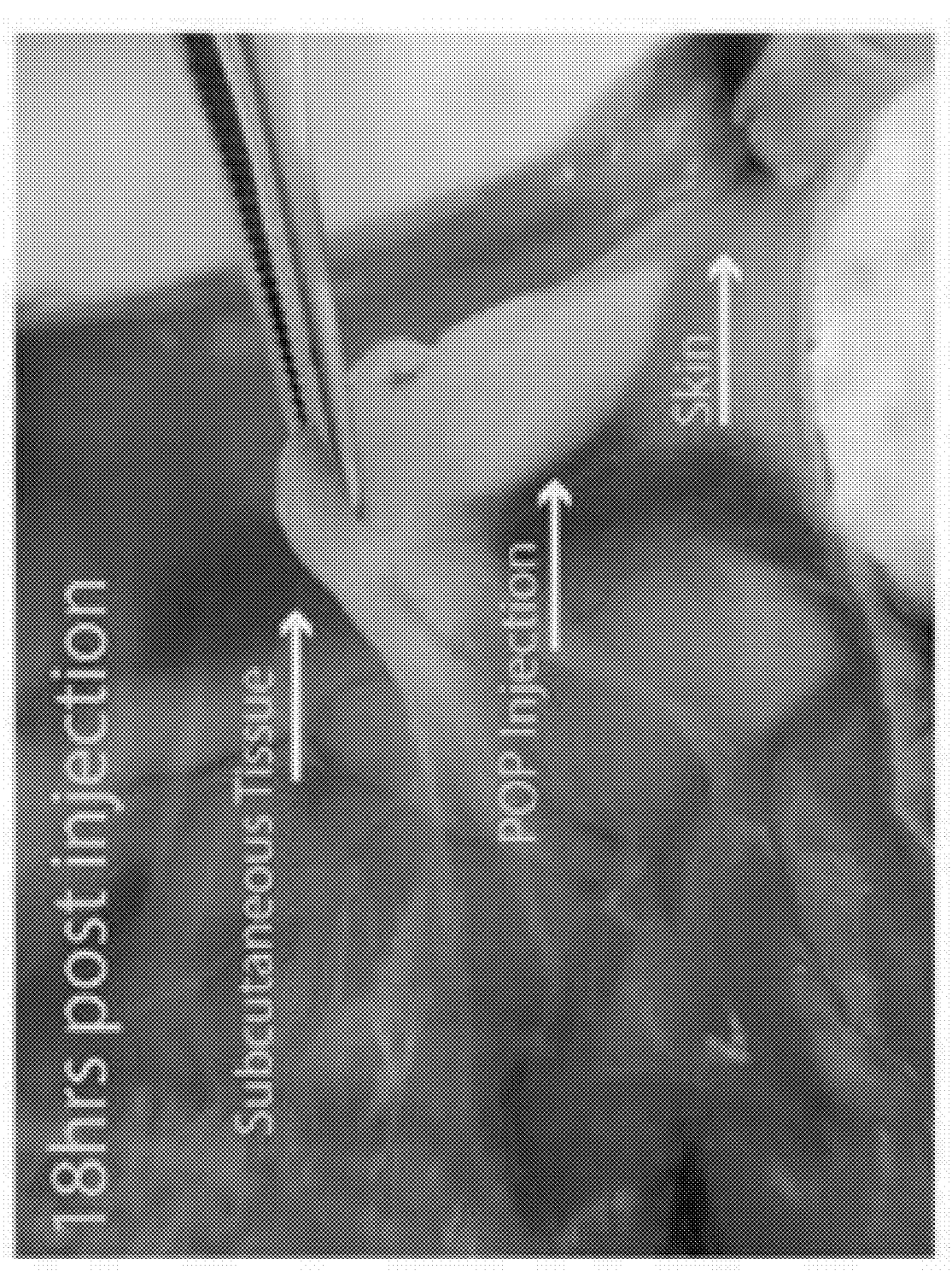
Figure 6F:
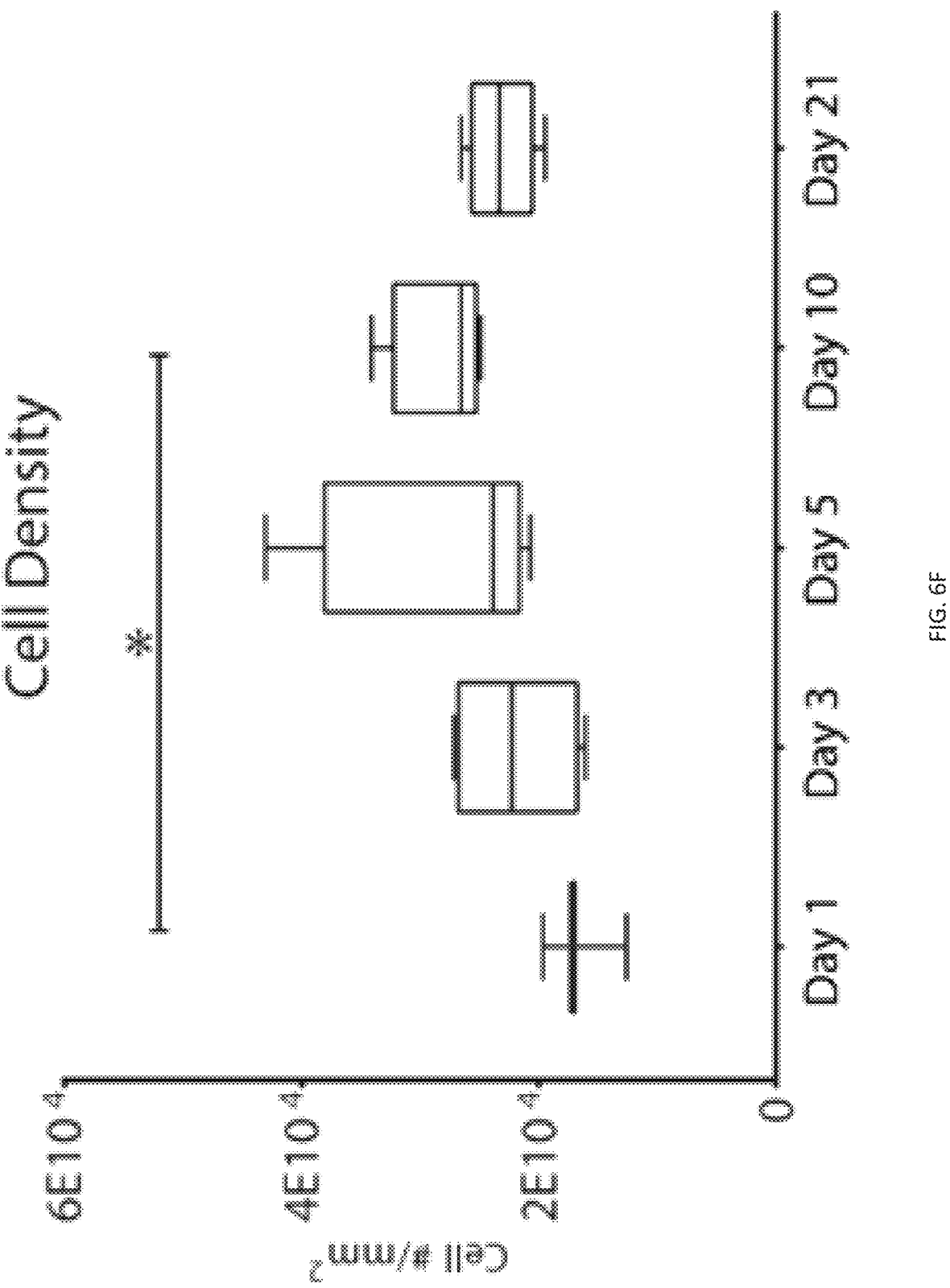
Figure 6G:
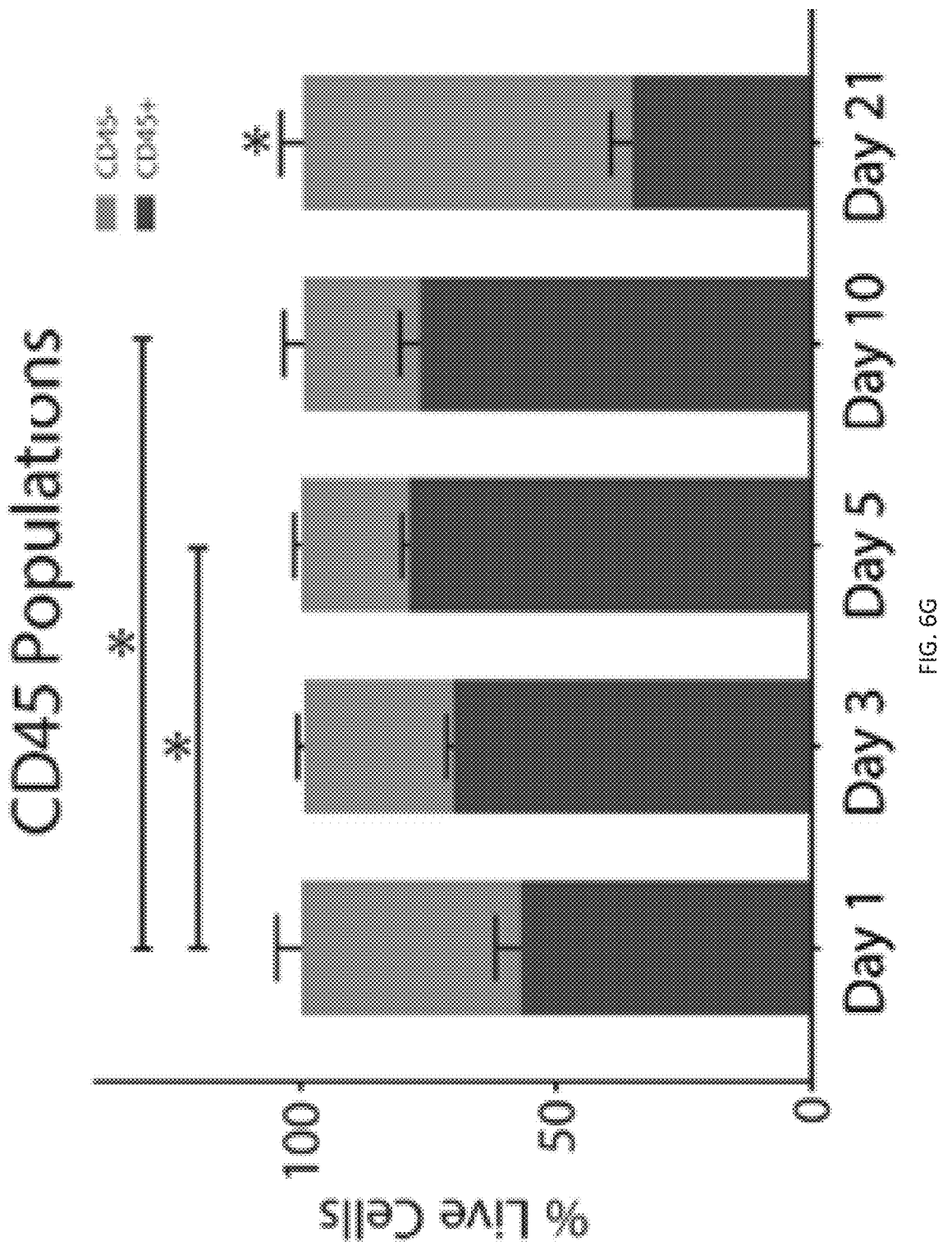
Figure 6H:
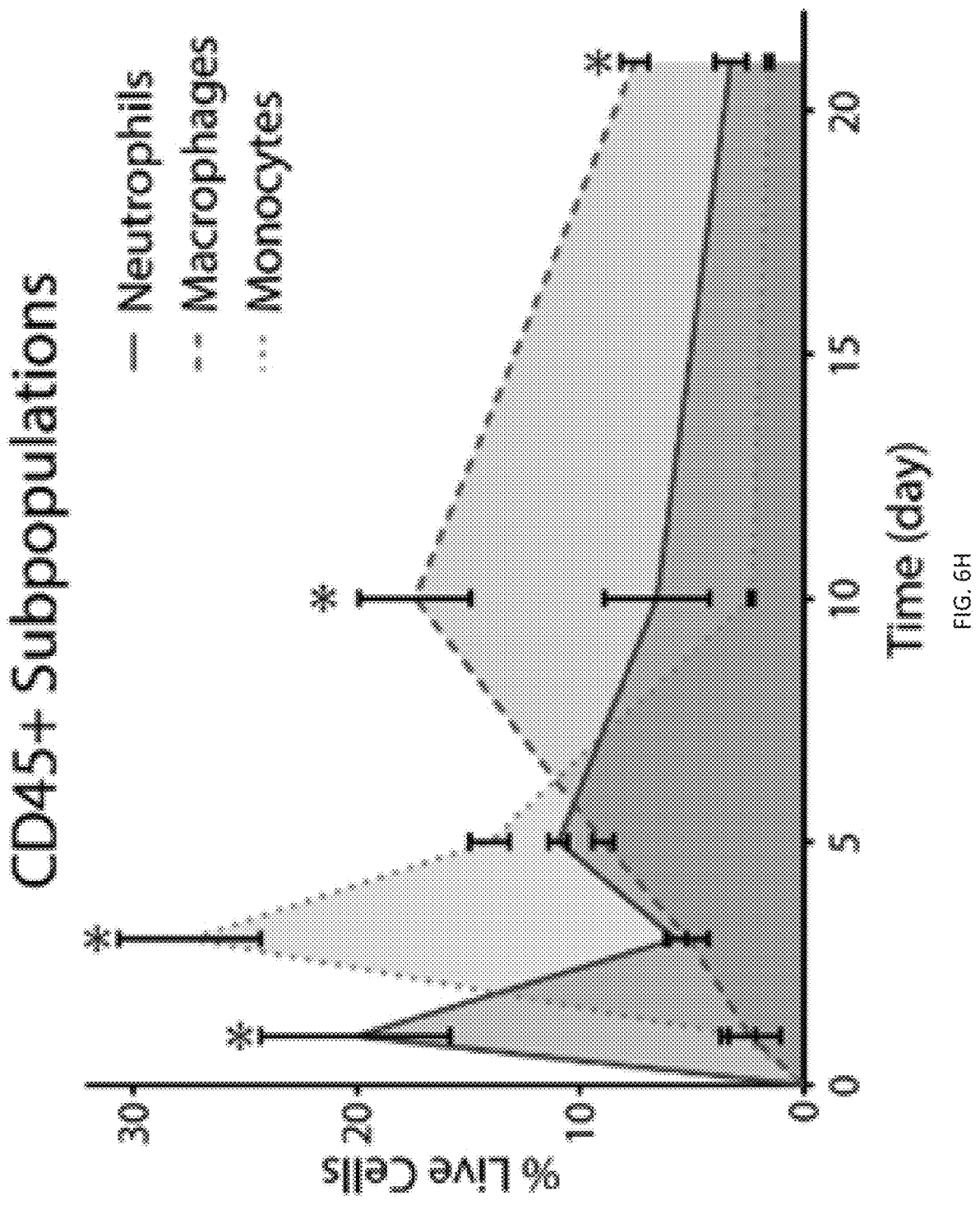
Figure 61:
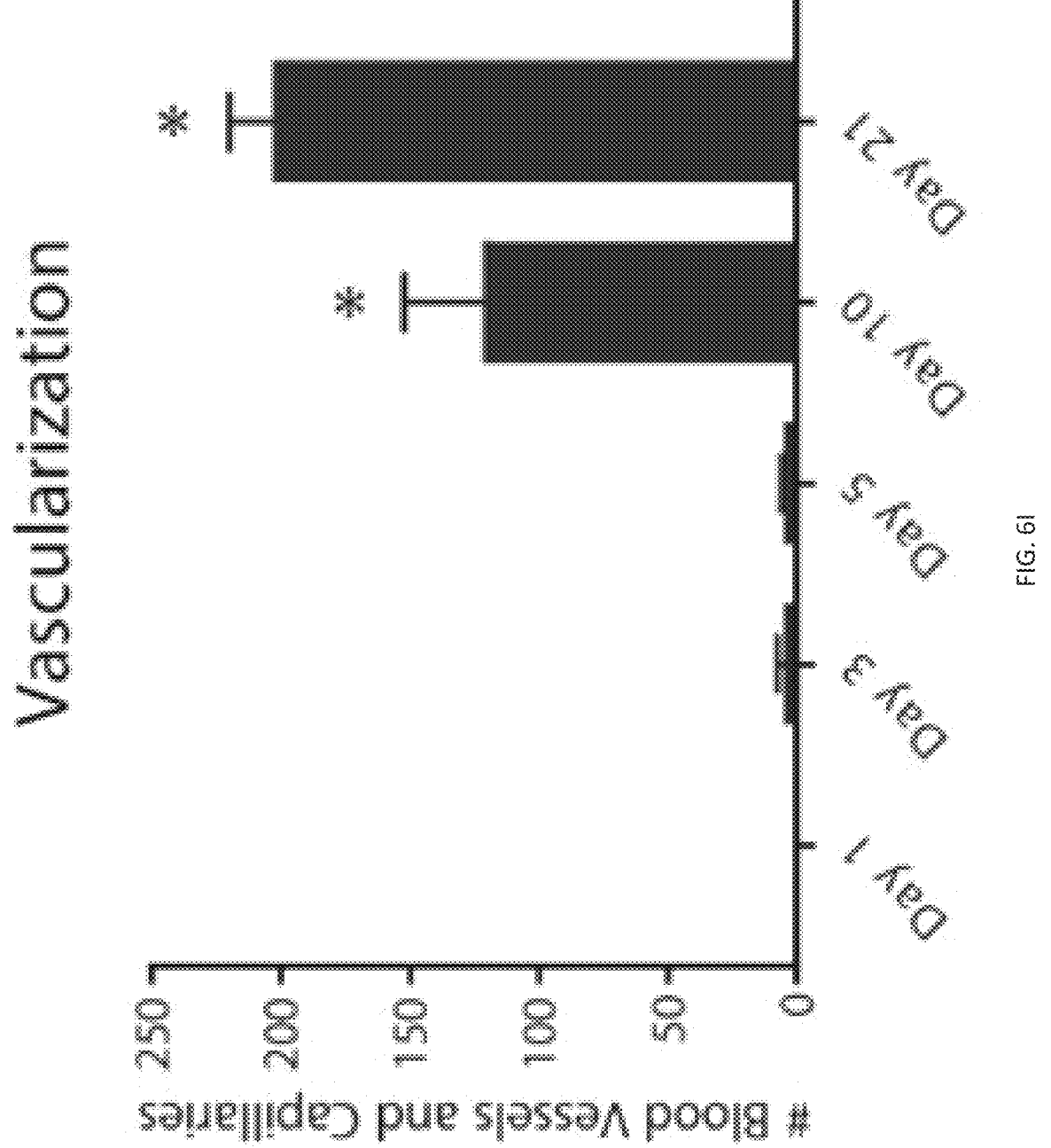
Figure 6J:
Figure 20A:
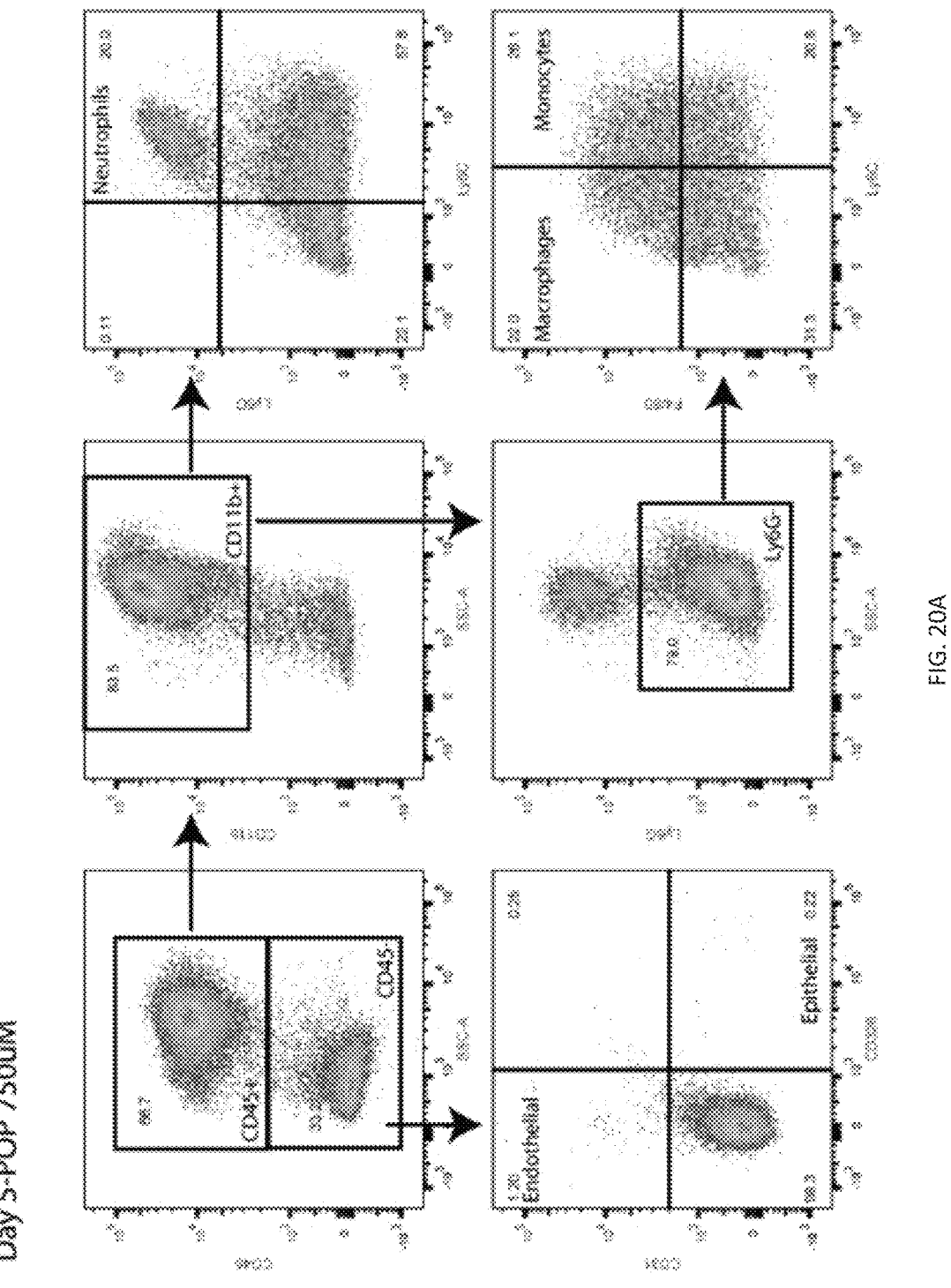
FIG. 20A-FIG. 20C: Flow gates for comparison groups. Additional example flow gates are shown for (FIG. 20A) Day 5 750 μM E1-H5-25%-120, (FIG. 20B) Day 5 Matrigel, and (FIG. 20C) Day 20 Matrigel.
Figure 20B:
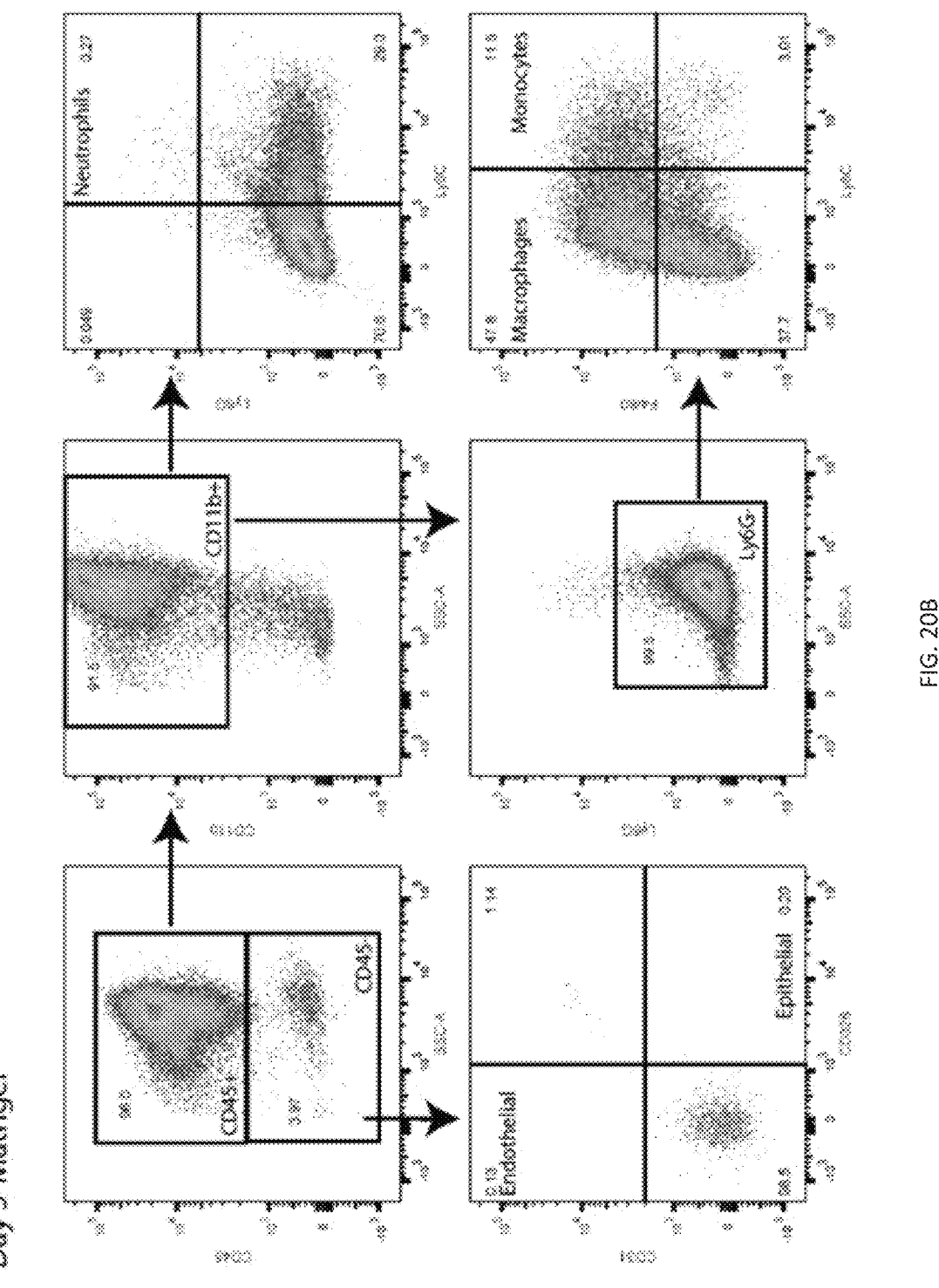
Figure 20C:
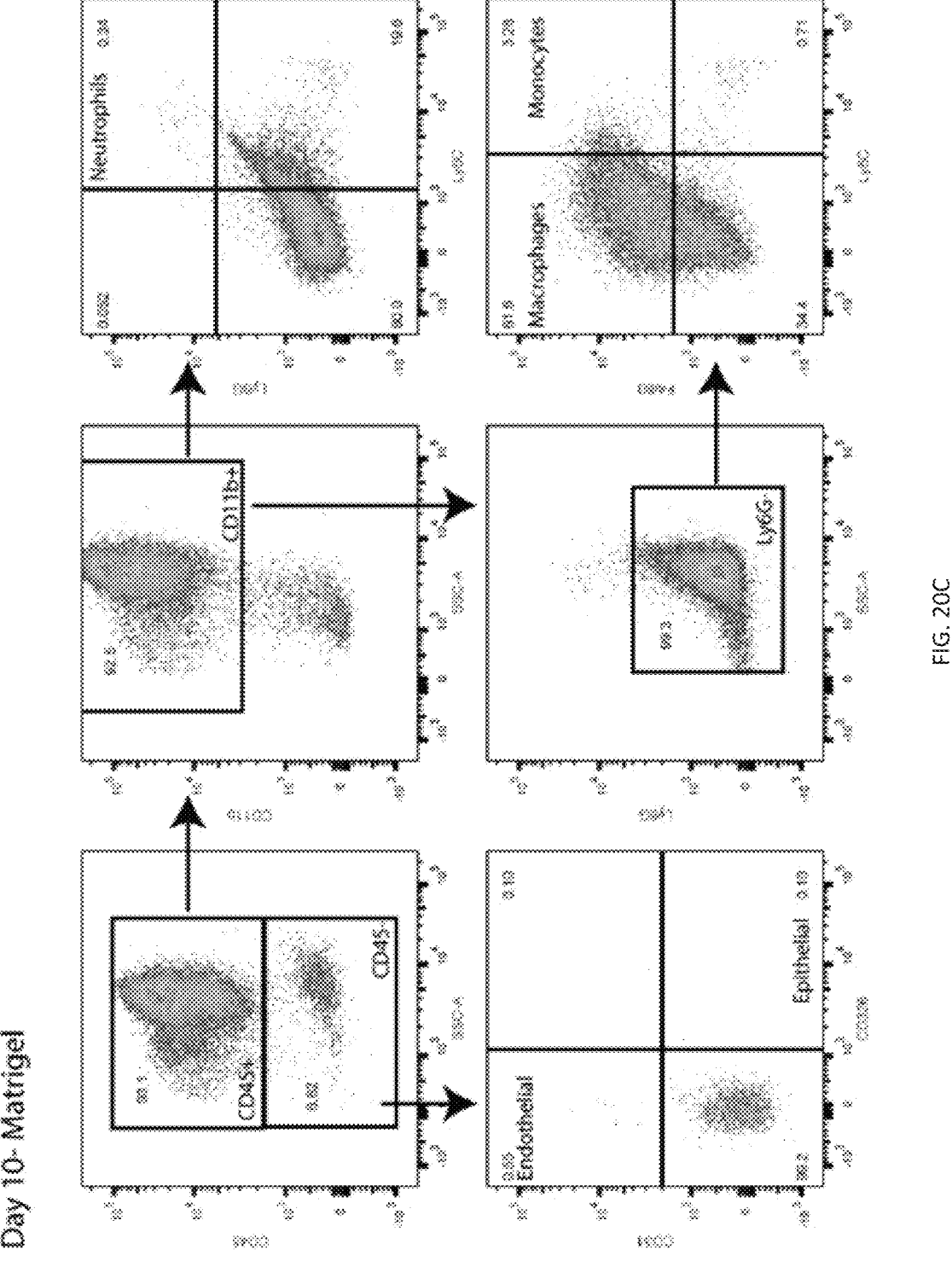
Figure 21A:
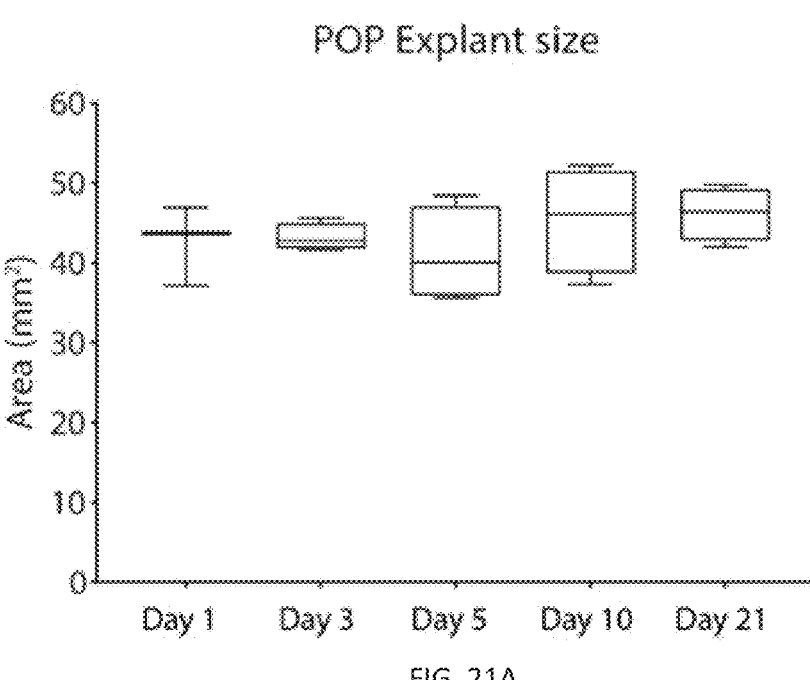
FIG. 21A-FIG. 21E: Additional cell subtype analysis.
Figure 21B:
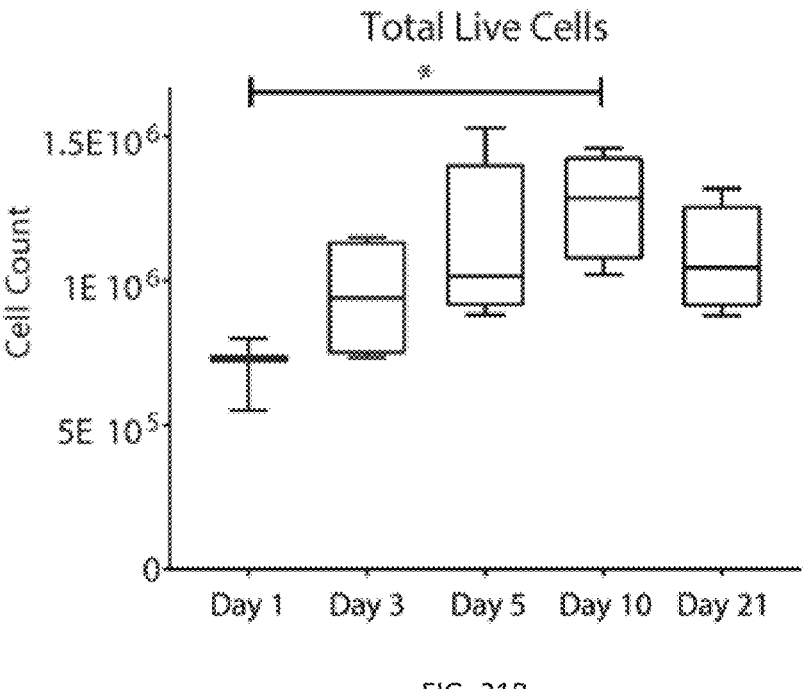
Figure 21C:
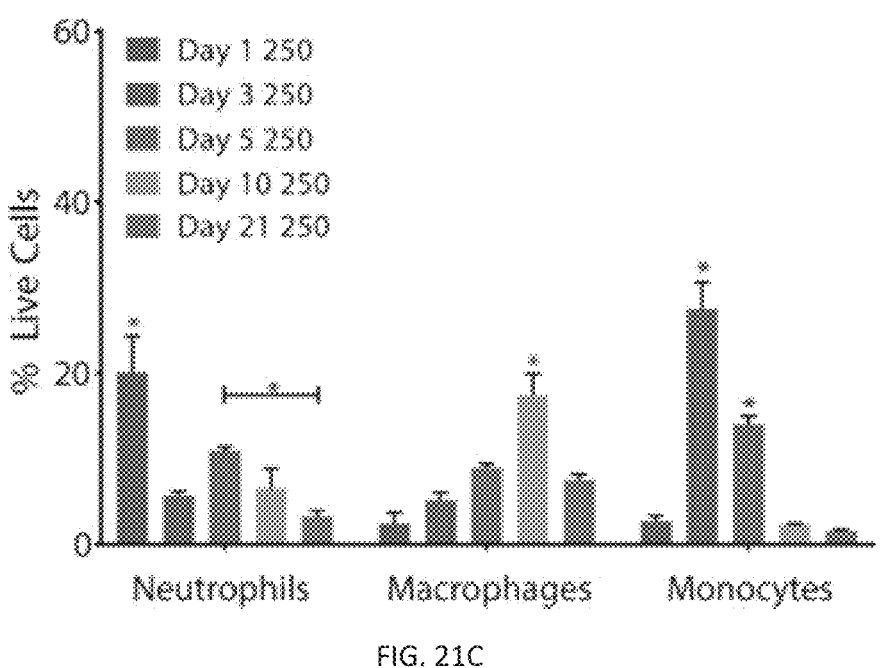
Figure 21D:
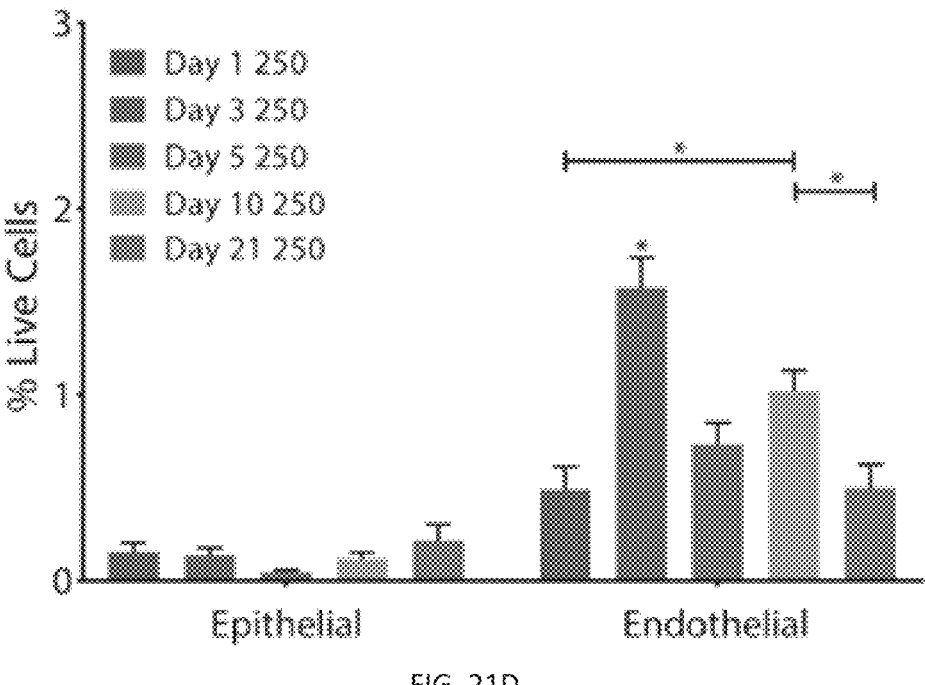
Figure 21E:
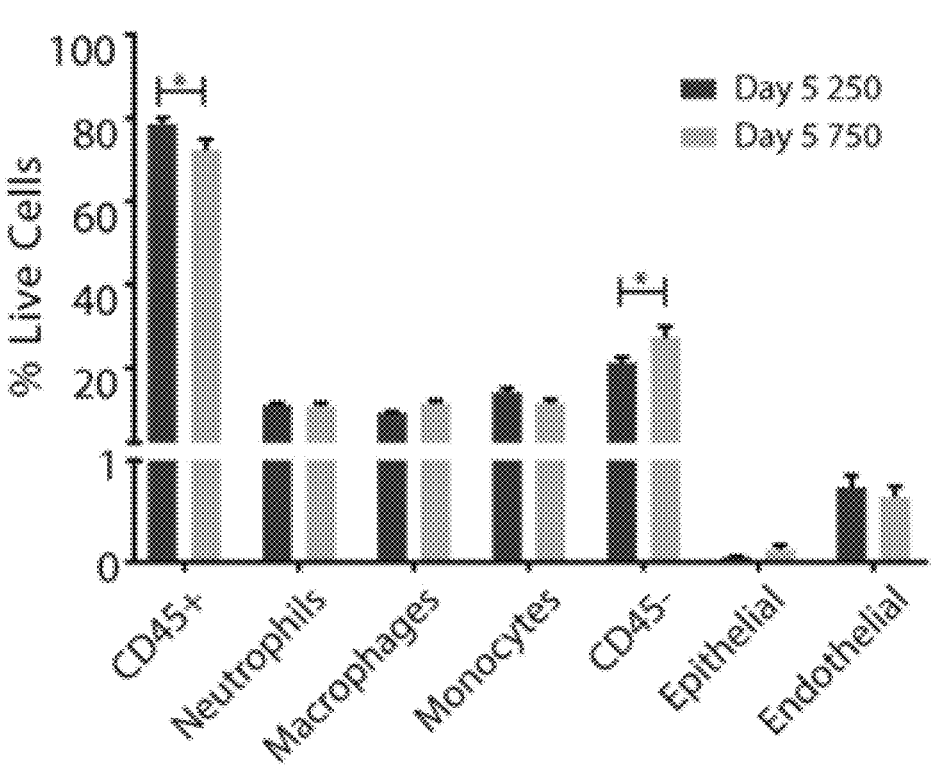
Figure 22A:
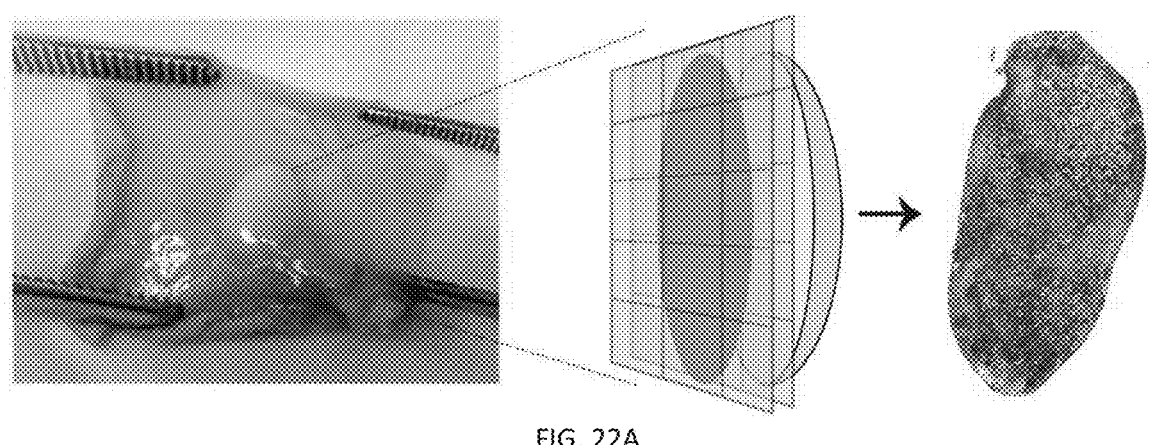
FIG. 22A-FIG. 22C: Additional Histological Analysis.
Figure 22B:
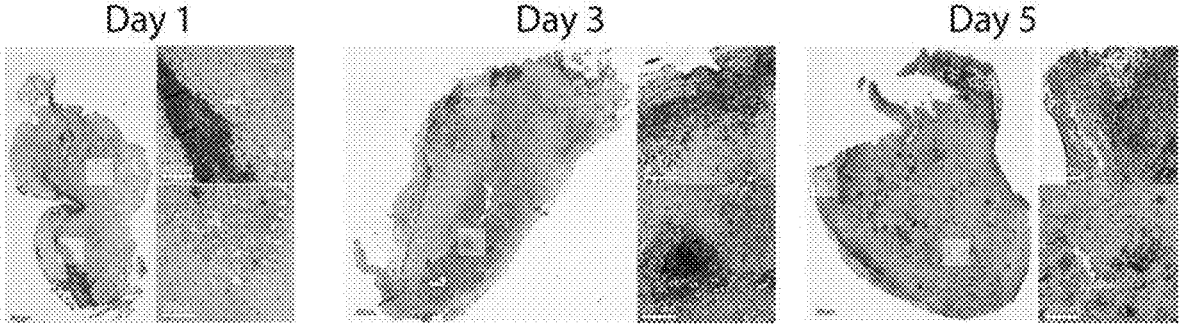
Figure 22C:
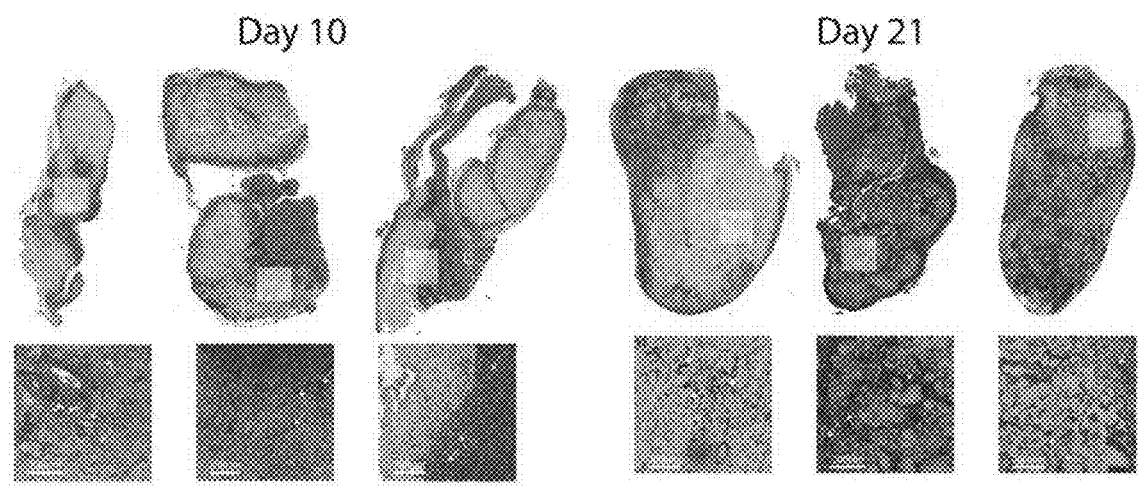
Figure 23A:
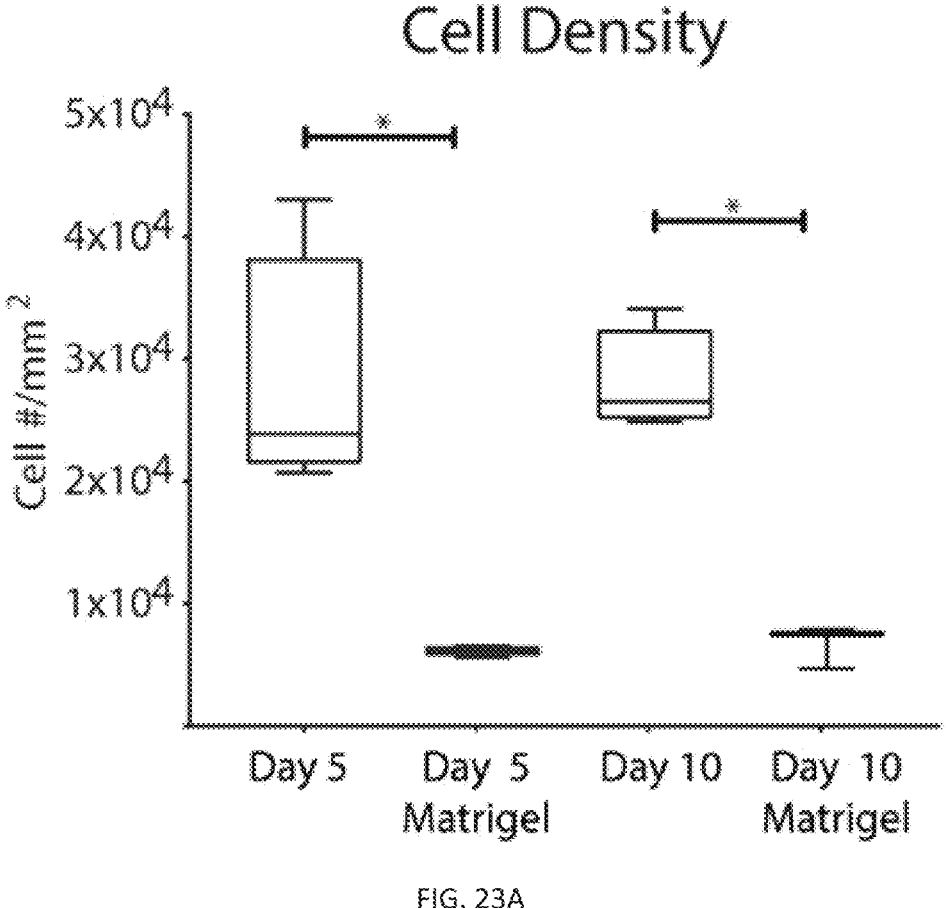
Figure 23B:
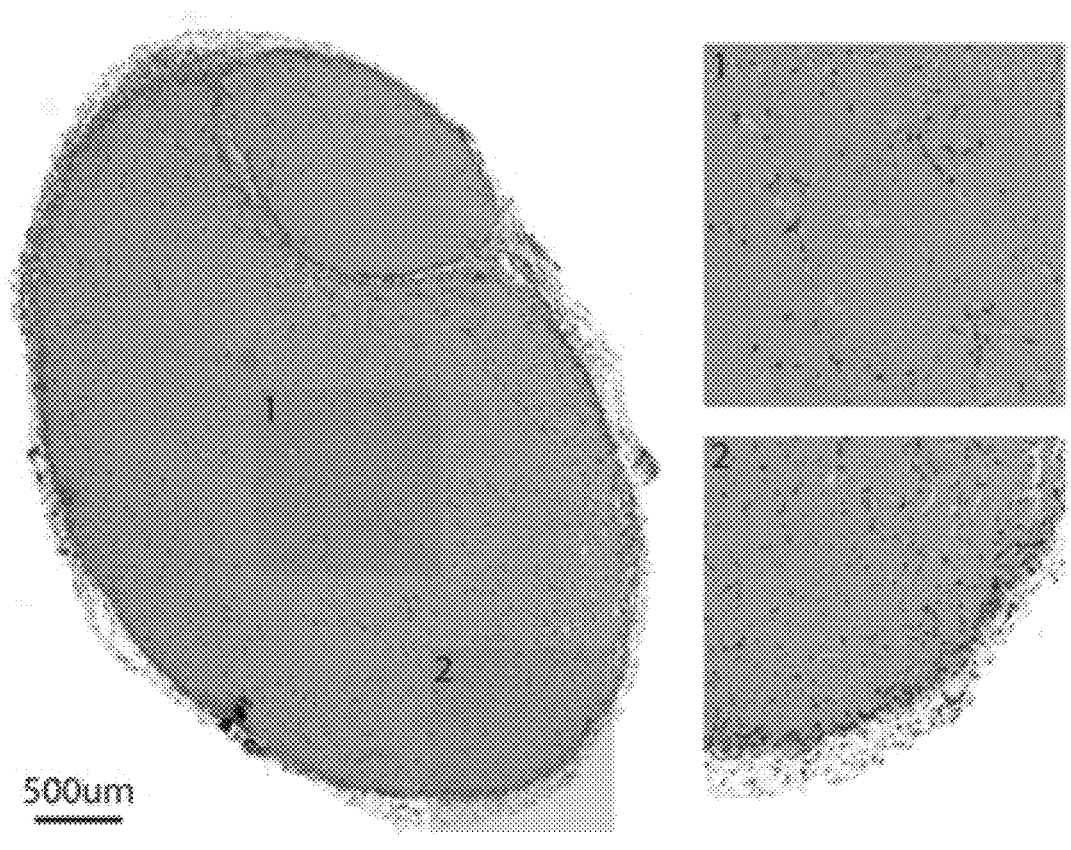
Figure 23C:
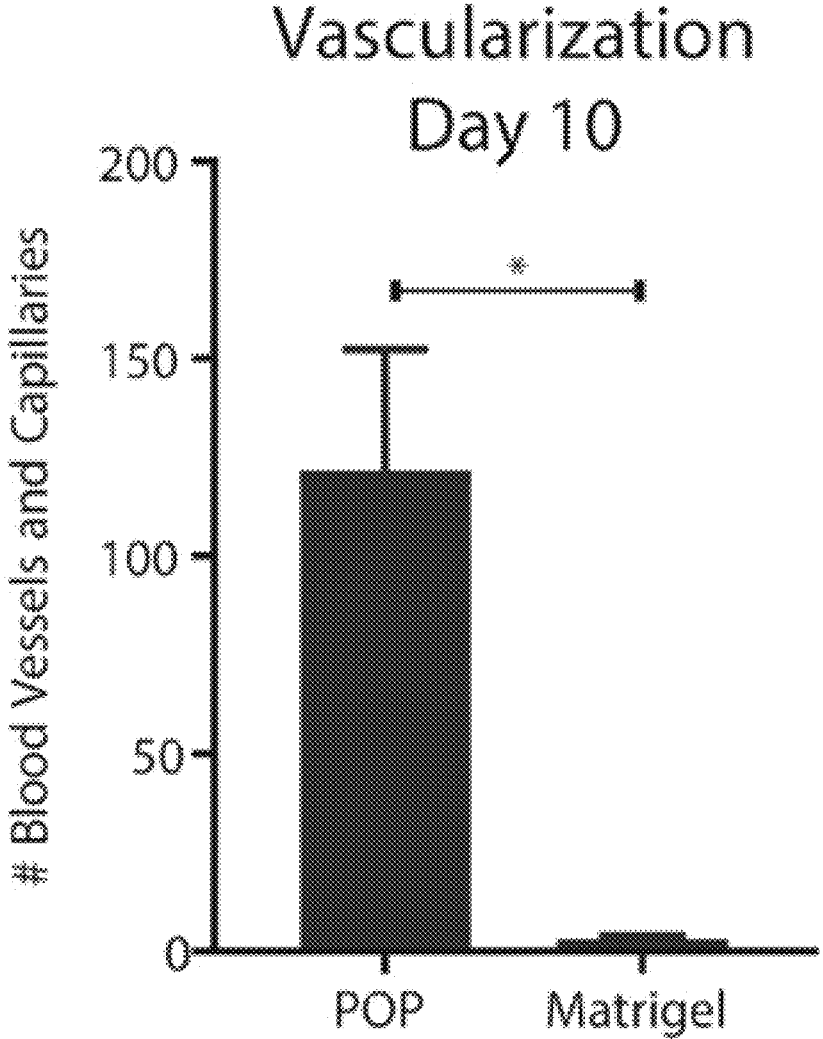
Figure 23E:
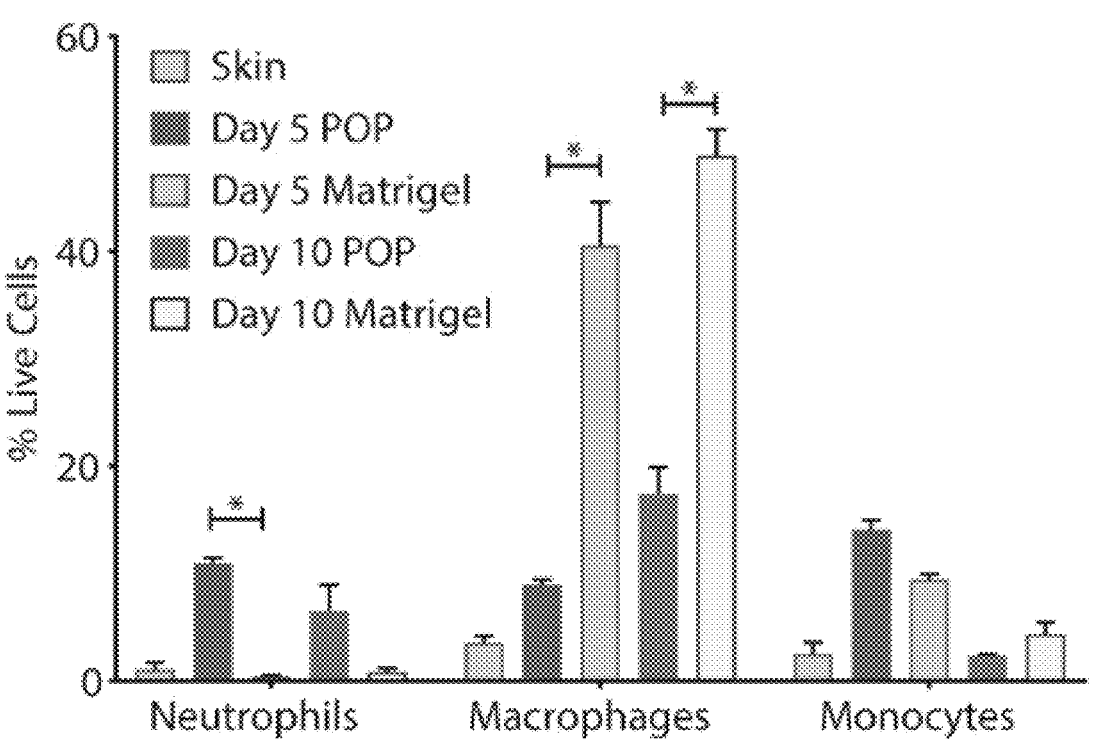
Figure 23F:
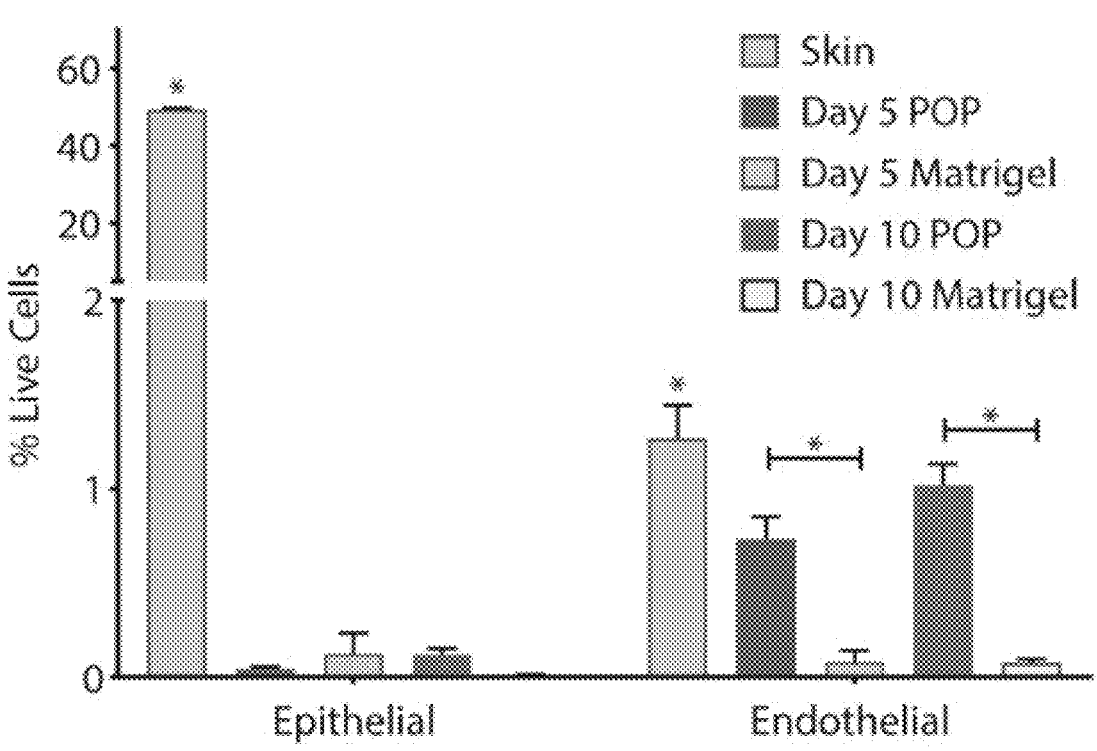
Figure 24A:
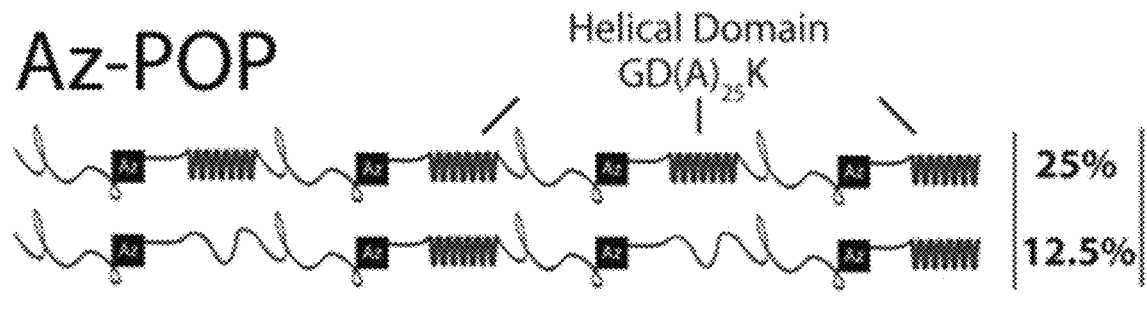
Figure 24B:
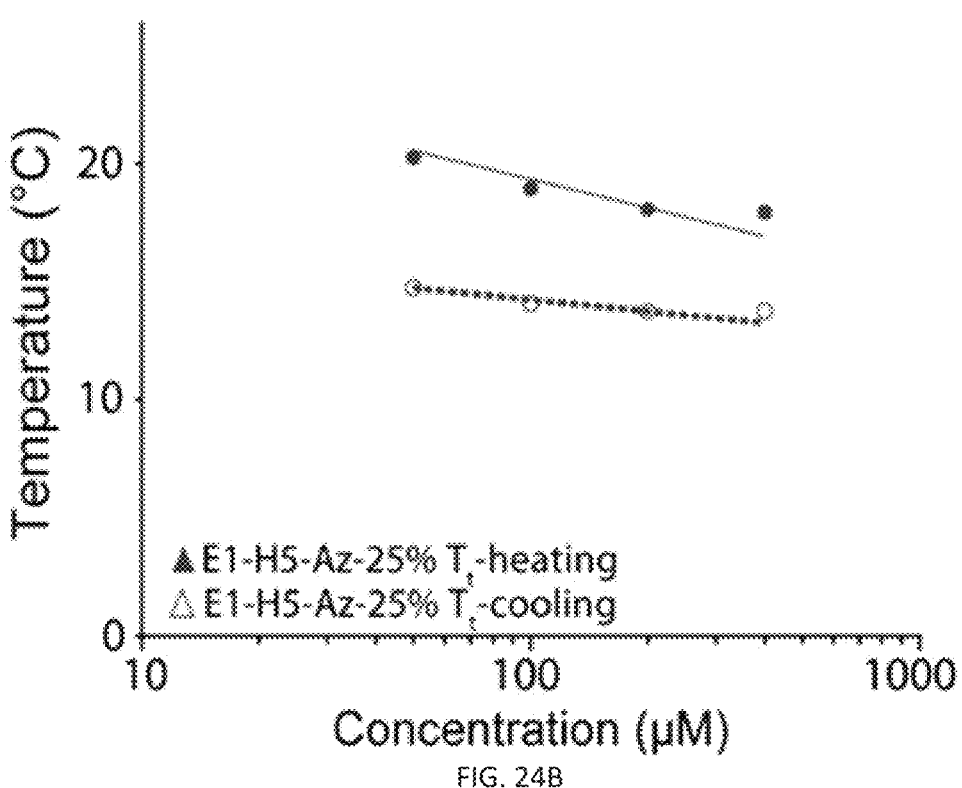
Figure 24C:
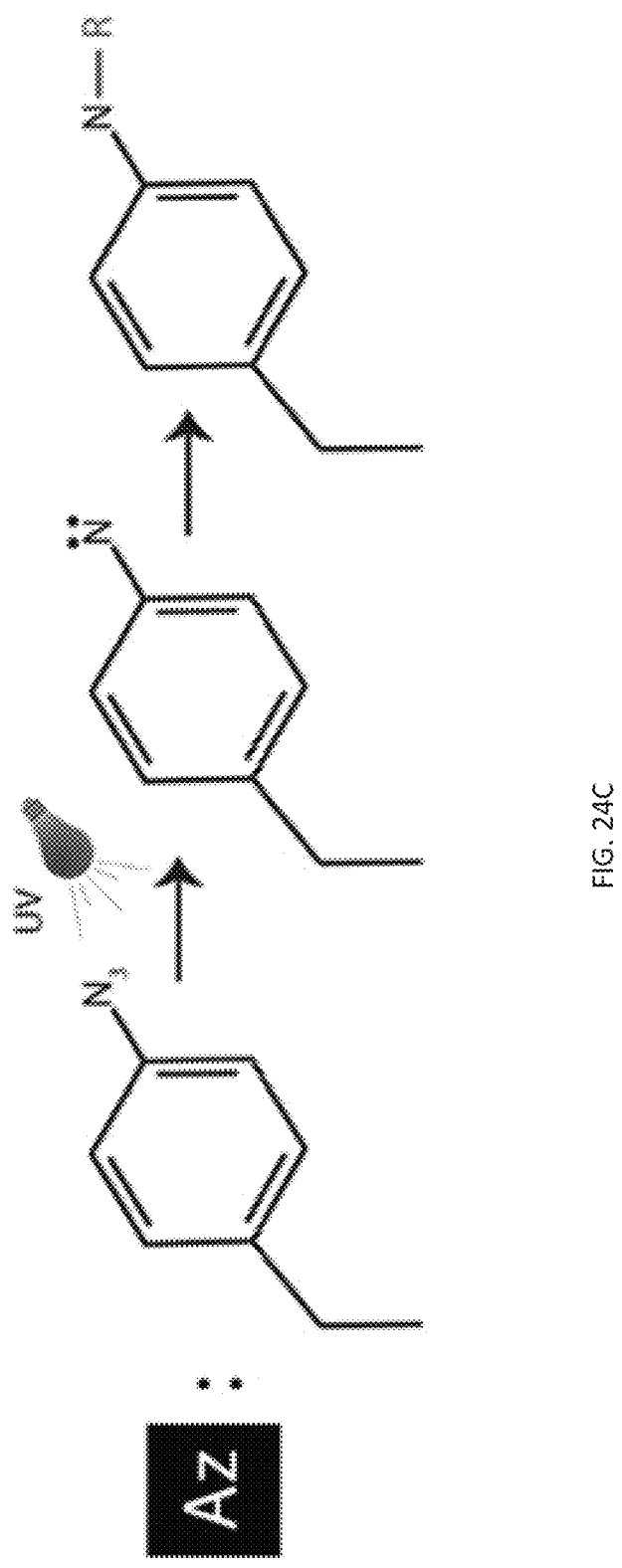
Figure 24E:
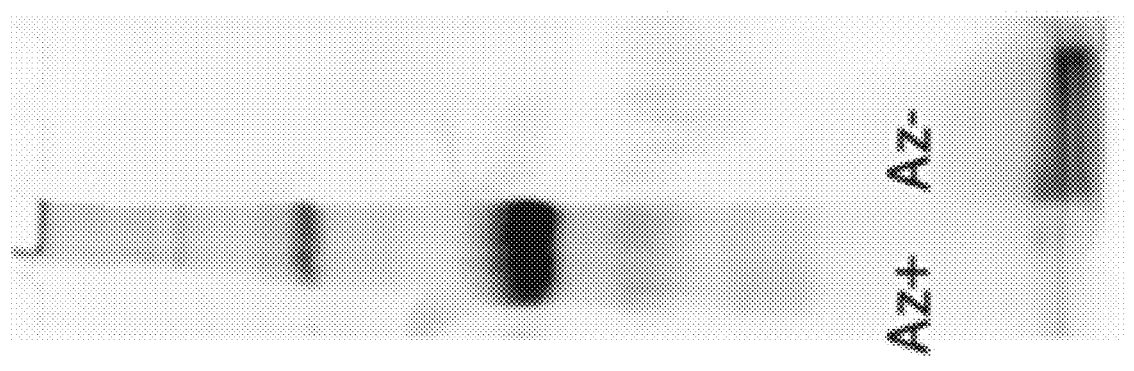
Figure 24D:
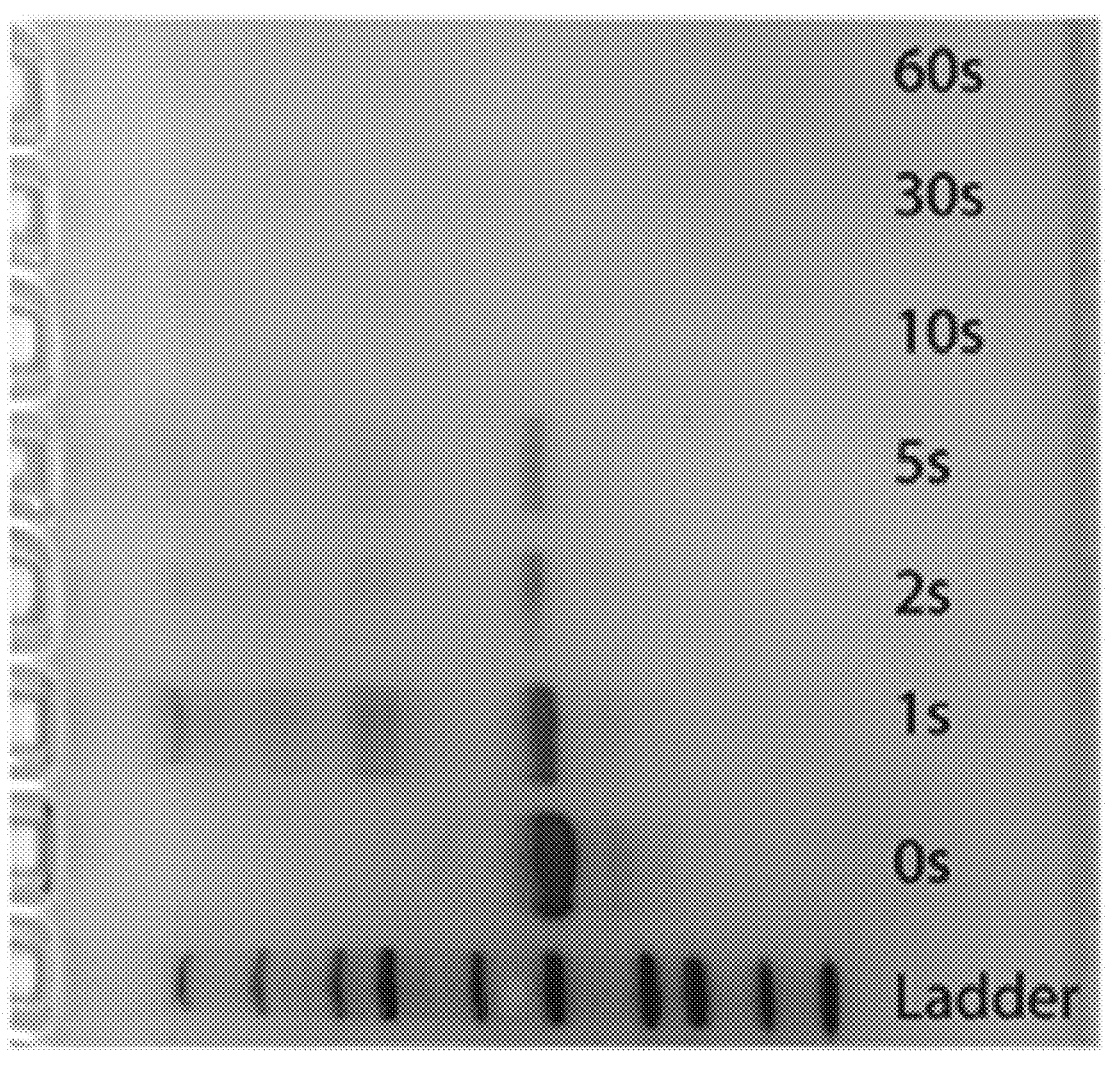
Figure 24F:
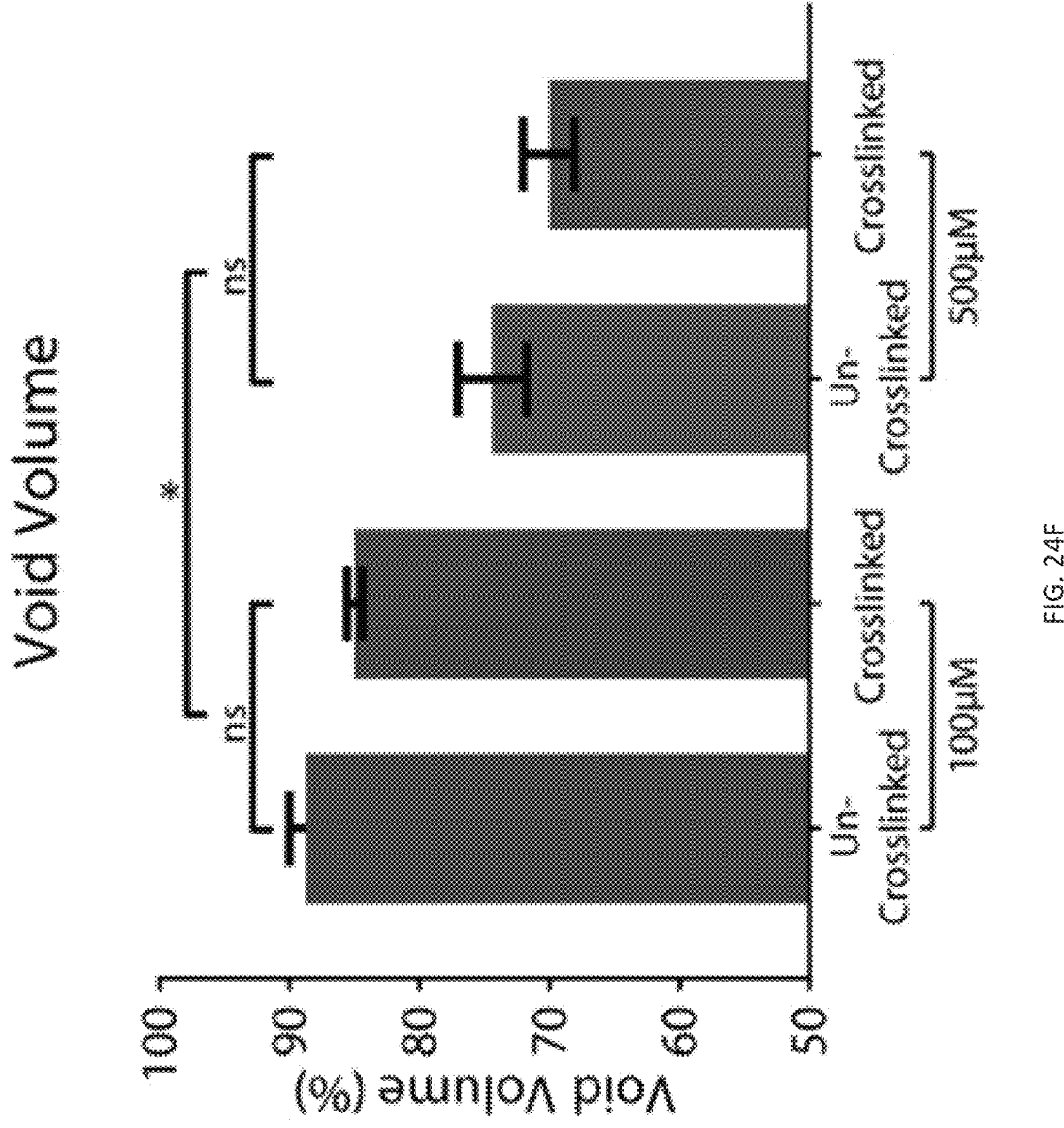
Figure 25A:
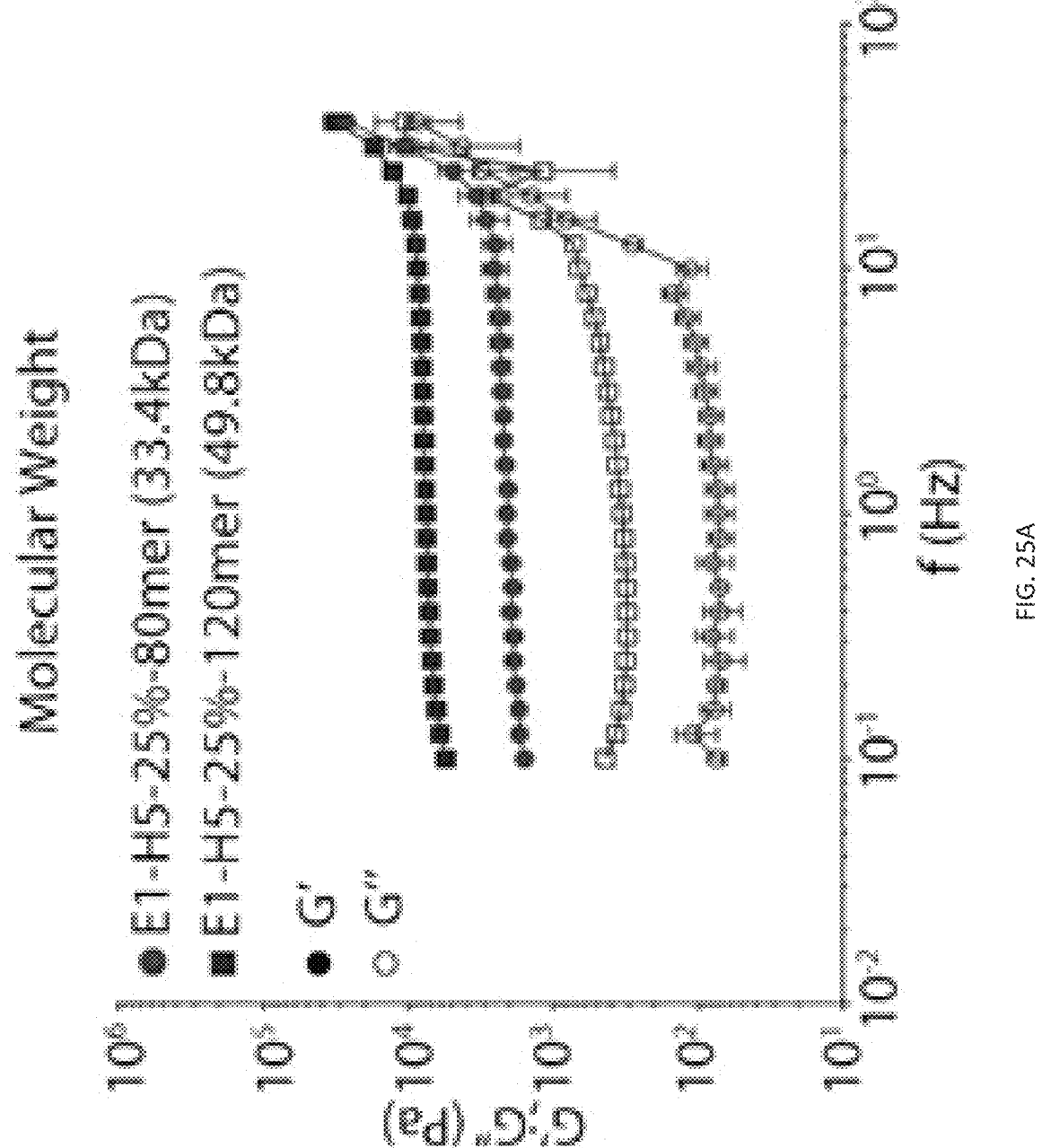
FIG. 25A-FIG. 25G: Methods of altering mechanical stability.
Figure 25B:
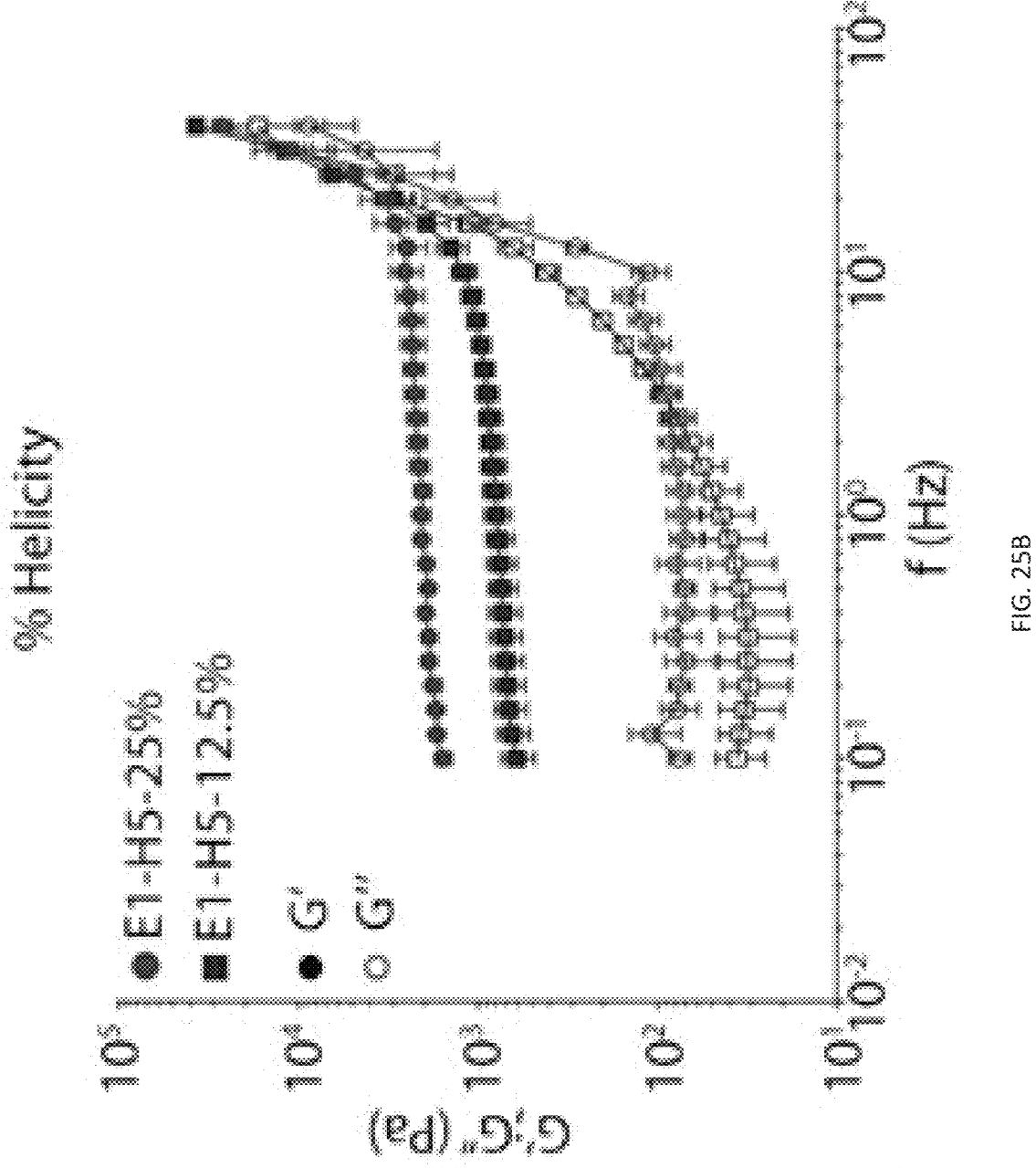
Figure 25C:
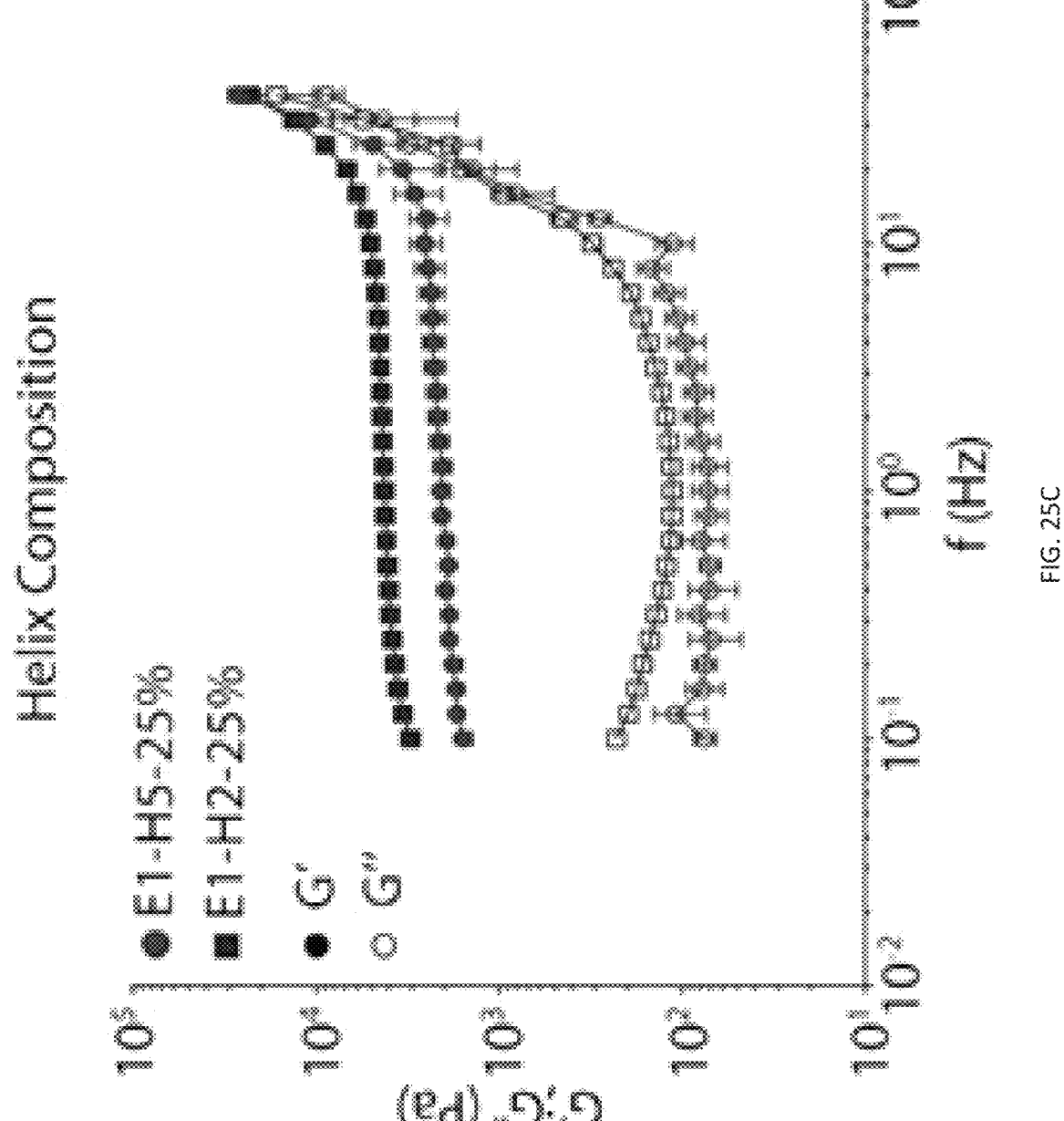
Figure 25D:
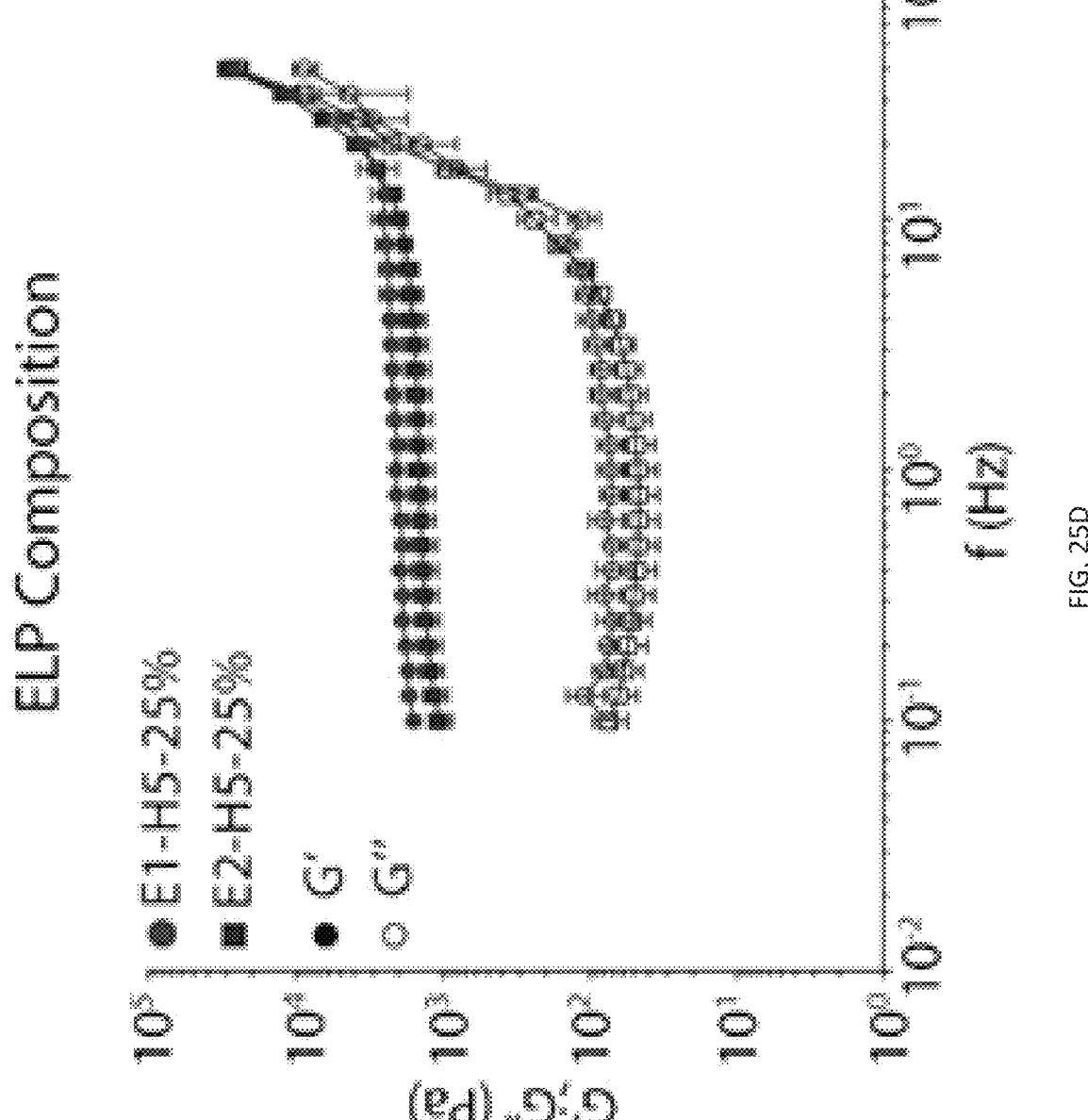
Figure 25E:
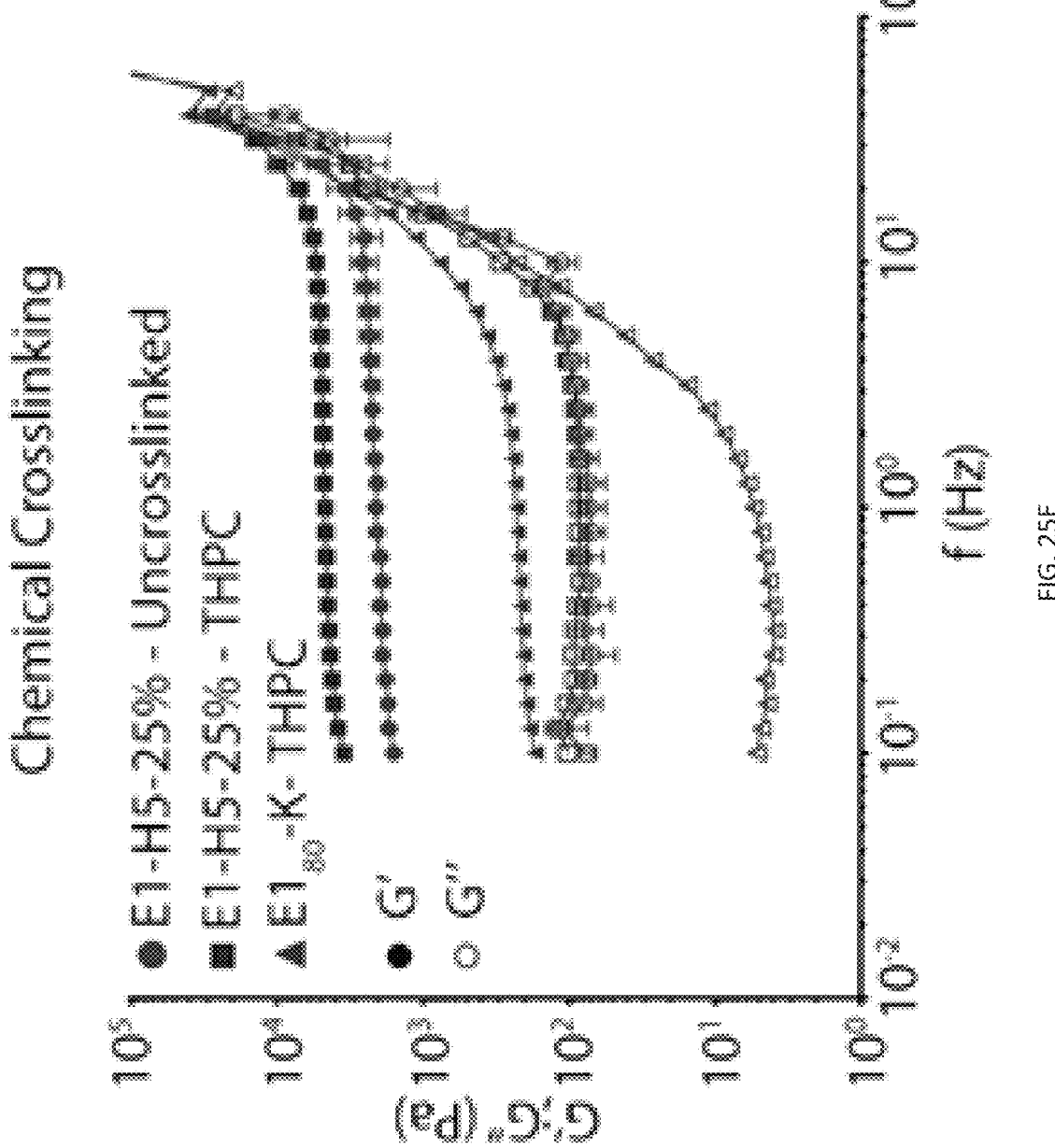
Figure 25F:
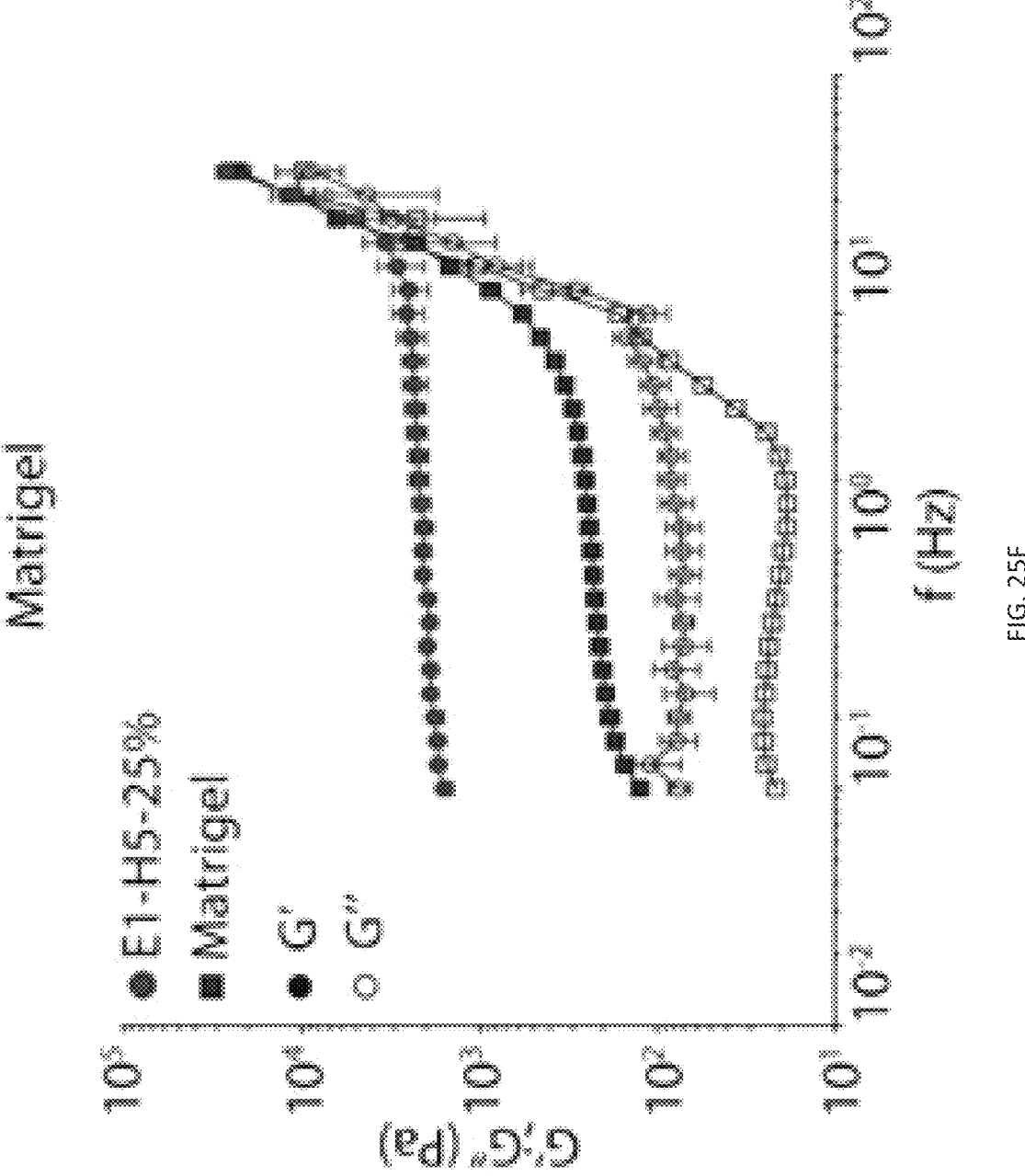
Figure 25G:
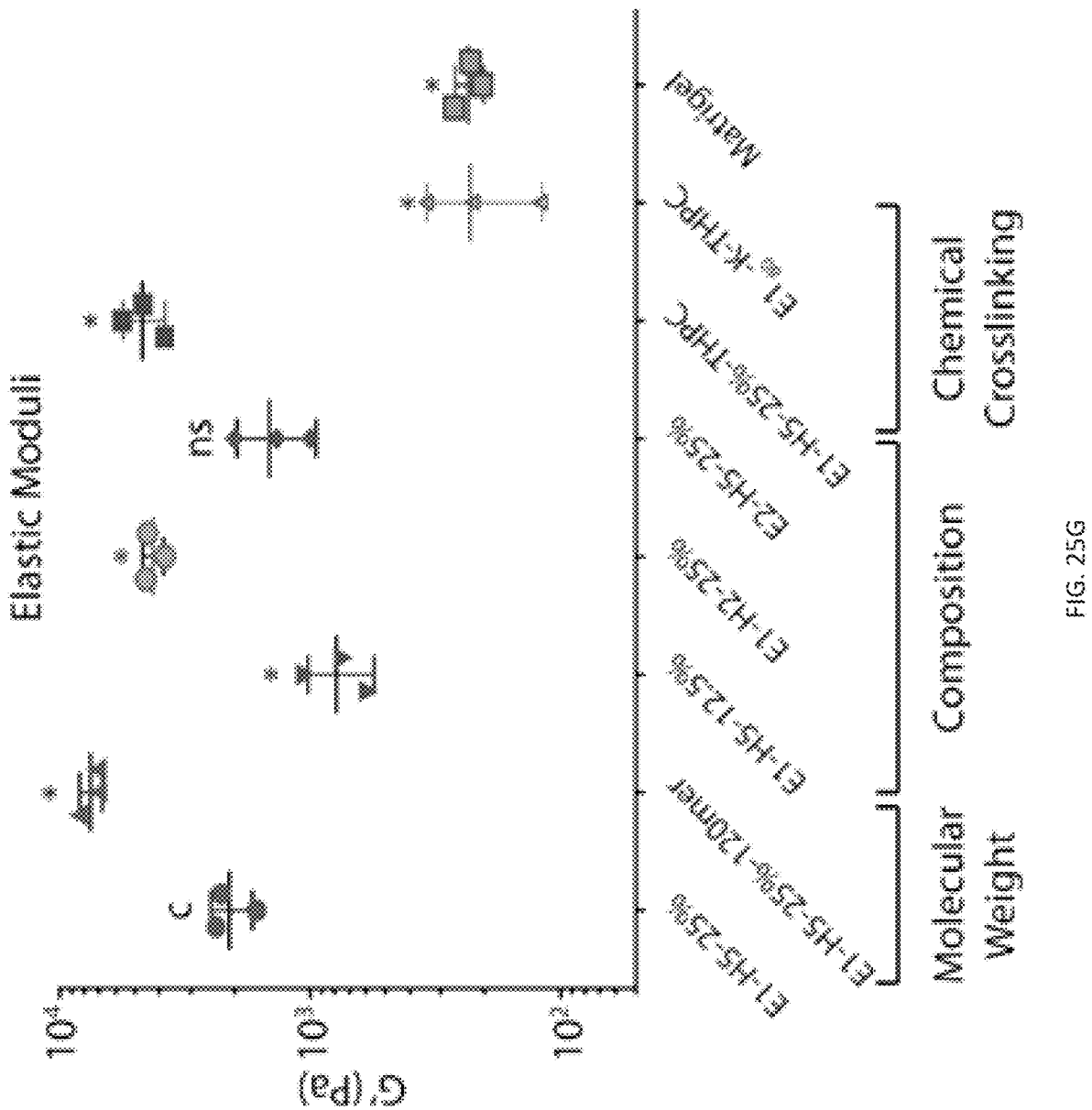

For analysis of POP persistence in the s.c. space and cell recruitment, C57BL/6 mice receiving endotoxin purified (<1 EU/mL) s.c. injections of E1-H5-25%-120 (200 μL at 250 μM, 50 kDa) were monitored over 21 days. Injected depots were excised and either fixed for histological evaluation or processed to extract cells for flow cytometry (FIG. 18-FIG. 20). POPs rapidly and robustly integrate into the s.c. space, creating mechanical connections with surrounding tissue within 24 h (FIG. 6E) and show no significant decrease in size after 21 days (FIG. 6D, FIG. 18, FIG. 15). Initial cell recruitment is high, with cell density peaking at day 10 (FIG. 6F). Recruited cells show the POP depots to undergo a wound-healing response with an initial, mild inflammatory phase that resolves over time followed by angiogenesis and proliferation of non-immune cells. Hematopoietic-derived cells (CD45+) steadily increase up to day 10 with neutrophils, inflammatory monocytes, and macrophages peaking on days 1, 3, and 10 respectively (FIG. 6G-FIG. 6H). By day 21, all hematopoietic derived cells drop off dramatically and non-hematopoietic cells become the dominant population (FIG. 6G-FIG. 6H and FIG. 21). Curiously, E1-H5-25%-120 injected at 750 μM POP concentration did not show significant differences in any recruited cell subtypes from 250 μM (FIG. 21) despite the decrease in porosity. Histology of POP depots supports the presence of a high cellular density, extensive cellular infiltration from surrounding tissue, and no strong fibrin capsule formation (FIG. 22). POPs also show a high degree of vascularization with capillaries and some larger vessels emerging by day 10—with some branching vessels even visible to the unaided eye (FIG. 6D and FIG. 6I-FIG. 6J). The vasculature becomes more uniformly distributed throughout the depots by day 21 (FIG. 22).

Because fully disordered ELPs disseminate too quickly to form explantable depots, we injected equivalent weight percentages of Matrigel to provide a comparison to an established injectable scaffold. Compared to Matrigel, POPs recruit a greater number of cells, including non-hematopoietic cells, and show dramatically increased mechanical integration and vascularization than Matrigel (FIG. 23). POPs are therefore more useful than Matrigel for applications requiring increased integration of the scaffold surrounding tissue, whereas Matrigel may be more useful for applications requiring greater isolation of the material from surrounding tissue. The angiogenesis of POPs with minimal, resolving inflammation is promising for the use of POPs as an injectable material for regenerative medicine.

Using molecularly engineered polypeptides that precisely encode ordered and disordered segments along the polymer chain, we have developed a simple, modular, and tunable material system to evaluate the impact of molecular order and disorder at the primary sequence level on the structure and properties of the resulting material. By encoding helical domains into ELPs, we show that thermally triggered phase separation does not lead to dense coacervates, but instead drives the hierarchical assembly of porous, viscoelastic networks that are reminiscent of cross-linked elastin. Though the physically cross-linked POP networks retain the thermal reversibility of fully disordered ELPs, the aggregation and dissolution temperatures can be independently controlled by specifying the composition and mass fraction of the disordered and ordered domains respectively. These polymers assemble into 3D scaffolds in vivo that are notably more stable than controls, which are disordered ELP sequences. Analysis of explanted POP depots reveals a progression from mild inflammation that resolves with time, to migration of cells within the scaffold, followed by proliferation and vascularization, indicating that POPs promote wound healing and tissue growth. As the field of intrinsically disordered proteins has expanded, knowledge of the biological importance of the synergy between disordered regions and ordered domains is growing; yet limited information exists on functionalizing these interactions for biomedical applications. Our biopolymer platform is an important step towards uncovering design rules that combine order and disorder to develop a new generation of functional protein biomaterials.

Example 8

UV Crosslinkable POPs

Gene fragments were cloned into a modified pet-24 vector via recursive directional ligation by plasmid reconstruction into chemically competent E. coli. Following their complete synthesis, genes were isolated via restriction digest, and the appropriate fragment cloned into another modified pet-24 vector with a pTac promoter and rrnB terminator instead of the T7 promoter and terminator of the original vector. The plasmids were then con-transfected into c321.ΔA E. coli alongside a pEvol tRNA/aaRS vector with two copies of pAcFRS.1.t1 synthetase—the c321.ΔA genome has previously been edited to remove all instances of the amber stop codon, and the tRNA/aaRS pair has been optimized to recognize the amber stop codon and attach to para-azidophenylalanine (N. W. Choi, J. Kim, S. C. Chapin, T. Duong, E. Donohue, P. Pandey, W. Broom, W. A. Hill, P. S. Doyle, Anal Chem 2012, 84, 9370, which is incorporated by reference herein in its entirety). Liquid cell cultures from 25% glycerol stocks were grown overnight (~16 hr) in 25 mL 2×YT starter cultures containing 45 μg/mL kanamycin and 25 μg/mL chloramphenicol at 37° C. and 200 rpm. Starter cultures were then transferred to 1 L 2×YT cultures the following morning and grown for ~8 hr in the presence of 45 μg/mL kanamycin, 25 μg/mL chloramphenicol, 0.2% arabinose, and 1 mM pAzF at 34° C. and 200 rpm. 1 mM IPTG was then added to induce xPOP expression, and cultures were grown for an additional ~16 hr overnight. Proteins were purified using inverse transition cycling as previously described for non-crosslinkable POPs. Purity was determined via SDS-PAGE gel electrophoresis. Samples were then lyophilized and stored at −20° C. All protocols were completed under low-light conditions to avoid undesirable pAzF crosslinking during synthesis and purification. xPOP transition behavior was characterized using a Cary 100 UV-Vis spectrophotometer monitoring optical density at 650 nm. Samples in 1×PBS were heated and cooled at 1° C./min and the point at which the first derivative of the curves was found to be largest in magnitude were recorded as the heating and cooling Tts. Characterization of the UV crosslinkable POPs can be seen in FIG. 24.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A partially ordered polypeptide (POP) comprising: a plurality of disordered domains; and a plurality of structured domains, wherein the POP exhibits phase transition behavior.

Clause 2. The polypeptide of clause 1, wherein the disordered domain comprises at least one of: (i) an amino acid sequence of $[VPGXG]_m$ (SEQ ID NO:1), wherein X is any amino acid except proline and m is an integer greater than or equal to 1; (ii) a PG motif comprising an amino acid sequence selected from PG, $P(X)_nG$ (SEQ ID NO:2), and $(B)_mP(X)_nG(Z)$ p (SEQ ID NO:3), or a combination thereof, wherein m, n, and p are independently an integer from 1 to 15, and wherein U, X, and Z are independently any amino acid; (iii) a non-repetitive polypeptide comprising a sequence of at least 60 amino acids, wherein at least about 10% of the amino acids are proline (P), and wherein at least about 20% of the amino acids are glycine (G); (iv) a non-repetitive polypeptide comprising a sequence of at least 60 amino acids, wherein at least about 40% of the amino acids are selected from the group consisting of valine (V), alanine (A), leucine (L), lysine (K), threonine (T), isoleucine (I), tyrosine (Y), serine (S), and phenylalanine (F); and (v) a non-repetitive polypeptide comprising a sequence of at least 60 amino acids, wherein the sequence does not contain three contiguous identical amino acids, wherein any 5-10 amino acid subsequence does not occur more than once in the non-repetitive polypeptide, and wherein when the non-repetitive polypeptide comprises a subsequence starting and ending with proline (P), the subsequence further comprises at least one glycine (G).

Clause 3. The polypeptide of clause 2, wherein the disordered domain comprises an amino acid sequence of $[VPGXG]_m$ (SEQ ID NO:1), wherein X is Val, or Ala, or mixture of Ala and Val, and wherein m is an integer from 1 to 50.

Clause 4. The polypeptide of clause 3, wherein X is a mixture of Ala and Val in a ratio from 10:1 to 1:10 (Ala:Val).

Clause 5. The polypeptide of clause 4, wherein X is a mixture of Ala and Val in a ratio of 1:1 or 1:4.

Clause 6. The polypeptide of any one of clauses 1-5, wherein the structured domain comprises at least one of: (i) a polyproline domain, each polyproline domain comprising at least 5 proline residues and having at least about 50% of the amino acids in a PPI polyproline helical conformation or a PPII polyproline helical conformation; and (ii) a polyalanine domain, each polyalanine domain comprising at least 5 alanine residues and having at least about 50% of the amino acids in an alpha-helical conformation.

Clause 7. The polypeptide of clause 6, wherein the structured domain comprises a polyalanine domain.

Clause 8. The polypeptide of clause 7, wherein at least about 60% of the amino acids in each polyalanine domain are in an alpha-helical conformation.

Clause 9. The polypeptide of clause 7 or 8, wherein the polyalanine domain comprises an amino acid sequence of $[B_p(A)_qZ_r]_n$ (SEQ ID NO:4) or $[(BA_s)_tZ_r]_n$ (SEQ ID NO:5), wherein B is Lys, Arg, Asp, or Glu; A is Ala; Z is Lys, Arg, Asp, or Glu; n is an integer from 1 to 50; p is an integer from 0 to 2; q is an integer from 1 to 50; r is an integer from 0 to 2; s is an integer from 1 to 5; and t is an integer from 1 to 50.

Clause 10. The polypeptide of any one of clauses 1-5 and 7-9, wherein the structured domain comprises $(A)_{25}$ (SEQ ID NO:6), $K(A)_{25}K$ (SEQ ID NO:7), $(KAAAA)_5K$ (SEQ ID NO:8), or $D(A)_{25}K$ (SEQ ID NO:9), or a combination thereof.

Clause 11. The polypeptide of any one of the preceding clauses, wherein the POP comprises alternating disordered domains and structured domains.

Clause 12. The polypeptide of any one of the preceding clauses, wherein about 4% to about 75% of the POP comprises structured domains.

Clause 13. The polypeptide of any one of the preceding clauses, wherein the POP is soluble below a lower critical solution temperature (LCST).

Clause 14. The polypeptide of any one of the preceding clauses, wherein the POP has a transition temperature of heating (Tt-heating) and a transition temperature of cooling (Tt-cooling).

Clause 15. The polypeptide of clause 14, wherein the transition temperature of heating (Tt-heating) and transition temperature of cooling (Tt-cooling) are identical.

Clause 16. The polypeptide of clause 14, wherein the transition temperature of heating (Tt-heating) is greater than the transition temperature of cooling (Tt-cooling).

Clause 17. The polypeptide of any one of clauses 14-16, wherein the transition temperature of heating (Tt-heating) is concentration-dependent.

Clause 18. The polypeptide of any one of clauses 14-16, wherein the transition temperature of cooling (Tt-cooling) is concentration-independent.

Clause 19. The polypeptide of any one of clauses 14-16, wherein the Tt-heating is primarily determined by the disordered domains, and wherein the Tt-cooling is primarily determined by the structured domains.

Clause 20. The polypeptide of any one of clauses 14-18, wherein the POP forms an aggregate above the Tt-heating.

Clause 21. The polypeptide of clause 20, wherein the aggregate resolubilizes when cooled to below the Tt-cooling.

Clause 22. The polypeptide of clause 20, wherein the aggregate is a stable three-dimensional matrix.

Clause 23. The polypeptide of clause 20, wherein the aggregate is fractal-like.

Clause 24. The polypeptide of clause 20, wherein the aggregate is porous with a void volume.

Clause 25. The polypeptide of clause 24, wherein the void volume is tunable.

Clause 26. A scaffold comprising a plurality of the polypeptide of any one of clauses 1-25 at a temperature greater than the transition temperature, such that the polypeptide forms an aggregate.

Clause 27. A cellular scaffold comprising the scaffold of clause 26, and a plurality of cells.

Clause 28. A method for forming a cellular scaffold, the method comprising: mixing cells with a plurality of the polypeptide of any one of clauses 1-25 at a first temperature less than the transition temperature of the polypeptide, such that the polypeptide does not form an aggregate; and incubating the polypeptides at a second temperature suitable for cellular growth and greater than the transition temperature, such that the polypeptides form an aggregate with the cells encapsulated within, to form the cellular scaffold.

Clause 29. The method of clause 28, further comprising implanting the cellular scaffold into a subject.

Clause 30. A method for forming a cellular scaffold, the method comprising: mixing cells with a plurality of the polypeptide of any one of clauses 1-25 to form a mixture, at a first temperature less than the transition temperature of the polypeptide, such that the polypeptide does not form an aggregate; and injecting the mixture at the first temperature into a subject, wherein the subject is at a second temperature greater than the transition temperature, such that the polypeptides form an aggregate with the cells encapsulated within, to form the cellular scaffold in the subject.

Clause 31. A method for forming a scaffold, the method comprising: injecting into a subject a plurality of the polypeptide of any one of clauses 1-23 at a first temperature less than the transition temperature of the polypeptide, such that the polypeptide does not form an aggregate prior to injection, wherein the subject is at a second temperature greater than the transition temperature, such that the polypeptides form an aggregate to form the scaffold in the subject.

Clause 32. The method of any one of clauses 28-30, wherein the cells within the scaffold integrate into the surrounding cells or tissues of the subject.

Clause 33. The method of any one of clauses 28-31, wherein the cells of the subject surrounding the scaffold integrate into the scaffold.

Clause 34. The method of clause 32, wherein the cells within the scaffold modify the surrounding cells or tissues of the subject.

Clause 35. The method of any one of clauses 29-34, wherein the cells within the scaffold, the cells integrating into the scaffold, or the cells modified by the scaffold form new vasculature.

Clause 36. The method of clause 28, further comprising: reducing the temperature to the first temperature, such that the aggregate/scaffold solubilizes; and separating the cells from the solubilized scaffold.

Clause 37. The method of clause 36, wherein the separating step comprises centrifugation.

Clause 38. The scaffold or method of any one of clauses 26-30 and 32-37, wherein the cells comprise stem cells, bacterial cells, or human tissue cells.

Clause 39. The scaffold or method of any one of clauses 26-38, wherein the scaffold has low immunogenicity or low antigenicity.

Clause 40. The scaffold or method of any one of clauses 26-39, wherein the scaffold promotes at least one of cell growth, recruitment, and differentiation.

Clause 41. A drug delivery composition comprising: a plurality of POPs according to any one of clauses 1-25, self-assembled into an aggregate above the $T_t$-heating; and an agent encapsulated within the aggregate.

Clause 42. The drug delivery composition of clause 41, wherein the agent recruits dendritic cells.

Clause 43. A method of delivering an agent to a subject, the method comprising: encapsulating the agent in an aggregate, the aggregate comprising a plurality of POPs according to any one of clauses 1-25; and administering the aggregate to the subject.

Clause 44. A method of treating a disease in a subject in need thereof, the method comprising administering the drug delivery composition of clause 41 to the subject.

Clause 45. The method of clause 44, wherein administering the drug delivery composition results in the formation of new vasculature, wound healing, or a combination thereof in the subject.

Clause 46. A method of increasing the maximum tolerated dose of an agent, the method comprising: encapsulating the agent in an aggregate of POPs according to any one of clauses 1-25; and administering the agent-encapsulated aggregate to a subject.

Clause 47. The composition of clause 41 or the method of any one of clauses 43-46, wherein the agent comprises a small molecule, a polynucleotide, a polypeptide, a carbohydrate, or a combination thereof.

```
Sequences
                                        (SEQ ID NO: 1)
[VPGXG]_m (SEQ ID NO: 2)
P(X)_nG (SEQ ID NO: 3)
(B)_mP(X)_nG(Z)_p (SEQ ID NO: 4)
[Bp(A)_qZr]_n (SEQ ID NO: 5)
[(BA_s)_rZr]_n (SEQ ID NO: 6)
(A)_25

(SEQ ID NO: 7)
K(A)_25K (SEQ ID NO: 8)
(KAAAA)_5K (SEQ ID NO: 9)
D(A)_25K (SEQ ID NO: 10)
PXXG (SEQ ID NO: 11)
PXXXG (SEQ ID NO: 12)
PXXXXG (SEQ ID NO: 13)
PXXXXXG (SEQ ID NO: 14)
PXXXXXXG (SEQ ID NO: 15)
PXXXXXXXG (SEQ ID NO: 16)
PXXXXXXXXG (SEQ ID NO: 17)
PXXXXXXXXXG (SEQ ID NO: 18)
PXXXXXXXXXXG (SEQ ID NO: 19)
PXXXXXXXXXXXG (SEQ ID NO: 20)
PXXXXXXXXXXXXG (SEQ ID NO: 21)
PXXXXXXXXXXXXXG (SEQ ID NO: 22)
PXXXXXXXXXXXXXXG (SEQ ID NO: 23)
PXXXXXXXXXXXXXXXG (SEQ ID NO: 24)
TGTGGGTGTTCCGGGCGTAGGTGTCCCAGGTGTGGGCGTA
CCGGGCGTTGGTGTTCCTGGTGTCGGCGTGCCGGG
```

-continued                                                          -continued (SEQ ID NO: 25)

CGGCACGCCGACACCAGGAACACCAACGCCCGGTACGCCC

ACACCTGGGACACCTACGCCCGGAACACCCACACC (SEQ ID NO: 26)

CGTGGGTGTTCCGGGCGTAGGTGTCCCAGGTGCGGGCGTA

CCGGGCGTTGGTGTTCCTGGTGTCGGCGTGCCGGG (SEQ ID NO: 27)

CGGCACGCCGACACCAGGAACACCAACGCCCGGTACGCCC

GCACCTGGGACACCTACGCCCGGAACACCCACGCC (SEQ ID NO: 28)

CGCCGGAGTGCCAGGCGTGGGTGTTCCAGGAGCAGGCGTT

CCAGGTGTGGGTGTTCCTGG (SEQ ID NO: 29)

AGGAACACCCACACCTGGAACGCCTGCTCCTGGAACACCC

ACGCCTGGCACTCCGGCGCC (SEQ ID NO: 30)

TGCGGCCGCAGCTGCGGCGGCAGCCGCGGCTGCCGCGGCT

GCAGCGGCAGCCGCGGCTGCGGCGGCCGCAGCTGCGGG (SEQ ID NO: 31)

CGCAGCTGCGGCCGCCGCAGCCGCGGCTGCCGCTGCAGCC

GCGGCAGCCGCGGCTGCCGCCGCAGCTGCGGCCGCACC (SEQ ID NO: 32)

TAAAGCGGCCGCAGCTGCGGCGGCAGCCGCGGCTGCCGCG

GCTGCAGCGGCAGCCGCGGCTGCGGCGGCCGCAGCTGCGA

AAGG (SEQ ID NO: 33)

TTTCGCAGCTGCGGCCGCCGCAGCCGCGGCTGCCGCTGCA

GCCGCGGCAGCCGCGGCTGCCGCCGCAGCTGCGGCCGCTT

TACC (SEQ ID NO: 34)

TAAAGCGGCCGCAGCTAAAGCCGCGGCAGCGAAAGCAGCC

GCGGCGAAAGCCGCAGCTGCGAAAGCGGCAGCCGCGAAGG

G (SEQ ID NO: 35)

CTTCGCGGCTGCCGCTTTCGCAGCTGCGGCTTTCGCCGCG

GCTGCTTTCGCTGCCGCGGCTTTAGCTGCGGCCGCTTTAC

C (SEQ ID NO: 36)

TGATGCGGCCGCAGCTGCGGCGGCAGCCGCGGCTGCCGCG

GCTGCAGCGGCAGCCGCGGCTGCGGCGGCCGCAGCTGCGA

AAGG (SEQ ID NO: 37)

TTTCGCAGCTGCGGCCGCCGCAGCCGCGGCTGCCGCTGCA

GCCGCGGCAGCCGCGGCTGCCGCCGCAGCTGCGGCCGCAT

CACC (SEQ ID NO: 38)

AAAAA (SEQ ID NO: 39)

VPGVG

_____

SEQUENCE LISTING

Sequence total quantity: 39
SEQ ID NO: 1              moltype = AA  length = 5
FEATURE                   Location/Qualifiers
REPEAT                    1..5
                          note = sequence 1-5 may repeat one or more times
VARIANT                   4
                          note = X is any amino acid except proline
source                    1..5
                          mol_type = protein
                          organism = synthetic construct
SEQUENCE: 1
VPGXG                                                                5

SEQ ID NO: 2              moltype =   length =
SEQUENCE: 2
000

SEQ ID NO: 3              moltype = AA  length = 47
FEATURE                   Location/Qualifiers
VARIANT                   2..15
                          note = Asx at positions 2-15 can either be present or absent
VARIANT                   17..31
                          note = X is any amino acid independent of Glx at positions
                           32-47
source                    1..47
                          mol_type = protein
                          organism = synthetic construct
VARIANT                   32..47
                          note = Glx at positions 32-47 are independent of X at
                           positions 17-31
VARIANT                   17..31
                          note = where any one or all amino acids at positions 18-31
                           can be either present or absent

```
SEQUENCE: 3
BBBBBBBBBB BBBBBPXXXX XXXXXXXXXX XGZZZZZZZZ ZZZZZZZ                          47

SEQ ID NO: 4              moltype = AA  length = 54
FEATURE                   Location/Qualifiers
VARIANT                   1..2
                          note = Any or all Asx at positions 1-2 can be either
                           present or absent
REPEAT                    1..54
                          note = sequence 1-54 may repeat 1-50 times
VARIANT                   4..52
                          note = Any one or all Ala at positions 4-52 can be either
                           present or absent
VARIANT                   53..54
                          note = Any or all Glx at positions 53-54 can be either
                           present or absent
source                    1..54
                          mol_type = protein
                          organism = synthetic construct
SEQUENCE: 4
BBAAAAAAAA AAAAAAAAAA AAAAAAAAAA AAAAAAAAAA AAAAAAAAAA AAZZ           54

SEQ ID NO: 5              moltype =   length =
SEQUENCE: 5
000

SEQ ID NO: 6              moltype = AA  length = 25
FEATURE                   Location/Qualifiers
source                    1..25
                          mol_type = protein
                          organism = synthetic construct
SEQUENCE: 6
AAAAAAAAAA AAAAAAAAAA AAAAA                                          25

SEQ ID NO: 7              moltype = AA  length = 27
FEATURE                   Location/Qualifiers
source                    1..27
                          mol_type = protein
                          organism = synthetic construct
SEQUENCE: 7
KAAAAAAAAA AAAAAAAAAA AAAAAAK                                        27

SEQ ID NO: 8              moltype = AA  length = 26
FEATURE                   Location/Qualifiers
source                    1..26
                          mol_type = protein
                          organism = synthetic construct
SEQUENCE: 8
KAAAAKAAAA KAAAAKAAAA KAAAK                                          26

SEQ ID NO: 9              moltype = AA  length = 27
FEATURE                   Location/Qualifiers
source                    1..27
                          mol_type = protein
                          organism = synthetic construct
SEQUENCE: 9
DAAAAAAAAA AAAAAAAAAA AAAAAAK                                        27

SEQ ID NO: 10             moltype =   length =
SEQUENCE: 10
000

SEQ ID NO: 11             moltype =   length =
SEQUENCE: 11
000

SEQ ID NO: 12             moltype =   length =
SEQUENCE: 12
000

SEQ ID NO: 13             moltype =   length =
SEQUENCE: 13
000

SEQ ID NO: 14             moltype =   length =
SEQUENCE: 14
000

SEQ ID NO: 15             moltype =   length =
```

```
SEQUENCE: 15
000

SEQ ID NO: 16              moltype =   length =
SEQUENCE: 16
000

SEQ ID NO: 17              moltype =   length =
SEQUENCE: 17
000

SEQ ID NO: 18              moltype =   length =
SEQUENCE: 18
000

SEQ ID NO: 19              moltype =   length =
SEQUENCE: 19
000

SEQ ID NO: 20              moltype =   length =
SEQUENCE: 20
000

SEQ ID NO: 21              moltype =   length =
SEQUENCE: 21
000

SEQ ID NO: 22              moltype =   length =
SEQUENCE: 22
000

SEQ ID NO: 23              moltype =   length =
SEQUENCE: 23
000

SEQ ID NO: 24              moltype = DNA   length = 75
FEATURE                    Location/Qualifiers
source                     1..75
                           mol_type = other DNA
                           organism = synthetic construct
SEQUENCE: 24
tgtgggtgtt ccgggcgtag gtgtcccagg tgtgggcgta ccgggcgttg gtgttcctgg   60
tgtcggcgtg ccggg                                                    75

SEQ ID NO: 25              moltype = DNA   length = 75
FEATURE                    Location/Qualifiers
source                     1..75
                           mol_type = other DNA
                           organism = synthetic construct
SEQUENCE: 25
cggcacgccg acaccaggaa caccaacgcc cggtacgccc acacctggga cacctacgcc   60
cggaacaccc acacc                                                    75

SEQ ID NO: 26              moltype = DNA   length = 75
FEATURE                    Location/Qualifiers
source                     1..75
                           mol_type = other DNA
                           organism = synthetic construct
SEQUENCE: 26
cgtgggtgtt ccgggcgtag gtgtcccagg tgcgggcgta ccgggcgttg gtgttcctgg   60
tgtcggcgtg ccggg                                                    75

SEQ ID NO: 27              moltype = DNA   length = 75
FEATURE                    Location/Qualifiers
source                     1..75
                           mol_type = other DNA
                           organism = synthetic construct
SEQUENCE: 27
cggcacgccg acaccaggaa caccaacgcc cggtacgccc gcacctggga cacctacgcc   60
cggaacaccc acgcc                                                    75

SEQ ID NO: 28              moltype = DNA   length = 60
FEATURE                    Location/Qualifiers
source                     1..60
                           mol_type = other DNA
                           organism = synthetic construct
SEQUENCE: 28
cgccggagtg ccaggcgtgg gtgttccagg agcaggcgtt ccaggtgtgg gtgttcctgg   60
```

-continued

```
SEQ ID NO: 29            moltype = DNA   length = 60
FEATURE                  Location/Qualifiers
source                   1..60
                         mol_type = other DNA
                         organism = synthetic construct
SEQUENCE: 29
aggaacaccc acacctggaa cgcctgctcc tggaacaccc acgcctggca ctccggcgcc   60

SEQ ID NO: 30            moltype = DNA   length = 78
FEATURE                  Location/Qualifiers
source                   1..78
                         mol_type = other DNA
                         organism = synthetic construct
SEQUENCE: 30
tgcggccgca gctgcggcgg cagccgcggc tgccgcggct gcagcggcag ccgcggctgc   60
ggcggccgca gctgcggg                                                 78

SEQ ID NO: 31            moltype = DNA   length = 78
FEATURE                  Location/Qualifiers
source                   1..78
                         mol_type = other DNA
                         organism = synthetic construct
SEQUENCE: 31
cgcagctgcg gccgccgcag ccgcggctgc cgctgcagcc gcggcagccg cggctgccgc   60
cgcagctgcg gccgcacc                                                 78

SEQ ID NO: 32            moltype = DNA   length = 84
FEATURE                  Location/Qualifiers
source                   1..84
                         mol_type = other DNA
                         organism = synthetic construct
SEQUENCE: 32
taaagcggcc gcagctgcgg cggcagccgc ggctgccgcg gctgcagcgg cagccgcggc   60
tgcggcggcc gcagctgcga aagg                                          84

SEQ ID NO: 33            moltype = DNA   length = 84
FEATURE                  Location/Qualifiers
source                   1..84
                         mol_type = other DNA
                         organism = synthetic construct
SEQUENCE: 33
tttcgcagct gcggccgccg cagccgcggc tgccgctgca gccgcggcag ccgcggctgc   60
cgccgcagct gcggccgctt tacc                                          84

SEQ ID NO: 34            moltype = DNA   length = 81
FEATURE                  Location/Qualifiers
source                   1..81
                         mol_type = other DNA
                         organism = synthetic construct
SEQUENCE: 34
taaagcggcc gcagctaaag ccgcggcagc gaaagcagcc gcggcgaaag ccgcagctgc   60
gaaagcggca gccgcgaagg g                                             81

SEQ ID NO: 35            moltype = DNA   length = 81
FEATURE                  Location/Qualifiers
source                   1..81
                         mol_type = other DNA
                         organism = synthetic construct
SEQUENCE: 35
cttcgcggct gccgctttcg cagctgcggc tttcgccgcg gctgctttcg ctgccgcggc   60
tttagctgcg gccgctttac c                                             81

SEQ ID NO: 36            moltype = DNA   length = 84
FEATURE                  Location/Qualifiers
source                   1..84
                         mol_type = other DNA
                         organism = synthetic construct
SEQUENCE: 36
tgatgcggcc gcagctgcgg cggcagccgc ggctgccgcg gctgcagcgg cagccgcggc   60
tgcggcggcc gcagctgcga aagg                                          84

SEQ ID NO: 37            moltype = DNA   length = 84
FEATURE                  Location/Qualifiers
source                   1..84
                         mol_type = other DNA
                         organism = synthetic construct
SEQUENCE: 37
tttcgcagct gcggccgccg cagccgcggc tgccgctgca gccgcggcag ccgcggctgc   60
cgccgcagct gcggccgcat cacc                                          84
```

```
SEQ ID NO: 38          moltype = AA  length = 5
FEATURE                Location/Qualifiers
source                 1..5
                       mol_type = protein
                       organism = synthetic construct
SEQUENCE: 38
AAAAA                                                              5

SEQ ID NO: 39          moltype = AA  length = 5
FEATURE                Location/Qualifiers
source                 1..5
                       mol_type = protein
                       organism = synthetic construct
SEQUENCE: 39
VPGVG                                                              5
```

The invention claimed is:

1. A partially ordered polypeptide comprising:
a plurality of disordered domains, each comprising a PG or a GP motif; and
a plurality of self-interacting domains, each self-interacting domain comprising a polyalanine domain, at least about 25% of the amino acids in the polyalanine domain being alanine residues,
wherein the partially ordered polypeptide exhibits phase transition behavior defined by a transition temperature, the partially ordered polypeptide forming an aggregate above the transition temperature.

2. The polypeptide of claim 1, wherein at least one disordered domain comprises an amino acid sequence of $(VPGXG)_m$ (SEQ ID NO:1), wherein X is any amino acid except proline and m is an integer greater than or equal to 1.

3. The polypeptide of claim 1, wherein the polyalanine domain comprises at least 4 consecutive alanine residues.

4. The polypeptide of claim 3, wherein the polyalanine domain comprises at least about 50% of its amino acids in an alpha-helical conformation.

5. The polypeptide of claim 4, wherein the polyalanine domain comprises at least about 90% of its amino acids in the alpha-helical conformation.

6. The polypeptide of claim 1, wherein at least about 50% of the amino acids in the polyalanine domain are alanine residues.

7. The polypeptide of claim 1, wherein the polyalanine domain comprises $(A)_{25}$ (SEQ ID NO: 6), $K(A)_{25}K$ (SEQ ID NO:7), or $D(A)_{25}K$ (SEQ ID NO:9), or a combination thereof.

8. The polypeptide of claim 1, wherein the polypeptide is soluble below the transition temperature.

9. The polypeptide of claim 1, wherein the aggregate is a porous network.

10. The polypeptide of claim 1, wherein the transition temperature is concentration dependent.

11. The polypeptide of claim 1, wherein the transition temperature is dependent on a ratio between the plurality of disordered domains and the plurality of self-interacting domains within the polypeptide.

12. The polypeptide of claim 1, wherein about 4% to about 75% of the polypeptide comprises self-interacting domains.

13. The polypeptide of claim 1, wherein the interaction strength between the plurality of disordered domains is between about 0.05 kcal/mol and about 0.40 kcal/mol.

14. The polypeptide of claim 13, wherein the interaction strength between the plurality of disordered domains is between about 0.35 kcal/mol and about 0.40 kcal/mol.

15. The polypeptide of claim 1, wherein the interaction strength between the plurality of self-interacting domains is at least about 1 kcal/mol.

16. The polypeptide of claim 1, wherein the polypeptide exhibits reversible phase transition behavior.

17. The polypeptide of claim 1, wherein the aggregate has a void volume between about 60% and about 90%.

18. The polypeptide of claim 1, wherein the aggregate is crosslinked by a chemical crosslinker.

19. The polypeptide of claim 1, wherein the aggregate is crosslinked by exposure to ultraviolet light.

20. A method for forming a cellular scaffold, the method comprising:
mixing cells with a plurality of the polypeptide of claim 1 at a first temperature less than the transition temperature of the polypeptide, such that the polypeptide does not form an aggregate;
heating the mixture to a second temperature greater than or equal to the transition temperature of the polypeptide, such that the polypeptide forms an aggregate; and
injecting the aggregate at the second temperature into a subject.

21. The method of claim 20, wherein the cells comprise stem cells.

* * * * *